(12) United States Patent
Kemp et al.

(10) Patent No.: US 11,319,287 B2
(45) Date of Patent: *May 3, 2022

(54) CYANOPYRROLIDINES AS DUB INHIBITORS FOR THE TREATMENT OF CANCER

(71) Applicant: MISSION THERAPEUTICS LIMITED, Cambridge (GB)

(72) Inventors: Mark Kemp, Cambridge (GB); Martin Stockley, Cambridge (GB); Alison Jones, Cambridge (GB)

(73) Assignee: MISSION THERAPEUTICS LIMITED, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/843,339

(22) Filed: Apr. 8, 2020

(65) Prior Publication Data

US 2020/0231542 A1    Jul. 23, 2020

Related U.S. Application Data

(62) Division of application No. 15/738,900, filed as application No. PCT/GB2016/052130 on Jul. 14, 2016, now Pat. No. 10,669,234.

(30) Foreign Application Priority Data

Jul. 14, 2015   (GB) ..................... 1512270
Mar. 18, 2016  (GB) ..................... 1604642

(51) Int. Cl.
| | |
|---|---|
| *C07D 207/16* | (2006.01) |
| *C07D 413/14* | (2006.01) |
| *C07D 403/06* | (2006.01) |
| *C07D 403/14* | (2006.01) |
| *C07D 413/06* | (2006.01) |
| *C07D 417/12* | (2006.01) |
| *C07D 417/14* | (2006.01) |
| *C07D 471/04* | (2006.01) |
| *C07D 401/06* | (2006.01) |
| *C07D 401/14* | (2006.01) |
| *C07D 209/04* | (2006.01) |
| *A61P 25/28* | (2006.01) |
| *A61P 35/00* | (2006.01) |

(52) U.S. Cl.
CPC ............ *C07D 207/16* (2013.01); *A61P 25/28* (2018.01); *A61P 35/00* (2018.01); *C07D 209/04* (2013.01); *C07D 401/06* (2013.01); *C07D 401/14* (2013.01); *C07D 403/06* (2013.01); *C07D 403/14* (2013.01); *C07D 413/06* (2013.01); *C07D 413/14* (2013.01); *C07D 417/12* (2013.01); *C07D 417/14* (2013.01); *C07D 471/04* (2013.01); *C07B 2200/07* (2013.01)

(58) Field of Classification Search
CPC .................................................. C07D 207/16
See application file for complete search history.

(56) References Cited

FOREIGN PATENT DOCUMENTS

WO    2012040527 A2    3/2012

*Primary Examiner* — Susanna Moore

(57) ABSTRACT

The present invention relates to novel compounds and method for the manufacture of inhibitors of deubiquitylating enzymes (DUBs). In particular, the invention relates to the inhibition of ubiquitin C-terminal hydrolase L1 (UCHL1) and ubiquitin C-terminal hydrolase 30 or ubiquitin specific peptidase 30 (USP30). The invention further relates to the use of DUB inhibitors in the treatment of cancer and conditions involving mitochondrial dysfunction. Compounds of the invention include compounds having the formula (I)

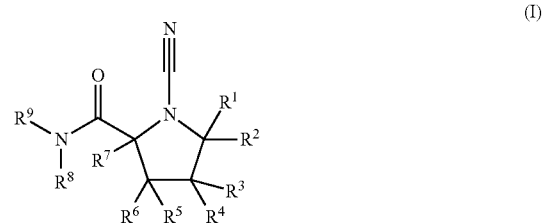

(I)

or a pharmaceutically acceptable salt thereof, wherein $R^1$, $R^2$, $R^3$, $R^4$, $R^5$, $R^6$, $R^7$, $R^8$ and $R^9$ are as defined herein.

15 Claims, 2 Drawing Sheets

Expression and purification of FLAG-UCHL1 from mammalian cells

UCHL1 kinetic assay for high throughput screening of compounds using an isopeptide linked substrate

USP30 kinetic assay for high throughput screening of compounds using an isopeptide linked substrate

CYANOPYRROLIDINES AS DUB INHIBITORS FOR THE TREATMENT OF CANCER

CROSS-REFERENCE TO RELATED APPLICATIONS

This application is a Divisional of U.S. patent application Ser. No. 15/738,900, filed Dec. 21, 2017, which in turn is a National Stage Application of PCT/GB2016/052130, filed Jul. 14, 2016, which claims priority from UK Patent Application No. 1512270.8, filed on Jul. 14, 2015 and UK Patent Application No. 1604642.7, filed on Mar. 18, 2016. The priority of said PCT, UK and US Patent Applications are claimed. Each of the prior mentioned applications is hereby incorporated by reference herein in its entirety.

The present invention relates to novel compounds and methods for the manufacture of inhibitors of deubiquitylating enzymes (DUBs). In particular, the invention relates to the inhibition of ubiquitin C-terminal hydrolase L1 (UCHL1) and ubiquitin C-terminal hydrolase 30 or ubiquitin specific peptidase 30 (USP30). The invention further relates to the use of DUB inhibitors in the treatment of cancer and conditions involving mitochondrial dysfunction.

BACKGROUND TO THE INVENTION

The listing or discussion of an apparently prior-published document in this specification should not necessarily be taken as an acknowledgement that the document is part of the state of the art or is common general knowledge.

Ubiquitin is a small protein consisting of 76 amino acids that can be reversibly attached to protein substrates. Protein ubiquitylation regulates many cellular functions including cell cycle progression, apoptosis, modification of cell surface receptors, regulation of DNA transcription and DNA repair. Thus, the ubiquitin proteasome system has been implicated in the pathogenesis of numerous disease states including inflammation, viral infection, metabolic dysfunction, CNS disorders, and oncogenesis (Clague et al., Physiol Rev 93:1289-1315, 2013).

Ubiquitin and ubiquitin-like proteins (Ubls) are cleaved from protein substrates by isopeptidases called deubiquitylating enzymes (DUBs). There are approximately 100 DUBs in human cells, divided into sub-families based on sequence homology: ubiquitin C-terminal hydrolases (UCHs), ubiquitin-specific proteases (USPs), ovarian tumour proteases (OTUs), Machado-Josephin domain proteases (MJDs), JAB1/MPN/MOV34 metalloproteases (JAMMs) or Sentrin-specific proteases (SENPs). The UCH family consisting of UCHL1, UCHL3, UCHL5 and BAP1 are cysteine proteases that operate through an active site thiol. UCHs are believed to preferentially cleave small protein substrates and to be involved in the processing and recycling of ubiquitin (Komander et al., Nat Rev Mol Cell Biol 10:550-563, 2009).

UCHL1 is a 223 amino acid protein whose expression is normally limited to the brain, peripheral nervous system, ovaries and testis in mammals. However, expression of UCHL1 has been reported to be up-regulated in several pathological conditions including cancer. Transgenic mice over-expressing UCHL1 are prone to malignancy, primarily lymphomas and lung tumours, demonstrating that UCHL1 is an oncogene (Hussain et al., Leukemia 24:1641-1655, 2010). The oncogenic function of UCHL1 is further supported by a number of clinical studies demonstrating that UCHL1 expression in tumours (including breast, colorectal, osteosarcoma and pancreatic) is inversely correlated with patient survival (Hurst-Kennedy et al., Biochem Res Int, 2012, Zheng et al., Cancer Lett 359:36-46). Thus, pharmacological inhibition of UCHL1 would serve as novel treatment for such cancers.

Ubiquitin is a master regulator of mitochondrial dynamics. Mitochondria are dynamic organelles whose biogenesis, fusion and fission events are regulated by the post-translational regulation via ubiquitylation of many key factors such as mitofusins. While ubiquitin ligases such as parkin are known to ubiquitylate a number of mitochondrial proteins, until recently, deubiquitylating enzymes remained elusive. USP30 is a 517 amino acid protein which is found in the mitochondrial outer membrane. It is the sole deubiquitylating enzyme bearing a mitochondrial addressing signal and has been shown to deubiquitylate a number of mitochondrial proteins. It has been demonstrated that USP30 opposes parkin-mediated mitophagy and that reduction of USP30 activity can rescue parkin-mediated defects in mitophagy.

Mitochondrial dysfunction can be defined as diminished mitochondrial content (mitophagy or mitochondrial biogenesis), as a decrease in mitochondrial activity and oxidative phosphorylation, but also as modulation of reactive oxygen species (ROS) generation. Hence a role for mitochondrial dysfunctions in a very large number of aging processes and pathologies including but not limited to, neurodegenerative diseases (e.g. Parkinson's disease (PD), Alzheimer's disease, Huntington's disease, Amyotrophic Lateral Sclerosis (ALS), multiple sclerosis), cancer, diabetes, metabolic disorders, cardio-vascular diseases, psychiatric diseases (e.g. Schizophrenia), and osteoarthritis.

For example, Parkinson's disease affects around 10 million people worldwide (Parkinson's Disease Foundation) and is characterised by the loss of dopaminergic neurons in the substantia nigra. The exact mechanisms underlying PD are unclear; however mitochondrial dysfunction is increasingly appreciated as a key determinant of dopaminergic neuronal susceptibility in PD and is a feature of both familial and sporadic disease, as well as in toxin-induced Parkinsonism. Parkin is one of a number of proteins that have been implicated with early onset PD. While most PD cases are linked to defects in alpha-synuclein, 10% of Parkinson's cases are linked to specific genetic defects, one of which is in the ubiquitin E3 ligase parkin. Parkin and the protein kinase PTEN-induced putative kinase 1 (PINK1) collaborate to ubiquitylate mitochondrial membrane proteins of damaged mitochondria resulting in mitophagy. Dysregulation of mitophagy results in increased oxidative stress, which has been described as a characteristic of PD. Inhibition of USP30 could therefore be a potential strategy for the treatment of PD. For example, PD patients with parkin mutations leading to reduced activity could be therapeutically compensated by inhibition of USP30.

It has been reported that depletion of USP30 enhances mitophagic clearance of mitochondria and also enhances parkin-induced cell death. USP30 has also been shown to regulate BAX/BAK-dependent apoptosis independently of parkin over expression. Depletion of USP30 sensitises cancer cells to BH-3 mimetics such as ABT-737, without the need for parkin over expression. Thus, an anti-apoptotic role has been demonstrated for USP30 and USP30 is therefore a potential target for anti-cancer therapy.

The ubiquitin-proteasome system has gained interest as a target for the treatment of cancer following the approval of the proteasome inhibitor bortezomib (Velcade®) for the treatment of multiple myeloma. Extended treatment with bortezomib is limited by its associated toxicity and drug resistance. However, therapeutic strategies that target specific aspects of the ubiquitin-proteasome pathway upstream of the proteasome, such as DUBs, are predicted to be better tolerated (Bedford et al., Nature Rev 10:29-46, 2011). Thus, there is a need for compounds and pharmaceutical compositions to inhibit DUBs such as UCHL1, USP30, USP7, USP47, BAP1, UCHL3 or SENP6 for the treatment of indications where DUB activity is observed, including, although not limited to, cancer.

SUMMARY OF THE INVENTION

In accordance with a first aspect of the invention there is provided a compound of formula (I)

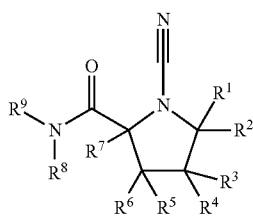

(I)

or a pharmaceutically acceptable salt thereof, wherein:

$R^1$, $R^2$ and $R^7$ each independently represent a hydrogen atom or optionally substituted $C_1$-$C_6$ alkyl;

$R^3$, $R^4$, $R^5$ and $R^6$ each independently represent a hydrogen atom, a halogen atom, cyano, optionally substituted $C_1$-$C_6$ alkyl, optionally substituted $C_1$-$C_6$ alkoxy, an optionally substituted 3 to 10 membered cycloalkyl or heterocyclyl, or an optionally substituted 5 to 10 membered heteroaryl or aryl;

$R^8$ represents optionally substituted $C_1$-$C_3$ alkyl or forms an optionally substituted 5 to 10 membered monocyclic or bicyclic heterocyclyl or heteroaryl ring with $R^9$ wherein the ring optionally comprises one or more additional heteroatoms;

$R^9$ represents an optionally substituted 3 to 10 membered cycloalkyl or heterocyclyl or optionally substituted 5 to 10 membered monocylic or bicyclic heteroaryl or aryl, or forms an optionally substituted 5 to 10 membered monocyclic or bicyclic heterocyclyl or heteroaryl ring with $R^8$ wherein the ring optionally comprises one or more additional heteroatoms.

When $R^9$ represents a 3 to 10 membered monocyclic or bicyclic cycloalkyl or heterocyclyl ring or a 5 to 10 membered monocyclic or bicyclic heteroaryl or aryl ring, or when $R^8$ and $R^9$ together form a monocyclic or bicyclic heterocyclic or heteroaryl ring, the ring may be substituted with one or more $R^{14}$ which is attached to the ring through Q, wherein each occurrence of $R^{14}$ independently represents an optionally substituted 3 to 10 membered cycloalkyl or heterocyclyl, or a 5 to 10 membered heteroaryl or aryl, and wherein each occurrence of Q is independently selected from a covalent bond, an oxygen atom, a sulphur atom, —$NR^{11}$—, —$CONR^{11}$—, —$NR^{11}CO$—, —$NR^{11}CONR^{12}$—, —$CO$—, —$C(O)O$—, —$SO$—, —$SO_2$—, —$SO_2NR^{11}$—, —$NR^{11}SO_2$—, —$NR^{11}SO_2NR^{12}$—, —$NR^{11}C(O)O$—, —$NR^{11}C(O)OR^{13}$—, or an optionally substituted —$C_1$-$C_6$ alkylene, an optionally substituted —$C_1$-$C_6$ alkyleneoxy, or an optionally substituted —$C_2$-$C_6$ alkenylene group.

$R^{11}$ and $R^{12}$ each independently represent a hydrogen atom or an optionally substituted $C_1$-$C_6$ alkyl and $R^{13}$ represents an optionally substituted $C_1$-$C_6$ alkylene.

When $R^9$ represents a 3 to 10 membered monocyclic or bicyclic cycloalkyl or heterocyclyl ring or a 5 to 10 membered monocyclic or bicyclic heteroaryl or aryl ring, or when $R^8$ and $R^9$ together form a monocyclic or bicyclic heterocyclic or heteroaryl ring, in addition or as an alternative to substitution with $R^{14}$, the ring may be substituted with one or more $R^{10}$ substituents, wherein the substituents are selected from a halogen atom, oxo, cyano, —$OR^{11a}$, —$SR^{11a}$, —$NO_2$, —$NR^{11a}R^{12a}$, —$CONR^{11a}R^{12a}$, —$NR^{11a}COR^{12a}$, —$NR^{11a}CONR^{12a}R^{13a}$, —$COR^{11a}$, —$C(O)OR^{11a}$, —$SO_2R^{11a}$, —$SO_2N^{11a}R^{12a}$, —$NR^{11a}SO_2R^{12a}$, —$NR^{11a}SO_2NR^{12a}R^{13a}$, —$NR^{11a}C(O)OR^{12a}$, or an optionally substituted —$C_1$-$C_6$ alkyl, optionally substituted —$C_1$-$C_6$ alkoxy or optionally substituted —$C_2$-$C_6$ alkenyl group.

$R^{11a}$, $R^{12a}$ and $R^{13a}$ each independently represent a hydrogen atom or an optionally substituted $C_1$-$C_6$ alkyl.

DETAILED DESCRIPTION OF THE INVENTION

Figure 1:
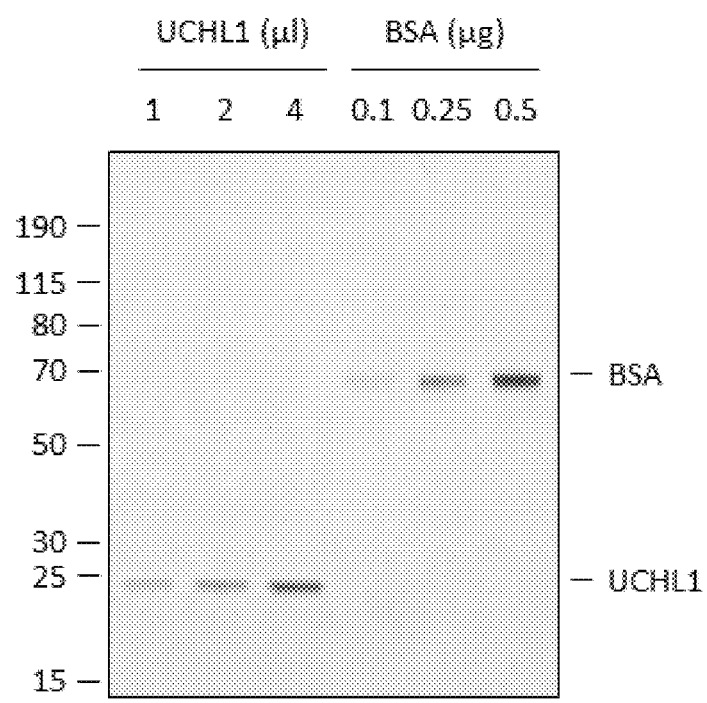
FIG. 1 provides an image of FLAG-UCHL1 purified from mammalian cells. FLAG-purified protein or the indicated concentrations of BSA were separated by SDS-PAGE and stained with Imperial (Pierce Biotechnology).
Figure 2:
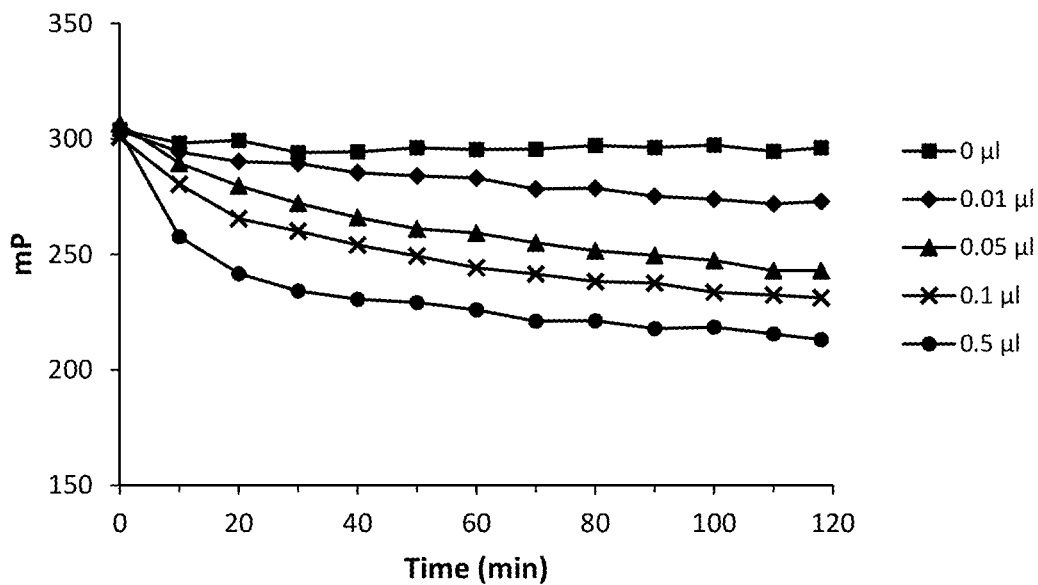
FIG. 2 is a graph showing proteolytic activity of purified FLAG-UCHL1 using a fluorescence polarisation assay. Various volumes of purified UCHL1 as indicated were incubated with a TAMRA labelled peptide linked to ubiquitin via an isopeptide bond.
Figure 3:
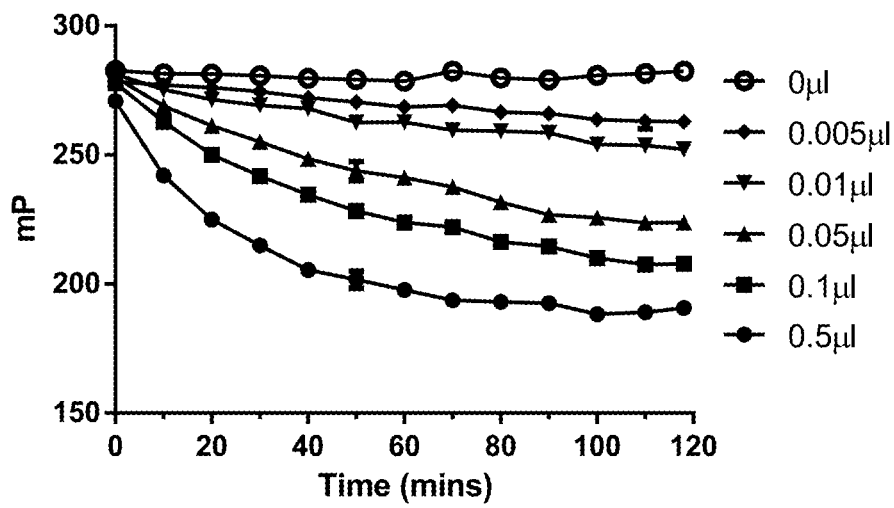
FIG. 3 is a graph showing proteolytic activity of USP30 measured using a fluorescence polarisation assay. Various volumes of purified USP30 as indicated were incubated with a TAMRA labelled peptide linked to ubiquitin via an isopeptide bond.

The definitions and explanations below are for the terms as used throughout this entire document including both the specification and the claims. Reference to compounds as described herein (e.g. a compound of formula (I)), includes reference to formula (I), including any sub-generic embodiments thereof, e.g. formulas (II), (III), (IIIa), (IV) and (V).

Where any group of the compounds of formula (I) have been referred to as optionally substituted, this group may be substituted or unsubstituted. Substitution may be by one or more of the specified substituents which may be the same or different. It will be appreciated that the number and nature of substituents will be selected to avoid any sterically undesirable combinations.

In the context of the present specification, unless otherwise stated an alkyl, alkylene, alkoxy, alkenyloxy, alkenyl, or alkynyl substituent (or linker) group or an alkyl, alkenyl moiety in a substituent group may be linear or branched. Alkyl, alkylene and alkenyl chains may also include intervening heteroatoms such as oxygen.

$C_x$-$C_y$ alkyl refers to a saturated aliphatic hydrocarbon group having x-y carbon atoms which may be linear or branched. For example $C_1$-$C_6$ alkyl contains from 1 to 6 carbon atoms. "Branched" means that at least one carbon branch point is present in the group. For example, tert-butyl and isopropyl are both branched groups. Examples of $C_1$-$C_6$ alkyl groups include methyl, ethyl, propyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-pentyl, 3-methyl-1-pentyl, 4-methyl-1-pentyl, 2-methyl-2- pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, tert-butyl, n-pentyl, isopentyl, neopentyl and n-hexyl.

A $C_x$-$C_y$ alkylene group or moiety may be linear or branched and refers to a divalent hydrocarbon group having one less hydrogen atom from $C_x$-$C_y$ alkyl as defined above. Examples of $C_1$-$C_6$ alkylene groups include methylene, ethylene, n-propylene, n-butylene, methylmethylene and dimethylmethylene.

$C_2$-$C_6$ alkenyl refers to a linear or branched hydrocarbon chain radical containing at least two carbon atoms and at least one double bond. Examples of alkenyl groups include ethenyl, propenyl, 2-propenyl, 1-butenyl, 2-butenyl, 1-hexenyl, 2-methyl-1-propenyl, 1,2-butadienyl, 1,3-pentadienyl, 1,4-pentadienyl and 1-hexadienyl.

$C_2$-$C_6$ alkynyl refers to a linear or branched hydrocarbon chain radical containing at least two carbon atoms and at least one triple bond. Examples of alkenyl groups include ethynyl, propynyl, 2-propynyl, 1-butynyl, 2-butynyl and 1-hexynyl.

$C_1$-$C_6$ alkoxy refers to a group or part of a group having an —O—$C_x$-$C_y$ alkyl group according to the definition of $C_x$-$C_y$ alkyl above. Examples of $C_1$-$C_6$ alkoxy include methoxy, ethoxy, propoxy, isopropoxy, butoxy, pentoxy and hexoxy.

A $C_1$-$C_6$ alkeneoxy group or moiety may be linear or branched and refers to a divalent hydrocarbon group having one less hydrogen atom from $C_1$-$C_6$ alkoxy as defined above. Examples of $C_1$-$C_6$ alkyleneoxy groups include methyleneoxy, ethyleneoxy, n-propyleneoxy and n-butyleneoxy.

The term "halogen" or "halo" refers to chlorine, bromine, fluorine or iodine atoms.

The term "oxo" means =O.

For the avoidance of doubt it will be understood that a 3 to 10 membered cycloalkyl or heterocyclyl ring, or a 5 to 10 membered heteroaryl or aryl ring as defined according to $R^3$, $R^4$, $R^5$, $R^6$, $R^8$, $R^9$ and $R^{14}$ does not include any unstable ring structures or, in the case of heteroaryl and heterocyclic rings systems, any O—O, O—S or S—S bonds. The ring systems may be monocyclic or bicyclic. A substituent if present may be attached to any suitable ring atom which may be a carbon atom or, in the case of heteroaryl and heterocyclic ring systems, a heteroatom. Substitution on a ring may also include a change in the ring atom at the position of the substitution. For example, substitution on a phenyl ring may include a change in the ring atom at the position of substitution from carbon to nitrogen, resulting in a pyridine ring.

"$C_x$-$C_y$ cycloalkyl" refers to a monocyclic or bicyclic non-aromatic hydrocarbon group of x-y carbon atoms. For example $C_3$-$C_{10}$ cycloalkyl refers to a hydrocarbon ring containing 3 to 10 carbon atoms. Examples of $C_3$-$C_{10}$ cycloalkyl are cyclopropyl, cyclobutyl, cyclopentyl, cyclohexyl, cyclopentyl, cyclohexyl, cycloheptyl, cyclooctyl and decahydronaphthalenyl.

An "aryl" group/moiety refers to any monocyclic or bicyclic hydrocarbon group comprising at least one aromatic group, for example having up to 10 carbon atom ring members. Examples of aryl groups include phenyl and naphthyl. Bicyclic rings may be fused aromatic rings where both rings are aromatic, for example, naphthalenyl, or may be fused rings where one of the rings is non-aromatic, for example, tetrahydronaphthyl.

"Heteroaryl" groups may be monocyclic or bicyclic. Bicyclic rings may be fused aromatic rings where both rings are aromatic or may be fused rings where one of the rings is non-aromatic. In instances where $R^9$ is a heteroaryl ring, the ring attached to the amide nitrogen may be an aromatic ring which can be fused to a further aromatic or non-aromatic ring. In instances where $R^8$ and $R^9$ together form a heteroaryl ring which incorporates the amide nitrogen, the ring can be fused to a further aromatic or non-aromatic ring. Heteroaryl rings comprise 1, 2 or 3 heteroatoms selected from oxygen, sulphur and nitrogen. When the heteroatom is nitrogen it may be oxidised. Examples of heteroaryl groups include pyridinyl, pyrazinyl, pyrimidinyl, pyridazinyl, furyl, thiophenyl, pyrrolyl, oxazolyl, thiazolyl, pyrazolyl, triazolyl, tetrazolyl, indolyl, indolizinyl, isoindolyl, indolinyl, purinyl, furazanyl, imidazolyl, indazolyl, isothiazolyl, isoxazolyl, oxadiazolyl, oxazinanyl, tetrazolyl, thiadiazolyl, benzofuranyl, isobenzofuranyl, tetrahydrofuranyl, benzothiophenyl, isobenzothiophenyl, benzimidazolyl, benzothiazolyl, napthyridinyl, pteridinyl, pyrazinyl, 4H-quinolizinyl, quinolinyl, isoquinolinyl, cinnolinyl, phthalazinyl, quinazolinyl, imidazopyridinyl, pyrazolopyridinyl, thiazolopyridinyl, indolinyl, isoindolinyl, triazinyl, pyridazinyl, dihydrophyridinyl, quinoxalinyl, benzodioxolyl, pyrrolopyridinyl, pyrazolopyridinyl and pyrrolopyrazinyl.

"Heterocyclyl" groups may also be monocyclic or comprise two or more fused rings which may be saturated or partially unsaturated comprising 1, 2 or 3 heteroatoms selected from oxygen, sulphur and nitrogen. In instances where $R^9$ is a bicyclic heterocyclyl ring, the ring attached to the amide nitrogen may be a non-aromatic ring which can be fused to a further aromatic or non-aromatic ring. In instances where $R^8$ and $R^9$ together form a heterocyclyl ring which incorporates the amide nitrogen, the ring can be fused to a further aromatic or non-aromatic ring. Examples of heterocyclyl groups include azetidinyl, pyrrolidinyl, piperidinyl, azepanyl, diazepanyl, dihydrofuranyl (e.g. 2,3-dihydrofuranyl, 2,5-dihydrofuranyl), 4,5-dihydro-1H-maleimido, dioxolanyl, morpholinyl, oxazolidinyl, piperazinyl, tetrahydrofuranyl, thiomorpholinyl, dihydropyranyl (e.g. 3,4-dihydropyranyl, 3,6-dihydropyranyl), homopiperazinyl, dioxanyl, hexahydropyrimidinyl, pyrazolinyl, pyrazolidinyl, pyridazinyl, 4H-quinolizinyl, quinuclinyl, tetrahydropyranyl, tetrahydropyridinyl, tetrahydropyrimidinyl, tetrahydrothiophenyl, tetramethylenesulfoxide, thiazolidinyl, hydantoinyl, benzopyranyl, tetrahydrothiazolopyridinyl, tetrahydroquinolinyl, benzomorpholinyl, tetrahydroisoquinolinyl and tetrahydropyrrolopyrazolyl.

"Optionally substituted" as applied to any group means that the said group may if desired be substituted with one or more substituents, which may be the same or different. Examples of suitable substituents for "substituted" and "optionally substituted" moieties, include halo, $C_1$-$C_6$ alkyl or $C_1$-$C_3$ alkyl, hydroxy, $C_1$-$C_6$ alkoxy or $C_1$-$C_3$ alkoxy, cyano, amino, nitro or $SF_5$ (a known mimetic of $NO_2$), aryl, heteroaryl, heterocyclyl, $C_3$-$C_6$ cycloalkyl, $C_{1-3}$ alkylamino, $C_{2-6}$ alkenylamino, di-$C_1$-$C_3$ alkylamino, $C_1$-$C_3$ acylamino, di-$C_1$-$C_3$ acylamino, carboxy, $C_1$-$C_3$ alkoxycarbonyl, carbamoyl, mono-$C_{1-3}$ carbamoyl, di-$C_1$-3 carbamoyl or any of the above in which a hydrocarbyl moiety is itself substituted by halo. In certain instances, optional substituents for alkyl, alkoxy, alkenyl, alkylene, alkyleneoxy or alkenylene may be selected from halogen, hydroxyl, thiol, cyano, amino, nitro and $SF_5$. In certain instances, optional substituents for cycloalkyl, aryl, heterocyclyl and heteroaryl rings may be selected from halogen, hydroxyl, thiol, cyano, amino, nitro, $SF_5$, alkyl or alkoxy wherein the alkyl or alkoxy is optionally substituted with one or more halogen. In groups containing an oxygen atom such as hydroxy and alkoxy, the oxygen atom can be replaced with sulphur to make groups such as thio (SH) and thio-alkyl (S-alkyl). Optional substituents therefore include groups such as S-methyl. In thio-alkyl groups, the sulphur atom may be further oxidised to make a sulfoxide or sulfone, and thus optional substituents therefore includes groups such as S(O)-alkyl and S(O)$_2$-alkyl.

Substituted groups thus include for example Br, Cl, F, CN, Me, Et, Pr, OMe, OEt, OPr, C(CH$_3$)$_3$, CH(CH$_3$)$_2$, CF$_3$, OCF$_3$, C(O)NHCH$_3$, cyclopropyl, phenyl, etc. In the case of aryl groups, the substitutions may be in the form of rings from adjacent carbon atoms in the aryl ring, for example cyclic acetals such as O—CH$_2$—O.

The term "treat" or "treating" or "treatment" includes prophylaxis and means to ameliorate, alleviate symptoms, eliminate the causation of the symptoms either on a temporary or permanent basis, or to prevent or slow the appearance of symptoms of the named disorder or condition. The compounds of the invention are useful in the treatment of humans and non-human animals.

The dose of the compound is that amount effective to prevent occurrence of the symptoms of the disorder or to treat some symptoms of the disorder from which the patient suffers. By "effective amount" or "therapeutically effective amount" or "effective dose" is meant that amount sufficient to elicit the desired pharmacological or therapeutic effects, thus resulting in effective prevention or treatment of the disorder. Prevention of the disorder is manifested by delaying the onset of the symptoms of the disorder to a medically significant extent. Treatment of the disorder is manifested by a decrease in the symptoms associated with the disorder or an amelioration of the reoccurrence of the symptoms of the disorder.

Pharmaceutically acceptable salts of the compounds of the invention include but are not limited to addition salts (for example phosphates, nitrates, sulphates, borates, acetates, maleates, citrates, fumarates, succinates, methanesulphonates, benzoates, salicylates and hydrohalides), salts derived from organic bases (such as lithium, potassium and sodium), salts of amino acids (such as glycine, alanine, valine, leucine, isoleucine, cysteine, methionine and proline), inorganic bases (such as triethylamine, hydroxide, choline, thiamine and N—N'-diacetylethylenediamine). Other pharmaceutically acceptable salts include ammonium salts, substituted ammonium salts and aluminium salts. Further pharmaceutically acceptable salts include quaternary ammonium salts of the compounds of the invention.

General methods for the production of salts are well known to the person skilled in the art. Such salts may be formed by conventional means, for example by reaction of a free acid or a free base form of a compound with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound in the form of a salt with another counter-ion, for example using a suitable ion exchange resin.

Where compounds of the invention exist in different enantiomeric and/or diastereoisomeric forms, the invention relates to these compounds prepared as isomeric mixtures or racemates whether present in an optically pure form or as mixtures with other isomers. Enantiomers differ only in their ability to rotate plane-polarized light by equal amounts in opposite directions and are denoted as the (+)/(S) or (−)/(R) forms respectively. Individual enantiomers or isomers may be prepared by methods known in the art, such as optical resolution of products or intermediates (for example chiral chromatographic separation e.g. chiral HPLC, or an asymmetric synthesis approach). Similarly where compounds of the invention exist as alternative tautomeric forms e.g. keto/enol, amide/imidic acid, the invention relates to the individual tautomers in isolation, and to mixtures of the tautomers in all proportions.

Included herein is the compound according to formula (II)

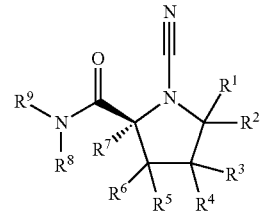

(II)

or a pharmaceutically acceptable salt thereof, wherein $R^1$, $R^2$, $R^3$, $R^4$, $R^5$, $R^6$, $R^7$, $R^8$ and $R^9$ are defined above for compounds of formula (I).

Isotopes

The compounds described herein may contain one or more isotopic substitutions, and a reference to a particular element includes within its scope all isotopes of the element. For example, a reference to hydrogen includes within its scope $^1$H, $^2$H (D), and $^3$H (T). Similarly, references to carbon and oxygen include within their scope respectively $^{12}$C, $^{13}$C and $^{14}$C and $^{16}$O and $^{18}$O. Examples of isotopes include $^2$H, $^3$H, $^{11}$C, $^{13}$C, $^{14}$C, $^{36}$Cl, $^{18}$F, 123, 125, 13N, 15N, 150, 170, 180, $^{32}$P and 35S.

In an analogous manner, a reference to a particular functional group also includes within its scope isotopic variations, unless the context indicates otherwise. For example, a reference to an alkyl group such as an ethyl group also covers variations in which one or more of the hydrogen atoms in the group is in the form of a deuterium or tritium isotope, e.g. as in an ethyl group in which all five hydrogen atoms are in the deuterium isotopic form (a perdeuteroethyl group). Deuterium may be referred to throughout as "deutero".

The isotopes may be radioactive or non-radioactive. In one embodiment, the compounds contain no radioactive isotopes. Such compounds are preferred for therapeutic use. In another embodiment, however, the compounds may contain one or more radioisotopes. Compounds containing such radioisotopes may be useful in a diagnostic context.

Certain isotopically labelled compounds of formula (I), for example, those incorporating a radioactive isotope, are useful in drug and/or substrate tissue distribution studies. The radioactive isotopes i.e. $^3$H and $^{14}$C are particularly useful for this purpose in view of their ease of incorporation and ready means of detection. Substitution with heavier isotopes i.e. $^2$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining receptor occupancy. Isotopically labelled compounds of formula (I) can generally be prepared by conventional techniques known to those skilled in the art or by processes analogous to those described in the accompanying examples and preparations using an appropriate isotopically labelled reagent in place of the non-labelled reagent previously employed.

Crystalline and Amorphous Forms

The compounds of formula (I) may exist in crystalline or amorphous form and some of the crystalline forms may exist as polymorphs, which are included within the scope of the present invention. Polymorphic forms of compounds of formula (I) may be characterised and differentiated using a number of conventional analytical techniques, including, but not limited to, infra-red spectra, Raman spectra, X-ray powder diffraction, differential scanning calorimetry, thermogravimetric analysis and solid state nuclear magnetic resonance.

Accordingly, in further embodiments, the invention provides a compound according to any described embodiments in a crystalline form. The compound may be from 50% to 100% crystalline, and more particularly is at least 50% crystalline, or at least 60% crystalline, or at least 70% crystalline, or at least 80% crystalline, or at least 90% crystalline, or at least 95% crystalline, or at least 98% crystalline, or at least 99% crystalline, or at least 99.5% crystalline, or at least 99.9% crystalline, for example 100% crystalline. The compound may alternatively be in an amorphous form.

The invention described herein relates to all crystal forms, solvates and hydrates of any of the disclosed compounds however so prepared. To the extent that any of the compounds disclosed herein have acid or basic centres such as carboxylates or amino groups, then all salt forms of said compounds are included herein. In the case of pharmaceutical uses, the salt should be seen as being a pharmaceutically acceptable salt.

The invention relates to any solvates of the compounds and their salts. Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulfoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGE), differential scanning calorimetry (DSC) and X-ray crystallography.

The solvates can be stoichiometric or non-stoichiometric solvates. Particular solvates may be hydrates, and examples of hydrates include hemihydrates, monohydrates and dihydrates. For a more detailed discussion of solvates and the methods used to make and characterise them, see Bryn et al., Solid-State Chemistry of Drugs, Second Edition, published by SSCI, Inc of West Lafayette, Ind., USA, 1999, ISBN 0-967-06710-3.

The invention relates to pharmaceutically functional derivatives of compounds as defined herein including ester derivatives and/or derivatives that have, or provide for, the same biological function and/or activity as any relevant compound of the invention. Thus, for the purposes of this invention, the term also includes prodrugs of compounds as defined herein.

The term "prodrug" of a relevant compound includes any compound that, following oral or parenteral administration, is metabolised in vivo to form that compound in an experimentally-detectable amount, and within a predetermined time (e.g. within a dosing interval of between 6 and 24 hours (i.e. once to four times daily).

Prodrugs of compounds may be prepared by modifying functional groups present on the compound in such a way that the modifications are cleaved, in vivo when such prodrug is administered to a mammalian subject. The modifications typically are achieved by synthesizing the parent compound with a prodrug substituent. Prodrugs include compounds wherein a hydroxyl, amino, sulfhydryl, carboxyl or carbonyl group in a compound is bonded to any group that may be cleaved in vivo to regenerate the free hydroxyl, amino, sulfhydryl, carboxyl or carbonyl group, respectively.

Examples of prodrugs include, but are not limited to, esters and carbamates of hydroxyl functional groups, ester groups of carboxyl functional groups, N-acyl derivatives and N-Mannich bases. General information on prodrugs may be found e.g. in Bundegaard, H. "Design of Prodrugs" p. 1-92, Elsevier, New York-Oxford (1985).

Compounds of the invention may be metabolised in vivo. Metabolites of compounds of formula (I) are also within the scope of the present invention. The term 'metabolites' refers to all molecules derived from any of the compounds according to the present invention in a cell or organism, preferably mammal. Preferably the term relates to molecules which differ from any molecule which is present in any such cell or organism under physiological conditions.

A treatment defined herein may be applied as a sole therapy of may involve, in addition to the compounds of the invention, conventional surgery or radiotherapy or chemotherapy. Furthermore, compounds of formula (I) can also be used in combination with existing therapeutic agents for the treatment of conditions associated with cancer, including small molecule therapeutics or antibody based therapeutics.

The disclosure includes compounds having the formula (I)

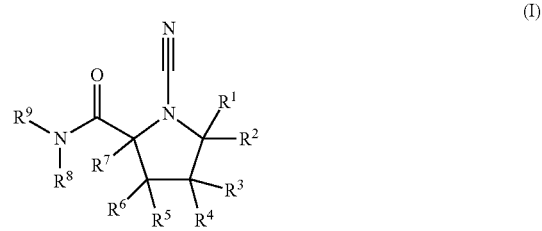

or a pharmaceutically acceptable salt thereof, wherein:

$R^1$, $R^2$ and $R^7$ each independently represent a hydrogen atom or optionally substituted $C_1$-$C_6$ alkyl;

$R^3$, $R^4$, $R^5$ and $R^6$ each independently represent a hydrogen atom, a halogen atom, cyano, optionally substituted $C_1$-$C_6$ alkyl, optionally substituted $C_1$-$C_6$ alkoxy, an optionally substituted 3 to 10 membered cycloalkyl or heteroaryl, or an optionally substituted 5 to 10 membered heteroaryl or aryl;

$R^8$ represents an optionally substituted $C_1$-$C_3$ alkyl or forms an optionally substituted monocyclic or bicyclic 5 to 10 membered heterocyclyl or heteroaryl ring with $R^9$ wherein the ring optionally comprises one or more additional heteroatoms, optionally selected from N, O and S;

$R^9$ represents an optionally substituted 3 to 10 membered cycloalkyl or heterocyclyl or optionally substituted 5 to 10 membered heteroaryl or aryl, or $R^9$ forms an optionally substituted 5 to 10 membered monocyclic or bicyclic heterocyclyl or heteroaryl ring with $R^8$ wherein the ring optionally comprises one or more additional heteroatoms, optionally selected from N, O and S.

In one embodiment, $R^9$ may represent a 3 to 10 membered (e.g. 3, 4, 5, 6, 7, 8, 9 or 10 membered cycloalkyl or heterocyclyl ring or a 5 to 10 membered (e.g. 5, 6, 7, 8, 9 or 10 membered) heteroaryl or aryl ring, wherein the ring is optionally substituted. The ring may be monocyclic or bicyclic.

In another embodiment, $R^9$ represents an optionally substituted 5 or 6 membered heteroaryl or aryl ring.

In an alternative embodiment, $R^9$ represents an optionally substituted 9 or 10 membered bicyclic heteroaryl or aryl ring.

When $R^9$ represents an optionally substituted 3 to 10 membered cycloalkyl or heterocyclic ring or an optionally substituted 5 to 10 membered heteroaryl or aryl ring, the ring may be selected from morpholinyl, piperidinyl, pyrrolidinyl, diazepanyl, piperazinyl, pyridazinyl, pyrazinyl, pyrazolyl, cyclopropyl, cyclohexyl, cyclopentyl, pyridinyl, imidazolyl, indolinyl, isoindolinyl, pyrimidinyl, isoxazolyl, dihydroindenyl, dihydroisoquinolinyl, tetrahydropyranyl, benzothiazolyl, phenyl, oxadiazolyl, triazolyl and thiazolyl.

When $R^9$ represents an optionally substituted 3 to 10 membered cycloalkyl or heterocyclic ring or an optionally substituted 5 to 10 membered heteroaryl or aryl ring, the ring may be selected from morpholinyl, piperidinyl, pyrrolidinyl, diazepanyl, piperazinyl, pyridazinyl, pyrazinyl, pyrazolyl, cyclopropyl, cyclohexyl, cyclopentyl, pyridinyl, imidazolyl, indolinyl, isoindolinyl, pyrimidinyl, isoxazolyl, dihydroindenyl, dihydroisoquinolinyl, tetrahydropyranyl, benzothiazolyl, phenyl, oxadiazolyl and triazolyl.

In one embodiment, the 3 to 10 membered cycloalkyl or heterocyclyl ring or 5 to 10 membered heteroaryl or aryl ring of $R^9$ is selected from thiazolyl, benzothiazolyl or isoxazolyl. In a further embodiment, $R^9$ is thiazolyl.

In one embodiment, the 3 to 10 membered cycloalkyl or heterocyclyl ring or 5 to 10 membered heteroaryl or aryl ring of $R^9$ is thiazolyl or benzothiazolyl, for example, thiazol-2-yl or benzothiazol-2-yl.

When $R^9$ represents a 3 to 10 membered cycloalkyl or heterocyclyl ring or a 5 to 10 membered heteroaryl or aryl ring, $R^8$ may be methyl or ethyl.

In one embodiment, $R^9$ forms an optionally substituted 5 to 10 (e.g. 5, 6, 7, 8, 9 or 10) membered monocylic or bicyclic ring with $R^8$ wherein the ring optionally comprises one or more (e.g. 1, 2 or 3) additional heteroatoms independently selected from nitrogen, oxygen and sulphur.

In one embodiment, $R^8$ and $R^9$ together form a 5 or 6 membered heterocyclyl or heteroaryl ring which is optionally substituted.

In another embodiment, $R^8$ and $R^9$ together form a 9 or 10 membered monocyclic or bicyclic heterocyclyl or heteroaryl ring which is optionally substituted.

In one particular embodiment, $R^8$ and $R^9$ together with the nitrogen to which they are attached form a 9 membered bicyclic ring. The bicyclic ring may be a 5 membered pyrrolidine ring, which incorporates the nitrogen to which $R^8$ and $R^9$ are attached, fused to a 6 membered aromatic ring. The 6 membered aryl ring may be phenyl or a heteroaryl ring containing one or two nitrogen ring atoms.

The bicyclic ring may be optionally substituted with one or more $R^{10}$ and/or one or more $R^{14}$ substituents as defined herein.

In one embodiment, the 5 to 10 membered monocyclic or bicyclic heterocyclyl or heteroaryl ring formed by $R^8$ and $R^9$ is selected from optionally substituted isoindolinyl, indolinyl, benzomorpholinyl, pyrrolopyridinyl, tetrahydropyrrolopyrazolyl and tetrahydroisoquinolinyl, for example, indolin-lyl or benzomorpholin-1-yl.

In one embodiment, the 5 to 10 membered monocyclic or bicyclic heterocyclyl or heteroaryl ring formed by $R^8$ and $R^9$ is selected from optionally substituted isoindolinyl, indolinyl, benzomorpholinyl, pyrrolopyridinyl and tetrahydropyrrolopyrazole, for example, indolin-lyl or benzomorpholin-1-yl.

In one embodiment, the 5 to 10 membered heterocyclyl or heteroaryl ring formed by $R^8$ and $R^9$ is selected from optionally substituted isoindolinyl, indolinyl and benzomorpholinyl, for example, indolin-lyl or benzomorpholin-1-yl.

When $R^9$ represents a ring, or when $R^8$ and $R^9$ together form a ring, the ring may be substituted with $R^{14}$ and/or one or more of $R^{10}$, wherein $R^{14}$ is attached to the ring through Q. Preferably, the ring is at least substituted with $R^{14}$, via Q. The ring may be substituted with further $R^{14}$ substituents via Q.

When the ring is substituted with more than one $R^{14}$, via Q, each occurrence of $R^{14}$ and Q may be the same or different. In one embodiment, when $R^9$ represents a ring, or when $R^8$ and $R^9$ together form a ring, the ring is substituted with one or two $R^{14}$ substituents. The ring may be substituted with one $R^{14}$ substituent. Alternatively, the ring may be substituted with two $R^{14}$ substituents which may be the same or different. Substitution with $R^{14}$ is always via Q.

Each $R^{10}$ may be independently selected from a halogen atom, oxo, cyano, —$OR^{11a}$, —$SR^{11}a$, —$NO_2$, —$NR^{11a}R^{12a}$, —$CONR^{11a}R^{12a}$, —$NR^{11a}COR^{12a}$, —$NR^{11a}CONR^{12a}R^{13a}$, —$COR^{11a}$, —$C(O)OR^{11a}$, —$SO_2R^{11a}$, —$SO_2NR^{11a}R^{12a}$, —$NR^{11a}SO_2R^{12a}$, —$NR^{11a}SO_2NR^{12a}R^{13a}$, —$NR^{11a}C(O)OR^{12a}$, or an optionally substituted —$C_1$-$C_6$ alkyl, optionally substituted —$C_1$-$C_6$ alkoxy, or optionally substituted —$C_2$-$C_6$ alkenyl group.

$R^{11a}$, $R^{12a}$ and $R^{13a}$ each independently represent a hydrogen atom or an optionally substituted $C_1$-$C_6$ alkyl.

Q may be selected from a covalent bond, an oxygen atom, a sulphur atom, —$NR^{11}$—, —$CONR^{11}$—, —$NR^{11}CO$—, —$NR^{11}CONR^{12}$—, —CO—, —C(O)O—, —SO—, —$SO_2$—, —$SO_2NR^{11}$—, —$NR^{11}SO_2$—, —$NR^{11}SO_2NR^{12}$—, —$NR^{11}C(O)O$—, —$NR^{11}C(O)OR^{13}$—, or an optionally substituted —$C_1$-$C_6$ alkylene, an optionally substituted —$C_1$-$C_6$ alkyleneoxy or an optionally substituted —$C_2$-$C_6$ alkenylene group.

$R^{11}$ and $R^{12}$ each independently represent a hydrogen atom or an optionally substituted $C_1$-$C_6$ alkyl and $R^{13}$ represents an optionally substituted $C_1$-$C_6$ alkylene group. For example, $R^{11}$ and $R^{12}$ each independently represent a hydrogen atom or $C_1$-$C_3$ alkyl.

In instances where the ring represented by $R^9$, or $R^9$ and $R^8$ together, is substituted with $R^{14}$ and/or one or more $R^{10}$, substitution at the ring may also include a change in the ring atom at the position of the substitution.

$R^{14}$ represents an optionally substituted 3 to 10 membered cycloalkyl or heterocyclyl or a 5 to 10 membered heteroaryl or aryl.

In one embodiment, $R^1$ represents optionally substituted $C_1$-$C_6$ alkyl. In one embodiment, $R^1$ represents optionally substituted $C_1$-$C_2$ alkyl (e.g, methyl or ethyl). In one embodiment, $R^1$ represents $C_1$-$C_6$ alkyl, $C_1$-$C_4$ alkyl, $C_1$-$C_3$ alkyl or $C_1$-$C_2$ alkyl, methyl or substituted methyl and $R^2$, $R^3$, $R^4$, $R^5$, $R^6$ and $R^7$ each independently represent hydrogen. The optional substituents for the alkyl may be selected from halogen, hydroxyl, thiol, cyano, amino, nitro and $SF_5$.

In one embodiment, $R^2$ represents optionally substituted $C_1$-$C_6$ alkyl. In one embodiment, $R^2$ represents optionally substituted $C_1$-$C_2$ alkyl (e.g, methyl or ethyl). In one embodiment, $R^2$ represents $C_1$-$C_6$ alkyl, $C_1$-$C_4$ alkyl, $C_1$-$C_3$ alkyl or $C_1$-$C_2$ alkyl, methyl or substituted methyl and $R^1$, $R^3$, $R^4$, $R^5$, $R^6$ and $R^7$ each independently represent hydrogen. The optional substituents for the alkyl may be selected from halogen, hydroxyl, thiol, cyano, amino, nitro and $SF_5$.

In one embodiment, $R^3$ represents a halogen atom. In one embodiment, $R^3$ represents F. In one embodiment, $R^3$ represents cyano. In one embodiment, $R^3$ represents optionally substituted $C_1$-$C_6$ alkyl. In one embodiment, $R^3$ represents optionally substituted $C_1$-$C_2$ alkyl (e.g., methyl or ethyl). In one embodiment, $R^3$ represents optionally substituted $C_1$-$C_6$ alkoxy. In one embodiment, $R^3$ represents optionally substituted $C_1$-$C_2$ alkoxy (e.g, OMe or OEt). In one embodiment, $R^3$ represents an optionally substituted 3 to 10 membered cycloalkyl or heterocyclyl, or a 5 to 10 membered heteroaryl or aryl. In one embodiment, $R^3$ represents an optionally substituted 5 or 6 membered aryl or heteroaryl. In one embodiment, $R^3$ represents optionally substituted phenyl. In one embodiment, $R^3$ represents a hydrogen atom, a halogen atom, $C_1$-$C_3$ alkyl, $C_1$-$C_3$ alkoxy or a 6 membered aryl and $R^1$, $R^2$, $R^4$, $R^5$, $R^6$ and $R^7$ each independently represent hydrogen. The optional substituents for the alkyl and alkoxy may be selected from halogen, hydroxyl, thiol, cyano, amino, nitro and $SF_5$.

In one embodiment, $R^4$ represents a halogen atom. In one embodiment, $R^4$ represents F. In one embodiment, $R^4$ represents cyano. In one embodiment, $R^4$ represents optionally substituted $C_1$-$C_6$ alkyl. In one embodiment, $R^4$ represents optionally substituted $C_1$-$C_2$ alkyl (e.g., methyl or ethyl). In one embodiment, $R^4$ represents optionally substituted $C_1$-$C_6$ alkoxy. In one embodiment, $R^4$ represents optionally substituted $C_1$-$C_2$ alkoxy (e.g, OMe or OEt). In one embodiment, $R^4$ represents an optionally substituted 3 to 10 membered cycloalkyl or heterocyclyl, or an optionally substituted 5 to 10 membered heteroaryl or aryl. In one embodiment, $R^4$ represents an optionally substituted 5 or 6 membered aryl or heteroaryl. In one embodiment, $R^4$ represents optionally substituted phenyl. In one embodiment, $R^4$ represents a hydrogen atom, a halogen atom, $C_1$-$C_3$ alkyl, $C_1$-$C_3$ alkoxy or a 6 membered aryl and $R^1$, $R^2$, $R^3$, $R^5$, $R^6$ and $R^7$ each independently represent hydrogen. The optional substituents for the alkyl and alkoxy may be selected from halogen, hydroxyl, thiol, cyano, amino, nitro and $SF_5$.

In one embodiment, when $R^3$ is other than hydrogen, $R^1$, $R^2$, $R^4$, $R^5$, $R^6$ and $R^7$ each independently represent hydrogen. In another embodiment, when $R^4$ is other than hydrogen, $R^1$, $R^2$, $R^3$, $R^5$, $R^6$ and $R^7$ each independently represent hydrogen. In a further embodiment, when both $R^3$ and $R^4$ are not hydrogen, $R^1$, $R^2$, $R^5$, $R^6$ and $R^7$ each independently represent hydrogen, for example, when $R^3$ and $R^4$ are both a halogen atom, such as F.

In one embodiment, $R^5$ represents a halogen atom. In one embodiment, $R^5$ represents F. In one embodiment, $R^5$ represents cyano. In one embodiment, $R^5$ represents optionally substituted $C_1$-$C_6$ alkyl. In one embodiment, $R^5$ represents optionally substituted $C_1$-$C_2$ alkyl (e.g., methyl or ethyl). In one embodiment, $R^5$ represents optionally substituted $C_1$-$C_6$ alkoxy. In one embodiment, $R^5$ represents optionally substituted $C_1$-$C_2$ alkoxy (e.g, OMe or OEt). In one embodiment, $R^5$ represents an optionally substituted 3 to 10 membered cycloalkyl or heterocyclyl, or an optionally substituted 5 to 10 membered heteroaryl or aryl. In one embodiment, $R^5$ represents an optionally substituted 5 or 6 membered aryl or heteroaryl. In one embodiment, $R^5$ represents optionally substituted phenyl. In one embodiment, $R^5$ represents a hydrogen atom, a halogen atom, $C_1$-$C_3$ alkyl, $C_1$-$C_3$ alkoxy or a 6 membered aryl and $R^1$, $R^2$, $R^3$, $R^4$, $R^6$ and $R^7$ each independently represent hydrogen. The optional substituents for the alkyl and alkoxy may be selected from halogen, hydroxyl, thiol, cyano, amino, nitro and $SF_5$.

In one embodiment, $R^6$ represents a halogen atom. In one embodiment, $R^6$ represents F. In one embodiment, $R^6$ represents cyano. In one embodiment, $R^6$ represents optionally substituted $C_1$-$C_6$ alkyl. In one embodiment, $R^6$ represents optionally substituted $C_1$-$C_2$ alkyl (e.g, methyl or ethyl). In one embodiment, $R^6$ represents optionally substituted $C_1$-$C_6$ alkoxy. In one embodiment, $R^6$ represents optionally substituted $C_1$-$C_2$ alkoxy (e.g, OMe or OEt). In one embodiment, $R^6$ represents an optionally substituted 3 to 10 membered cycloalkyl or heterocyclyl, or an optionally substituted 5 to 10 membered heteroaryl or aryl. In one embodiment, $R^6$ represents an optionally substituted 5 or 6 membered aryl or heteroaryl. In one embodiment, $R^6$ represents optionally substituted phenyl. In one embodiment, $R^6$ represents a hydrogen atom, a halogen atom, $C_1$-$C_3$ alkyl, $C_1$-$C_3$ alkoxy or a 6 membered aryl and $R^1$, $R^2$, $R^3$, $R^4$, $R^5$ and $R^7$ each independently represent hydrogen. The optional substituents for the alkyl and alkoxy may be selected from halogen, hydroxyl, thiol, cyano, amino, nitro and $SF_5$.

In one embodiment, when $R^5$ is other than hydrogen, $R^1$, $R^2$, $R^3$, $R^4$, $R^6$ and $R^7$ each independently represent hydrogen. In another embodiment, when $R^6$ is other than hydrogen, $R^1$, $R^2$, $R^3$, $R^4$, $R^5$ and $R^7$ each independently represent hydrogen. In a further embodiment, when both $R^5$ and $R^6$ are not hydrogen, $R^1$, $R^2$, $R^3$, $R^4$ and $R^7$ each independently represent hydrogen, for example, when $R^5$ and $R^6$ are both a halogen atom, such as F.

In one embodiment, $R^7$ represents optionally substituted $C_1$-$C_6$ alkyl. In one embodiment, $R^7$ represents optionally substituted $C_1$-$C_2$ alkyl (e.g, methyl or ethyl). In one embodiment, $R^7$ represents $C_1$-$C_6$ alkyl, $C_1$-$C_4$ alkyl, $C_1$-$C_3$ alkyl or $C_1$-$C_2$ alkyl, methyl or substituted methyl and $R^1$, $R^2$, $R^3$, $R^4$, $R^5$ and $R^6$ each independently represent hydrogen. The optional substituents for the alkyl may be selected from halogen, hydroxyl, thiol, cyano, amino, nitro and $SF_5$.

In one embodiment, $R^1$, $R^2$ and $R^7$ each independently represent a hydrogen atom or $C_1$-$C_6$ alkyl, and $R^3$, $R^4$, $R^5$ and $R^6$ each independently represent a hydrogen atom, a halogen atom, cyano, $C_1$-$C_6$ alkyl, $C_1$-$C_6$ alkoxy, or an unsubstituted 3 to 6 membered cycloalkyl, aryl, heteroaryl or heterocyclyl ring, wherein the alkyl and alkoxy may optionally substituted with one or more substituents selected from halogen, hydroxyl, thiol, cyano, amino, nitro and $SF_5$.

In another embodiment, $R^1$, $R^2$ and $R^7$ each independently represent a hydrogen atom or $C_1$-$C_6$ alkyl, and $R^3$, $R^4$, $R^5$ and $R^6$ each independently represent a hydrogen atom, a halogen atom, cyano, $C_1$-$C_6$ alkyl or $C_1$-$C_6$ alkoxy, wherein the alkyl and alkoxy may optionally substituted with one or more substituents selected from halogen, hydroxyl, thiol, cyano, amino, nitro and $SF_5$.

In one embodiment, $R^1$, $R^2$, $R^3$, $R^4$, $R^5$, $R^6$ and $R^7$ each represent hydrogen.

Each $R^{10}$ independently represents a halogen atom, oxo, cyano, $-OR^{11a}$, $-SR^{11a}$, $-NO_2$, $-NR^{11a}R^{12a}$, $-CONR^{11a}R^{12a}$, $-NR^{11a}COR^{12a}$, $-NR^{11a}CONR^{12a}R^{13a}$, $-COR^{11a}$, $-C(O)OR^{11a}$, $-SO_2R^{11a}$, $-SO_2NR^{11a}R^{12a}$, $-NR^{11a}SO_2R^{12a}$, $-NR^{11a}SO_2NR^{12a}R^{13a}$, $-NR^{11a}C(O)OR^{12a}$, or an optionally substituted $-C_1$-$C_6$ alkyl, optionally substituted $-C_1$-$C_6$ alkoxy, or optionally substituted $-C_2$-$C_6$ alkenyl group.

In one embodiment, each $R^{10}$ may be independently selected from a halogen atom (e.g. fluorine, chlorine or bromine), oxo, cyano, $-OR^{11a}$, $-SR^{11a}$, $-NO_2$, $-NR^{11a}R^{12a}$, $-CONR^{11a}R^{12a}$, $-NR^{11a}COR^{12a}$, $-NR^{11a}CONR^{12a}R^{13a}$, $-COR^{11a}$, $-C(O)OR^{11a}$, —$SO_2R^{11a}$, —$SO_2NR^{11a}R^{12a}$, —$NR^{11a}SO_2R^{12a}$, —$NR^{11a}SO_2NR^{12a}R^{13a}$, —$NR^{11a}C(O)OR^{12a}$, or an optionally substituted $C_1$-$C_6$ alkyl, $C_1$-$C_4$ alkyl or $C_1$-$C_3$ alkyl, an optionally substituted $C_1$-$C_6$ alkoxy, $C_1$-$C_4$ alkoxy or $C_1$-$C_3$ alkoxy, or an optionally substituted $C_2$-$C_6$ alkenyl or $C_2$-$C_4$ alkenyl group.

In another embodiment, each $R^{10}$ may be independently selected from a halogen atom (e.g. fluorine, chlorine or bromine), oxo, cyano, —$OR^{11a}$ (e.g. hydroxyl), —$SR^{11a}$, (e.g. SH), —$NO_2$ (or the mimetic $SF_5$), —$NR^{11a}R^{12a}$ (e.g. amino or N,N-dimethyamino), —$CONR^{11a}R^{12a}$ (e.g. amido), —$NR^{11a}COR^{12a}$ (e.g. N-acetyl), —$NR^{11a}CONR^{12a}R^{13a}$, $COR^{11a}$ (e.g. acetyl), —$C(O)OR^{11a}$ (e.g. methoxycarbonyl or ethoxycarbonyl), —$SO_2R^{11a}$ (e.g. methylsulphonyl), —$SO_2NR^{11a}R^{12a}$ (e.g. dimethylaminosulphonyl), —$NR^{11a}SO_2R^{12a}$, $NR^{11a}SO_2NR^{12a}R^{13a}$, $NR^{11a}C(O)OR^{12a}$ or an optionally substituted $C_1$-$C_4$ alkyl (e.g. propyl, isopropyl or tert butyl) or $C_1$-$C_2$ alkyl (e.g. methyl or ethyl or $CF_3$), $C_1$-$C_4$ alkoxy (e.g. methoxy or methoxymethyl), or a $C_2$-$C_4$ alkenyl (e.g. vinyl) group.

In another embodiment, each $R^{10}$ may be independently selected from a halogen atom, cyano, optionally substituted $C_1$-$C_6$ alkyl for example $C_1$-$C_3$ alkyl, optionally substituted $C_1$-$C_6$ alkoxy for example $C_1$-$C_3$ alkoxy, or —$CONR^{11a}R^{12a}$, for example —$CONH_2$, —CONHMe or —CONHEt.

In a further embodiment, each $R^{10}$ may be independently selected from a halogen atom, optionally substituted $C_1$-$C_6$ alkyl for example $C_1$-$C_3$ alkyl, optionally substituted $C_1$-$C_6$ alkoxy for example $C_1$-$C_3$ alkoxy, or —$CONR^{11a}R^{12a}$, for example —$CONH_2$, —CONHMe or —CONHEt. In an even further embodiment, each $R^{10}$ is independently selected from methyl, ethyl, cyano and fluorine.

In particular, when $R^9$ is thiazole, each $R^{10}$ may be independently selected from methyl, ethyl, cyano and fluorine.

More particularly, when $R^9$ is thiazole, each $R^{10}$ may be independently selected from methyl, ethyl and cyano.

$R^{11a}$, $R^{12a}$ and $R^{13a}$ each independently represent a hydrogen atom or optionally substituted $C_1$-$C_6$ alkyl, $C_1$-$C_4$ alkyl or $C_1$-$C_2$ alkyl.

Q represents a covalent bond, an oxygen atom, a sulphur atom, —$NR^{11}$—, —$CONR^{11}$—, —$NR^{11}CO$—, —$NR^{11}CONR^{12}$—, —CO—, —C(O)O—, —SO—, —$SO_2$—, —$SO_2NR^{11}$—, —$NR^{11}SO_2$—, —$NR^{11}SO_2NR^{12}$—, —$NR^{11}C(O)O$—, —$NR^{11}C(O)OR^{13}$—, or an optionally substituted —$C_2$-$C_6$ alkylene, optionally substituted —$C_1$-$C_6$ alkyleneoxy or an optionally substituted —$C_2$-$C_6$ alkenylene group.

In one embodiment, Q may be selected from a covalent bond, an oxygen atom, a sulphur atom, —$NR^{11}$—, —$CONR^{11}$—, —$NR^{11}CO$—, —$NR^{11}CONR^{12}$—, —CO—, —C(O)O—, —SO—, —$SO_2$—, —$SO_2NR^1$—, —$NR^{11}SO_2$—, —$NR^{11}SO_2NR^{12}$—, —$NR^{11}C(O)O$—, —$NR^{11}C(O)OR^{13}$—, or an optionally substituted $C_1$-$C_6$ alkylene, $C_1$-$C_4$ alkylene or $C_1$-$C_3$ alkylene, an optionally substituted $C_1$-$C_6$ alkyleneoxy, $C_1$-$C_4$ alkyleneoxy or $C_1$-$C_3$ alkyleneoxy or an optionally substituted $C_2$-$C_6$ alkenylene or $C_2$-$C_4$ alkenylene group.

In a further embodiment, Q represents a covalent bond, an oxygen atom, $C_1$-$C_3$ alkylene (e.g. methylene, ethylene or straight or branched propylene) or $C_1$-$C_3$ alkyleneoxy.

$R^{11}$ and $R^{12}$ each independently represent a hydrogen atom or optionally substituted $C_1$-$C_6$ alkyl, $C_1$-$C_4$ alkyl or $C_1$-$C_2$ alkyl, and $R^{13}$ represents an optionally substituted $C_1$-$C_6$ alkylene, $C_1$-$C_4$ alkylene or $C_1$-$C_2$ alkylene.

In one embodiment, $R^{11}$ and $R^{12}R^{13}$ each independently represent a hydrogen atom or $C_1$-$C_2$ alkyl (e.g. methyl or ethyl). $R^{13}$ may represent $C_1$-$C_2$ alkylene (e.g. methylene or ethylene).

In one embodiment, $R^{14}$ represents a monocyclic or bicyclic 3 to 10 membered (e.g. 3, 4, 5, 6, 7, 8, 9 or 10 membered) cycloalkyl or heterocyclyl ring or 5 to 10 membered (e.g. 5, 6, 7, 8, 9 or 10 membered) heteroaryl or aryl ring, such as morpholinyl, piperidinyl, pyrrolidinyl, diazepanyl, piperazinyl, pyridazinyl, pyrazinyl, pyrazolyl, cyclopropyl, cyclohexyl, cyclopentyl, pyridinyl, imidazolyl, indolinyl, isoindolinyl, pyrimidinyl, isoxazolyl, dihydroindenyl, dihydroisoquinolinyl, tetrahydropyranyl, tetrahydrofuranyl, imidazopyridinyl, phenyl, oxadiazolyl, triazolyl, thiazolyl, quinolinyl, pyrrolopyridinyl, pyrazolopyridinyl, pyrrolopyrazinyl and benzodioxolyl, which may be optionally substituted.

In one embodiment, $R^{14}$ represents a monocyclic or bicyclic 3 to 10 membered (e.g. 3, 4, 5, 6, 7, 8, 9 or 10 membered) cycloalkyl or heterocyclyl ring or 5 to 10 membered (e.g. 5, 6, 7, 8, 9 or 10 membered) heteroaryl or aryl ring, such as morpholinyl, piperidinyl, pyrrolidinyl, diazepanyl, piperazinyl, pyridazinyl, pyrazinyl, pyrazolyl, cyclopropyl, cyclohexyl, cyclopentyl, pyridinyl, imidazolyl, indolinyl, isoindolinyl, pyrimidinyl, isoxazolyl, dihydroindenyl, dihydroisoquinolinyl, tetrahydropyranyl, phenyl, oxadiazolyl, and triazolyl, which may be optionally substituted.

$R^{14}$ may be selected from phenyl, isoxazolyl, pyridinyl, pyrazolyl, cyclopropyl, tetrahydrofuran, pyrimidinyl, pyrrolopyridinyl, pyrazinyl, imidazopyridinyl, benzodioxolyl, triazolyl, imidazolyl, quinolinyl, benzodioxolyl and indazolyl.

$R^{14}$ may be selected from phenyl, isoxazolyl, pyridinyl, pyrazolyl, cyclopropyl, tetrahydrofuran, pyrimidinyl, pyrrolopyridinyl, pyrazinyl, imidazopyridinyl, benzodioxolyl, triazolyl and imidazolyl.

In another embodiment, $R^{14}$ represents an optionally substituted 5 or 6 membered heteroaryl or aryl ring. The ring may be selected from substituted or unsubstituted phenyl, isoxazolyl, pyridinyl, pyrimidinyl, pyrazolyl, thiazolyl, triazolyl, imidazolyl or pyrazinyl.

In another embodiment, $R^{14}$ represents an optionally substituted 5 or 6 membered heteroaryl or aryl ring. The ring may be selected from substituted or unsubstituted phenyl, isoxazolyl, pyridinyl, pyrimidinyl, pyrazolyl or pyrazinyl.

In another embodiment, $R^{14}$ represents an optionally substituted 9 or 10 membered bicyclic heteroaryl or aryl ring. For example, the ring may be substituted or unsubstituted indolinyl, quinolinyl, pyrrolopyridinyl, pyrazolopyridinyl, pyrrolopyrazinyl, benzodioxolyl or indazolyl.

In another embodiment, $R^{14}$ represents an optionally substituted 9 or 10 membered bicyclic heteroaryl or aryl ring. For example, the ring may be substituted or unsubstituted indolinyl, quinolinyl, pyrrolopyridinyl, pyrazolopyridinyl, pyrrolopyrazinyl or benzodioxolyl.

In another embodiment, $R^{14}$ represents an optionally substituted 9 or 10 membered bicyclic heteroaryl or aryl ring. For example, the ring may be substituted or unsubstituted indolinyl.

In another embodiment, $R^{14}$ represents substituted or unsubstituted pyrazolyl.

In one embodiment, when $R^9$ represents a ring, or when $R^8$ and $R^9$ together form a ring, the ring is substituted with two $R^{14}$ substituents. In particular, one of the $R^{14}$ rings may be an optionally substituted 6 membered aryl and the other $R^{14}$ ring may be an optionally substituted 5 or 6 membered heteroaryl. In a particular embodiment, each $R^{14}$ ring is either unsubstituted or substituted with one or more substituents as defined below.

$R^{14}$ may be optionally substituted with one or more substituents each independently selected from a halogen atom, oxo, cyano, —$OR^{15}$, $SR^{15}$, —$NO_2$, —$NR^{15}R^{16}$, —$CONR^{15}R^{16}$, —$NR^{15}COR^{16}$, —$NR^{15}CONR^{16}R^{17}$, —$COR^{15}$, —$C(O)OR^{15}$, —$SO_2R^{15}$, —$SO_2NR^{15}R^{16}$, —$NR^{15}SO_2R^{16}$, —$NR^{15}SO_2NR^{16}R^{17}$, —$NR^{15}C(O)OR^{16}$, or an optionally substituted —$C_1$-$C_6$ alkyl, optionally substituted —$C_1$-$C_6$ alkoxy, optionally substituted —$C_1$-$C_6$ alkylene, optionally substituted —$C_1$-$C_6$ alkyleneoxy, optionally substituted —$C_2$-$C_6$ alkenyl or optionally substituted —$C_2$-$C_6$ alkenylene group, optionally substituted 3 to 10 membered cycloalkyl or heterocyclyl or optionally substituted 5 to 10 membered heteroaryl or aryl, wherein the optionally substituted —$C_1$-$C_6$ alkylene, —$C_1$-$C_6$ alkyleneoxy or —$C_2$-$C_6$ alkenylene group is attached to an optionally substituted 3 to 10 membered cycloalkyl or heterocyclyl or optionally substituted 5 to 10 membered heteroaryl or aryl.

In one embodiment, $R^{14}$ is substituted with one or more substituents each independently selected from a halogen atom, oxo, cyano, —$OR^{16}$, —$SR^{15}$, —$NO_2$, —$NR^{15}R^{16}$, —$CONR^{15}R^{16}$, —$NR^{15}COR^{16}$, —$NR^{15}CONR^{16}R^{17}$, —$COR^{15}$, —$C(O)OR^{15}$, —$SO_2R^{15}$, —$SO_2NR^{15}R^{16}$, —$NR^{15}SO_2R^{16}$, —$NR^{15}SO_2NR^{16}R^{17}$, —$NR^{15}C(O)OR^{16}$, or an optionally substituted —$C_1$-$C_6$ alkyl, optionally substituted —$C_1$-$C_6$ alkoxy, optionally substituted alkenyl, or optionally substituted —$C_3$-$C_6$ cycloalkyl.

$R^{14}$ may be substituted with one or more substituents selected from fluorine, chlorine, cyano, nitro, methyl, ethyl, cyclopropyl, $CF_3$, methoxy, ethoxy, methoxymethyl, methoxyethoxy, propoxy, $OCF_3$, C(O)NHMe, NHC(O)Me, NMeC(O)Me, NMeS(O)$_2$Me, S(O)$_2$Me, $NH_2$, NHMe and $N(Me)_2$.

$R^{14}$ may be substituted with one or more substituents selected from fluorine, chlorine, cyano, methyl, ethyl, $CF_3$, methoxy, C(O)NHMe, NHC(O)Me, $NH_2$, NHMe, and cyclopropyl.

In all cases described herein, $R^{15}$, $R^{16}$ and $R^{17}$ each independently represent a hydrogen atom or an optionally substituted $C_1$-$C_6$ alkyl, or an optionally substituted 3 to 10 membered cycloalkyl or heterocyclyl or optionally substituted 5 to 10 membered heteroaryl or aryl. In one embodiment, $R^1$, $R^{16}$ and $R^{17}$ each independently represent a hydrogen atom or optionally substituted $C_1$-$C_3$ alkyl.

In one embodiment, the $R^{14}$ ring is substituted with one, two or three substituents.

In instances where $R^{14}$ is substituted, substitution at the $R^{14}$ ring may also include a change in the ring atom at the position of the substitution.

In a further embodiment, $R^8$ forms a 5 to 10 membered monocylic or bicyclic heterocyclyl or heteroaryl ring with $R^9$ which is substituted with $R^{14}$, wherein $R^{14}$ is attached to the ring via Q and represents an optionally substituted 5 or 6 membered heteroaryl or aryl ring, wherein Q is selected from a covalent bond, an oxygen atom or optionally substituted $C_1$-$C_3$ alkylene.

In a still further embodiment, $R^9$ represents a 3 to 10 membered cycloalkyl or heterocyclyl ring or a 5 to 10 membered heteroaryl or aryl ring which is substituted with $R^{14}$, wherein $R^{14}$ is attached to the ring via Q and represents an optionally substituted 5 or 6 membered heteroaryl or aryl ring, wherein Q is selected from a covalent bond, an oxygen atom or optionally substituted $C_1$-$C_3$ alkylene.

In an embodiment of the invention there is provided a compound of formula (IIIa):

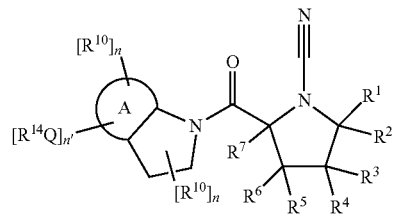

(IIIa)

or a pharmaceutically acceptable salt thereof, wherein:
each occurrence of n is independently 0, 1, 2, or 3, and when n is 2 or 3, each $R^{10}$ can be the same or different;
n' is 0, 1 or 2, and when n' is 2, each $R^{14}$ and each Q can be the same or different;
ring A is an 6 membered aryl ring optionally containing one or two nitrogen ring atoms; and
$R^1$, $R^2$, $R^3$, $R^4$, $R^5$, $R^6$, $R^7$, $R^{10}$, $R^{14}$, Q and n are as defined herein.

In one embodiment, $R^1$, $R^2$, $R^5$, $R^6$ and R may each represent hydrogen;
$R^3$ and $R^4$ may each independently represent a hydrogen atom, a halogen atom, optionally substituted $C_1$-$C_3$ alkyl or optionally substituted $C_1$-$C_3$ alkoxy;
$R^{10}$ may represent halogen, optionally substituted $C_1$-$C_3$ alkyl, optionally substituted $C_1$-$C_3$ alkoxy, or $CONR^{11a}R^{12a}$, wherein $R^{11a}$ and $R^{12a}$ each independently represent hydrogen or $C_1$-$C_3$ alkyl;
ring A is phenyl, pyridinyl or diazinyl;
n is 0 or 1;
n' is 1 or 2;
Q may represent a covalent bond, an oxygen atom, optionally substituted —$C_1$-$C_3$ alkylene or optionally substituted $C_1$-$C_3$ alkyleneoxy; and
each $R^{14}$ represents an optionally substituted 5 or 6 membered heteroaryl or aryl.

In one embodiment, ring A is phenyl.
In another embodiment, ring A is pyridyl or pyrimidyl.
In an embodiment of the invention there is provided a compound of formula (III):

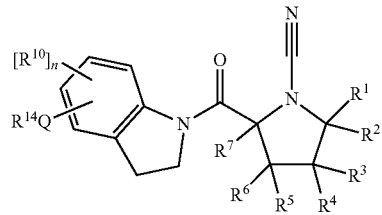

(III)

or a pharmaceutically acceptable salt thereof, wherein:
$R^1$, $R^2$ and $R^7$ each independently represent a hydrogen atom or optionally substituted $C_1$-$C_6$ alkyl;
$R^3$, $R^4$, $R^5$ and $R^6$ each independently represent a hydrogen atom, a halogen atom, cyano, optionally substituted $C_1$-$C_6$ alkyl, optionally substituted $C_1$-$C_6$ alkoxy, an optionally substituted 3 to 10 membered cycloalkyl or heteroaryl, or an optionally substituted 5 to 10 membered heteroaryl or aryl;
Each $R^{10}$ is independently selected from a halogen atom, oxo, cyano, —$OR^{11a}$, —$SR^{11a}$, —$NO_2$, —$NR^{11a}R^{12a}$, —$CONR^{11a}R^{12a}$, —$NR^{11a}COR^{12a}$, —$NR^{11a}CONR^{12a}R^{13a}$, —$COR^{11a}$, —$C(O)OR^{11a}$, —$SO_2R^{11a}$, —$SO_2NR^{11a}R^{12a}$, —NR$^{11a}$SO$_2$R$^{12a}$, —NR$^{11a}$SO$_2$NR$^{12a}$R$^{13a}$, —NR$^{11a}$C(O)OR$^{12a}$, or an optionally substituted —C$_1$-C$_6$ alkyl, optionally substituted —C$_1$-C$_6$ alkoxy, or —C$_2$-C$_6$ alkenyl group;

R$^{11a}$, R$^{12a}$ and R$^{13a}$ each independently represent a hydrogen atom or an optionally substituted C$_1$-C$_6$ alkyl;

n is 0, 1, 2 or 3, and when n is 2 or 3, each R$^{10}$ can be the same or different;

Q is selected from a covalent bond, an oxygen atom, a sulphur atom, —NR$^{11}$—, —CONR$^{11}$—, —NR$^{11}$CO—, —NR$^{11}$CONR$^{12}$—, —CO—, —C(O)O—, —SO—, —SO$_2$—, —SO$_2$NR$^{11}$—, —NR$^{11}$SO$_2$—, —NR$^{11}$SO$_2$NR$^{12}$—, —NR$^{11}$C(O)O—, —NR$^{11}$C(O)OR$^{13}$—, or an optionally substituted —C$_1$-C$_6$ alkylene, optionally substituted —C$_1$-C$_6$ alkyleneoxy or an optionally substituted —C$_2$-C$_6$ alkenylene group;

R$^{11}$ and R$^{12}$ each independently represent a hydrogen atom or an optionally substituted C$_1$-C$_6$ alkyl, and R$^{13}$ represents an optionally substituted C$_1$-C$_6$ alkylene group; and R$^{14}$ represents an optionally substituted 3 to 10 membered monocyclic or bicyclic cycloalkyl or heterocyclyl or a 5 to 10 membered monocyclic or bicyclic heteroaryl or aryl.

In one embodiment, R$^1$, R$^2$, R$^5$, R$^6$ and R$^7$ may each represent hydrogen;

R$^3$ and R$^4$ may each independently represent a hydrogen atom, a halogen atom, optionally substituted C$_1$-C$_3$ alkyl or optionally substituted C$_1$-C$_3$ alkoxy;

R$^{10}$ may represent halogen, optionally substituted C$_1$-C$_3$ alkyl, optionally substituted C$_1$-C$_3$ alkoxy, or CONR$^{11a}$R$^{12a}$, wherein R$^{11a}$ and R$^{12a}$ each independently represent hydrogen or C$_1$-C$_3$ alkyl;

n is 0 or 1;

Q may represent a covalent bond, an oxygen atom, optionally substituted —C$_1$-C$_3$ alkylene or optionally substituted C$_1$-C$_3$ alkyleneoxy; and R$^{14}$ represents an optionally substituted 5 or 6 membered heteroaryl or aryl.

In a further embodiment of the invention there is provided a compound of formula (IV):

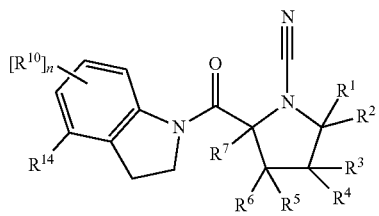

(IV)

or a pharmaceutically acceptable salt thereof, wherein:
R$^1$, R$^2$, R$^5$, R$^6$ and R$^7$ each independently represent a hydrogen atom or optionally substituted C$_1$-C$_3$ alkyl;

R$^3$ and R$^4$ each independently represent a hydrogen atom, a halogen atom or optionally substituted C$_1$-C$_3$ alkyl or optionally substituted C$_1$-C$_3$ alkoxy;

n is 0, 1 or 2; wherein if n is 2, each R$^{10}$ can be the same or different;

each R$^{10}$ independently represents a halogen atom, optionally substituted C$_1$-C$_3$ alkyl, optionally substituted C$_1$-C$_3$ alkoxy, —CONH$_2$, —CONHMe or —CONHEt; and R$^{14}$ represents an optionally substituted 3 to 10 membered monocyclic or bicyclic cycloalkyl or heterocyclyl or an optionally substituted 5 to 10 membered monocyclic or bicyclic heteroaryl or aryl.

Preferably, R$^{14}$ represents an optionally substituted 5 or 6 membered heteroaryl, aryl or heterocyclyl.

R$^{14}$ may be selected from morpholinyl, piperidinyl, pyrrolidinyl, diazepanyl, piperazinyl, pyridazinyl, pyrazinyl, pyrazolyl, cyclopropyl, cyclohexyl, cyclopentyl, pyridinyl, imidazolyl, indolinyl, isoindolinyl, pyrimidinyl, isoxazolyl, dihydroindenyl, dihydroisoquinolinyl, tetrahydropyranyl, phenyl, oxadiazolyl, triazolyl, pyrrolopyridinyl, thiazolyl, pyrazolopyridinyl, pyrrolopyrazinyl, benzodioxolyl and quinolinyl. In one embodiment, R$^{14}$ is pyrazolyl.

In a further embodiment, there is provided a compound of formula (IV):

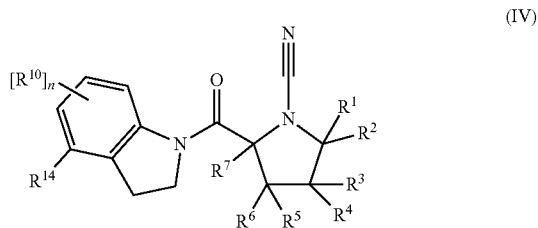

(IV)

or a pharmaceutically acceptable salt thereof, wherein:
R$^1$, R$^2$, R$^5$, R$^6$ and R$^7$ each independently represent a hydrogen atom or optionally substituted C$_1$-C$_3$ alkyl;

R$^3$ and R$^4$ each independently represent a hydrogen atom, a halogen atom or optionally substituted C$_1$-C$_3$ alkyl or optionally substituted C$_1$-C$_3$ alkoxy;

n is 0, 1 or 2; wherein if n is 2, each R$^{10}$ can be the same or different;

each R$^{10}$ independently represents a halogen atom, optionally substituted C$_1$-C$_3$ alkyl or optionally substituted C$_1$-C$_3$ alkoxy; and R$^{14}$ represents an optionally substituted 3 to 10 membered monocyclic or bicyclic cycloalkyl or heterocyclyl or an optionally substituted 5 to 10 membered monocyclic or bicyclic heteroaryl or aryl.

R$^{14}$ may be selected from morpholinyl, piperidinyl, pyrrolidinyl, diazepanyl, piperazinyl, pyridazinyl, pyrazinyl, pyrazolyl, cyclopropyl, cyclohexyl, cyclopentyl, pyridinyl, imidazolyl, indolinyl, isoindolinyl, pyrimidinyl, isoxazolyl, dihydroindenyl, dihydroisoquinolinyl, tetrahydropyranyl, phenyl, oxadiazolyl and triazolyl. In one embodiment, R$^{14}$ is pyrazolyl.

For formula (IV), R$^{14}$ may be substituted with one or more substituents each independently selected from a halogen atom, oxo, cyano, —OR$^{15}$, —SR$^{15}$, —NO$_2$, —NR$^{15}$R$^{16}$, —CONR$^{15}$R$^{16}$, —NR$^{15}$COR$^{16}$, —NR$^{15}$CONR$^{16}$R$^{11}$, —COR$^{15}$, —C(O)OR$^{15}$, —SO$_2$R$^{15}$, —SO$_2$NR$^{15}$R$^{16}$, —NR$^{15}$SO$_2$R$^{16}$, —NR$^{15}$SO$_2$NR$^{16}$R$^{17}$, —NR$^{15}$C(O)OR$^{16}$, or an optionally substituted —C$_1$-C$_6$ alkyl, optionally substituted —C$_1$-C$_6$ alkoxy, optionally substituted —C$_1$-C$_6$ alkylene, optionally substituted —C$_1$-C$_6$ alkyleneoxy, optionally substituted —C$_2$-C$_6$ alkenyl, optionally substituted —C$_2$-C$_6$ alkenylene group, optionally substituted 3 to 10 membered cycloalkyl or heterocyclyl or optionally substituted 5 to 10 membered heteroaryl or aryl, wherein the optionally substituted —C$_1$-C$_6$ alkylene, —C$_1$-C$_6$ alkyleneoxy or —C$_2$-C$_6$ alkenylene group is attached to an optionally substituted 3 to 10 membered cycloalkyl or heterocyclyl or optionally substituted 5 to 10 membered heteroaryl or aryl.

R$^{15}$, R$^{16}$ and R$^{17}$ each independently represent a hydrogen atom or an optionally substituted C$_1$-C$_6$ alkyl, or an optionally substituted 3 to 10 membered cycloalkyl or heterocyclyl or optionally substituted 5 to 10 membered heteroaryl or aryl. In one embodiment, $R^{15}$, $R^{16}$ and $R^{17}$ each independently represent a hydrogen atom or optionally substituted $C_1$-$C_3$ alkyl.

The compound may be of the formula:

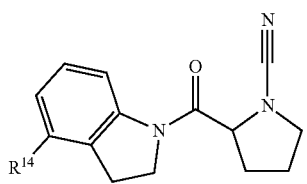

(V)

wherein $R^{14}$ represents an optionally substituted 5 or 6 membered heterocyclyl, heteroaryl or aryl.

$R^{14}$ may be substituted with one or more substituents each independently selected from cyano, optionally substituted $C_1$-$C_3$ alkyl, optionally substituted $C_3$-$C_6$ cycloalkyl, optionally substituted $C_1$-$C_3$ alkoxy, —NHCOMe, —NH$_2$, —NHMe.

$R^{14}$ may be substituted with one or more substituents each independently selected from cyano, optionally substituted $C_1$-$C_3$ alkyl, optionally substituted $C_3$-$C_6$ cycloalkyl or optionally substituted $C_1$-$C_3$ alkoxy.

Examples of novel compounds of formula (I) include:
(S)-2-(4-ethoxyindoline-1-carbonyl)pyrrolidine-1-carbonitrile
(S)-2-(4-isopropoxyindoline-1-carbonyl)pyrrolidine-1-carbonitrile
(S)-2-(4-phenoxyindoline-1-carbonyl)pyrrolidine-1-carbonitrile
(S)-2-(5-phenoxyindoline-1-carbonyl)pyrrolidine-1-carbonitrile
(S)-1-cyano-N-ethyl-N-(4-phenylthiazol-2-yl)pyrrolidine-2-carboxamide
(S)-2-(4-phenylindoline-1-carbonyl)pyrrolidine-1-carbonitrile
(S)-2-(5-(3,5-dimethylisoxazol-4-yl)indoline-1-carbonyl)pyrrolidine-1-carbonitrile
(S)-2-(4-(3-methoxyphenyl)indoline-1-carbonyl)pyrrolidine-1-carbonitrile
(S)-2-(4-(4-methoxyphenyl)indoline-1-carbonyl)pyrrolidine-1-carbonitrile
(S)-2-(4-(2,6-dimethylphenyl)indoline-1-carbonyl)pyrrolidine-1-carbonitrile
(S)-2-(4-(2-methoxyphenyl)indoline-1-carbonyl)pyrrolidine-1-carbonitrile
3-(1-(cyano-L-prolyl)indolin-4-yl)-N-methylbenzamide
(S)-2-(4-cyclopropylindoline-1-carbonyl)pyrrolidine-1-carbonitrile
(2S,4S)-4-methoxy-2-(4-phenylindoline-1-carbonyl)pyrrolidine-1-carbonitrile
(2S,4R)-4-methoxy-2-(4-phenylindoline-1-carbonyl)pyrrolidine-1-carbonitrile
(S)-2-(5-(5-methylisoxazol-4-yl)indoline-1-carbonyl)pyrrolidine-1-carbonitrile
(S)-2-(5-phenylindoline-1-carbonyl)pyrrolidine-1-carbonitrile
(S)-2-(5-(5-(trifluoromethyl)-1H-pyrazol-4-yl)indoline-1-carbonyl)pyrrolidine-1-carbonitrile
(S)-2-(4-(5-(trifluoromethyl)-1H-pyrazol-4-yl)indoline-1-carbonyl)pyrrolidine-1-carbonitrile
(S)-2-(4-(1H-pyrazol-4-yl)indoline-1-carbonyl)pyrrolidine-1-carbonitrile
(S)-2-(4-(5-methyl-1H-pyrazol-4-yl)indoline-1-carbonyl)pyrrolidine-1-carbonitrile
(S)-2-(4-(4-cyanophenyl)indoline-1-carbonyl)pyrrolidine-1-carbonitrile
(S)-2-(4-(3-cyanophenyl)indoline-1-carbonyl)pyrrolidine-1-carbonitrile
(S)-2-(4-(2-cyanophenyl)indoline-1-carbonyl)pyrrolidine-1-carbonitrile
(S)-2-(4-(3,5-dimethyl-1H-pyrazol-4-yl)indoline-1-carbonyl)pyrrolidine-1-carbonitrile
(S)-2-(4-(1H-pyrazol-3-yl)indoline-1-carbonyl)pyrrolidine-1-carbonitrile
(S)-2-(4-(1H-pyrrolo[2,3-b]pyridin-3-yl)indoline-1-carbonyl)pyrrolidine-1-carbonitrile
(S)-4,4-difluoro-2-(4-(5-(trifluoromethyl)-1H-pyrazol-4-yl)indoline-1-carbonyl)pyrrolidine-1-carbonitrile
(2S,4S)-4-fluoro-2-(4-(5-(trifluoromethyl)-1H-pyrazol-4-yl)indoline-1-carbonyl)pyrrolidine-1-carbonitrile
(S)-4,4-difluoro-2-(4-(5-methyl-1H-pyrazol-4-yl)indoline-1-carbonyl)pyrrolidine-1-carbonitrile
(S)-2-(5-(1H-pyrazol-5-yl)indoline-1-carbonyl)pyrrolidine-1-carbonitrile
(S)-2-(4-phenylisoindoline-2-carbonyl)pyrrolidine-1-carbonitrile
(S)-2-(5-phenylisoindoline-2-carbonyl)pyrrolidine-1-carbonitrile
(S)-2-(4-(pyridin-2-yl)indoline-1-carbonyl)pyrrolidine-1-carbonitrile
(S)-2-(4-(pyridazin-4-yl)indoline-1-carbonyl)pyrrolidine-1-carbonitrile
(S)-2-(4-(pyrimidin-4-yl)indoline-1-carbonyl)pyrrolidine-1-carbonitrile
(S)-2-(4-(3-cyclopropyl-1H-pyrazol-4-yl)indoline-1-carbonyl)pyrrolidine-1-carbonitrile
(S)-2-(4-(2-aminopyrimidin-4-yl)indoline-1-carbonyl)pyrrolidine-1-carbonitrile
(S)-2-(4-(pyridin-4-yl)indoline-1-carbonyl)pyrrolidine-1-carbonitrile
(S)-2-(4-(5-methylisoxazol-4-yl)indoline-1-carbonyl)pyrrolidine-1-carbonitrile
(S)-2-(4-(3,5-dimethylisoxazol-4-yl)indoline-1-carbonyl)pyrrolidine-1-carbonitrile
(S)-2-(4-(pyridin-3-yl)indoline-1-carbonyl)pyrrolidine-1-carbonitrile
(S)-2-(6-phenylindoline-1-carbonyl)pyrrolidine-1-carbonitrile
(S)-2-(8-phenyl-3,4-dihydro-2H-benzo[b][1,4]oxazine-4-carbonyl)pyrrolidine-1-carbonitrile
(S)-2-(5-phenyl-1,2,3,4-tetrahydroquinoline-1-carbonyl)pyrrolidine-1-carbonitrile
(S)-1-cyano-N-(4-(2-methoxyphenyl)thiazol-2-yl)-N-methylpyrrolidine-2-carboxamide
(S)-1-cyano-N-(4-(3-methoxyphenyl)thiazol-2-yl)-N-methylpyrrolidine-2-carboxamide
(S)-1-cyano-N-methyl-N-(4-(pyridin-2-yl)thiazol-2-yl)pyrrolidine-2-carboxamide
(S)-1-cyano-N-methyl-N-(4-(pyridin-3-yl)thiazol-2-yl)pyrrolidine-2-carboxamide
(S)-1-cyano-N-methyl-N-(4-(pyridin-4-yl)thiazol-2-yl)pyrrolidine-2-carboxamide
(2S)-1-cyano-N-methyl-N-(4-(tetrahydrofuran-3-yl)thiazol-2-yl)pyrrolidine-2-carboxamide
(S)—N-(4-(3-chlorophenyl)thiazol-2-yl)-1-cyano-N-methylpyrrolidine-2-carboxamide
(S)—N-(4-(2-chlorophenyl)thiazol-2-yl)-1-cyano-N-methylpyrrolidine-2-carboxamide (S)-1-cyano-N-methyl-N-(4-phenylthiazol-2-yl)pyrrolidine-2-carboxamide
(S)-1-cyano-N-methyl-N-(1-phenyl-1H-pyrazol-3-yl)pyrrolidine-2-carboxamide
(S)-1-cyano-N-(4-isopropylthiazol-2-yl)-N-methylpyrrolidine-2-carboxamide
(S)-1-cyano-N-methyl-N-(3-phenylisoxazol-5-yl)pyrrolidine-2-carboxamide
(S)—N-(5-benzylthiazol-2-yl)-1-cyano-N-methylpyrrolidine-2-carboxamide
(S)-1-cyano-N-methyl-N-(5-phenylthiazol-2-yl)pyrrolidine-2-carboxamide
(S)—N-(4-(tert-butyl)thiazol-2-yl)-1-cyano-N-methylpyrrolidine-2-carboxamide
(S)—N-(4-(4-chlorophenyl)thiazol-2-yl)-1-cyano-N-methylpyrrolidine-2-carboxamide
(S)—N-(3-(2-chlorophenyl)isoxazol-5-yl)-1-cyano-N-methylpyrrolidine-2-carboxamide
(2S,4S)-1-cyano-N-methyl-4-phenyl-N-(4-phenylthiazol-2-yl)pyrrolidine-2-carboxamide
(S)—N-(3-(3-chlorophenyl)isoxazol-5-yl)-1-cyano-N-methylpyrrolidine-2-carboxamide
(S)-1-cyano-N-(3-(3-methoxyphenyl)isoxazol-5-yl)-N-methylpyrrolidine-2-carboxamide
(S)-1-cyano-N-methyl-N-(5-phenylisoxazol-3-yl)pyrrolidine-2-carboxamide
(S)—N-(3-(4-chlorophenyl)isoxazol-5-yl)-1-cyano-N-methylpyrrolidine-2-carboxamide
(S)—N-(4-(4-acetamidophenyl)thiazol-2-yl)-1-cyano-N-methylpyrrolidine-2-carboxamide
(S)—N-(4-(3-acetamidophenyl)thiazol-2-yl)-1-cyano-N-methylpyrrolidine-2-carboxamide ethyl 4-(1-(cyano-L-prolyl)indolin-4-yl)-1-(4-methoxybenzyl)-1H-pyrazole-5-carboxylate
(2S,4S)-1-cyano-4-methoxy-N-methyl-N-(4-phenylthiazol-2-yl)pyrrolidine-2-carboxamide
(S)-2-(4-(3-methylisoxazol-4-yl)indoline-1-carbonyl)pyrrolidine-1-carbonitrile
(S)-2-(4-(1H-imidazol-1-yl)indoline-1-carbonyl)pyrrolidine-1-carbonitrile
4-(1-(cyano-L-prolyl)indolin-4-yl)-1H-pyrazole-5-carbonitrile
(S)-2-(5-phenyl-1,2,3,4-tetrahydroisoquinoline-2-carbonyl)pyrrolidine-1-carbonitrile
(S)-2-(4-(2-aminopyridin-4-yl)indoline-1-carbonyl)pyrrolidine-1-carbonitrile
(S)-1-cyano-N-(4-(6-cyanopyridin-2-yl)thiazol-2-yl)-N-methylpyrrolidine-2-carboxamide
(S)-1-cyano-N-(4-(2-cyanopyridin-4-yl)thiazol-2-yl)-N-methylpyrrolidine-2-carboxamide
(S)-1-cyano-N-(4-(4-cyanopyridin-2-yl)thiazol-2-yl)-N-methylpyrrolidine-2-carboxamide
(S)-1-cyano-N-(4-(6-cyano-3-methylpyridin-2-yl)thiazol-2-yl)-N-methylpyrrolidine-2-carboxamide
(S)-1-cyano-N-(4-(6-methoxypyridin-2-yl)thiazol-2-yl)-N-methylpyrrolidine-2-carboxamide
(S)-1-cyano-N-methyl-N-(4-(6-(trifluoromethyl)pyridin-2-yl)thiazol-2-yl)pyrrolidine-2-carboxamide
(S)-1-cyano-N-(4-(6-cyano-5-methoxypyridin-2-yl)thiazol-2-yl)-N-methylpyrrolidine-2-carboxamide
(S)-1-cyano-N-(4-(6-cyano-5-methylpyridin-2-yl)thiazol-2-yl)-N-methylpyrrolidine-2-carboxamide
1-(cyano-L-prolyl)-4-phenylindoline-6-carboxamide
1-(cyano-L-prolyl)-N-ethyl-4-phenylindoline-6-carboxamide
1-(cyano-L-prolyl)-4-(3-ethylphenyl)-N-methylindoline-6-carboxamide
1-(cyano-L-prolyl)-N-methyl-4-(quinolin-6-yl)indoline-6-carboxamide
1-(cyano-L-prolyl)-N-methyl-4-(1H-pyrrolo[2,3-b]pyridin-3-yl)indoline-6-carboxamide
(S)-2-(6-(1H-imidazol-2-yl)-4-phenylindoline-1-carbonyl)pyrrolidine-1-carbonitrile
(S)-2-(4-phenyl-6-(4H-1,2,4-triazol-3-yl)indoline-1-carbonyl)pyrrolidine-1-carbonitrile
(S)-2-(6-(5-methyl-4H-1,2,4-triazol-3-yl)-4-phenylindoline-1-carbonyl)pyrrolidine-1-carbonitrile
(S)-2-(4-(4-cyanophenyl)-6-(5-methyl-4H-1,2,4-triazol-3-yl)indoline-1-carbonyl)pyrrolidine-1-carbonitrile
(S)-2-(4-(3-cyanophenyl)-6-(5-methyl-4H-1,2,4-triazol-3-yl)indoline-1-carbonyl)pyrrolidine-1-carbonitrile
(2S,4S)-4-fluoro-2-(4-(5-methyl-1H-pyrazol-4-yl)indoline-1-carbonyl)pyrrolidine-1-carbonitrile
N-(4-(1-(cyano-L-prolyl)indolin-4-yl)pyridin-2-yl)acetamide
(S)-2-(4-(5-(trifluoromethyl)-1H-pyrazol-4-yl)-2,3-dihydro-1H-pyrrolo[3,2-c]pyridine-1-carbonyl)pyrrolidine-1-carbonitrile
1-(cyano-L-prolyl)-N-methyl-4-(4-(trifluoromethyl)phenyl)indoline-6-carboxamide
1-(cyano-L-prolyl)-4-(3-cyanophenyl)-N-methylindoline-6-carboxamide
1-(cyano-L-prolyl)-4-(4-cyanophenyl)-N-methylindoline-6-carboxamide
4-(4-chlorophenyl)-1-(cyano-L-prolyl)-N-methylindoline-6-carboxamide
1-(cyano-L-prolyl)-N-methyl-4-(m-tolyl)indoline-6-carboxamide
4-(2-chlorophenyl)-1-(cyano-L-prolyl)-N-methylindoline-6-carboxamide
1-(cyano-L-prolyl)-4-(3,4-dichlorophenyl)-N-methylindoline-6-carboxamide
4-(benzo[d][1,3]dioxol-5-yl)-1-(cyano-L-prolyl)-N-methylindoline-6-carboxamide
(S)—N-(5-(3-chlorophenyl)isoxazol-3-yl)-1-cyano-N-methylpyrrolidine-2-carboxamide
(S)-1-cyano-N-(5-(3-cyanophenyl)isoxazol-3-yl)-N-methylpyrrolidine-2-carboxamide
(S)-1-cyano-N-(5-(3-methoxyphenyl)isoxazol-3-yl)-N-methylpyrrolidine-2-carboxamide
(S)—N-(4-(3-chlorophenyl)thiazol-2-yl)-1-cyano-N-ethylpyrrolidine-2-carboxamide
(S)-1-cyano-N-(4-(5-cyanopyridin-3-yl)thiazol-2-yl)-N-methylpyrrolidine-2-carboxamide
(S)-2-(1-phenyl-1,4,5,6-tetrahydropyrrolo[3,2-c]pyrazole-4-carbonyl)pyrrolidine-1-carbonitrile
(S)-2-(4-(3-chlorophenyl)indoline-1-carbonyl)pyrrolidine-1-carbonitrile
(S)-2-(5-(4-cyanophenyl)isoindoline-2-carbonyl)pyrrolidine-1-carbonitrile
(S)-2-(5-(3-cyanophenyl)isoindoline-2-carbonyl)pyrrolidine-1-carbonitrile
(S)-2-(5-(3-(trifluoromethyl)-1H-pyrazol-4-yl)isoindoline-2-carbonyl)pyrrolidine-1-carbonitrile
4-(1-(cyano-L-prolyl)indolin-4-yl)nicotinonitrile
(S)-2-(4-(1H-pyrrolo[2,3-b]pyridin-4-yl)indoline-1-carbonyl)pyrrolidine-1-carbonitrile
(S)-2-(4-(6-aminopyridin-2-yl)indoline-1-carbonyl)pyrrolidine-1-carbonitrile
(S)-2-(4-(6-aminopyrazin-2-yl)indoline-1-carbonyl)pyrrolidine-1-carbonitrile
(S)-2-(4-(2-(methylamino)pyrimidin-4-yl)indoline-1-carbonyl)pyrrolidine-1-carbonitrile (S)-2-(4-(2-aminopyrimidin-5-yl)indoline-1-carbonyl)pyrrolidine-1-carbonitrile
(S)-2-(4-(1H-pyrazolo[3,4-b]pyridin-3-yl)indoline-1-carbonyl)pyrrolidine-1-carbonitrile
(S)-2-(4-(5H-pyrrolo[2,3-b]pyrazin-7-yl)indoline-1-carbonyl)pyrrolidine-1-carbonitrile
(S)—N-(4-(3-chloro-4-fluorophenyl)thiazol-2-yl)-1-cyano-N-methylpyrrolidine-2-carboxamide
(S)-1-cyano-N-methyl-N-(4-(3-(trifluoromethyl)phenyl)thiazol-2-yl)pyrrolidine-2-carboxamide
(S)-1-cyano-N-(4-(3-cyanophenyl)thiazol-2-yl)-N-methylpyrrolidine-2-carboxamide
(S)-1-cyano-N-(4-(3-ethylphenyl)thiazol-2-yl)-N-methylpyrrolidine-2-carboxamide
(S)-2-(5-(3-(trifluoromethoxy)phenyl)isoindoline-2-carbonyl)pyrrolidine-1-carbonitrile
(S)-2-(5-(3-methyl-1H-indazol-6-yl)isoindoline-2-carbonyl)pyrrolidine-1-carbonitrile
(S)-2-(5-(1-methyl-H-indazol-5-yl)isoindoline-2-carbonyl)pyrrolidine-1-carbonitrile
(S)-2-(5-(4-(methylsulfonyl)phenyl)isoindoline-2-carbonyl)pyrrolidine-1-carbonitrile
(S)-2-(5-(2-cyanophenyl)isoindoline-2-carbonyl)pyrrolidine-1-carbonitrile
(S)-2-(5-(3-nitrophenyl)isoindoline-2-carbonyl)pyrrolidine-1-carbonitrile
(S)-2-(5-(3-cyano-2-fluorophenyl)isoindoline-2-carbonyl)pyrrolidine-1-carbonitrile
(S)-1-cyano-N-methyl-N-(4-(3-(N-methylacetamido)phenyl)thiazol-2-yl)pyrrolidine-2-carboxamide
(S)-1-cyano-N-methyl-N-(4-(3-(N-methylmethylsulfonamido)phenyl)thiazol-2-yl)pyrrolidine-2-carboxamide
(S)-1-cyano-N-(4-(6-cyano-3-methoxypyridin-2-yl)thiazol-2-yl)-N-methylpyrrolidine-2-carboxamide
(S)-1-cyano-N-(4-(6-isopropoxypyridin-2-yl)thiazol-2-yl)-N-methylpyrrolidine-2-carboxamide
(S)-1-cyano-N-(4-(6-cyano-5-ethoxypyridin-2-yl)thiazol-2-yl)-N-methylpyrrolidine-2-carboxamide
(S)-1-cyano-N-(4-(6-cyano-5-(dimethylamino)pyridin-2-yl)thiazol-2-yl)-N-methylpyrrolidine-2-carboxamide
(S)-1-cyano-N-(4-(6-cyano-3-(2-methoxyethoxy)pyridin-2-yl)thiazol-2-yl)-N-methylpyrrolidine-2-carboxamide
(S)-1-cyano-N-(4-(6-cyano-3-ethoxypyridin-2-yl)thiazol-2-yl)-N-methylpyrrolidine-2-carboxamide
(S)-1-cyano-N-(4-(6-cyanopyridin-2-yl)-5-ethylthiazol-2-yl)-N-methylpyrrolidine-2-carboxamide
(S)-1-cyano-N-(4-(6-cyanopyridin-2-yl)-5-methylthiazol-2-yl)-N-methylpyrrolidine-2-carboxamide
(S)-1-cyano-N-(4-(3-(methoxymethyl)phenyl)thiazol-2-yl)-N-methylpyrrolidine-2-carboxamide
(S)-1-cyano-N-(5-cyano-4-phenylthiazol-2-yl)-N-methylpyrrolidine-2-carboxamide
(S)-1-cyano-N-(4-(6-cyclopropylpyridin-2-yl)thiazol-2-yl)-N-methylpyrrolidine-2-carboxamide
(S)-1-cyano-N-(4-(3-cyanophenyl)-5-fluorothiazol-2-yl)-N-methylpyrrolidine-2-carboxamide or pharmaceutically acceptable salts thereof.

It should be noted that each of the chemical compounds listed above represents a particular and independent aspect of the invention.

According to a further aspect of the invention there is provided a process for the preparation of a compound of formula (I) or a pharmaceutically acceptable salt thereof comprising the steps of reacting an acid of formula (VI) with a compound $R^9$—$NHR^8$ to form an amide:

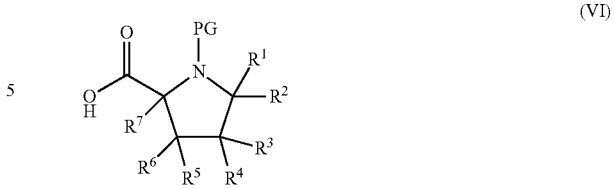

Where $R^1$ to $R^9$ are as defined elsewhere and PG is an amine protecting group. The protecting group may be but is not limited to BOC. It is clear to a person skilled in the art to combine or adjust such a protecting chemical group. After coupling of $R^9$—$NHR^8$ to form an amide, the protecting group may be removed to leave the free amine according to formula (VII) which can then be treated with cyanogen bromide to form compounds according to formula (I).

According to a further aspect of the invention there is provided a process for the preparation of a compound of formula (I) or a pharmaceutically acceptable salt thereof comprising the steps of reacting an amine of formula (VII) with cyanogen bromide to form N—CN compounds:

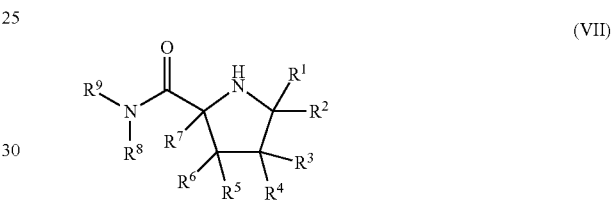

According to a further aspect of the invention there is provided a pharmaceutical composition comprising a compound of the invention.

Pharmaceutical compositions of this invention comprise any of the compounds of the invention combined with any pharmaceutically acceptable carrier, adjuvant or vehicle. Examples of pharmaceutically acceptable carriers, are known to those skilled in the art and include but are not limited to preserving agents, fillers, disintegrating agents, wetting agents, emulsifying agents, suspending agents, sweetening agents, flavouring agents, perfuming agents, antibacterial agents, antifungal agents, lubricating agents and dispersing agents, depending on the nature of the mode of administration and dosage forms. The compositions may be in the form of, for example, tablets, capsules, powders, granules, elixirs, lozenges, suppositories, syrups and liquid preparations including suspensions and solutions. The term "pharmaceutical composition" in the context of this invention means a composition comprising an active agent and comprising additionally one or more pharmaceutically acceptable carriers. The composition may further contain ingredients selected from, for example, diluents, adjuvants, excipients, vehicles, preserving agents, fillers, disintegrating agents, wetting agents, emulsifying agents, suspending agents, sweetening agents, flavouring agents, perfuming agents, antibacterial agents, antifungal agents, lubricating agents and dispersing agents, depending on the nature of the mode of administration and dosage forms.

According to a further aspect of the invention there is provided a compound of the disclosure or pharmaceutical composition thereof for use in therapy. In particular the compounds of the invention have use in the treatment of cancer and more particularly in the treatment of cancers linked to DUB activity.

The compounds described herein may also be used in the manufacture of a medicament for the treatment of a cancer linked to DUB activity.

In a further aspect of the invention there is provided a method of treatment or prevention of a cancer, the method comprising administering a pharmaceutically effective amount of a compound of the invention or a pharmaceutical composition thereof to an individual suffering from a cancer.

UCHL1 is overexpressed in many tumour types. In a further aspect of the invention there is provided a method of treatment or prevention of a cancer linked to UCHL1 activity, the method comprising administering a pharmaceutically effective amount of a compound disclosed herein or a pharmaceutical composition thereof to an individual suffering from a cancer linked to UCHL1 activity The compounds or compositions according to the invention may be used to treat cancer. References to "cancer" or "tumour" include but are not limited to breast, ovarian, prostate, lung, kidney, gastric, colon, testicular, head and neck, pancreas, brain, melanoma, bone or other cancers of tissue organs and cancers of the blood cells such as lymphomas and leukaemias. Particular cancers include lymphoma, multiple myeloma, colorectal cancer, and non-small cell lung carcinoma.

The compounds or compositions according to the invention may be used to treat additional diseases linked to UCHL1 activity. For example a disease linked to UCHL1 activity may be selected from neurodegenerative disorders (such as Alzheimer's disease, Parkinson's disease), chronic obstructive pulmonary disease (COPD), inflammation, viral infections, including MERS or SARS, bacterial infections, including TB, or metabolic disorders.

Certain compounds of the invention also show activity against USP30 and are therefore useful in the treatment of disorders or diseases linked to USP30 activity. USP30 is a 517 amino acid protein which is found in the mitochondrial outer membrane. It is the sole deubiquitylating enzyme bearing a mitochondrial addressing signal and has been shown to deubiquitylate a number of mitochondrial proteins. Mitochondrial dysfunction can be defined as diminished mitochondrial content (mitophagy or mitochondrial biogenesis), as a decrease in mitochondrial activity and oxidative phosphorylation, but also as modulation of reactive oxygen species (ROS) generation. Hence mitochondrial dysfunction plays a role in a very large number of aging processes and pathologies.

The compounds or compositions of the invention may be used to treat a condition involving mitochondrial dysfunction.

The condition involving mitochondrial dysfunction may be selected from a condition involving a mitophagy defect, a condition involving a mutation in mitochondrial DNA, a condition involving mitochondrial oxidative stress, a condition involving a defect in mitochondrial membrane potential, mitochondrial biogenesis, a condition involving a defect in mitochondrial shape or morphology, and a condition involving a lysosomal storage defect.

In particular, the condition involving mitochondrial dysfunction may be selected from a neurodegenerative disease; multiple sclerosis (MS), mitochondrial myopathy, encephalopathy, lactic acidosis, and stroke-like episodes (MELAS) syndrome; Leber's hereditary optic neuropathy (LHON); cancer; neuropathy, ataxia, retinitis pigmentosa-maternally inherited Leigh syndrome (NARP-MILS); Danon disease; diabetes; diabetic nephropathy; metabolic disorders; heart failure; ischemic heart disease leading to myocardial infarction; psychiatric diseases, for example schizophrenia; multiple sulfatase deficiency (MSD); mucolipidosis II (ML II); mucolipidosis III (ML III); mucolipidosis IV (ML IV); GM1-gangliosidosis (GM1); neuronal ceroid-lipofuscinoses (NCL1); Alpers disease; Barth syndrome; Beta-oxidation defects; carnitine-acyl-carnitine deficiency; carnitine deficiency; creatine deficiency syndromes; co-enzyme Q10 deficiency; complex I deficiency; complex II deficiency; complex III deficiency; complex IV deficiency; complex V deficiency; COX deficiency; chronic progressive external ophthalmoplegia syndrome (CPEO); CPT I deficiency; CPT II deficiency; glutaric aciduria type II; Kearns-Sayre syndrome; lactic acidosis; long-chain acyl-CoA dehydrogenase deficiency (LCHAD); Leigh disease or syndrome; lethal infantile cardiomyopathy (LIC); Luft disease; glutaric aciduria type II; medium-chain acyl-CoA dehydrogenase deficiency (MCAD); myoclonic epilepsy and ragged-red fiber (MERRF) syndrome; mitochondrial cytopathy; mitochondrial recessive ataxia syndrome; mitochondrial DNA depletion syndrome; myoneurogastointestinal disorder and encephalopathy; Pearson syndrome; pyruvate dehydrogenase deficiency; pyruvate carboxylase deficiency; POLG mutations; medium/short-chain 3-hydroxyacyl-CoA dehydrogenase (M/SCHAD) deficiency; and very long-chain acyl-CoA dehydrogenase (VLCAD) deficiency.

The condition involving mitochondrial dysfunction may be a CNS disorder, for example a neurodegenerative disease.

Neurodegenerative diseases include, but are not limited to, Parkinson's disease, Alzheimer's disease, amyotrophic lateral sclerosis (ALS), Huntington's disease, ischemia, stroke, dementia with Lewy bodies, and frontotemporal dementia. The compounds of the invention are useful in the treatment of Parkinson's disease, including, but not limited to, PD related to mutations in α-synuclein, parkin and PINK1, autosomal recessive juvenile Parkinson's disease (AR-JP) where parkin is mutated.

The compounds of the invention or pharmaceutical compositions thereof as described herein may be combined with one or more additional agents. The compounds may be combined with an additional anti-tumour therapeutic agent, for example chemotherapeutic drugs or inhibitors of other regulatory proteins. In one embodiment the additional anti-tumour therapeutic agent is selected from a PARP (poly ADP ribose polymerase) inhibitor, a BRCA2 inhibitor and an ATM inhibitor. In another embodiment the PARP (poly ADP ribose polymerase) inhibitor is an inhibitory RNA (RNAi) molecule (PARPi). In a further embodiment PARP inhibitors may be selected from one or more of Iniparib (BSI 201), Olaparib (AZD-2281), Rucaparib (AG014699, PF-01367338) and Veliparib (ABT-888), MK-4827, CEP-9722, E7016(GPI-21016), LT-673, MP-124, NMS-P118. In a further embodiment the additional anti-tumour agent is a chemotherapeutic agent. Chemotherapeutic agents may be selected from olaparib, mitomycin C, cisplatin, carboplatin, oxaliplatin, ionizing radiation (IR), camptothecin, irinotecan, topotecan, temozolomide, taxanes, 5-fluoropyrimidines, gemcitabine, and doxorubicin.

The pharmaceutical compositions of the invention may be administered in any effective manner suitable for targeting cancer cells, for example orally in any orally acceptable dosage form including, but not limited to tablets, dragees, powders, elixirs, syrups, liquid preparations including suspensions, sprays, inhalants, tablets, lozenges, emulsions, solutions, cachets, granules and capsules. Such dosage forms are prepared according to techniques known in the art of pharmaceutical formulation. When in the form of sprays or inhalants the pharmaceutical compositions may be administered nasally. Suitable formulations for this purpose are known to those skilled in the art.

The pharmaceutical compositions of the invention may be administered by injection and may be in the form of a sterile liquid preparation for injection, including liposome preparations. The pharmaceutical compositions of the invention may also be in the form of suppositories for rectal administration. These are formulated so that the pharmaceutical composition is solid at room temperature and liquid at body temperature to allow release of the active compound.

The dosages may be varied depending upon the requirements of the patient, the severity of the condition being treated, and the compound being employed. Determination of the proper dosage for a particular situation is within the remit of the person skilled in the skill of the art. Generally, treatment is initiated with smaller dosages which are less than the optimal dose of the compound. Thereafter the dosage is increased by small increments until the optimum effect under the circumstances is reached.

The magnitude of an effective dose of a compound will, of course, vary with the nature of the severity of the condition to be treated and with the particular compound and its route of administration. The selection of appropriate dosages is within the ability of one of ordinary skill in this art, without undue burden. The daily dose range is about 10 μg to about 100 mg per kg body weight of a human and non-human animal and in general may be around 10 μg to 30 mg per kg body weight per dose. The above dose may be given from one to three times per day.

Synthetic Methodologies

Compounds of the invention may be prepared via a variety of synthetic routes. Exemplary routes to certain compounds of the invention are shown below. Representative compounds of the present invention can be synthesized in accordance with the general synthetic methods described below and are illustrated more particularly in the schemes that follow. Since the schemes are an illustration, the invention should not be construed as being limited by the chemical reactions and conditions expressed. The preparation of the various starting materials used in the schemes is well within the skill of persons versed in the art. Those skilled in the art appreciate that, where appropriate, the individual transformations within a scheme can be completed in a different order. The following schemes describe general synthetic methods whereby intermediate and target compounds of the present invention may be prepared. Additional representative compounds and stereoisomers, racemic mixtures, diastereomers and enantiomers thereof can be synthesized using the intermediates prepared in accordance to the general schemes and other materials, compounds and reagents known to those skilled in the art. All such compounds, stereoisomers, racemic mixtures, diastereomers and enantiomers thereof are intended to be encompassed within the scope of the present invention.

All the compounds were characterised by either liquid chromatography-mass spectroscopy (LCMS) or $^1$H NMR or both.

Abbreviations:
Ar Aryl
BEH Ethylene Bridged Hybrid
BOC Tert-butoxycarbonyl
br Broad (NMR signal)
d Doublet (NMR signal)
dba dibenzylideneacetone
DCC N,N'-Dicyclohexylcarbodiimide
DCM Dichloromethane
DIPC N,N'-Diisopropylcarbodiimide
DIPEA Diisopropylethylamine
DMF N,N-Dimethylformamide
DMSO Dimethylsulphoxide
dppf 1,1'-Bis(diphenylphosphino)ferrocene
ES Electrospray
EtOAc Ethyl acetate
EtOH Ethanol
g gram(s)
h Hour(s)
HATU 1-[Bis(dimethylamino)methylene]-1H-1,2,3-triazolo[4,5-b]pyridinium 3-oxid hexafluorophosphate
m Multiplet (NMR signal)
M Molar
MeCN Acetonitrile
MeOH Methanol
min Minutes
rt Room temperature
RT Retention time
s Singlet (NMR signal)
t Triplet (NMR signal)
TEA Triethylamine
TBTU N,N,N',N'-Tetramethyl-O-(benzotriazol-1-yl)uronium tetrafluoroborate
TFA Trifluoroacetic acid
THF Tetrahydrofuran
TLC Thin layer chromatography Analytical Methods:

| Method C | |
|---|---|
| Column | BEH C18, 50 × 2.1 mm, 1.7 μm or equivalent |
| Mobile Phase | (A) 5 mM Ammonium Acetate + 0.1% Formic acid in water |
| | (B) 0.1% Formic acid in MeCN |
| Flow Rate | 0.55 mL/min |

| | Time | % B |
|---|---|---|
| Gradient | 0.01 | 5 |
| | 0.40 | 5 |
| | 0.80 | 35 |
| | 1.20 | 55 |
| | 2.50 | 100 |
| | 3.30 | 100 |
| | 3.31 | 5 |
| | 4.00 | 5 |

| Method D | |
|---|---|
| Column | X-bridge C18, 150 × 4.6 mm, 5 μm or equivalent |
| Mobile Phase | (A) 0.1% Ammonia in water |
| | (B) 0.1% Ammonia in MeCN |
| Flow Rate | 1.0 mL/min |

| | Time | % B |
|---|---|---|
| Gradient | 0.01 | 10 |
| | 5.00 | 90 |
| | 7.00 | 100 |
| | 11.00 | 100 |
| | 11.01 | 10 |
| | 12.00 | 10 |

| Method H | |
|---|---|
| Column | X-bridge C18, 50 × 4.6 mm, 3.5 μm or equivalent |
| Mobile Phase | (A) 0.1% Ammonia in water |
| | (B) 0.1% Ammonia in MeCN |
| Flow Rate | 1.0 mL/min |

| | Time | % B |
|---|---|---|
| Gradient | 0.01 | 5 |
| | 5.00 | 90 |
| | 5.80 | 95 |
| | 7.20 | 95 |
| | 7.21 | 5 |
| | 10.00 | 5 |

Method J

| | | |
|---|---|---|
| Column | BEH C18, 50 × 2.1 mm, 1.7 μm or equivalent | |
| Mobile Phase | (A) 5 mM Ammonium acetate + 0.1% Formic acid in water | |
| | (B) 0.1% Formic acid in MeCN | |
| Flow Rate | 0.45 mL/min | |

| | Time | % B |
|---|---|---|
| Gradient | 0.01 | 2 |
| | 0.50 | 2 |
| | 5.00 | 90 |
| | 6.00 | 95 |
| | 7.00 | 95 |
| | 7.01 | 2 |
| | 8.00 | 2 |

Method X

| | | |
|---|---|---|
| Column | Agilent TC-C18, 50 × 2.1 mm, 5 μm | |
| Mobile Phase | (A) 0.04% TFA in water | |
| | (B) 0.02% TFA in MeCN | |
| Flow Rate | 0.8 mL/min | |

| | Time (min) | B % |
|---|---|---|
| Gradient | 0 | 0 |
| | 0.4 | 1 |
| | 3.4 | 100 |
| | 4 | 100 |
| Temperature | 50° C. | |

Method Y

| | | |
|---|---|---|
| Column | XBridge ShieldRP18, 50 × 2.1 mm, 5 μm | |
| Mobile Phase | (A) 0.05% NH3 in water | |
| | (B) MeCN | |
| Flow Rate | 0.8 mL/min | |

| | Time (min) | B % |
|---|---|---|
| Gradient | 0 | 0 |
| | 0.4 | 5 |
| | 3.4 | 100 |
| | 4 | 100 |
| Temperature | 40° C. | |

Method Z

| | | |
|---|---|---|
| Column | Agilent TC-C18, 50 × 2.1 mm, 5 μm or equivalent | |
| Mobile Phase | (A) 0.04% TFA in water | |
| | (B) 0.02% TFA in MeCN | |
| Flow Rate | 0.80 mL/min | |

| | Time | % B |
|---|---|---|
| Gradient | 0.01 | 10 |
| | 3.40 | 100 |
| | 4.00 | 100 |
| | 4.01 | 10 |
| | 4.50 | 10 |

Intermediate A 5-Benzyl-N-methylthiazol-2-amine

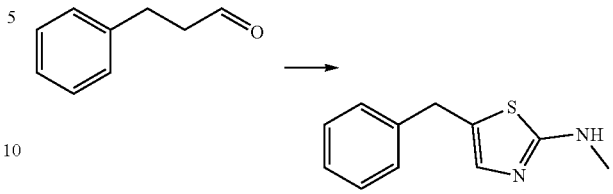

Bromine (0.38 ml, 7.45 mmol) was added dropwise to a solution of 3-phenylpropanal (CAS Number 104-53-0) (1.0 g, 7.45 mmol) in DCM (10 ml) at 0° C. The reaction mixture was stirred at rt for 16 h. The resulting reaction mixture was concentrated under reduced pressure. The resulting residue was dissolved in ethanol (10 ml) and N-methyl thiourea (1.34 g, 14.9 mmol) was added at rt. The obtained reaction mixture was heated at 80° C. for 4 h. The resulting reaction mixture was cooled to rt, diluted with water (30 ml) and extracted with EtOAc (3×30 ml). The combined organic phase was dried over $Na_2SO_4$, filtered and concentrated under reduced pressure. The resulting residue was purified by flash chromatography (10% MeOH in DCM) yielding 5-benzyl-N-methylthiazol-2-amine (0.60 g, 2.93 mmol). LCMS: Method C, 1.638 min, MS: ES+ 205.14.

Intermediate B Tert-butyl (S)-2-(4-bromoindoline-1-carbonyl)pyrrolidine-1-carboxylate

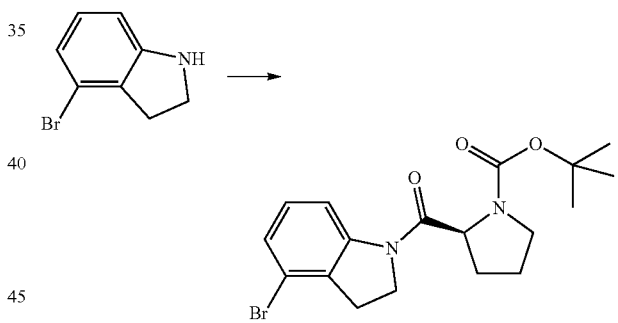

To a solution of (tert-butoxycarbonyl)-L-proline (CAS Number 15761-39-4) (6.52 g, 30.3 mmol) in THF (50 ml) was added HATU (14.4 g, 37.87 mmol) and DIPEA (6.52 g, 50.5 mmol) at rt. The reaction mixture was stirred for 1 h. 4-Bromoindoline (CAS Number 86626-38-2) (5 g, 25.25 mmol) was added to the reaction mixture. The reaction mixture was stirred at rt for 15 h. The resulting reaction mixture was combined with 10 other batches prepared on the same scale by an identical method, then poured into saturated $NaHCO_3$ solution (1000 ml). The resulting mixture was extracted with EtOAc (2×1000 ml). The combined organic phase was collected, dried over $Na_2SO_4$, filtered and concentrated under reduced pressure. The resulting residue was purified by column chromatography (12-15% EtOAc in hexane). The material obtained from chromatographic purification was suspended in saturated $NaHCO_3$ solution (300 ml) and stirred for 30 min. The resulting solid precipitates were collected by filtration under reduced pressure, washed with hexane (200 ml) and dried yielding tert-butyl (S)-2-(4-bromoindoline-1-carbonyl)pyrrolidine-1-carboxylate (Intermediate B, 65 g, 164.94 mmol). LCMS: Method C, 2.483 min, MS: ES+ 395.21; ¹H NMR (400 MHz, DMSO-d6) δ ppm 7.95-8.13 (m, 1H), 7.12-7.22 (m, 2H), 4.45-4.55 (m, 1H), 4.15-4.30 (m, 2H), 3.36-3.47 (m, 2H), 3.14-3.18 (m, 2H), 2.28-2.33 (m, 1H), 1.88-1.96 (m, 3H), 1.20-1.50 (m, 9H).

Intermediate C Tert-butyl
4-bromo-3-cyclopropyl-1H-pyrazole-1-carboxylate

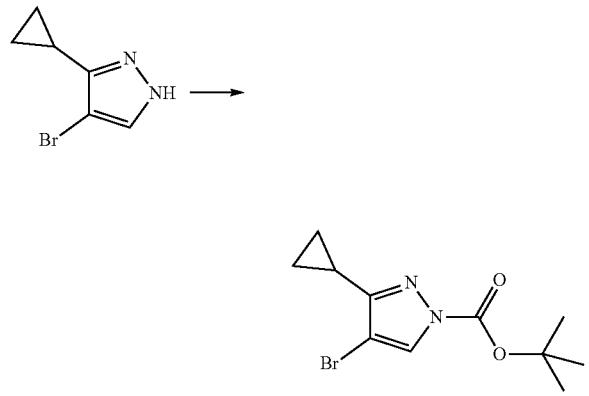

To a solution of methyl 4-bromo-3-cyclopropyl-1H-pyrazole (CAS Number 957345-28-7) (0.5 g, 2.67 mmol) in DCM (10 ml) were added TEA (0.324 g, 3.20 mmol) and 4-dimethylaminopyridine (0.033 g, 0.26 mmol) at 0° C. BOC anhydride (0.641 g, 2.9 mmol) was added to the reaction mixture at 0° C. The reaction mixture stirred at rt for 3 h. The resulting reaction mixture was poured into water (20 ml) and extracted with DCM (2×15 ml). The combined organic phase was collected, dried over Na₂SO₄, filtered and concentrated under reduced pressure yielding tert-butyl 4-bromo-3-cyclopropyl-1H-pyrazole-1-carboxylate (0.54 g, 1.88 mmol). This material was used directly for the next step without further purification. LCMS: Method C, 2.607 min, MS: ES+ 287.3.

Scheme 1

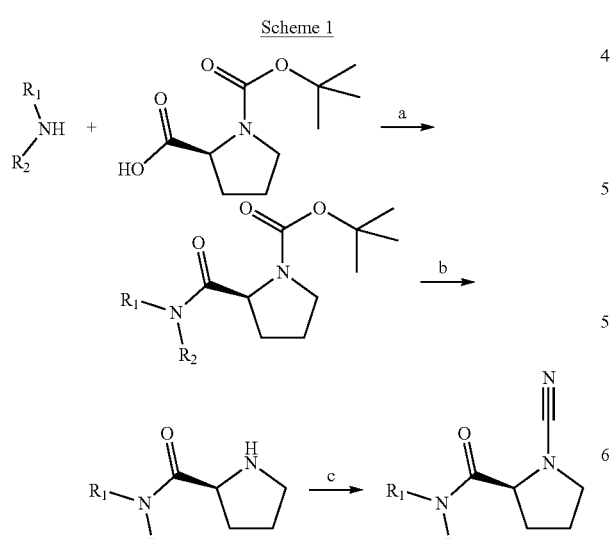

Reagents and conditions: a) HATU, DIPEA, DMF; b) TFA, DCM; c) cyanogen bromide, K₂CO₃, THF.

Example 1 (S)-2-(4-Ethoxyindoline-1-carbonyl)
pyrrolidine-1-carbonitrile (Prepared According to Scheme 1)

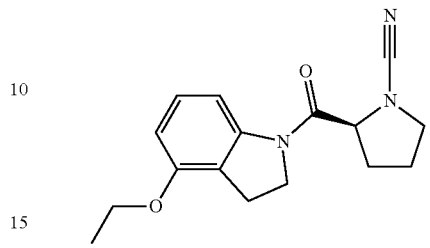

Step a. To a solution of BOC-L-proline (0.71 g, 3.30 mmol) in DMF (12 ml) were added HATU (1.25 g, 3.30 mmol) and DIPEA (0.71 g, 5.50 mmol) at 0° C. The reaction mixture was stirred at 0° C. for 15 min. 4-Ethoxyindoline (CAS Number 220657-56-7) (0.45 g, 2.70 mmol) was dissolved in DMF (2 ml) and added dropwise to the reaction mixture at 0° C. The reaction mixture was stirred at rt for 30 min. The resulting reaction mixture was poured into water (50 ml) and extracted with EtOAc (5×50 ml). The combined organic phase was collected, dried over Na₂SO₄, filtered and concentrated under reduced pressure yielding tert-butyl (S)-2-(4-ethoxyindoline-1-carbonyl)pyrrolidine-1-carboxylate (0.53 g, 1.47 mmol). This material was used directly for the next step without further purification. LCMS: Method C, 2.485 min, MS: ES+ 361.29.

Step b. To a solution of tert-butyl (S)-2-(4-ethoxyindoline-1-carbonyl)pyrrolidine-1-carboxylate (0.50 g, 1.30 mmol) in DCM (2 ml) was added TFA (2 ml) at rt. The reaction mixture was stirred at rt for 1 h. The resulting reaction mixture was concentrated under reduced pressure yielding (S)-4-ethoxy-1-prolylindoline TFA salt (0.42 g, 1.12 mmol). This material was used directly for the next step without further purification. LCMS: Method C, 1.733 min, MS: ES+ 261.26.

Step c. To a solution of (S)-4-ethoxy-1-prolylindoline TFA salt (0.40 g, 1.06 mmol) in THF (15 ml) was added K₂CO₃ (0.88 g, 6.40 mmol) at 0° C. Cyanogen bromide (0.13 g, 1.28 mmol) was added to the reaction mixture at 0° C. The reaction mixture was stirred at rt for 1 h. The resulting reaction mixture was filtered off and the filtrate was concentrated under reduced pressure. The residue was purified by column chromatography (42% EtOAc in hexane) yielding the title compound (0.16 g, 0.56 mmol). LCMS: Method J, 3.727 min, MS: ES+ 286.5.

Compounds in Table 1 were synthesised using a procedure similar to that described for Example 1.

TABLE 1
| Example Number | R₁R₂N— | Name | Amine CAS Number | LCMS method | LCMS RT | MS ES+ |
|---|---|---|---|---|---|---|
| 2 |  | (S)-2-(4-isopropoxyindoline-1-carbonyl)pyrrolidine-1-carbonitrile | 1395034-52-2 | J | 4.02 | 300.32 |
| 3 |  | (S)-2-(4-phenoxyindoline-1-carbonyl)pyrrolidine-1-carbonitrile | 930790-14-0 | H | 4.77 | 333.94 |
| 4 |  | (S)-2-(5-phenoxyindoline-1-carbonyl)pyrrolidine-1-carbonitrile | 930790-08-2 | H | 4.70 | 333.94 |
| 5 |  | (S)-1-cyano-N-ethyl-N-(4-phenylthiazol-2-yl)pyrrolidine-2-carboxamide | 5039-15-6 | J | 4.57 | 327.88 |
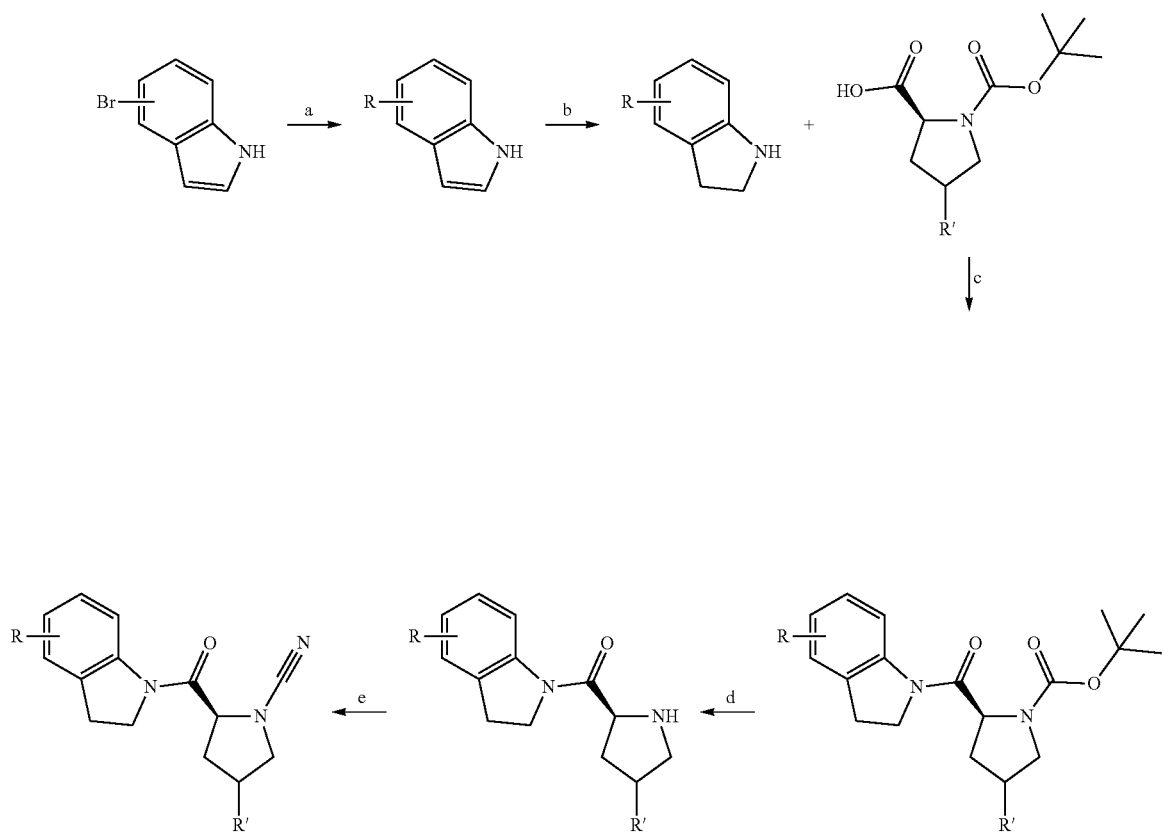
Scheme 2

Reagents and conditions: a) RB(OH)$_2$, Pd(PPh$_3$)$_4$, K$_2$CO$_3$, toluene, EtOH, water; b) AcOH, NaCNBH$_3$; c) HATU, DIPEA, THF; d) TFA, DCM, rt; e) cyanogen bromide, K$_2$CO$_3$, THF.

Example 6 (S)-2-(4-Phenylindoline-1-carbonyl)pyrrolidine-1-carbonitrile (Prepared According to Scheme 2)

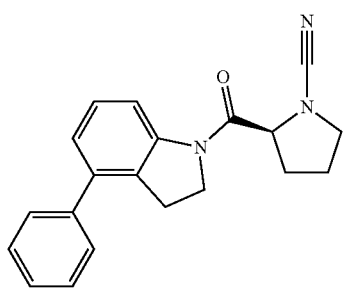 [SMILES: N#CN1CCC[C@H]1C(=O)N1CCc2c(-c3ccccc3)cccc21]

Step a. A solution of 4-bromo-1H-indole (CAS Number 52488-36-5) (0.5 g, 2.55 mmol) and phenylboronic acid (0.310 g, 2.55 mmol) in toluene (5 ml), ethanol (2.5 ml) and water (1.2 ml) was prepared in a glass vial. K$_2$CO$_3$ (1.4 g, 10.20 mmol) was added to the reaction mixture at rt. The reaction mixture was degassed for 10 min. Pd(PPh$_3$)$_4$ (0.147 g, 0.13 mmol) was added to the reaction mixture at rt. The glass vial was sealed and subjected to heating at 100° C. (external temperature) for 2 h. The resulting reaction mixture was poured into water (50 ml) and extracted with EtOAc (3×50 ml). The combined organic phase was collected, dried over Na$_2$SO$_4$, filtered and concentrated under reduced pressure. The resulting residue was purified by flash chromatography (15% EtOAc in hexane) yielding 4-phenyl-1H-indole (0.430 g, 2.22 mmol). LCMS: Method C, 2.355 min, MS: ES+194.19.

Step b. To a solution of 4-phenyl-1H-indole (0.4 g, 2.07 mmol) in acetic acid (5 ml) was added NaCNBH$_3$ (0.156 g, 2.48 mmol) portion wise at 10° C. The reaction mixture was stirred at rt for 1 h. The resulting reaction mixture was poured into ice cold aqueous 1M NaOH solution (50 ml) and extracted with EtOAc (3×50 ml). The combined organic phase was dried over Na$_2$SO$_4$, filtered and concentrated under reduced pressure. The resulting residue was purified by flash chromatography (20% EtOAc in hexane) yielding 4-phenylindoline (0.280 g, 1.43 mmol). LCMS: Method C, 1.689 min, MS: ES+ 196.40.

Step c. To a solution of 4-phenylindoline (0.250 g, 1.28 mmol) in DMF (5 ml) was added BOC-L-proline (0.275 g, 1.28 mmol) at rt. HATU (0.974 g, 2.56 mmol) and DIPEA (0.5 ml, 2.56 mmol) were added to the reaction mixture rt. The reaction mixture was stirred at rt for 16 h. The resulting reaction mixture was poured into water (50 ml) and extracted with EtOAc (3×30 ml). The combined organic phase was collected, dried over Na$_2$SO$_4$, filtered and concentrated under reduced pressure. The resulting residue was purified by flash chromatography (25% EtOAc in hexane) yielding tert-butyl (S)-2-(4-phenylindoline-1-carbonyl)pyrrolidine-1-carboxylate (0.290 g, 0.74 mmol). LCMS: Method C, 2.509 min, MS: ES+ 393.33.

Step d. To a solution of (S)-2-(4-phenylindoline-1-carbonyl)pyrrolidine-1-carboxylate (0.25 g, 0.63 mmol) in DCM (5 ml) was added TFA (0.15 ml) at 0° C. The reaction mixture was stirred at rt for 2 h. The resulting reaction mixture was concentrated under reduced pressure. The resulting residue was triturated with DCM (2×5 ml) yielding (S)-4-phenyl-1-prolylindoline TFA salt (0.185 g). This material was used directly for the next step without further purification.

Step e. To a solution of (S)-4-phenyl-1-prolylindoline TFA salt (0.18 g, 0.62 mmol) in THF (3 ml) was added K$_2$CO$_3$ (0.255 g, 1.85 mmol) at 0° C. The reaction stirred at 0° C. for 5 min. Cyanogen bromide (0.065 g, 0.61 mmol) was added to the reaction mixture at 0° C. The reaction mixture was stirred at rt for 1 h. The resulting reaction mixture was poured into water (50 ml) and extracted with EtOAc (3×30 ml). The combined organic phase was collected, dried over Na$_2$SO$_4$, filtered and concentrated under reduced pressure. The resulting residue was purified by flash chromatography (20% EtOAc in hexane) yielding the title compound (0.070 g, 0.22 mmol). LCMS: Method C, 2.135 min, MS: ES+ 318.60.

Compounds in Table 2 were synthesised using a procedure similar to that described for Example 6.

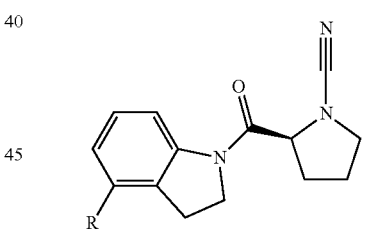

TABLE 2

| Example Number | R— | Name | Boronic Acid CAS Number | LCMS method | LCMS RT | MS ES+ |
|---|---|---|---|---|---|---|
| 7 | (3,5-dimethylisoxazol-4-yl) | (S)-2-(5-(3,5-dimethylisoxazol-4-yl)indoline-1-carbonyl)pyrrolidine-1-carbonitrile | 16114-47-9 | J | 3.50 | 337.31 |
| 8 | (3-methoxyphenyl) | (S)-2-(4-(3-methoxyphenyl)indoline-1-carbonyl)pyrrolidine-1-carbonitrile | 10365-98-7 | H | 4.64 | 347.94 |

TABLE 2-continued

| Example Number | R— | Name | Boronic Acid CAS Number | LCMS method | LCMS RT | MS ES+ |
|---|---|---|---|---|---|---|
| 9 | 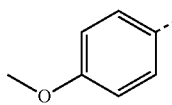 | (S)-2-(4-(4-methoxyphenyl)indoline-1-carbonyl)pyrrolidine-1-carbonitrile | 5720-07-0 | H | 4.61 | 347.94 |
| 10 | 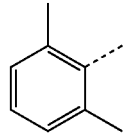 | (S)-2-(4-(2,6-dimethylphenyl)indoline-1-carbonyl)pyrrolidine-1-carbonitrile | 100379-00-8 | H | 5.18 | 346.03 |
| 11 | 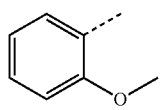 | (S)-2-(4-(2-methoxyphenyl)indoline-1-carbonyl)pyrrolidine-1-carbonitrile | 5720-06-9 | H | 4.68 | 348.01 |
| 12 | 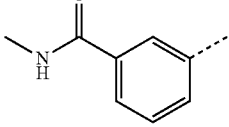 | 3-(1-(cyano-L-prolyl)indolin-4-yl)-N-methylbenzamide | 832695-88-2 | H | 3.60 | 374.99 |
| 13 |  | (S)-2-(4-cyclopropylindoline-1-carbonyl)pyrrolidine-1-carbonitrile | 411235-57-9 | J | 3.90 | 283.21 |
| 112 | 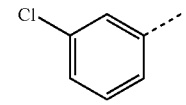 | (S)-2-(4-(3-chlorophenyl)indoline-1-carbonyl)pyrrolidine-1-carbonitrile | 63503-60-6 | J | 4.75 | 352.62 |

Compounds in Table 3 were synthesised using a procedure similar to that described for Example 6 using phenylboronic acid in step c.

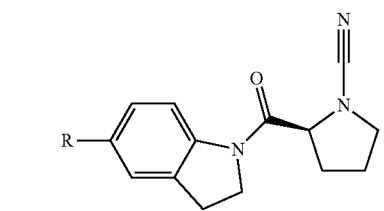

TABLE 3

| Example Number | Name | Step c starting material | LCMS method | LCMS RT | MS ES+ |
|---|---|---|---|---|---|
| 14 | (2S,4S)-4-methoxy-2-(4-phenylindoline-1-carbonyl)-pyrrolidine-1-carbonitrile | (2S,4S)-1-tert-Butoxycarbonyl-4-methoxy-pyrrolidine-2-carboxylic acid (CAS Number 83623-93-2) | J | 4.30 | 348 |
| 15 | (2S,4R)-4-methoxy-2-(4-phenylindoline-1-carbonyl)-pyrrolidine-1-carbonitrile | (2S,4R)-1-(tert-butoxy-carbonyl)-4-methoxy-pyrrolidine-2-carboxylic acid (prepared according to Bioorganic and Medicinal Chemistry 14 (2006) 2725-2746) | J | 4.16 | 348 |

Compounds in Table 4 were synthesised using a procedure similar to that described for Example 6 using 5-bromoindole in step a.

TABLE 4
| Example Number | R- | Name | Boronic Acid/Ester CAS Number | LCMS method | LCMS RT | MS ES+ |
|---|---|---|---|---|---|---|
| 16 | 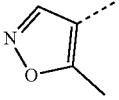 | (S)-2-(5-(5-methylisoxazol-4-yl)indoline-1-carbonyl)pyrroldine-1-carbonitrile | 1346808-41-0 | H | 3.86 | 323.03 |
| 17 | 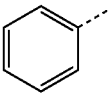 | (S)-2-(5-phenylindoline-1-carbonyl)pyrrolidine-1-carbonitrile | 98-80-6 | J | 4.23 | 318.21 |
| 18 | 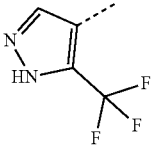 | (S)-2-(5-(5-(trifluoromethyl)-1H-pyrazol-4-yl)indoline-1-carbonyl)pyrrolidine-1-carbonitrile | 1218790-40-9 | H | 3.74 | 375.99 |
Scheme 3
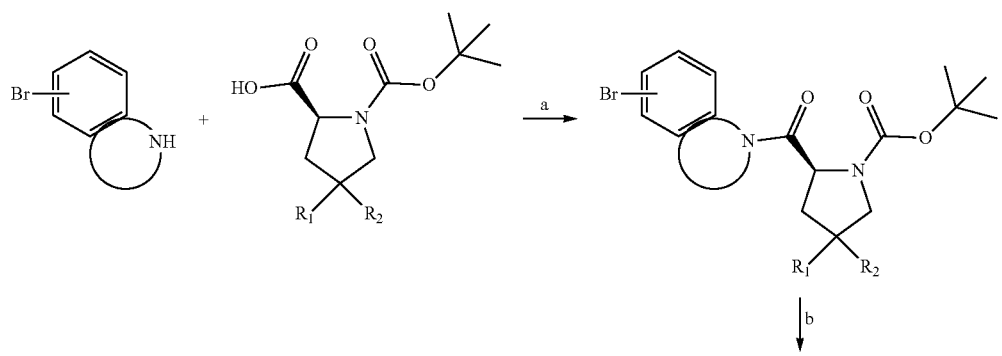
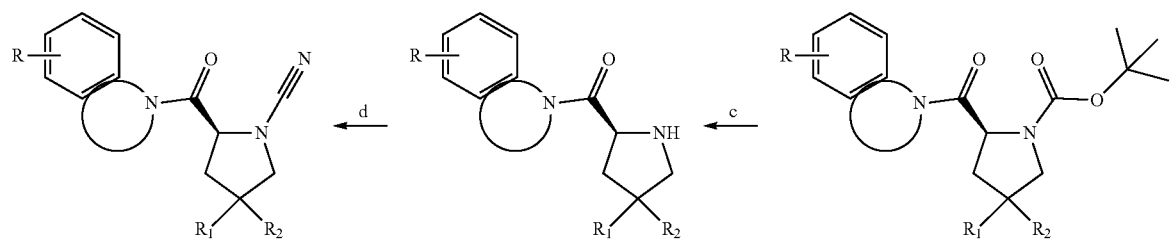

Reagents and conditions: a) HATU, DIPEA, THF; b) RB(OH)$_2$, Pd(dppf)Cl$_2$, NaHCO$_3$, DMF, water; c) TFA, DCM, rt; d) cyanogen bromide, K$_2$CO$_3$, THF.

Example 19 (S)-2-(4-(5-(Trifluoromethyl)-1H-pyrazol-4-yl)indoline-1-carbonyl)pyrrolidine-1-carbonitrile (Prepared According to Scheme 3)

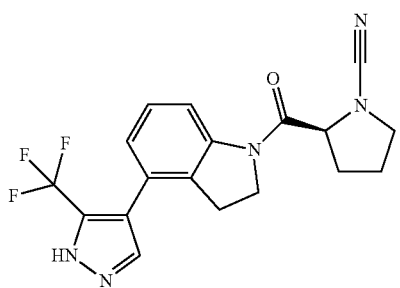 [SMILES: N#CN1CCC[C@H]1C(=O)N1CCc2c(-c3cn[nH]c3C(F)(F)F)cccc21]

Step a. Tert-butyl (S)-2-(4-bromoindoline-1-carbonyl)pyrrolidine-1-carboxylate was prepared according to the method described for Intermediate B.

Step b. A solution of Intermediate B (1.0 g, 2.53 mmol), 4-(4,4,5,5-tetramethyl-1,3,2-dioxaborolan-2-yl)-5-(trifluoromethyl)-1H-pyrazole (CAS Number 1218790-40-9) (0.66 g, 2.53 mmol) and NaHCO$_3$ (0.43 g, 5.06 mmol) in DMF: water (9:1, 15 ml) was stirred at rt in a microwave tube. The reaction mixture and degassed for 15 min. Pd(dppf)Cl$_2$ (0.19 g, 0.25 mmol) was added and the reaction mixture was heated at 110° C. for 1.5 h in microwave. The resulting reaction mixture was combined with 14 other batches prepared on the same scale by an identical method, then poured into water (500 ml). The resulting mixture was extracted with EtOAc (3×250 ml). The combined organic phase was washed with brine solution (200 ml), dried over Na$_2$SO$_4$, filtered and concentrated under reduced pressure. The resulting residue was purified by column chromatography (50% EtOAc in hexane). The material obtained from chromatographic purification was azeotropically distilled with a mixture of hexane:diethyl ether (1:1, 200 ml) yielding tert-butyl (S)-2-(4-(5-(trifluoromethyl)-1H-pyrazol-4-yl)indoline-1-carbonyl)pyrrolidine-1-carboxylate (12.0 g, 26.6 mmol). LCMS: Method C, 2.254 min, MS: ES+ 451.6.

Step c. To a solution of tert-butyl (S)-2-(4-(5-(trifluoromethyl)-1H-pyrazol-4-yl)indoline-1-carbonyl)pyrrolidine-1-carboxylate (3.0 g, 6.66 mmol) in DCM (45 ml) was added TFA (6 ml) at rt. The reaction mixture was stirred at rt for 1 h. The resulting reaction mixture was combined with 3 other batches prepared on the same scale by an identical method, then concentrated under reduced pressure. The obtained residue was triturated with diethyl ether (2×50 ml) yielding (S)-1-prolyl-4-(5-(trifluoromethyl)-1H-pyrazol-4-yl)indoline TFA salt (12.0 g, 25.86 mmol). LCMS: Method C, 1.718 min, MS: ES+ 351. This material was used directly for the next step without further purification.

Step d. To a solution of (S)-1-prolyl-4-(5-(trifluoromethyl)-1H-pyrazol-4-yl)indoline TFA salt (3.0 g, 6.46 mmol) in THF (30 ml) was added K$_2$CO$_3$ (1.96 g, 14.22 mmol) at 0° C. Cyanogen bromide (0.68 g, 6.46 mmol) was added to the reaction mixture at 0° C. The reaction mixture was stirred at rt for 30 min. The resulting reaction mixture was combined with 3 other batches prepared on the same scale by an identical method, then poured into water (250 ml). The resulting mixture was extracted with EtOAc (2×200 ml). The combined organic phase was collected, washed with brine (200 ml), dried over Na$_2$SO$_4$, filtered and concentrated under reduced pressure. The resulting residue was purified by column chromatography (4% MeOH in DCM) yielding the title compound (5.559 g, 14.82 mmol). LCMS: Method H, 3.815 min, MS: ES+ 375.92; $^1$H NMR (400 MHz, DMSO-d6) δ ppm 13.82 (br s, 1 H), 8.16 (s, 1H), 8.12 (d, J=8 Hz, 1H), 7.26 (t, J=8 Hz, 1H), 6.97 (d, J=7.6 Hz, 1H), 4.71-4.74 (m, 1H), 4.24-4.31 (m, 1H), 3.99-4.06 (m, 1H), 3.48-3.57 (m, 2H), 2.98-3.13 (m, 2H), 2.26-2.33 (m, 1H), 1.87-2.02 (m, 3H).

Example 20 (S)-2-(4-(1H-Pyrazol-4-yl)indoline-1-carbonyl)pyrrolidine-1-carbonitrile (Prepared According to Scheme 3)

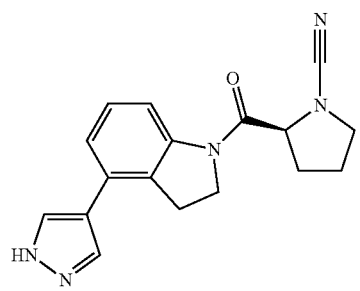 [SMILES: N#CN1CCC[C@H]1C(=O)N1CCc2c(-c3cn[nH]c3)cccc21]

Step a. Tert-butyl (S)-2-(4-bromoindoline-1-carbonyl)pyrrolidine-1-carboxylate was prepared according to the method described for Intermediate B.

Step b. A solution of Intermediate B (1.0 g, 2.53 mmol), 4-(4,4,5,5-tetramethyl-1,3,2-dioxaborolan-2-yl)-1H-pyrazole (CAS Number 269410-08-4) (0.74 g, 3.79 mmol) and NaHCO$_3$ (0.85 g, 10.12 mmol) in DMF:water (8:2, 15 ml) was stirred at rt in a microwave tube. The reaction mixture and degassed for 15 min. Pd(dppf)Cl$_2$.DCM complex (0.21 g, 0.25 mmol) was added and the reaction mixture was heated at 160° C. for 2 h in a microwave. The resulting reaction mixture was cooled to rt and poured into water (50 ml). The obtained mixture was extracted with EtOAc (3×75 ml). The combined organic layer was collected and mixed with similar organic layers obtained from 19 other batches prepared on the same scale by an identical method. The combined organic phase was dried over Na$_2$SO$_4$, filtered and concentrated under reduced pressure. The resulting residue was purified by column chromatography (70% EtOAc in hexane) yielding tert-butyl (S)-2-(4-(1H-pyrazol-4-yl)indoline-1-carbonyl)pyrrolidine-1-carboxylate (7.8 g, 20.4 mmol). LCMS: Method C, 1.998 min, MS: ES+ 383.6; $^1$H NMR (400 MHz, DMSO-d6) δ ppm 12.91-13.13 (br s, 1H), 7.82-8.14 (m, 3H), 7.15-7.27 (m, 2H), 4.49-4.57 (m, 1H), 4.16-4.33 (m, 2H), 3.25-3.44 (m, 4H), 2.22-2.32 (m, 1H), 1.80-1.99 (m, 3H), 1.24-1.40 (m, 9H).

Step c. To a solution of tert-butyl (S)-2-(4-(1H-pyrazol-4-yl)indoline-1-carbonyl)pyrrolidine-1-carboxylate (2.5 g, 6.54 mmol) in DCM (50 ml) was added TFA (7 ml) at rt. The reaction mixture was stirred at rt for 2 h. The resulting reaction mixture was combined with 2 other batches prepared on the same scale by an identical method, then concentrated under reduced pressure. The obtained residue was triturated with diethyl ether (2×100 ml) yielding (S)-1-prolyl-4-(1H-pyrazol-4-yl)indoline TFA salt (10.6 g).

LCMS: Method C, 1.549 min, MS: ES+ 283.42. This material was used directly for the next step without further purification.

Step d. A solution of (S)-1-prolyl-4-(1H-pyrazol-4-yl)indoline TFA salt (3.5 g, 8.83 mmol) and K$_2$CO$_3$ (3.6 g, 26.51 mmol) in THF (60 ml) was stirred at rt for 5 min. Cyanogen bromide (1.4 g, 13.25 mmol) was added to the reaction mixture at rt. The reaction mixture was stirred at rt for 30 min. The resulting reaction mixture was combined with 2 other batches prepared on the same scale by an identical method, then poured into water (250 ml). The resulting mixture was extracted with EtOAc (3×300 ml). The organic phase was collected and dried over Na$_2$SO$_4$, filtered and concentrated under reduced pressure. The resulting residue was purified by flash chromatography (1.5-2% MeOH in DCM) yielding the title compound (4.39 g, 14.29 mmol). LCMS: Method J, 3.164 min, MS: ES+308.42; $^1$H NMR (400 MHz, DMSO-d6) δ ppm 13.08 (br s, 1H), 8.10 (s, 1H), 8.0 (d, J=7.6 Hz, 1H), 7.88 (s, 1H), 7.30 (d, J=8 Hz, 1H), 7.21 (t, J=7.6 Hz, 1H), 4.73-4.76 (m, 1H), 4.29-4.35 (m, 1H), 4.04-4.14 (m, 1H), 3.48-3.57 (m, 2H), 3.27-3.30 (m, 2H), 2.28-2.37 (m, 1H), 1.87-1.98 (m, 3H).

Example 21 (S)-2-(4-(5-Methyl-1H-pyrazol-4-yl)indoline-1-carbonyl)pyrrolidine-1-carbonitrile (Prepared According to Scheme 3)

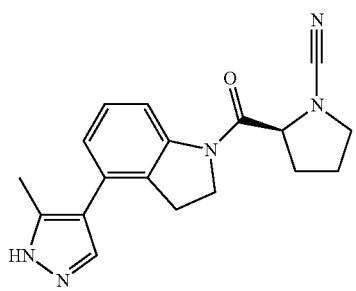 [SMILES: Cc1[nH]ncc1-c1cccc2c1CCN2C(=O)[C@@H]1CCCN1C#N]

Step a. Tert-butyl (S)-2-(4-bromoindoline-1-carbonyl)pyrrolidine-1-carboxylate was prepared according to the method described for Intermediate B.

Step b. A solution of Intermediate B (1.0 g, 2.53 mmol), 3-methylpyrazole-4-boronic acid, pinacol ester (CAS Number 936250-20-3) (0.63 g, 3.03 mmol) and NaHCO$_3$ (0.63 g, 7.5 mmol) in DMF:water (8:2, 15 ml) was stirred at rt in a microwave tube. The reaction mixture and degassed for 15 min. Pd(dppf)Cl$_2$ (0.19 g, 0.25 mmol) was added and the reaction mixture was heated at 120° C. for 1.5 h in microwave. The resulting reaction mixture was combined with 22 other batches prepared on the same scale by an identical method, then poured into water (500 ml). The resulting mixture was extracted with EtOAc (3×500 ml). The combined organic phase was dried over Na$_2$SO$_4$, filtered and concentrated under reduced pressure. The resulting residue was purified by flash chromatography (70% EtOAc in hexane) yielding tert-butyl (S)-2-(4-(5-methyl-1H-pyrazol-4-yl)indoline-1-carbonyl)pyrrolidine-1-carboxylate (11.1 g, 28.01 mmol). LCMS: Method C, 2.033 min, MS: ES+397.6.

Step c. To a solution of tert-butyl (S)-2-(4-(5-methyl-1H-pyrazol-4-yl)indoline-1-carbonyl)pyrrolidine-1-carboxylate (2.75 g, 6.94 mmol) in DCM (60 ml) was added TFA (8 ml) at rt. The reaction mixture was stirred at rt for 2 h, then combined with the reaction mixture of 3 other batches prepared on the same scale by an identical method, and concentrated under reduced pressure. The obtained residue was triturated with diethyl ether (2×100 ml) yielding (S)-4-(5-methyl-1H-pyrazol-4-yl)-1-prolylindoline TFA salt (12 g). LCMS: Method C, 1.472 min, MS: ES+ 297.29. This material was used directly for the next step without further purification.

Step d. To a solution of (S)-4-(5-methyl-1H-pyrazol-4-yl)-1-prolylindoline TFA salt (3.0 g, 7.3 mmol) in THF (45 ml) was added K$_2$CO$_3$ (3.03 g, 21.9 mmol) at rt. Cyanogen bromide (1.15 g, 10.96 mmol) was added to the reaction mixture at rt. The reaction mixture was stirred at rt for 30 min, then combined with the reaction mixture of 3 other batches prepared on the same scale by an identical method, and poured into water (250 ml) and extracted with EtOAc (3×250 ml). The organic phase was collected and dried over Na$_2$SO$_4$, filtered and concentrated under reduced pressure. The resulting residue was purified by flash chromatography (80% EtOAc in hexane) yielding the title compound (4.614 g, 14.37 mmol). LCMS: Method J, 3.244 min, MS: ES+ 322.50; $^1$H NMR (400 MHz, DMSO-d6) δ ppm 12.48 (br s, 1H), 8.03 (s, 1H), 7.55-7.65 (m, 1H), 7.22 (t, J=7.6 Hz, 1H), 6.99 (d, J=7.2, 1H), 4.69-4.72 (m, 1H), 4.21-4.28 (m, 1H), 4.03-4.10 (m, 1H), 3.48-3.59 (m, 2H), 3.10-3.17 (m, 2H), 2.29-2.38 (m, 1H), 2.24 (s, 3H), 1.94-2.03 (m, 3H).

Compounds in Table 5 were synthesised using a procedure similar to that described for Example 19.

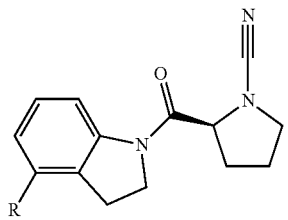

TABLE 5

| Example Number | R- | Name | Boronic Acid/Ester CAS Number | LCMS method | LCMS RT | MS ES+ |
|---|---|---|---|---|---|---|
| 22 | ![4-cyanophenyl] | (S)-2-(4-(4-cyanophenyl)indoline-1-carbonyl)pyrrolidine-1-carbonitrile | 126747-14-6 | J | 3.96 | 343.19 |

TABLE 5-continued

| Example Number | R- | Name | Boronic Acid/ Ester CAS Number | LCMS method | LCMS RT | MS ES+ |
|---|---|---|---|---|---|---|
| 23 | | (S)-2-(4-(3-cyanophenyl)indoline-1-carbonyl)pyrrolidine-1-carbonitrile | 150255-96-2 | J | 3.94 | 343.17 |
| 24 | | (S)-2-(4-(2-cyanophenyl)indoline-1-carbonyl)pyrrolidine-1-carbonitrile | 138642-62-3 | J | 3.85 | 343.22 |
| 25 | | (S)-2-(4-(3,5-dimethyl-1H-pyrazol-4-yl)indoline-1-carbonyl)pyrrolidine-1-carbonitrile | 857530-80-4 | J | 3.103/ 3.165 | 336.27/ 336.34 |
| 26 | | (S)-2-(4-(1H-pyrazol-3-yl)indoline-1-carbonyl)pyrrolidine-1-carbonitrile | 844501-71-9 | H | 3.34 | 308 |
| 27 | | (S)-2-(4-(1H-pyrrolo[2,3-b]pyridin-3-yl)indoline-1-carbonyl)pyrrolidine-1-carbonitrile | 942070-47-5 | H | 3.68 | 358.09 |

Compounds in Table 6 were synthesised using a procedure similar to that described for Example 19.

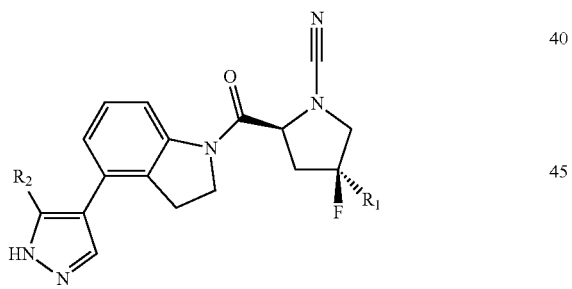

TABLE 6

| Example Number | R1 | R2 | Name | Fluoro pyrrolidine/ boronic ester CAS Number | LCMS method | LCMS RT | MS ES+ |
|---|---|---|---|---|---|---|---|
| 28 | F | $CF_3$ | (S)-4,4-difluoro-2-(4-(5-(trifluoromethyl)-1H-pyrazol-4-yl)indoline-1-carbonyl)pyrroldine-1-carbonitrile | 203866-15-3/ 1218790-40-9 | C | 2.12 | 412.70 |
| 29 | H | $CF_3$ | (2S,4S)-4-fluoro-2-(4-(5-(trifluoromethyl)-1H-pyrazol-4-yl)indoline-1-carbonyl)pyrrolidine-1-carbonitrile | 203866-13-1/ 1218790-40-9 | H | 3.70 | 393.89 |

TABLE 6-continued

| Example Number | R1 | R2 | Name | Fluoro pyrrolidine/ boronic ester CAS Number | LCMS method | LCMS RT | MS ES+ |
|---|---|---|---|---|---|---|---|
| 30 | F | CH$_3$ | (S)-4,4-difluoro-2-(4-(5-methyl-1H-pyrazol-4-yl)indoline-1-carbonyl)pyrrolidine-1-carbonitrile | 203866-15-3/ 936250-20-3 | H | 3.63 | 358.03 |

Compounds in Table 7 were synthesised using a procedure similar to that described for Example 20 using 5-bromoindoline (CAS Number 22190-33-6) in step a.

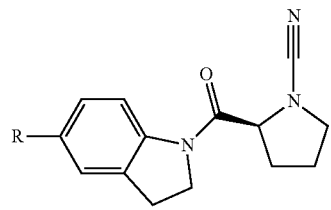

TABLE 7

| Example Number | R- | Name | Boronic Acid/Ester CAS Number | LCMS method | LCMS RT | MS ES+ |
|---|---|---|---|---|---|---|
| 31 | (1H-pyrazol-5-yl) | (S)-2-(5-(1H-pyrazol-5-yl)indoline-1-carbonyl)pyrrolidine-1-carbonitrile | 844501-71-9 | H | 3.29 | 307.93 |

Compounds in Table 8 were synthesised using a procedure similar to that described for Example 19.

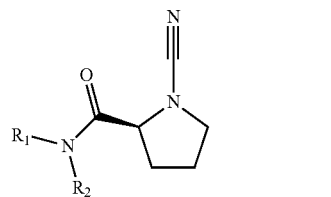

TABLE 8

| Example Number | R$_1$R$_2$N- | Name | Boronic Acid or Boronate/ Bromide CAS Number | LCMS method | LCMS RT | MS ES+ |
|---|---|---|---|---|---|---|
| 32 | 4-phenylisoindoline | (S)-2-(4-phenylisoindoline-2-carbonyl)pyrrolidine-1-carbonitrile | 98-80-6 923590-95-8 | H | 4.42 | 317.97 |

TABLE 8-continued

| Example Number | R₁R₂N- | Name | Boronic Acid or Boronate/ Bromide CAS Number | LCMS method | LCMS RT | MS ES+ |
|---|---|---|---|---|---|---|
| 33 | (phenyl-substituted isoindoline) | (S)-2-(5-phenylisoindoline-2-carbonyl)pyrrolidine-1-carbonitrile | 98-80-6 919346-89-7 | H | 4.45 | 317.97 |
| 113 | (4-cyanophenyl-substituted isoindoline) | (S)-2-(5-(4-cyano-phenyl)isoindoline-2-carbonyl)pyrrolidine-1-carbonitrile | 126747-14-6 919346-89-7 | H | 4.10 | 342.99 |
| 114 | (3-cyanophenyl-substituted isoindoline) | (S)-2-(5-(3-cyano-phenyl)isoindoline-2-carbonyl)pyrrolidine-1-carbonitrile | 150255-96-2 919346-89-7 | H | 4.18 | 342.99 |
| 115 | (3-(trifluoromethyl)-1H-pyrazol-4-yl-substituted isoindoline) | (S)-2-(5-(3-(trifluoromethyl)-1H-pyrazol-4-yl)isoindoline-2-carbonyl)pyrrolidine-1-carbonitrile | 1218790-40-9 919346-89-7 | J | 3.55 | 376.54 |
| 128 | (3-(trifluoromethoxy)phenyl-substituted isoindoline) | (S)-2-(5-(3-(trifluoromethoxy)phenyl)isoindoline-2-carbonyl)pyrrolidine-1-carbonitrile | 179113-90-7 919346-89-7 | Z | 3.03 | 402.1 |
| 129 | (3-methyl-1H-indazol-6-yl-substituted isoindoline) | (S)-2-(5-(3-methyl-1H-indazol-6-yl)isoindoline-2-carbonyl)pyrrolidine-1-carbonitrile | 1245816-26-5 919346-89-7 | X | 2.81 | 372.1 |
| 130 | (1-methyl-1H-indazol-5-yl-substituted isoindoline) | (S)-2-(5-(1-methyl-1H-indazol-5-yl)isoindoline-2-carbonyl)pyrrolidine-1-carbonitrile | 590418-08-9 919346-89-7 | X | 2.85 | 372.1 |
| 131 | (4-(methylsulfonyl)phenyl-substituted isoindoline) | (S)-2-(5-(4-(methylsulfonyl)phenyl)isoindoline-2-carbonyl)pyrrolidine-1-carbonitrile | 149104-88-1 919346-89-7 | Y | 2.35 | 396.2 |

TABLE 8-continued

| Example Number | $R_1R_2N-$ | Name | Boronic Acid or Boronate/ Bromide CAS Number | LCMS method | LCMS RT | MS ES+ |
|---|---|---|---|---|---|---|
| 132 | 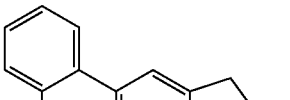 | (S)-2-(5-(2-cyanophenyl)isoindoline-2-carbonyl)pyrrolidine-1-carbonitrile | 138642-62-3 919346-89-7 | X | 2.90 | 343.2 |
| 133 | 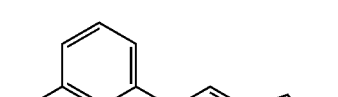 | (S)-2-(5-(3-nitrophenyl)isoindoline-2-carbonyl)pyrrolidine-1-carbonitrile | 13331-27-6 919346-89-7 | Y | 2.90 | 363.0 |
| 134 |  | (S)-2-(5-(3-cyano-2-fluorophenyl)isoindoline-2-carbonyl)pyrrolidine-1-carbonitrile | 957121-05-0 919346-89-7 | X | 2.95 | 361.1 |

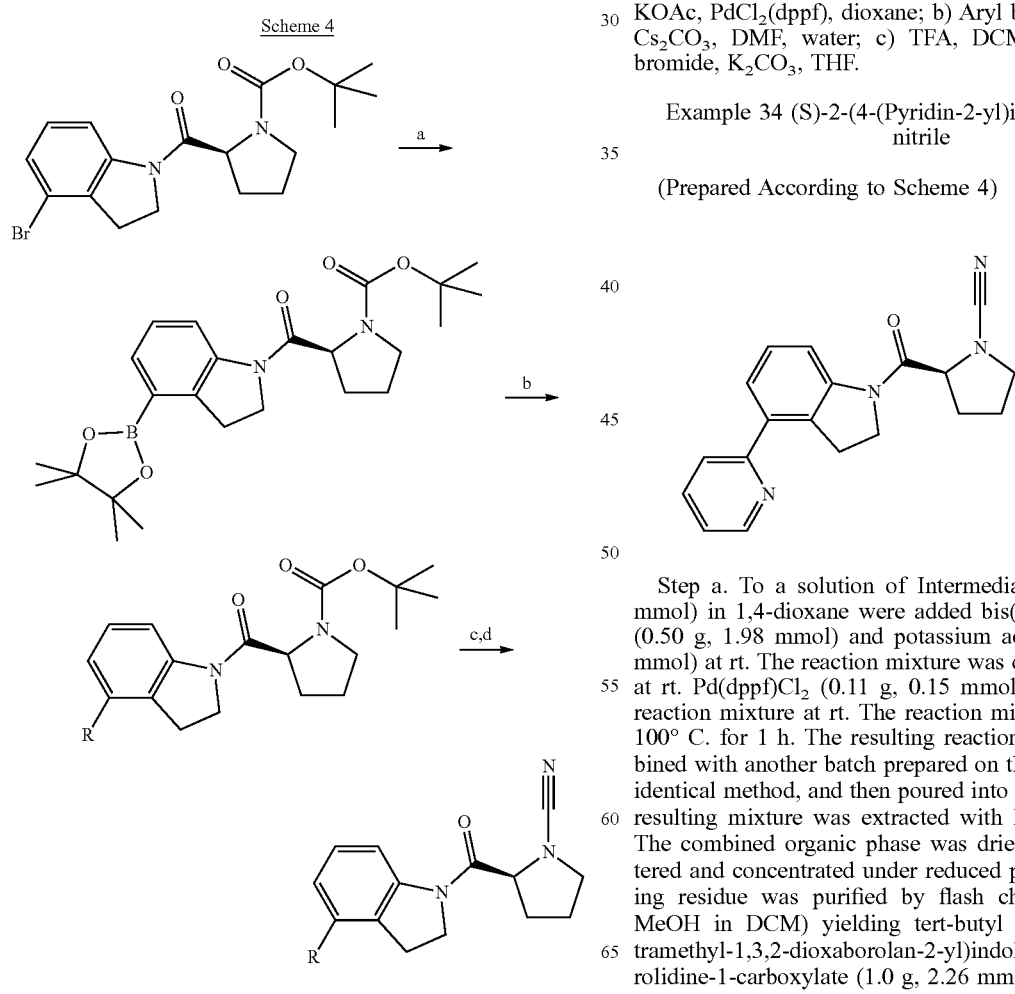

Reagents and conditions: a) Bis(pinacolato)diboron, KOAc, $PdCl_2$(dppf), dioxane; b) Aryl bromide, $Pd(PPh_3)_4$, $Cs_2CO_3$, DMF, water; c) TFA, DCM, rt; d) cyanogen bromide, $K_2CO_3$, THF.

Example 34 (S)-2-(4-(Pyridin-2-yl)indoline-1-carbonitrile (Prepared According to Scheme 4)

Step a. To a solution of Intermediate B (0.60 g, 1.52 mmol) in 1,4-dioxane were added bis(pinacolato) diboron (0.50 g, 1.98 mmol) and potassium acetate (0.44 g, 4.58 mmol) at rt. The reaction mixture was degassed for 30 min at rt. Pd(dppf)Cl$_2$ (0.11 g, 0.15 mmol) was added to the reaction mixture at rt. The reaction mixture was heated at 100° C. for 1 h. The resulting reaction mixture was combined with another batch prepared on the same scale by an identical method, and then poured into water (100 ml). The resulting mixture was extracted with EtOAc (2×100 ml). The combined organic phase was dried over $Na_2SO_4$, filtered and concentrated under reduced pressure. The resulting residue was purified by flash chromatography (5% MeOH in DCM) yielding tert-butyl (S)-2-(4-(4,4,5,5-tetramethyl-1,3,2-dioxaborolan-2-yl)indoline-1-carbonyl)pyrrolidine-1-carboxylate (1.0 g, 2.26 mmol). LCMS: Method C, 2.742 min, MS: ES+ 443.42.

Step b. To a solution of tert-butyl (S)-2-(4-(4,4,5,5-tetramethyl-1,3,2-dioxaborolan-2-yl)indoline-1-carbonyl)pyrrolidine-1-carboxylate (0.50 g, 1.13 mmol) in DMF:water (4:1, 10 ml) were added 2-bromopyridine (0.17 g, 1.13 mmol) and Cs$_2$CO$_3$ (1.10 g, 3.39 mmol) at rt. The reaction mixture was degassed for 15 min at rt. Pd(PPh$_3$)$_4$ (0.13 g, 0.11 mmol) was added to the reaction mixture at rt. The reaction mixture was heated at 100° C. for 1.5 h. The resulting reaction mixture was poured into water (200 ml) and extracted with EtOAc (4×70 ml). The combined organic phase was dried over Na$_2$SO$_4$, filtered and concentrated under reduced pressure. The resulting residue was purified by flash chromatography (51% EtOAc in hexane) yielding tert-butyl (S)-2-(4-(pyridin-2-yl)indoline-1-carbonyl)pyrrolidine-1-carboxylate (0.2 g, 0.50 mmol). LCMS: Method C, 2.222 min, MS: ES+394.45.

Steps c, d. The title compound was synthesised from the intermediate above using a procedure similar to that described for steps b, c of Example 1. LCMS: Method J, 3.263 min, MS: ES+ 319.3.

Compounds in Table 9 were synthesised using a procedure similar to that described for Example 34.

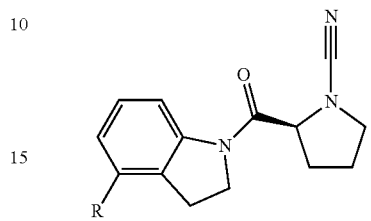

TABLE 9

| Example Number | R- | Name | Aryl halide CAS Number | LCMS method | LCMS RT | MS ES+ |
|---|---|---|---|---|---|---|
| 35 | (pyridazin-4-yl) | (S)-2-(4-(pyridazin-4-yl)indoline-1-carbonyl)pyrrolidine-1-carbonitrile | 115514-66-4 | H | 3.10 | 319.9 |
| 36 | (pyrimidin-4-yl) | (S)-2-(4-(pyrimidin-4-yl)indoline-1-carbonyl)pyrrolidine-1-carbonitrile | 17180-93-7 | H | 3.31 | 320.04 |
| 37 | (3-cyclopropyl-1H-pyrazol-4-yl) | (S)-2-(4-(3-cyclopropyl-1H-pyrazol-4-yl)indoline-1-carbonyl)pyrrolidine-1-carbonitrile | Intermediate C | J | 3.51 | 348.5 |
| 38 | (2-aminopyrimidin-4-yl) | (S)-2-(4-(2-aminopyrimidin-4-yl)indoline-1-carbonyl)pyrrolidine-1-carbonitrile | 343926-69-2 | J | 3.00 | 335.4 |
| 116 | (3-cyanopyridin-4-yl) | 4-(1-(cyano-L-prolyl)indolin-4-yl)nicotinonitrile | 154237-70-4 | H | 3.64 | 343.99 |
| 117 | (1H-pyrrolo[2,3-b]pyridin-4-yl) | (S)-2-(4-(1H-pyrrolo[2,3-b]pyridin-4-yl)indoline-1-carbonyl)pyrrolidine-1-carbonitrile | 348640-06-2 | H | 3.66 | 358.03 |
| 118 | (6-aminopyridin-2-yl) | (S)-2-(4-(6-aminopyridin-2-yl)indoline-1-carbonyl)pyrrolidine-1-carbonitrile | 19798-81-3 | C | 1.61 | 334.34 |
| 119 | (6-aminopyrazin-2-yl) | (S)-2-(4-(6-aminopyrazin-2-yl)indoline-1-carbonyl)pyrrolidine-1-carbonitrile | 33332-28-4 | C | 1.62 | 335.40 |

TABLE 9-continued

| Example Number | R- | Name | Aryl halide CAS Number | LCMS method | LCMS RT | MS ES+ |
|---|---|---|---|---|---|---|
| 120 | | (S)-2-(4-(2-(methylamino)pyrimidin-4-yl)indoline-1-carbonyl)pyrrolidine-1-carbonitrile | 22404-46-2 | C | 1.71 | 349.40 |
| 121 | | (S)-2-(4-(2-aminopyrimidin-5-yl)indoline-1-carbonyl)pyrrolidine-1-carbonitrile | 7752-82-1 | C | 1.60 | 335.50 |
| 122 | | (S)-2-(4-(1H-pyrazolo[3,4-b]pyridin-3-yl)indoline-1-carbonyl)pyrrolidine-1-carbonitrile | 68618-36-0 | C | 1.81 | 359.54 |
| 123 | | (S)-2-(4-(5H-pyrrolo[2,3-b]pyrazin-7-yl)indoline-1-carbonyl)pyrrolidine-1-carbonitrile | 56015-31-7 | C | 1.73 | 359.50 |

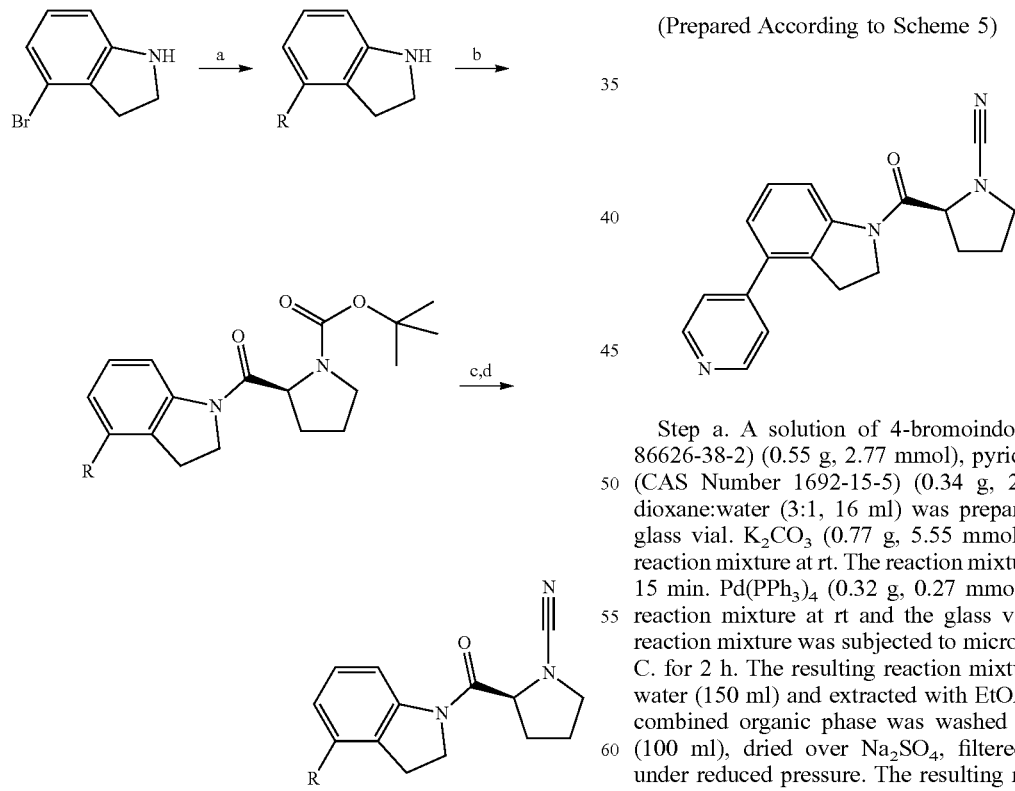

Scheme 5

Reagents and conditions: a) RB(OH)$_2$, Pd(PPh$_3$)$_4$, K$_2$CO$_3$, 1,4-dioxane, water; b) BOC-L-proline, HATU, DIPEA, THF; c) TFA, DCM, rt; d) cyanogen bromide, K$_2$CO$_3$, THF.

Example 39 (S)-2-(4-(Pyridin-4-yl)indoline-1-carbonitrile (Prepared According to Scheme 5)

Step a. A solution of 4-bromoindoline (CAS Number 86626-38-2) (0.55 g, 2.77 mmol), pyridin-4-ylboronic acid (CAS Number 1692-15-5) (0.34 g, 2.77 mmol) in 1,4-dioxane:water (3:1, 16 ml) was prepared in a microwave glass vial. K$_2$CO$_3$ (0.77 g, 5.55 mmol) was added to the reaction mixture at rt. The reaction mixture was degassed for 15 min. Pd(PPh$_3$)$_4$ (0.32 g, 0.27 mmol) was added to the reaction mixture at rt and the glass vial was sealed. The reaction mixture was subjected to microwave heating at 80° C. for 2 h. The resulting reaction mixture was poured into water (150 ml) and extracted with EtOAc (2×150 ml). The combined organic phase was washed with brine solution (100 ml), dried over Na$_2$SO$_4$, filtered and concentrated under reduced pressure. The resulting residue was purified by flash chromatography (20-55% EtOAc in hexane) yielding 4-(pyridin-4-yl)indoline (0.55 g). MS: ES+ 197.3.

Steps b, c and d. The title compound was synthesised from the intermediate above using a procedure similar to that described for steps a, b and c of Example 1. LCMS: Method H, 3.499 min, MS ES+318.97.

Compounds in Table 10 were synthesised using a procedure similar to that described for Example 39.

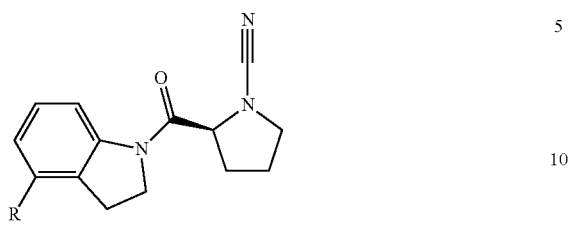

TABLE 10

| Example Number | R- | Name | Boronic Acid CAS Number | LCMS method | LCMS RT | MS ES+ |
|---|---|---|---|---|---|---|
| 40 | 5-methylisoxazol-4-yl | (S)-2-(4-(5-methylisoxazol-4-yl)indoline-1-carbonyl)pyrrolidine-1-carbonitrile | 1346808-41-0 | J | 3.70 | 323.5 |
| 41 | 3,5-dimethylisoxazol-4-yl | (S)-2-(4-(3,5-dimethylisoxazol-4-yl)indoline-1-carbonyl)pyrrolidine-1-carbonitrile | 16114-47-9 | H | 3.97 | 336.93 |
| 42 | pyridin-3-yl | (S)-2-(4-(pyridin-3-yl)indoline-1-carbonyl)pyrrolidine-1-carbonitrile | 1692-25-7 | H | 3.55 | 318.97 |

Scheme 6

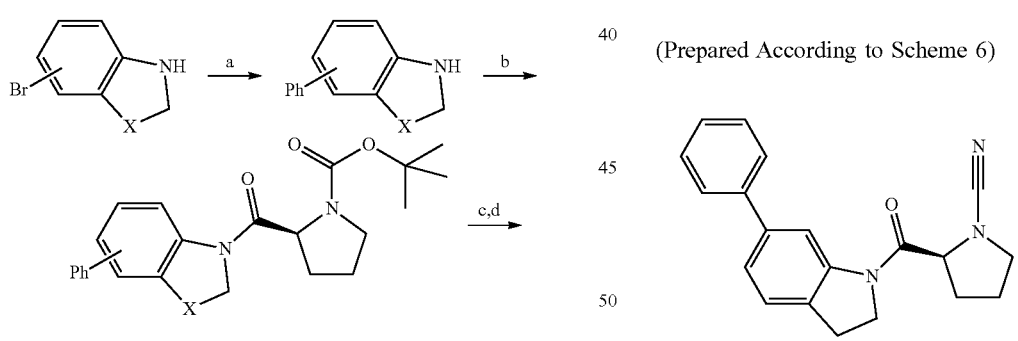

Reagents and conditions: a) PhB(OH)$_2$, Pd(dppf)Cl$_2$, NaHCO$_3$, DMF, water; b) BOC-L-proline, HATU, DIPEA, THF; c) TFA, DCM, rt; d) cyanogen bromide, K$_2$CO$_3$, THF.

Example 43 (S)-2-(6-Phenylindoline-1-carbonyl)pyrrolidine-1-carbonitrile (Prepared According to Scheme 6)

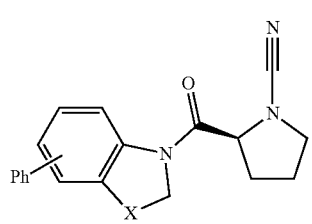

Step a. To a solution of 6-bromoindoline (CAS Number 63839-24-7) (1.0 g, 5.05 mmol) and phenylboronic acid (0.738 g, 6.06 mmol) in 1,4-dioxane (10 ml) and water (3 ml) was added K$_2$CO$_3$ (2.09 g, 15.15 mmol) at rt. The reaction mixture was degassed for 20 min. Dichlorobis(tri-o-tolylphosphine)palladium(II) (0.198 g, 0.25 mol) was added to the reaction mixture and heated at 90° C. (external temperature) for 2 h. The resulting reaction mixture was poured into water (50 ml) and extracted with EtOAc (3×50 ml). The combined organic phase was dried over Na$_2$SO$_4$, filtered and concentrated under reduced pressure. The resulting residue was purified by column chromatography (6% EtOAc in hexane) yielding 6-phenylindoline (0.63 g, 3.23 mmol). LCMS: Method C, 1.688 min, MS: ES+ 196.14.

Steps b, c and d. The title compound was synthesised from the intermediate above using a procedure similar to that described for steps a, b and c of Example 1. LCMS: Method H, 4.72 min, MS ES+318.10.

Compounds in Table 11 were synthesised using a procedure similar to that described for Example 43.

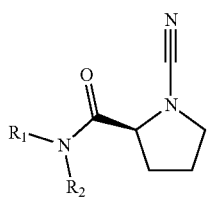

Example 46 (S)-1-Cyano-N-(4-(2-methoxyphenyl)thiazol-2-yl)-N-methylpyrrolidine-2-carboxamide (Prepared According to Scheme 7)

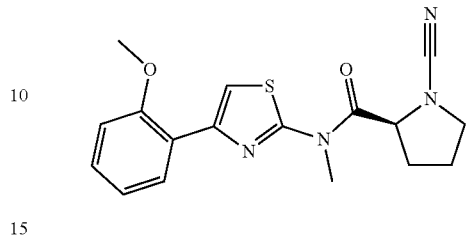

Step a. A solution of 2-bromo-1-(2-methoxyphenyl)ethan-1-one (CAS Number 31949-21-0) (0.200 g, 0.87 mmol) in

TABLE 11

| Example Number | R₁R₂N- | Name | Starting amine CAS Number | LCMS method | LCMS RT | MS ES+ |
|---|---|---|---|---|---|---|
| 44 | 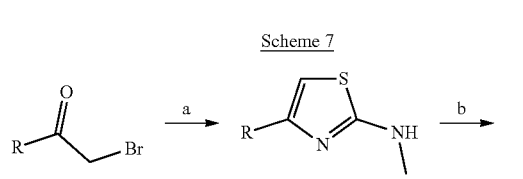 | (S)-2-(8-phenyl-3,4-dihydro-2H-benzo[b][1,4]oxazine-4-carbonyl)pyrrolidine-1-carbonitrile | 625394-65-2 | J | 4.24 | 334 |
| 45 | 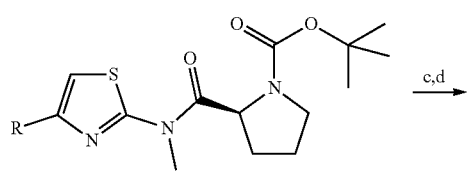 | (S)-2-(5-phenyl-1,2,3,4-tetrahydroquinoline-1-carbonyl)pyrrolidine-1-carbonitrile | 1073968-64-5 | H | 4.82 | 332.01 |

Scheme 7

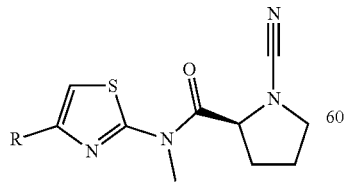

Reagents and conditions: a) N-methylthiourea, EtOH; b) BOC-L-proline, HATU, DIPEA, THF; c) TFA, DCM, rt; d) cyanogen bromide, K₂CO₃, THF.

ethanol (4 ml) was prepared in a microwave glass vial. N-Methylthiourea (0.086 g, 0.96 mmol) was added to the reaction mixture at rt. The glass vial was sealed and subjected to microwave irradiation at 80° C. for 10 min. The resulting reaction mixture was concentrated under vacuum. The obtained residue was triturated with pentane (5 ml) yielding 4-(2-methoxyphenyl)-N-methylthiazol-2-amine (0.232 g). This material was used directly for the next step without further purification. LCMS: Method C, 1.757 min, MS: ES+ 220.94.

Steps b, c and d. The title compound was synthesised from the intermediate above using a procedure similar to that described for steps a, b and c of Example 1. LCMS: Method J, 4.36 min, MS ES+342.90.

Compounds in Table 12 were synthesised using a procedure similar to that described for Example 46.

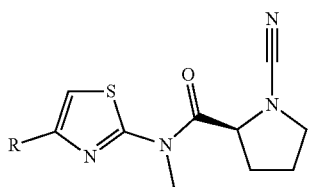

TABLE 12

| Example Number | R- | Name | α-Br ketone CAS Number | LCMS method | LCMS RT | MS ES+ |
|---|---|---|---|---|---|---|
| 47 | 3-methoxyphenyl | (S)-1-cyano-N-(4-(3-methoxyphenyl)thiazol-2-yl)-N-methylpyrrolidine-2-carboxamide | 5000-65-7 | J | 4.23 | 343.60 |
| 48 | pyridin-2-yl | (S)-1-cyano-N-methyl-N-(4-(pyridin-2-yl)thiazol-2-yl)pyrrolidine-2-carboxamide | 40086-66-6 | J | 3.03 | 313.96 |
| 49 | pyridin-3-yl | (S)-1-cyano-N-methyl-N-(4-(pyridin-3-yl)thiazol-2-yl)pyrrolidine-2-carboxamide | 17694-68-7 | J | 2.89 | 313.96 |
| 50 | pyridin-4-yl | (S)-1-cyano-N-methyl-N-(4-(pyridin-4-yl)thiazol-2-yl)pyrrolidine-2-carboxamide | 5349-17-7 | J | 2.47 | 313.93 |
| 51 | tetrahydrofuran-3-yl | (2S)-1-cyano-N-methyl-N-(4-(tetrahydrofuran-3-yl)thiazol-2-yl)pyrrolidine-2-carboxamide | 1101023-98-6 | J | 3.49 | 307.32 |
| 52 | 3-chlorophenyl | (S)-N-(4-(3-chlorophenyl)thiazol-2-yl)-1-cyano-N-methylpyrrolidine-2-carboxamide | 41011-01-2 | H | 5.20 | 346.85 |
| 53 | 2-chlorophenyl | (S)-N-(4-(2-chlorophenyl)thiazol-2-yl)-1-cyano-N-methylpyrrolidine-2-carboxamide | 5000-66-8 | H | 4.94 | 346.91 |
| 124 | 3-chloro-4-fluorophenyl | (S)-N-(4-(3-chloro-4-fluorophenyl)thiazol-2-yl)-1-cyano-N-methylpyrrolidine-2-carboxamide | 63529-30-6 | H | 5.19 | 365.01 |
| 125 | 3-(trifluoromethyl)phenyl | (S)-1-cyano-N-methyl-N-(4-(3-(trifluoromethyl)phenyl)thiazol-2-yl)pyrrolidine-2-carboxamide | 2003-10-3 | H | 5.16 | 380.98 |
| 126 | 3-cyanophenyl | (S)-1-cyano-N-(4-(3-cyanophenyl)thiazol-2-yl)-N-methylpyrrolidine-2-carboxamide | 50916-55-7 | H | 4.53 | 338.07 |
| 127 | 3-ethylphenyl | (S)-1-cyano-N-(4-(3-ethylphenyl)thiazol-2-yl)-N-methylpyrrolidine-2-carboxamide | 152074-06-1 | H | 5.02 | 340.13 |

Scheme 8

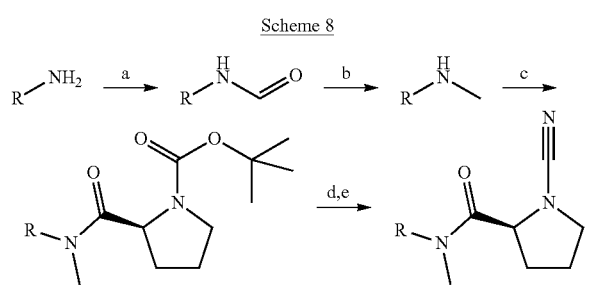

Reagents and conditions: a) Formic acid; b) LiAlH₄, THF; c) BOC-L-proline, HATU, DIPEA, THF; d) TFA, DCM, rt; e) cyanogen bromide, K₂CO₃, THF.

Example 54 (S)-1-cyano-N-methyl-N-(4-phenylthiazol-2-yl)pyrrolidine-2-carboxamide (Prepared According to Scheme 8)

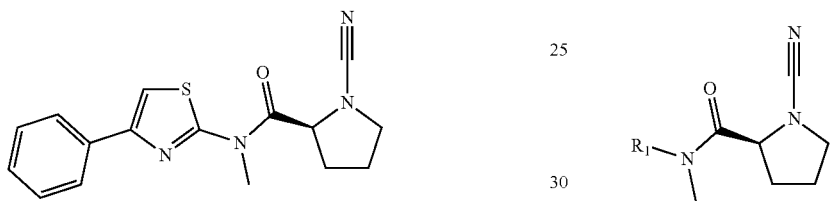

Step a. A mixture of acetic anhydride (12 ml) and formic acid (7.2 ml) was heated at 50° C. for 45 min. The resulting mixture was cooled to 0° C. 2-Amino-4-phenylthiazole (CAS Number 2010-06-2) (0.6 g, 3.41 mmol) was added to the above mixture at 0° C. The reaction mixture was stirred at rt for 2 h. The resulting reaction mixture was poured into saturated NaHCO₃ solution (20 ml) and extracted with EtOAc (3×20 ml). The combined organic phase was dried over Na₂SO₄, filtered and concentrated under reduced pressure yielding N-(4-phenylthiazol-2-yl)formamide (0.74 g). This material was used directly for the next step without further purification. LCMS: Method C, 1.917 min, MS: ES+ 204.98.

Step b. To a solution of N-(4-phenylthiazol-2-yl)formamide (0.74 g, 3.63 mmol) in THF (10 ml) was added 2 M lithium aluminium hydride in THF (5.4 ml, 10.88 mmol) dropwise at 0° C. The reaction mixture was stirred at rt for 1 h. The resulting reaction mixture was poured into cold NaHCO₃ solution (20 ml) and extracted with extracted with DCM (3×20 ml). The combined organic phase was dried over Na₂SO₄, filtered and concentrated under reduced pressure yielding N-methyl-4-phenylthiazol-2-amine (0.48 g, 2.52 mmol). This material was used directly for the next step without further purification. LCMS: Method C, 1.725 min, MS: ES+ 191.19.

Steps c, d and e. The title compound was synthesised from the intermediate above using a procedure similar to that described for steps a, b and c of Example 1. LCMS: Method H, 4.84 min, MS ES+313.1.

Compounds in Table 13 were synthesised using a procedure similar to that described for Example 54.

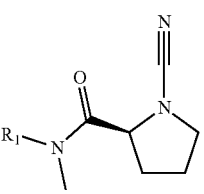

TABLE 13

| Example Number | R- | Name | Amine CAS Number | LCMS method | LCMS RT | MS ES+ |
|---|---|---|---|---|---|---|
| 55 | | (S)-1-cyano-N-methyl-N-(1-phenyl-1H-pyrazol-3-yl)pyrrolidine-2-carboxamide | 1128-56-9 | J | 3.62 | 296.39 |
| 56 | | (S)-1-cyano-N-(4-isopropylthiazol-2-yl)-N-methylpyrrolidine-2-carboxamide | 79932-20-0 | C | 2.09 | 279.23 |
| 57 | | (S)-1-cyano-N-methyl-N-(3-phenylisoxazol-5-yl)pyrrolidine-2-carboxamide | 4369-55-5 | J | 3.85 | 297.27 |

Example 58 (S)—N-(5-benzylthiazol-2-yl)-1-cyano-N-methylpyrrolidine-2-carboxamide (Prepared According to Scheme 1)

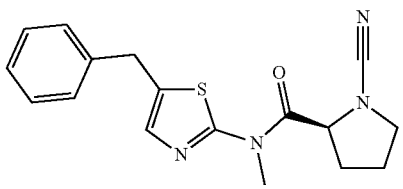 [SMILES: CN(C(=O)[C@@H]1CCCN1C#N)c1ncc(Cc2ccccc2)s1]

Step a. To a solution of BOC-L-proline (0.13 g, 1.22 mmol) in DMF (1 ml) was added HATU (0.35 g, 1.83 mmol) at rt. 5-Benzyl-N-methylthiazol-2-amine (Intermediate A, 0.125 g, 1.22 mmol) and TEA (0.51 ml, 3.67 mmol) were added to the reaction mixture at rt. The reaction mixture was stirred at rt for 5 h. The resulting reaction mixture was poured into water (20 ml) and extracted with EtOAc (3×20 ml). The combined organic phase was collected, washed with brine solution (20 ml), dried over Na$_2$SO$_4$, filtered and concentrated under reduced pressure. The resulting residue was purified by flash chromatography (50% EtOAc in hexane) yielding tert-butyl (S)-2-((5-benzylthiazol-2-yl)(methyl)carbamoyl)pyrrolidine-1-carboxylate (0.2 g, 0.49 mmol). LCMS: Method C, 2.619 min, MS: ES+ 402.21.

Step b. To a solution of tert-butyl(S)-2-((5-benzylthiazol-2-yl)(methyl)carbamoyl) pyrrolidine-1-carboxylate (0.2 g, 0.49 mmol) in DCM (3 ml) was added TFA (3.0 ml) at 0° C. The reaction mixture was stirred at rt for 1 h. The resulting reaction mixture was concentrated under reduced pressure yielding (S)—N-(5-benzylthiazol-2-yl)-N-methylpyrrolidine-2-carboxamide TFA salt (0.2 g, 0.48 mmol). This material was used directly for the next step without further purification. LCMS: Method C, 1.685 min, MS: ES+ 302.30.

Step c. To a solution of (S)—N-(5-benzylthiazol-2-yl)-N-methylpyrrolidine-2-carboxamide TFA salt (0.2 g, 0.66 mmol) in THF (4 ml) was added K$_2$CO$_3$ (0.5 g, 3.31 mmol) at 0° C. Cyanogen bromide (0.084 g, 0.79 mmol) was added to the reaction mixture at 0° C. The reaction mixture was stirred at rt for 2 h. The resulting reaction mixture was poured into water (20 ml) and extracted with EtOAc (3×20 ml). The combined organic phase was collected, dried over Na$_2$SO$_4$, filtered and concentrated under reduced pressure. The resulting residue was purified by flash chromatography (70% EtOAc in hexane) yielding the title compound (0.005 g, 0.02 mmol). LCMS: Method J, 4.090 min, MS: ES+327.22; $^1$H NMR (400 MHz, CDCl$_3$) δ ppm 7.24-7.34 (m, 6H), 4.78 (m, 1H), 4.10 (s, 2H), 3.71-3.76 (m, 4H), 3.58-3.64 (s, 1H), 2.35-2.39 (m, 1H), 2.03-2.10 (m, 3H).

Compounds in Table 14 were synthesised using a procedure similar to that described for Example 58.

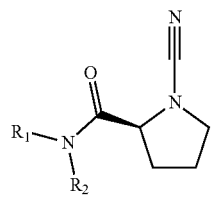

TABLE 14

| Example Number | R$_1$R$_2$N- | Name | Amine CAS Number | LCMS method | LCMS RT | MS ES+ |
|---|---|---|---|---|---|---|
| 59 | 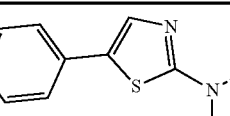 | (S)-1-cyano-N-methyl-N-(5-phenylthiazol-2-yl)pyrrolidine-2-carboxamide | 1344198-25-9 | H | 4.49 | 312.97 |
| 60 | 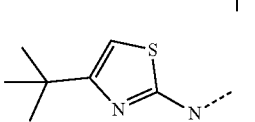 | (S)-N-(4-(tert-butyl)thiazol-2-yl)-1-cyano-N-methylpyrrolidine-2-carboxamide | 82202-31-1 | H | 5.05 | 293.05 |
| 61 | 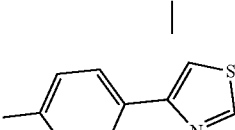 | (S)-N-(4-(4-chlorophenyl)thiazol-2-yl)-1-cyano-N-methylpyrrolidine-2-carboxamide | 21344-78-5 | X | 30.16 | 346.85 |
| 62 | 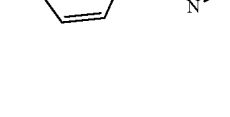 | (S)-N-(3-(2-chlorophenyl)isoxazol-5-yl)-1-cyano-N-methylpyrrolidine-2-carboxamide | 86685-91-8 (may be prepared according to Jpn. Kokai Tokkyo Koho, 59181267, 15 Oct. 1984) | H | 4.46 | 330.9 |

Compounds in Table 15 were synthesised using a procedure similar to that described for Example 1 using (2S,4S)—N—BOC-4-phenyl-pyrrolidine-2-carboxylic acid (CAS Number 96314-29-3) in step a.

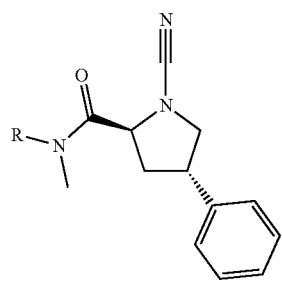

TABLE 15

| Example Number | R- | Name | Amine CAS Number | LCMS method | LCMS RT | MS ES+ |
|---|---|---|---|---|---|---|
| 63 | 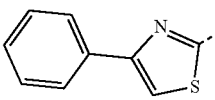 | (2S,4S)-1-cyano-N-methyl-4-phenyl-N-(4-phenylthiazol-2-yl)pyrrolidine-2-carboxamide | 2010-06-2 | H | 5.56 | 389.03 |

Scheme 9

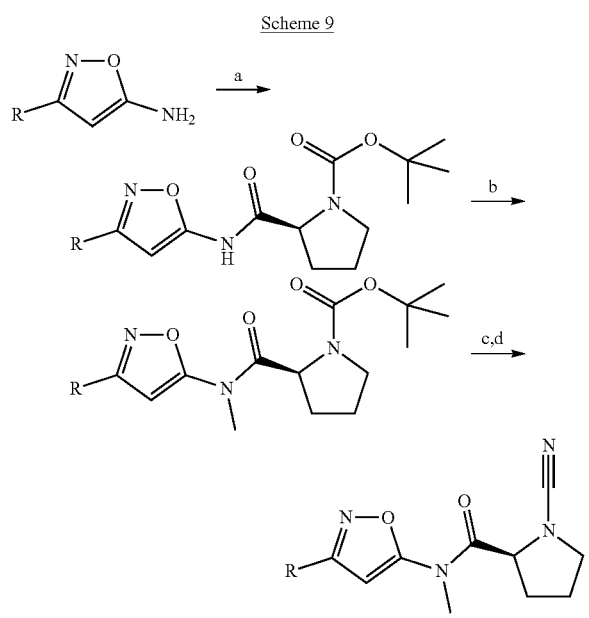

Reagents and conditions: a) BOC-L-proline, POCl$_3$, pyridine; b) NaH, MeI, DMF; c) TFA, DCM; d) cyanogen bromide, K$_2$CO$_3$, THF.

Example 64 (S)—N-(3-(3-Chlorophenyl)isoxazol-5-yl)-1-cyano-N-methylpyrrolidine-2-carboxamide (Prepared According to Scheme 9)

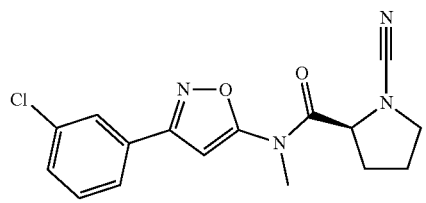 [SMILES: CN(C(=O)[C@@H]1CCCN1C#N)c1cc(-c2cccc(Cl)c2)no1]

Step a. To a solution of 3-(3-chlorophenyl)isoxazol-5-amine (CAS Number 86685-95-2) (0.127 g, 0.654 mmol) and BOC-L-proline (0.14 g, 0.654 mmol) in pyridine (3.1 ml) was added phosphorous oxychloride (0.2 g, 1.31 mmol) dropwise at −15° C. The reaction mixture was stirred at rt for 1 h. The resulting reaction mixture was poured into 10% copper sulphate solution (80 ml) and extracted with EtOAc (2×60 ml). The combined organic phase was washed with 10% citric acid solution (80 ml), saturated NaHCO$_3$ solution (80 ml), dried over Na$_2$SO$_4$, filtered and concentrated under reduced pressure yielding tert-butyl (S)-2-((3-(3-chlorophenyl)isoxazol-5-yl)carbamoyl)pyrrolidine-1-carboxylate (0.236 g, 0.60 mmol). This material was used directly for the next step without further purification. LCMS: Method C, 2.559 min, MS: ES+ 392.55.

Steps b, c and d. The title compound was synthesised from the intermediate above using a procedure similar to that described for steps a, b and c of Example 1. LCMS: Method H, 4.68 min, MS ES+330.9.

Compounds in Table 16 were synthesised using a procedure similar to that described for Example 64.

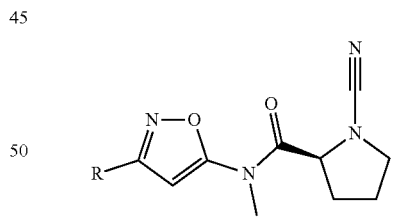

TABLE 16

| Example Number | R- | Name | Amine CAS Number | LCMS method | LCMS RT | MS ES+ |
|---|---|---|---|---|---|---|
| 65 | 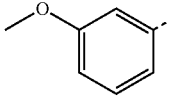 | (S)-1-cyano-N-(3-(3-methoxyphenyl)isoxazol-5-yl)-N-methylpyrrolidine-2-carboxamide | 119162-46-8 | J | 4.07 | 328.33 |

TABLE 16-continued

| Example Number | R- | Name | CAS Number | Amine LCMS method | LCMS RT | MS ES+ |
|---|---|---|---|---|---|---|
| 66 | phenyl | (S)-1-cyano-N-methyl-N-(5-phenylisoxazol-3-yl)pyrrolidine-2-carboxamide | 4369-55-5 | J | 3.99 | 297 |
| 67 | 4-methylphenyl | (S)-N-(3-(4-chlorophenyl)isoxazol-5-yl)-1-cyano-N-methylpyrrolidine-2-carboxamide | 33866-48-7 | H | 4.69 | 330.9 (+18) |

Example 68 (S)—N-(4-(4-acetamidophenyl)thiazol-2-yl)-1-cyano-N-methylpyrrolidine-2-carboxamide

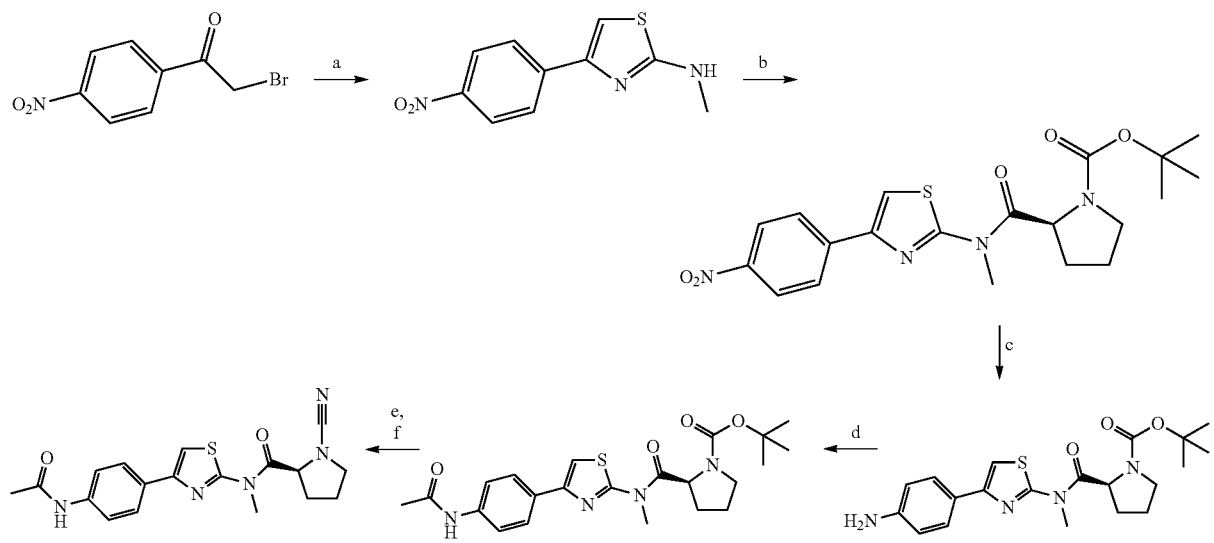

Step a. To a solution of 2-bromo-4'-nitroacetophenone (CAS Number 99-81-0) (2.0 g, 8.19 mmol) in ethanol (20 ml) was added 1-methylthiourea (0.73 g, 8.19 mmol) at rt. The reaction mixture was stirred at rt for 5 min and then heated at 70° C. for 3 h. The resulting reaction mixture was poured into water (100 ml) and extracted with EtOAc (3×100 ml). The combined organic phase was dried over Na₂SO₄, filtered and concentrated under reduced pressure. The obtained residue was triturated with diethyl ether (15 ml) yielding N-methyl-4-(4-nitrophenyl)thiazol-2-amine (1.8 g, 7.65 mmol). LCMS: Method C, 2.178 min, MS: ES+ 236.10.

Step b. To a solution of BOC-L-proline (1.97 g, 9.17 mmol) in THF (20 ml) were added HATU (4.36 g, 11.47 mmol) and DIPEA (1.97 g, 15.29 mmol) at 0° C. The reaction mixture was stirred at rt for 0.5 h. N-methyl-4-(4-nitrophenyl)thiazol-2-amine (1.8 g, 7.65 mmol) was added to the reaction mixture at rt. The reaction mixture was stirred at rt for 72 h. The resulting reaction mixture was poured into saturated NaHCO₃ solution (100 ml) and extracted with EtOAc (3×50 ml). The combined organic phase was washed with brine solution (50 ml), saturated NaHCO₃ solution (50 ml), dried over Na₂SO₄, filtered and concentrated under reduced pressure. The resulting residue was purified by flash chromatography (23% EtOAc in hexane) yielding tert-butyl (S)-2-(methyl(4-(4-nitrophenyl)thiazol-2-yl)carbamoyl)pyrrolidine-1-carboxylate (1.6 g, 3.7 mmol). LCMS: Method C, 2.613 min, MS: ES+433.46.

Step c. To a solution of tert-butyl (S)-2-(methyl(4-(4-nitrophenyl)thiazol-2-yl)carbamoyl)pyrrolidine-1-carboxylate (1.6 g, 3.7 mmol) in MeOH (20 ml) was added 10% dry Pd/C (0.6 g) at rt. The reaction mixture was purged with H₂ gas at rt for 6 h. The resulting reaction mixture was carefully filtered through celite hyflow and concentrated under reduced pressure. The obtained residue was triturated with diethyl ether (20 ml) yielding tert-butyl (S)-2-((4-(4-aminophenyl)thiazol-2-yl)(methyl)carbamoyl)pyrrolidine-1-carboxylate (1.0 g, 2.48 mmol). LCMS: Method C, 2.071 min, MS: ES+ 403.32.

Step d. To a solution of tert-butyl (S)-2-((4-(4-aminophenyl)thiazol-2-yl)(methyl)carbamoyl) pyrrolidine-1-carboxylate (0.4 g, 0.9 mmol) in THF (5 ml) was added K₂CO₃ (0.34 g, 2.48 mmol) at 0° C. Acetyl chloride (0.07 ml, 1.09 mmol) was added dropwise into the reaction mixture at 0° C. The reaction mixture was stirred at rt for 16 h. The resulting reaction mixture was poured into water (100 ml) and extracted with EtOAc (3×50 ml). The combined organic phase was collected, washed with saturated NaHCO₃ solution (100 ml), brine solution (20 ml), dried over Na₂SO₄, filtered and concentrated under reduced pressure. The resulting residue was purified by flash chromatography (53-100% EtOAc in hexane) yielding tert-butyl (S)-2-((4-(4-acetamidophenyl)thiazol-2-yl)(methyl)carbamoyl) pyrrolidine-1-carboxylate (0.36 g, 0.81 mmol). LCMS: Method J, 4.466 min, MS: ES+ 445.4.

Step e. To a solution of tert-butyl (S)-2-((4-(4-acetamidophenyl)thiazol-2-yl)(methyl)carbamoyl) pyrrolidine-1-carboxylate (0.13 g, 0.29 mmol) in DCM (2 ml) was added TFA (1 ml) at 0° C. The reaction mixture was stirred at 40° C. for 3 h. The resulting reaction mixture was concentrated under reduced pressure. The obtained residue was azeotropically distilled with DCM (2×15 ml) yielding (S)—N-(4-(4-acetamidophenyl)thiazol-2-yl)-N-methylpyrrolidine-2-carboxamide TFA salt (0.135 g, 0.29 mmol). This material was used directly for the next step without further purification.

Step f. To a solution of (S)—N-(4-(4-acetamidophenyl)thiazol-2-yl)-N-methylpyrrolidine-2-carboxamide TFA salt (0.13 g, 0.29 mmol) in THF (5 ml) was added K$_2$CO$_3$ (0.20 g, 1.4 mmol) at 0° C. Cyanogen bromide (0.037 g, 0.35 mmol) was added to the reaction mixture at 0° C. The reaction mixture was stirred at rt for 15 min. The resulting reaction mixture was poured into water (50 ml) and extracted with EtOAc (3×15 ml). The combined organic phase was collected, dried over Na$_2$SO$_4$, filtered and concentrated under reduced pressure. The resulting residue was purified by flash chromatography (85% EtOAc in hexane). The crude product obtained from flash chromatographic purification was further triturated with diethyl ether (2 ml), ethanol (2 ml), methyl tert-butyl ether (2 ml), DCM (2 ml) and finally dried. The resulting crude product was again purified by flash chromatography (2% MeOH in DCM). The product obtained from flash chromatographic purification was azeotropically distilled with ethanol (2×5 ml) yielding the title compound (0.028 g, 0.075 mmol). LCMS: Method J, 3.581 min, MS: ES+ 370.40.

Compounds in Table 17 were synthesised using a procedure similar to that described for Example 68.

Example 135 (S)-1-cyano-N-methyl-N-(4-(3-(N-methylacetamido)phenyl)thiazol-2-yl)pyrrolidine-2-carboxamide

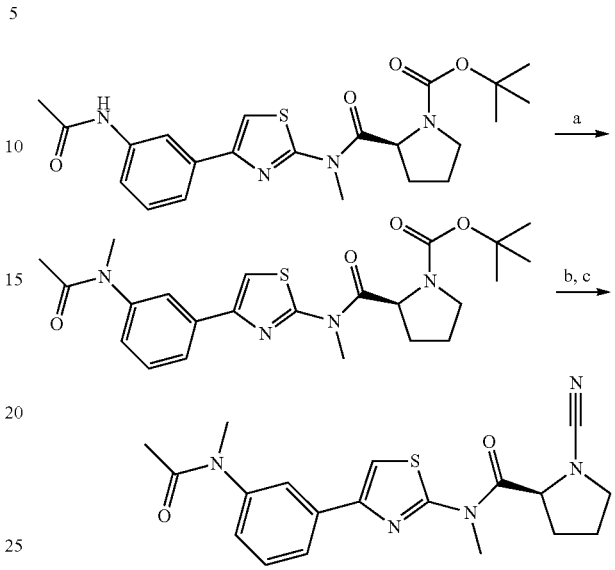

Step a. To a stirred solution of tert-butyl (S)-2-((4-(3-acetamidophenyl)thiazol-2-yl)(methyl)carbamoyl)pyrrolidine-1-carboxylate, (synthesised using a procedure similar to that described for Example 68, steps a-d) (0.35 g, 0.787 mmol) in DMF (7 ml) was added sodium hydride (60% dispersion in mineral oil) (0.047 g, 1.181 mmol) at 0° C. The reaction mixture was stirred at 0° C. for 15 min. Methyl iodide (0.13 g, 0.945 mmol) was added to the reaction mixture at 0° C. The reaction mixture was stirred at rt for 3 h. The resulting reaction mixture was diluted with saturated NaHCO$_3$ solution (50 ml) and extracted with EtOAc (3×25 ml). The combined organic phase was separated, dried over Na$_2$SO$_4$, filtered and concentrated under reduced pressure. The resulting crude material was purified by column chromatography (50% EtOAc in hexane) yielding tert-butyl (S)-2-(methyl(4-(3-(N-methylacetamido)phenyl)thiazol-2-yl)carbamoyl)pyrrolidine-1-carboxylate (0.16 g, 0.348 mmol). LCMS: Method C, 2.10 min, MS: ES+ 459.48; $^1$H NMR (400 MHz, DMSO-d6) δ ppm 7.94 (m, 1H), 7.91 (s, 1H), 7.84 (s, 1H), 7.51 (t, J=6.8 Hz, 1H), 7.30 (d, J=6.4 Hz, 1H), 4.90-4.93 (m, 1H), 3.82 (s, 3H), 3.37-3.47 (m, 2H), 3.20 (s, 3H), 2.33-2.37 (m, 1H), 1.86-1.97 (m, 3H), 1.81 (s, 3H), 1.22 (s, 9H).

Steps b, c. The title compound was synthesised from the intermediate above using a procedure similar to that

TABLE 17

| Example Number | R- | Name | Amine CAS Number | LCMS method | LCMS RT | MS ES+ |
|---|---|---|---|---|---|---|
| 69 | 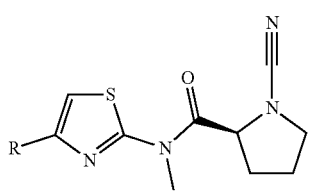 | (S)-N-(4-(3-acetamidophenyl)thiazol-2-yl)-1-cyano-N-methylpyrrolidine-2-carboxamide | 172848-45-2 | H | 3.68 | 370 | described for Example 68, steps e, f. LCMS: Method H, 3.73 min, MS: ES+ 384.07; ¹H NMR (400 MHz, DMSO-d6) δ ppm 7.88-7.94 (m, 3H), 7.52 (t, J=7.4 Hz, 1H), 7.30 (d, J=6.8 Hz, 1H), 5.14-5.17 (m, 1H), 3.77 (s, 3H), 3.53-3.58 (m, 2H), 3.20 (s, 3H), 2.38-2.45 (m, 2H), 2.02-2.09 (m, 1H), 1.91-1.97 (m, 1H), 1.77 (s, 3H).

Example 136 (S)-1-cyano-N-methyl-N-(4-(3-(N-methylmethylsulfonamido)phenyl)thiazol-2-yl)pyrrolidine-2-carboxamide

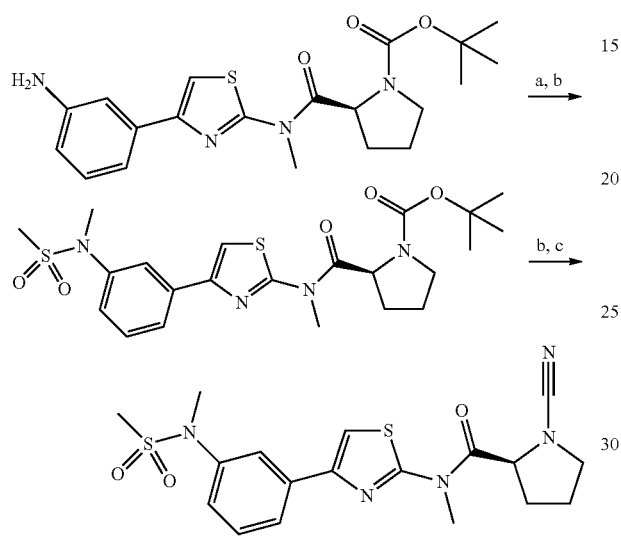

Step a. To a solution of tert-butyl (S)-2-((4-(3-aminophenyl)thiazol-2-yl)(methyl)carbamoyl) pyrrolidine-1-carboxylate (synthesised using a procedure similar to that described for Example 68, steps a-c) (0.6 g, 1.49 mmol) in pyridine (6 ml) was added methanesulfonyl chloride (0.173 ml, 2.23 mmol) at 0° C. The reaction mixture was stirred for 4 h at rt. The resulting reaction mixture was poured into cold water (100 ml) and extracted using EtOAc (50 ml×2). The organic layer was combined, dried over Na₂SO₄ and concentrated under reduced pressure to yield tert-butyl (S)-2-(methyl(4-(3-(methylsulfonamido) phenyl)thiazol-2-yl)carbamoyl) pyrrolidine-1-carboxylate (0.57 g, 1.18 mmol). LCMS: Method C, 2.073 min, MS: ES+ 481.6

Step b. To a solution of (S)-2-(methyl(4-(3-(methylsulfonamido) phenyl)thiazol-2-yl) carbamoyl) pyrrolidine-1-carboxylate (0.5 g, 1.04 mmol) in DMF (5 ml) was added K₂CO₃ (0.43 g, 3.12 mmol) at 0° C. and stirred at rt. Methyl iodide (0.22 g, 1.56 mmol) was added to the reaction mixture and stirred for 10 h at rt. The resulting reaction mixture was poured into cold water (100 ml) and extracted using EtOAc (100 ml×2). The organic layer was washed with brine (200 ml) and combined, dried over Na₂SO₄ and concentrated under reduced pressure to yield tert-butyl (S)-2-(methyl(4-(3-(N-methylmethylsulfonamido)phenyl)thiazol-2-yl)carbamoyl)-pyrrolidine-1-carboxylate (0.6 g, quantitative). LCMS: Method C, 2.55 min, MS: ES+ 495.2

Steps c, d. The title compound was synthesised from the intermediate above using a procedure similar to that described for Example 68, steps e, f. LCMS: Method H, 4.14 min, MS: ES+ 420.00; ¹H NMR (400 MHz, DMSO-d6) δ ppm 7.89-7.94 (m, 2H), 7.84 (s, 1H), 7.48 (t, J=8 Hz, 1H), 7.38-7.40 (m, 1H), 5.13-5.16 (m, 1H), 3.76 (s, 3H), 3.53-3.57 (m, 2H), 3.29 (s, 3H), 2.99 (s, 3H), 2.33-2.42 (m, 1H), 2.03-2.07 (m, 1H), 1.91-1.95 (m, 1H), 1.80-1.85 (m, 1H).

Example 70 Ethyl 4-(1-(cyano-L-prolyl)indolin-4-yl)-1-(4-methoxybenzyl)-1H-pyrazole-5-carboxylate

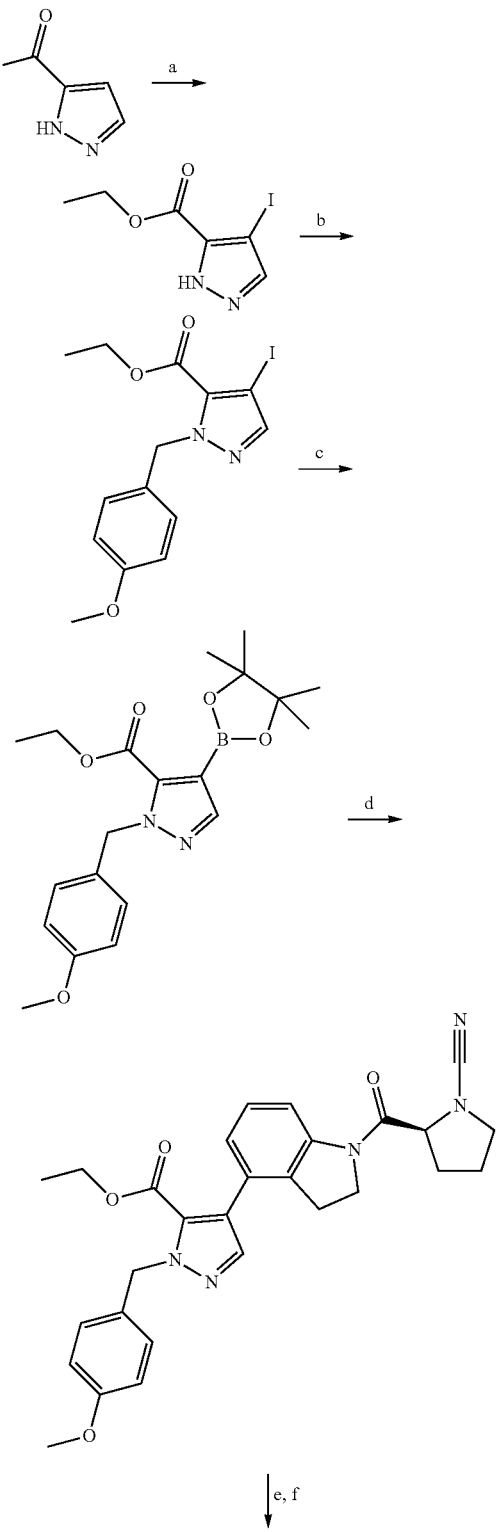

-continued

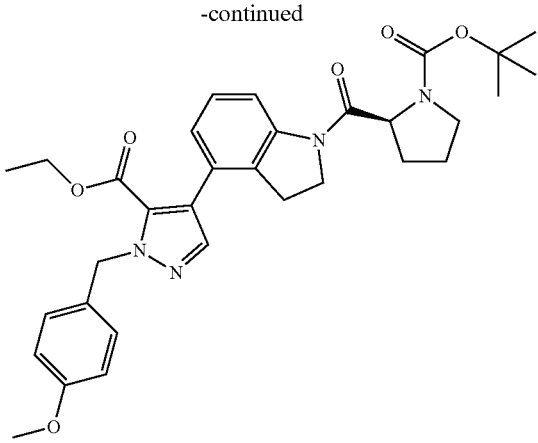

Step a. To a solution of ethyl 1H-pyrazole-5-carboxylate (CAS Number 5932-27-4) (5 g, 35.7 mmol) in MeCN (25 ml) were added N-iodosuccinimide (8.79 g, 39.24 mmol) and TFA (1.18 g, 10.35 mmol) at rt. The reaction mixture was stirred at rt for 16 h. The resulting reaction mixture was poured into water (250 ml) and extracted with EtOAc (3×150 ml). The combined organic phase was dried over $Na_2SO_4$, filtered and concentrated under reduced pressure yielding ethyl 4-iodo-1H-pyrazole-5-carboxylate (10.2 g). LCMS: Method C, 1.884 min, MS: ES+ 267.1. This material was used directly for the next step without further purification.

Step b. To a solution of 4-iodo-1H-pyrazole-5-carboxylate (10.2 g, 38.34 mmol) in MeCN (150 ml) were added $K_2CO_3$ (10.58 g, 76.69 mmol) and 4-methoxybenzyl chloride (7.35 g, 47.16 mmol) at rt. The reaction mixture was stirred at 70° C. for 4 h. The resulting reaction mixture was poured into water (500 ml) and extracted with EtOAc (3×150 ml). The combined organic phase was dried over $Na_2SO_4$, filtered and concentrated under reduced pressure. The resulting residue was purified by column chromatography (10% EtOAc in Hexane) yielding ethyl 4-iodo-1-(4-methoxybenzyl)-1H-pyrazole-5-carboxylate (7 g, 18.1 mmol) LCMS: Method C, 2.385 min, MS: ES+ 387.3.

Step c. To a solution of ethyl 4-iodo-1-(4-methoxybenzyl)-1H-pyrazole-5-carboxylate (0.5 g, 1.29 mmol) in THF (30 ml) was added 2-isopropoxy-4,4,5,5-tetramethyl-1,3,2-dioxaborolane (CAS Number 61676-62-8) (0.72 g, 3.88 mmol) at −78° C. n-Butyllithium (2.5M in hexane) (1.55 ml, 3.88 mmol) was added to the reaction mixture dropwise at −78° C. The reaction mixture was stirred at −78° C. for 1 h. The resulting reaction mixture was quenched with $NH_4Cl$ solution (200 ml) and extracted with EtOAc (3×100 ml). The combined organic phase was collected, dried over $Na_2SO_4$, filtered and concentrated under reduced pressure to yielding ethyl 1-(4-methoxybenzyl)-4-(4,4,5,5-tetramethyl-1,3,2-dioxaborolan-2-yl)-1H-pyrazole-5-carboxylate (0.58 g). This material was immediately used for the next step without further purification.

Step d. A solution of tert-butyl (S)-2-(4-bromoindoline-1-carbonyl)pyrrolidine-1-carboxylate (Intermediate B, 0.2 g, 0.51 mmol) in DMF (4 ml) and water (1 ml) was prepared in a microwave glass vial. $NaHCO_3$ (0.21 g, 2.53 mmol) and ethyl 1-(4-methoxybenzyl)-4-(4,4,5,5-tetramethyl-1,3,2-dioxaborolan-2-yl)-1H-pyrazole-5-carboxylate (0.586 g, 1.51 mmol) were added to the reaction mixture at rt. The reaction mixture was degassed at rt for 10 min. Pd(dppf)$Cl_2$ (0.037 g, 0.05 mmol) was added to the reaction mixture and the glass vial was sealed. The reaction mixture was subjected to microwave heating at 110° C. for 1 h. The resulting reaction mixture was poured into water (300 ml) and extracted with EtOAc (3×100 ml). The combined organic layer was washed with water (2×100 ml), dried over $Na_2SO_4$, filtered and concentrated under reduced pressure. The resulting residue was purified by column chromatography (30% EtOAc in Hexane) yielding ethyl 4-(1-((tert-butoxycarbonyl)-L-prolyl) indolin-4-yl)-1-(4-methoxybenzyl)-1H-pyrazole-5-carboxylate (0.24 g, 0.41 mmol) LCMS: Method C, 2.495 min, MS: ES+ 575.8.

Step e. To a solution of ethyl 4-(1-((tert-butoxycarbonyl)-L-prolyl)indolin-4-yl)-1-(4-methoxybenzyl)-1H-pyrazole-5-carboxylate (0.24 g, 0.41 mmol) in DCM (5 ml) was added TFA (0.28 ml, 1.67 mmol) at rt. The reaction mixture was stirred at rt for 30 min. The resulting reaction mixture was concentrated under reduced pressure. The resulting residue was azeotropically distilled using DCM (3×10 ml) yielding ethyl (S)-1-(4-methoxybenzyl)-4-(1-prolylindolin-4-yl)-1H-pyrazole-5-carboxylate TFA salt (0.18 g, 0.30 mmol) LCMS: Method C, 1.898 min, MS: ES+ 475.7. This material was used directly for the next step without further purification.

Step f. To a solution of ethyl (S)-1-(4-methoxybenzyl)-4-(1-prolylindolin-4-yl)-1H-pyrazole-5-carboxylate TFA salt (0.15 g, 0.25 mmol) in THF (4 ml) was added $K_2CO_3$ (0.14 g, 1.02 mmol) at rt. The reaction mixture was stirred at rt for 10 min. Cyanogen bromide (0.04 g, 0.38 mmol) was added to the reaction mixture at rt. The reaction mixture was stirred at rt for 1 h. The resulting reaction mixture was poured into water (100 ml) and extracted with EtOAc (3×50 ml). The combined organic phase was dried over $Na_2SO_4$, filtered and concentrated under reduced pressure. The resulting residue was purified by column chromatography (2.5% MeOH in DCM). The crude product obtained after chromatographic purification was triturated with diethyl ether (2×10 ml) yielding title compound (0.027 g, 0.054 mmol) LCMS: Method H, 4.497 min, MS: ES+ 500.06.

Example 71 (2S,4S)-1-Cyano-4-methoxy-N-methyl-N-(4-phenylthiazol-2-yl)pyrrolidine-2-carboxamide

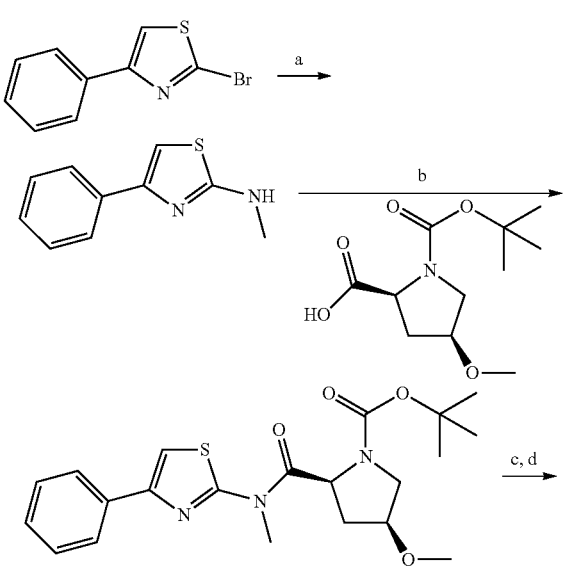

-continued

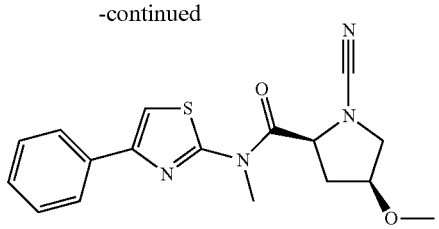

Step a. A solution of 2-bromo-4-phenylthiazole (CAS Number 57516-16-2) (5 g, 20.8 mmol) in 33% methylamine in ethanol (60 ml) was prepared at rt. The reaction mixture was heated at 80° C. for 96 h. The resulting reaction mixture was concentrated under reduced pressure. The resulting reside was purified by column chromatography (20% EtOAc in hexane) yielding N-methyl-4-phenylthiazol-2-amine (2.1 g, 11.03 mmol). LCMS: Method C, 1.723 min, MS: ES+ 191.14. $^1$H NMR (400 MHz, DMSO-d6) δ ppm 7.82-7.85 (dd, J=3.2 Hz, 6.4 Hz, 2H), 7.57-7.58 (d, J=4 Hz, 1H), 7.35-7.39 (m, 2H), 7.24-7.28 (m, 1H), 7.07 (s, 1H), 2.87-2.88 (d, J=4.8 Hz, 3H).

Step b. To a solution of (2S,4S)-1-(tert-butoxycarbonyl)-4-methoxypyrrolidine-2-carboxylic acid (CAS Number 83623-93-2) (0.077 g, 0.40 mmol) in DMF (3 ml) were added TBTU (0.196 g, 0.61 mmol) and DIPC (0.18 ml, 1.22 mmol) at rt. The reaction mixture was stirred at rt for 30 min. N-methyl-4-phenylthiazol-2-amine (0.1 g, 0.40 mmol) was added to the reaction mixture at rt and stirred for 16 h. The reaction mixture was further heated at 60° C. for additional 16 h. The resulting reaction mixture was poured into water (50 ml) and extracted with EtOAc (2×50 ml). The combined organic phase was washed with saturated NaHCO$_3$ (2×25 ml), citric acid (2×25 ml) and brine solution (50 ml). The collected organic phase was dried over Na$_2$SO$_4$, filtered and concentrated under reduced pressure yielding tert-butyl(2S, 4S)-4-methoxy-2-(methyl(4-phenylthiazol-2-yl)carbamoyl) pyrrolidine-1-carboxylate (0.2 g). This material was used directly for the next step without further purification. MS: ES+ 418.

Step c. To a solution of tert-butyl (2S,4S)-4-methoxy-2-(methyl(4-phenylthiazol-2-yl)carbamoyl)pyrrolidine-1-carboxylate (0.2 g, 0.47 mmol) in DCM (5 ml) was added TFA (2 ml) at 0° C. The reaction mixture was stirred at rt for 30 min. The resulting reaction mixture was concentrated under reduced pressure. The resulting residue was azeotropically distilled with DCM (2×5 ml) yielding (2S,4S)-4-methoxy-N-methyl-N-(4-phenylthiazol-2-yl) pyrrolidine-2-carboxamide TFA salt (0.2 g). This material was used directly for the next step without further purification.

Step d. To a solution of (2S,4S)-4-methoxy-N-methyl-N-(4-phenylthiazol-2-yl)pyrrolidine-2-carboxamide TFA salt (0.2 g, 0.46 mmol) in THF (5 ml) were added TEA (0.17 ml, 0.92 mmol) and cyanogen bromide (0.073 g, 0.53 mmol) at 0° C. The reaction mixture was stirred at rt for 30 min. The resulting reaction mixture was poured into water (30 ml) and extracted with EtOAc (2×15 ml). The combined organic phase was dried over Na$_2$SO$_4$, filtered and concentrated under reduced pressure. The resulting residue was purified by Preparative TLC (15% EtOAc in Hexane) yielding the title compound (0.030 g, 0.087 mmol). LCMS: Method J, 4.176 min, MS: ES+ 343.27; $^1$H NMR (400 MHz, DMSO-d6) δ ppm 7.96-7.98 (m, 2H), 7.76 (s, 1H), 7.43-7.47 (m, 2H), 7.34-7.36 (m, 1H), 5.12-5.16 (m, 1H), 4.03-4.06 (m, 1H), 3.74-3.78 (m, 1H), 3.71 (s, 3H), 3.52-3.55 (m, 1H), 3.16 (s, 3H), 2.64-2.70 (m, 1H), 2.55-2.56 (m, 1H).

Example 72 (S)-2-(4-(3-Methylisoxazol-4-yl)indoline-1-carbonyl)pyrrolidine-1-carbonitrile

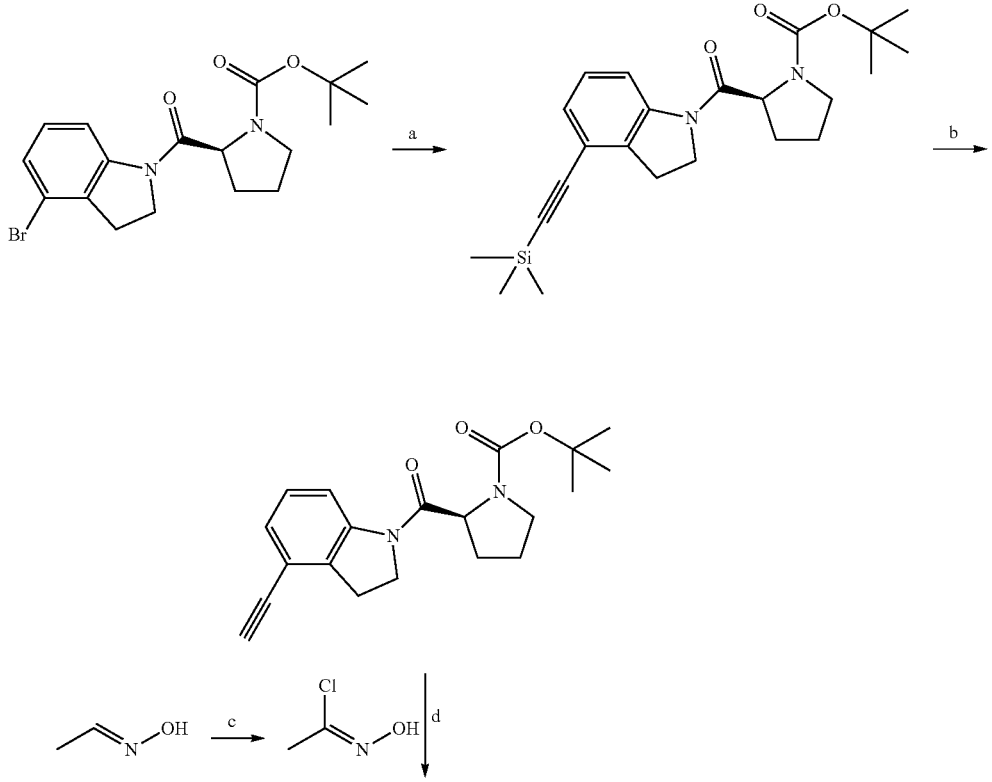

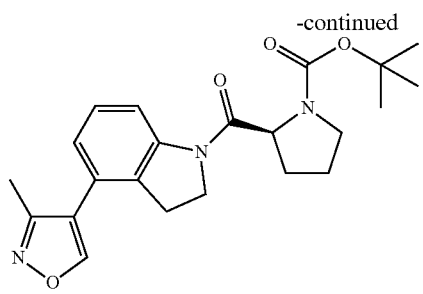 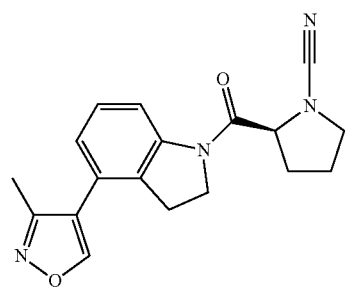

Step a. A solution of Intermediate B (0.3 g, 0.76 mmol) in DMF (7 ml) was prepared in microwave glass tube. Pd(PPh₃)₂Cl₂ (0.055 g, 0.07 mmol), TEA (0.2 ml, 1.52 mmol) and trimethylsilylacetylene (0.38 g, 3.86 mmol) were added to the reaction mixture at rt. The glass tube was sealed and subjected to microwave irradiation at 90° C. for 3 h. The resulting reaction mixture was poured into water (100 ml) and extracted with EtOAc (4×25 ml). The combined organic phase was collected, dried over Na₂SO₄, filtered and concentrated under reduced pressure. The resulting residue was purified by flash chromatography (15-20% EtOAc in hexane) yielding tert-butyl (S)-2-(4-((trimethylsilyl)ethynyl) indoline-1-carbonyl)pyrrolidine-1-carboxylate (0.23 g, 0.55 mmol). LCMS: Method C, 2.943 min, MS: ES+ 413.40.

Step b. To a solution of tert-butyl (S)-2-(4-((trimethylsilyl)ethynyl) indoline-1-carbonyl)pyrrolidine-1-carboxylate (0.22 g, 0.50 mmol) in MeOH (5 ml) was added K₂CO₃ (0.15 g, 1.01 mmol) at 0° C. The reaction mixture was stirred at rt for 30 min. The reaction mixture was filtered and concentrated under reduced pressure. The resulting residue was purified by column chromatography (20% EtOAc in hexane) yielding tert-butyl (S)-2-(4-ethynylindoline-1-carbonyl) pyrrolidine-1-carboxylate (0.2 g, 0.58 mmol). LCMS: Method C, 2.387 min, MS: ES+ 341.50.

Step c. To a solution of acetaldehyde oxime (0.30 g, 5.08 mmol) in DMF (10 ml) was added N-chlorosuccinimide (0.68 g, 5.08 mmol) at 0° C. The reaction mixture was stirred at rt for 2 h. The resulting reaction mixture was poured into water (100 ml) and extracted with EtOAc (2×50 ml). The combined organic phase was collected, dried over Na₂SO₄, filtered and concentrated under reduced pressure yielding N-hydroxyacetimidoyl chloride (0.28 g, 3.01 mmol). This material was used immediately for the next step without further purification.

Step d. To a solution of tert-butyl (S)-2-(4-ethynylindoline-1-carbonyl)pyrrolidine-1-carboxylate (0.20 g, 0.57 mmol) in THF (5 ml) were added N-hydroxyacetimidoyl chloride (0.28 g, 2.97 mmol) and TEA (0.25 ml, 1.71 mmol) at 0° C. The reaction mixture was stirred at rt for 24 h. The resulting reaction mixture was poured into water (170 ml) and extracted with EtOAc (3×50 ml). The combined organic phase was collected, dried over Na₂SO₄, filtered and concentrated under reduced pressure. The resulting residue was purified by column chromatography (50-60% EtOAc in hexane) yielding tert-butyl (S)-2-(4-(3-methylisoxazol-4-yl) indoline-1-carbonyl)pyrrolidine-1-carboxylate (0.15 g, 0.38 mmol). LCMS: Method H, 4.669 min, MS: ES+ 398.02.

Step e. To a solution of (S)-2-(4-(3-methylisoxazol-4-yl) indoline-1-carbonyl)pyrrolidine-1-carboxylate (0.14 g, 0.35 mmol) in DCM (3 ml) was added TFA (1.5 ml) at 0° C. The reaction mixture was stirred at rt for 1 h. The resulting reaction mixture was concentrated under reduced pressure yielding (S)-3-methyl-4-(1-prolylindolin-4-yl) isoxazole TFA salt (0.11 g, 0.26 mmol). This material was used directly for the next step without further purification. LCMS: Method C, 1.622 min, MS: ES+ 298.27.

Step f. To a solution of (S)-3-methyl-4-(1-prolylindolin-4-yl) isoxazole TFA salt (0.1 g, 0.24 mmol) in THF (3 ml) was added K₂CO₃ (0.1 g, 0.72 mmol) at rt. The reaction mixture was stirred at rt for 5 min. Cyanogen bromide (0.03 g, 0.29 mmol) was added to the reaction mixture at 0° C. The reaction mixture was stirred at rt for 1 h. The resulting reaction mixture was poured into water (50 ml) and extracted with EtOAc (2×50 ml). The organic phase was collected, dried over Na₂SO₄, filtered and concentrated under reduced pressure. The resulting residue was purified by flash chromatography (55-70% EtOAc in hexane) yielding the title compound (0.025 g, 0.08 mmol). LCMS: Method H, 3.907 min, MS: ES+ 322.96; ¹H NMR (400 MHz, DMSO-d6) δ ppm 8.24 (d, J=8.0 Hz, 1H), 7.52 (d, J=8.0 Hz, 1H), 7.37 (t, J=7.6 Hz, 1H), 6.80 (s, 1H), 4.74-4.77 (m, 1H), 4.34-4.41 (m, 1H), 4.09-4.16 (m, 1H), 3.48-3.58 (m, 2H), 3.39-3.43 (m, 2H), 2.31-2.37 (m, 4H), 1.99-2.06 (m, 1H), 1.87-1.94 (m, 2H).

Example 73 (S)-2-(4-(1H-imidazol-1-yl)indoline-1-carbonyl)pyrrolidine-1-carbonitrile

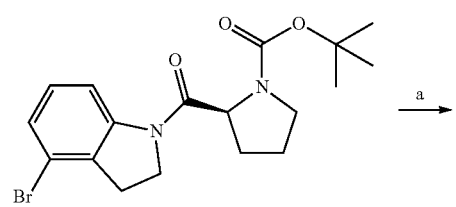

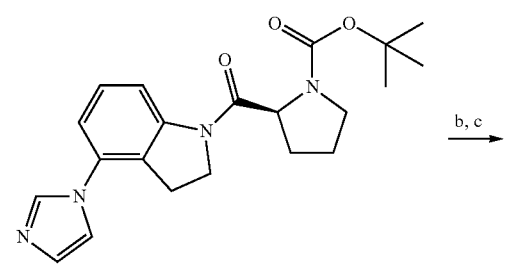

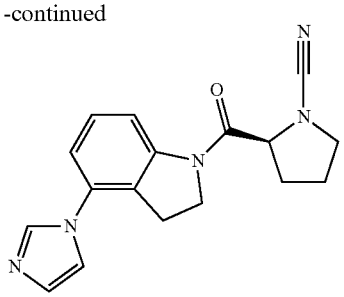

Step a. To a solution of Intermediate B (0.8 g, 2.02 mmol) in DMSO (15 ml) were added imidazole (0.14 g, 2.33 mmol), $K_2CO_3$ (0.42 g, 3.03 mmol), $Cs_2CO_3$ (0.99 g, 3.03 mmol) and CuI (0.04 g, 0.20 mmol) at rt. The reaction mixture was heated at 150° C. for 24 h. The resulting reaction mixture was poured into water (30 ml) and filtered through celite hyflow. The resulting filtrate was extracted with EtOAc (3×60 ml). The combined organic phase was collected, washed with brine (2×80 ml), dried over $Na_2SO_4$, filtered and concentrated under reduced pressure. The resulting residue was purified by flash chromatography (2-4% MeOH in DCM) yielding tert-butyl (S)-2-(4-(1H-imidazol-1-yl)indoline-1-carbonyl) pyrrolidine-1-carboxylate (0.25 g, 0.65 mmol). LCMS: Method C, 1.634 min, MS: ES+383.40.

Steps b, c. The title compound was synthesised from the intermediate above using a procedure similar to that described for steps b and c of Example 1. LCMS: Method J, 2.447 min, MS ES+ 308.37.

Example 74 4-(1-(Cyano-L-prolyl)indolin-4-yl)-1H-pyrazole-5-carbonitrile

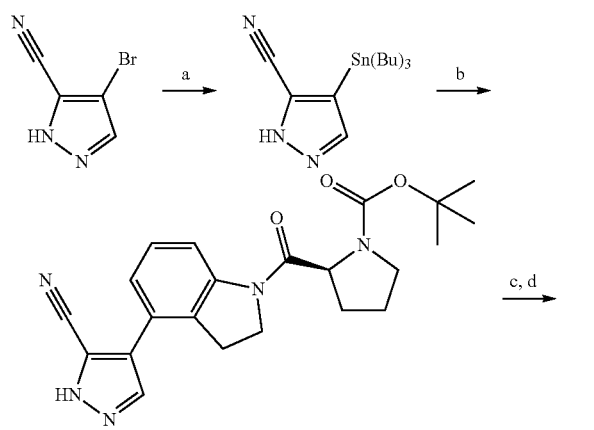

Step a. To a solution of 4-bromo-2H-pyrazole-3-carbonitrile (CAS Number 288246-16-2) (3 g, 17.4 mmol) in THF (10 ml) was added n-butyllithium (15% in hexane) (14.8 ml, 34.8 mmol) dropwise at −78° C. The reaction mixture was stirred at −78° C. for 1 h. Tri-n-butyl tin chloride (8.5 g, 26.16 mmol) was added to the reaction mixture at −78° C. The reaction mixture was stirred at rt for 2 h. The resulting reaction mixture was quenched with $NH_4Cl$ solution (150 ml) and extracted with EtOAc (3×100 ml). The combined organic phase was collected, dried over $Na_2SO_4$, filtered and concentrated under reduced pressure. The resulting residue was purified by column chromatography (12% EtOAc in hexane) yielding 4-(tributylstannyl)-1H-pyrazole-5-carbonitrile (3.2 g, 8.35 mmol). LCMS: Method C, 3.294 min, MS: ES+ 384.4.

Step b. To a solution of Intermediate B (0.2 g, 0.51 mmol) and 4-(tributylstannyl)-1H-pyrazole-5-carbonitrile (0.48 g, 1.26 mmol) in 1,4-dioxane (4 ml) were added tri(2-furyl)phosphine (0.023 g, 0.10 mmol) and LiCl (0.063 g, 1.52 mmol) at rt. The reaction mixture was degassed for 10 min. $Pd_2(dba)_3$ (0.023 g, 0.02 mmol) was added to the reaction mixture at rt. The reaction mixture was heated at 140° C. for 2 h. The resulting reaction mixture was combined with one other batch prepared on the same scale by an identical method, then poured into water (150 ml). The resulting mixture was extracted with EtOAc (3×100 ml). The combined organic phase was dried over $Na_2SO_4$, filtered and concentrated under reduced pressure. The resulting residue was purified by column chromatography (1% MeOH in DCM) yielding tert-butyl (S)-2-(4-(5-cyano-1H-pyrazol-4-yl)indoline-1-carbonyl)pyrrolidine-1-carboxylate (0.18 g, 0.44 mmol) LCMS: Method C, 2.010 min, MS: ES+352.3 (M-56).

Steps c, d. The title compound was synthesised from the intermediate above using a procedure similar to that described for steps b and c of Example 1. LCMS: Method H, 2.91 min, MS ES+ 333.01.

Example 75 (S)-2-(5-Phenyl-, 2,3,4-tetrahydroisoquinoline-2-carbonyl)pyrrolidine-1-carbonitrile

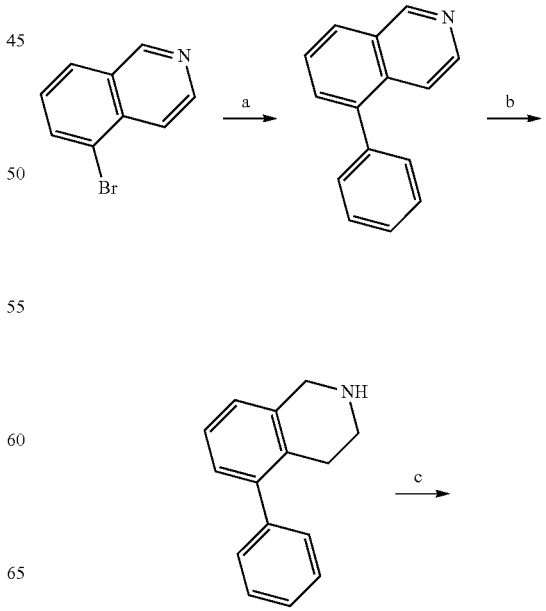

-continued

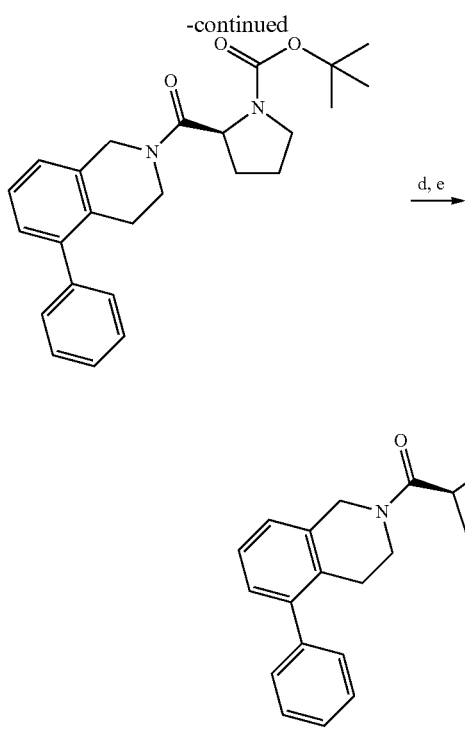

Step a. To a solution of 5-bromoisoquinoline (CAS Number 34784-04-8) (1 g, 4.8 mmol) in toluene (10 ml), water (5 ml) and EtOH (2.5 ml) were added $Na_2CO_3$ (1.02 g, 9.6 mmol) and phenylboronic acid (0.586 g, 4.8 mmol) at rt. The reaction mixture was degassed for 20 min. $Pd(PPh_3)_4$ (0.278 g, 0.24 mmol) was added to the reaction mixture at rt. The reaction mixture was heated at 90° C. for 18 h. The resulting reaction mixture was poured into water (100 ml) and extracted with EtOAc (2×50 ml). The combined organic phase was dried over $Na_2SO_4$, filtered and concentrated under reduced pressure. The resulting residue was purified by column chromatography (20% EtOAc in Hexane) yielding the 5-phenylisoquinoline (1 g, 4.87 mmol) LCMS: Method C, 1.782 min, MS: ES+ 205.8.

Step b. To a solution of 5-phenylisoquinoline (1 g, 4.87 mmol) in MeOH (7 ml) was added $PtO_2$ (0.8 g) at rt. The reaction mixture was purged with $H_2$ gas at rt for 6 h. The resulting reaction mixture was carefully filtered through celite hyflow and concentrated under reduced pressure yielding 5-phenyl-1,2,3,4-tetrahydroisoquinoline (0.6 g, 2.8 mmol). This material was used immediately for the next step without further purification. LCMS: Method C, 1.600 min, MS: ES+ 209.9.

Step c. To a solution of BOC-L-Proline (0.25 g, 1.15 mmol) in THF (5 ml) were added HATU (0.55 g, 1.44 mmol) and DIPEA (0.33 ml, 1.92 mmol) at 0° C. The reaction mixture was stirred at 0° C. for 15 min. 5-Phenyl-1,2,3,4-tetrahydroisoquinoline (0.2 g, 0.96 mmol) was added to the reaction mixture at 0° C. The reaction mixture was stirred at rt for 1 h. The resulting reaction mixture was poured into water (60 ml) and extracted with EtOAc (2×50 ml). The combined organic phase was dried over $Na_2SO_4$, filtered and concentrated under reduced pressure. The resulting residue was purified by column chromatography (3% MeOH in DCM) yielding the tert-butyl (S)-2-(5-phenyl-1,2,3,4-tetrahydroisoquinoline-2-carbonyl)pyrrolidine-1-carboxylate (0.2 g, 0.49 mmol). LCMS: Method C, 2.458 min, MS: ES+ 407.38.

Steps d, e. The title compound was synthesised from the intermediate above using a procedure similar to that described for steps b and c of Example 1. LCMS: Method J, 4.14 min, MS ES+ 332.23.

Example 76 (S)-2-(4-(2-Aminopyridin-4-yl)indoline-1-carbonyl)pyrrolidine-1-carbonitrile

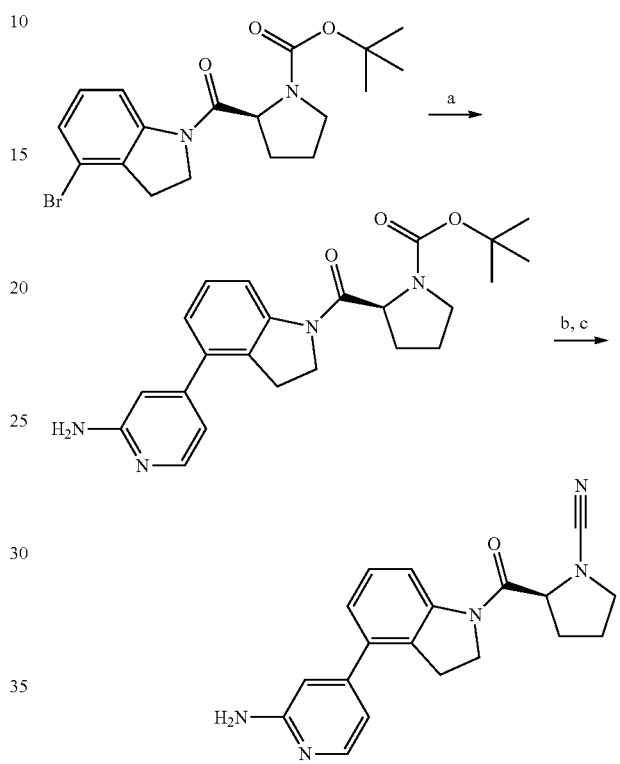

Step a. A solution of Intermediate B (0.3 g, 0.76 mmol) and 4-(4,4,5,5-tetramethyl-1,3,2-dioxaborolan-2-yl)pyridin-2-amine (CAS Number 1195995-72-2) (0.200 g, 0.91 mmol) in 1,4-dioxane:water (4:1, 5 ml) was prepared in a glass vial. $K_2CO_3$ (0.314 g, 2.27 mmol) was added to the reaction mixture at rt. The reaction mixture was degassed for 15 min. $Pd(PPh_3)_4$ (0.043 g, 0.037 mol) was added to the reaction mixture at rt. The glass vial was sealed and subjected to heating at 85° C. (external temperature) for 3 h. The resulting reaction mixture was poured into water (30 ml) and extracted with EtOAc (3×20 ml). The combined organic phase was collected, dried over $Na_2SO_4$, filtered and concentrated under reduced pressure. The resulting residue was purified by flash chromatography (2-3% MeOH in DCM) yielding tert-butyl (S)-2-(4-(2-aminopyridin-4-yl)indoline-1-carbonyl)-pyrrolidine-1-carboxylate (0.256 g, 0.63 mmol). LCMS: Method C, 1.68 min, MS: ES+409.47.

Step b. To a solution of tert-butyl (S)-2-(4-(2-aminopyridin-4-yl)indoline-1-carbonyl)pyrrolidine-1-carboxylate (0.250 g, 0.61 mmol) in DCM (5 ml) was added TFA (2.0 ml) at 0° C. The reaction mixture was stirred at rt for 1 h. The resulting reaction mixture was concentrated under reduced pressure. The obtained residue was azeotropically distilled with DCM (2×5 ml) and further triturated with diethyl ether (2×5 ml) yielding (S)-4-(2-aminopyridin-4-yl)-1-prolylindoline TFA salt (0.321 g). This material was used directly for the next step without further purification. LCMS: Method C, 1.414 min, MS: ES+ 309.48.

Step c. To a solution of (S)-4-(2-aminopyridin-4-yl)-1-prolylindoline TFA salt (0.321 g, 0.76 mmol) in THF (5 ml)

was added K$_2$CO$_3$ (0.314 g, 2.28 mmol) at 0° C. Cyanogen bromide (0.081 g, 0.76 mmol) was added to the reaction mixture at 0° C. The reaction mixture was stirred at rt for 1 h. The resulting reaction mixture was poured into water (30 ml) and extracted with EtOAc (3×20 ml). The combined organic phase was collected, dried over Na$_2$SO$_4$, filtered and concentrated under reduced pressure. The resulting residue was purified by flash chromatography (2-3% MeOH in DCM) yielding the title compound (0.051 g, 0.15 mmol). LCMS: Method J, 2.727 min, MS: ES+ 334.39.

Scheme 10

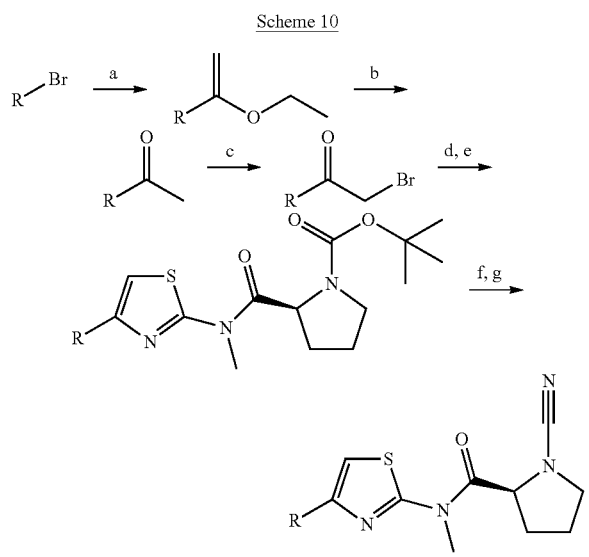

Reagents and conditions: a) 1-ethoxy-1-(tributylstannyl) ethylene, PdCl$_2$(PPh$_3$)$_2$, MeCN, 70° C.; b) 2.5 M aq. HCl, THF; c) Br$_2$, AcOH; d) N-methylthiourea, EtOH; e) BOC-L-proline, HATU, DIPEA, THF; f) TFA, DCM; g) cyanogen bromide, K$_2$CO$_3$, THF.

Example 77 (S)-1-Cyano-N-(4-(6-cyanopyridin-2-yl)thiazol-2-yl)-N-methylpyrrolidine-2-carboxamide (Prepared According to Scheme 10)

Step a. To a solution of 6-bromopicolinonitrile (CAS Number 122918-25-6) (1.0 g, 5.46 mmol) in acetonitrile (10 ml) was added 1-ethoxy-1-(tributylstannyl)ethylene (CAS Number 97674-02-7) (1.97 g, 5.46 mmol) at rt. The resulting reaction mixture was degassed for 10 min before addition of dichlorobis(triphenylphosphine)palladium(II) (0.19 g, 0.27 mmol) at rt. The reaction mixture was heated at 70° C. for 18 h. The resulting reaction mixture was cooled to rt, poured into water (20 ml) and extracted with EtOAc (3×25 ml). The combined organic phase was dried over Na$_2$SO$_4$, filtered and concentrated under reduced pressure. The resulting residue was purified by column chromatography (8% EtOAc in hexane) to yield 6-(1-ethoxyvinyl)picolinonitrile (0.48 g, 2.75 mmol). LCMS: Method C, 2.39 min, MS: ES+ 175.04.

Step b. To a solution of 6-(1-ethoxyvinyl)picolinonitrile (0.55 g, 3.15 mmol) in THF (20 ml) was added 2.5 M aqueous HCl solution (1.37 ml) at rt and stirred for 1 h. The resulting reaction mixture was poured into water (40 ml), neutralized with saturated NaHCO$_3$ solution and extracted with EtOAc (3×40 ml). The combined organic phase was dried over Na$_2$SO$_4$, filtered and concentrated under reduced pressure to yield 6-acetylpicolinonitrile (0.47 g, 3.21 mmol). LCMS: Method C, 1.88 min, MS: ES+ 147.09.

Step c. To a solution of 6-acetylpicolinonitrile (0.1 g, 0.68 mmol) in acetic acid (10 ml) was added bromine (0.108 g, 0.68 mmol) in glacial acetic acid (5 ml) drop wise at 15° C. The reaction mixture was stirred at rt for 20 h. The resulting reaction mixture was poured into saturated NaHCO$_3$ solution (30 ml) and neutralized with slow addition of solid Na$_2$CO$_3$. The obtained mixture was extracted with EtOAc (3×40 ml). The combined organic phase was dried over Na$_2$SO$_4$, filtered and concentrated under reduced pressure yielding 6-(2-bromoacetyl)picolinonitrile (0.4 g, 1.77 mmol). MS: ES+ 224.7; 226.7.

Steps d-g. The title compound was synthesised from the intermediate above using a procedure similar to that described for Example 46. LCMS: Method J, 3.80 min, MS: ES+ 339.47; $^1$H NMR (400 MHz, DMSO-d6) δ ppm 8.35 (dd, J=8.0, 0.8 Hz, 1H), 8.16 (t, J=8 Hz, 1H), 8.09 (s, 1H), 7.98 (dd, J=7.6, 0.8 Hz, 1H), 5.14-5.18 (m, 1H), 3.77 (s, 3H), 3.51-3.60 (m, 2H), 2.32-2.45 (m, 1H), 2.03-2.11 (m, 1H), 1.91-1.99 (m, 1H), 1.82-1.86 (m, 1H).

Compounds in Table 18 were synthesised using a procedure similar to that described for Example 77.

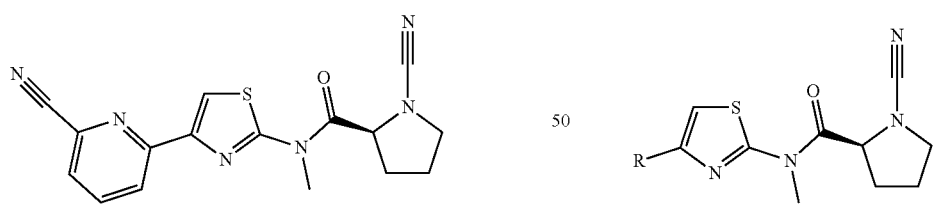

TABLE 18

| Example Number | R | Name | Aryl bromide CAS Number | LCMS method | LCMS RT | MS ES+ | $^1$H NMR (400 MHz, DMSO-d6) δ ppm |
|---|---|---|---|---|---|---|---|
| 78 | (2-cyanopyridin-3-yl) | (S)-1-cyano-N-(4-(2-cyanopyridin-4-yl)thiazol-2-yl)-N-methylpyrrolidine-2-carboxamide | 62150-45-2 | J | 3.74 | 339.43 | 8.81 (d, J = 5.2 Hz, 1 H), 8.57 (s, 1 H), 8.32 (s, 1 H), 8.24 (dd, J = 5.2, 1.6 Hz, 1 H), 5.15-5.18 (m, 1 H), 3.78 (s, 3 H), 3.53-3.60 (m, 2 H), 2.33-2.45 (m, 1 H), 2.03-2.10 (m, 1 H), 1.91-1.99 (m, 1 H), 1.83-1.85 (m, 1 H) |

TABLE 18-continued

| Example Number | R | Name | Aryl bromide CAS Number | LCMS method | LCMS RT | MS ES+ | 1H NMR (400 MHz, DMSO-d6) δ ppm |
|---|---|---|---|---|---|---|---|
| 79 | | (S)-1-cyano-N-(4-(4-cyanopyridin-2-yl)thiazol-2-yl)-N-methylpyrrolidine-2-carboxamide | 10386-27-3 | H | 4.01 | 339.00 | 8.86 (d, J = 4.8 Hz, 1 H), 8.41 (s, 1 H), 8.08 (s, 1 H), 7.81-7.83 (dd, J = 4.8, 1.2 Hz, 1 H), 5.15-5.18 (m, 1 H), 3.79 (s, 3 H), 3.50-3.58 (m, 2 H), 2.36-2.44 (m, 1 H), 2.06-2.10 (m, 1 H), 1.91-1.99 (m, 1 H), 1.79-1.86 (m, 1 H) |
| 80 | | (S)-1-cyano-N-(4-(6-cyano-3-methylpyridin-2-yl)thiazol-2-yl)-N-methylpyrrolidine-2-carboxamide | 450844-27-6 | J | 3.85 | 353.26 | 7.98 (d, J = 8 Hz, 1 H), 7.92-7.93 (m, 2 H), 5.14-5.17 (m, 1 H), 3.71 (s, 3 H), 3.53-3.58 (m, 2 H), 2.68 (s, 3 H), 2.33-2.44 (m, 1 H), 2.03-2.09 (m, 1 H), 1.95-1.99 (m, 1 H), 1.84-1.94 (m, 1 H) |
| 81 | | (S)-1-cyano-N-(4-(6-methoxypyridin-2-yl)thiazol-2-yl)-N-methylpyrrolidine-2-carboxamide | 40473-07-2 | H | 4.79 | 343.86 | 7.93 (s, 1 H), 7.77-7.81 (t, J = 7.6 Hz, 1 H), 7.65 (d, J = 6.8 Hz, 1 H), 6.77 (dd, J = 4.0, 0.8 Hz, 1 H), 5.14-5.16 (m, 1 H), 3.94 (s, 3 H), 3.76 (s, 3 H), 3.53-3.57 (m, 2 H), 2.37-2.42 (m, 1 H), 2.04-2.08 (m, 1 H), 1.92-1.96 (m, 1 H), 1.81-1.86 (m, 1 H) |
| 82 | | (S)-1-cyano-N-methyl-N-(4-(6-(trifluoromethyl)pyridin-2-yl)thiazol-2-yl)pyrrolidine-2-carboxamide | 189278-27-1 | H | 4.99 | 381.91 | 8.34 (d, J = 8.0 Hz, 1 H), 8.20 (t, J = 7.6 Hz, 1 H), 8.04 (s, 1 H), 7.85 (d, J = 7.6 Hz, 1 H), 5.14-5.17 (m, 1 H), 3.78 (s, 3 H), 3.53-3.58 (m, 2 H), 2.38-2.43 (m, 1 H), 2.04-2.10 (m, 1 H), 1.91-1.96 (m, 1 H), 1.79-1.86 (m, 1 H) |
| 137 | | (S)-1-cyano-N-(4-(6-cyano-3-methoxypyridin-2-yl)thiazol-2-yl)-N-methylpyrrolidine-2-carboxamide | 1112851-37-2 | J | 3.50 | 369.48 | 8.05 (s, 1 H), 8.02-8.03 (d, 1 H J = 2.8 Hz), 7.74-7.76 (d, 1 H J = 8.8 Hz), 5.14-5.17 (m, 1 H), 4.01 (s, 3 H), 3.74 (s, 3 H), 3.53-3.57 (m, 2 H), 2.37-2.42 (m, 1H), 2.01-2.08 (m, 1 H), 1.91-1.97 (m, 1 H), 1.80-1.85 (m, 1H) |
| 138 | | (S)-1-cyano-N-(4-(6-isopropoxypyridin-2-yl)thiazol-2-yl)-N-methyl pyrrolidine-2-carboxamide | 463336-87-0 | J | 4.94 | 372.38 | 7.86 (s, 1 H), 7.76 (t, J = 8.4 Hz, 1 H), 7.60 (d, J = 8.0 Hz, 1 H), 6.69 (d, J = 8.0 Hz, 1 H), 5.35-5.42 (m, 1 H), 5.13-5.16 (m, 1 H), 3.75 (s, 3 H), 3.51-3.60 (m, 2 H), 2.37-2.42 (m, 1 H), 2.03-2.10 (m, 1 H), 1.94-1.99 (m, 1 H), 1.78-1.92 (m, 1 H), 1.34 (d, J = 6.4 Hz, 6 H) |

Example 83 (S)-1-Cyano-N-(4-(6-cyano-5-methoxy-pyridin-2-yl)thiazol-2-yl)-N-methylpyrrolidine-2-carboxamide

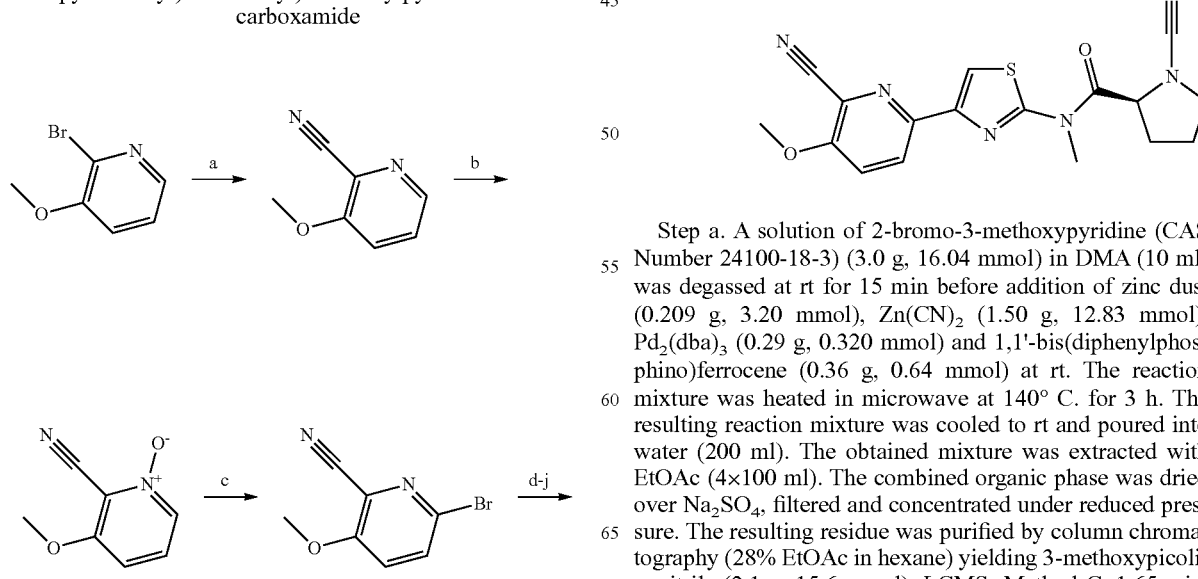

Step a. A solution of 2-bromo-3-methoxypyridine (CAS Number 24100-18-3) (3.0 g, 16.04 mmol) in DMA (10 ml) was degassed at rt for 15 min before addition of zinc dust (0.209 g, 3.20 mmol), Zn(CN)$_2$ (1.50 g, 12.83 mmol), Pd$_2$(dba)$_3$ (0.29 g, 0.320 mmol) and 1,1'-bis(diphenylphosphino)ferrocene (0.36 g, 0.64 mmol) at rt. The reaction mixture was heated in microwave at 140° C. for 3 h. The resulting reaction mixture was cooled to rt and poured into water (200 ml). The obtained mixture was extracted with EtOAc (4×100 ml). The combined organic phase was dried over Na$_2$SO$_4$, filtered and concentrated under reduced pressure. The resulting residue was purified by column chromatography (28% EtOAc in hexane) yielding 3-methoxypicolinonitrile (2.1 g, 15.6 mmol). LCMS: Method C, 1.65 min, MS: ES+ 135.04; ¹H NMR (400 MHz, DMSO-d6) δ ppm 8.31 (d, J=4.4 Hz, 1H), 7.73-7.80 (m, 2H), 3.97 (s, 3H).

Step b. To a solution 3-methoxypicolinonitrile (1.9 g, 14.16 mmol) in DCM (50 ml) was added m-chloroperbenzoic acid (55-75% in water) (6.11 g, 21.24 mmol) portion wise at rt. The reaction mixture was heated at 65° C. for 30 h. The resulting reaction was cooled to rt and poured into saturated NaHCO₃ solution (800 ml). The obtained mixture was extracted with EtOAc (5×200 ml). The combined organic phase was washed with saturated NaHCO₃ solution (350 ml), dried over Na₂SO₄, filtered and concentrated under reduced pressure. The resulting residue was purified by column chromatography (4% MeOH in DCM) yielding 2-cyano-3-methoxypyridine 1-oxide (1.65 g, 10.98 mmol). LCMS: Method H, 2.15 min, MS: ES+ 150.92

Step c. A mixture of 2-cyano-3-methoxypyridine-1-oxide (1.6 g, 10.65 mmol) and POBr₃ (10.69 g, 37.3 mmol) was heated at 90° C. for 1 h. The resulting reaction mixture was cooled to rt and poured into ice cold water (200 ml). The obtained mixture was neutralized by slow addition of saturated NaHCO₃ solution (700 ml). The obtained mixture was extracted with EtOAc (4×300 ml). The combined organic phase was dried over Na₂SO₄, filtered and concentrated under reduced pressure. The resulting residue was purified by column chromatography (9.5% EtOAc in hexane) yielding 6-bromo-3-methoxypicolinonitrile (0.45 g, 2.12 mmol). LCMS: Method C, 2.00 min, MS: ES+ 213.05; ¹H NMR (400 MHz, DMSO-d6) δ ppm 7.98 (d, J=9.2 Hz, 1H), 7.80 (d, J=9.2 Hz, 1H), 3.97 (s, 3H)

Steps d-j. The title compound was synthesised from the intermediate above using a procedure similar to that described for Example 77. LCMS: Method J, 3.91 min, MS: ES+ 369.23; ¹H NMR (400 MHz, DMSO-d6) δ ppm 8.32 (d, J=8.8 Hz, 1H), 7.88-7.90 (m, 2H), 5.14-5.17 (m, 1H), 4.02 (s, 3H), 3.76 (s, 3H), 3.51-3.60 (m, 2H), 2.37-2.45 (m, 1H), 2.03-2.10 (m, 1H), 1.91-1.97 (m, 1H), 1.78-1.86 (m, 1H).

Example 84 (S)-1-Cyano-N-(4-(6-cyano-5-methylpyridin-2-yl)thiazol-2-yl)-N-methylpyrrolidine-2-carboxamide

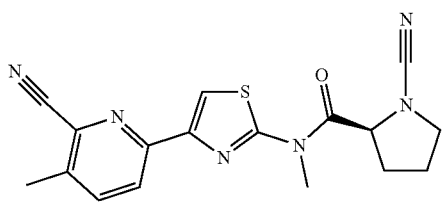 [SMILES: Cc1ccc(-c2csc(N(C)C(=O)[C@@H]3CCCN3C#N)n2)nc1C#N]

The title compound was synthesised using a procedure similar to that described for Example 83 using 2-bromo-3-methylpyridine (CAS Number 3430-17-9) in step a. LCMS: Method H, 4.49 min, MS: ES+ 351.90; ¹H NMR (400 MHz, DMSO-d6) δ ppm 8.25 (d, J=8.0 Hz, 1H), 8.02-8.05 (m, 2H), 5.14-5.17 (m, 1H), 3.76 (s, 3H), 3.53-3.58 (m, 2H), 2.51 (s, 3H), 2.33-2.45 (m, 1H), 2.03-2.09 (m, 1H), 1.91-1.95 (m, 1H), 1.80-1.85 (m, 1H).

Example 139 (S)-1-cyano-N-(4-(6-cyano-5-ethoxy-pyridin-2-yl)thiazol-2-yl)-N-methylpyrrolidine-2-carboxamide

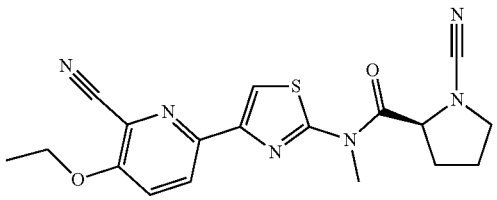 [SMILES: CCOc1ccc(-c2csc(N(C)C(=O)[C@@H]3CCCN3C#N)n2)nc1C#N]

The title compound was synthesised using a procedure similar to that described for Example 83 using 2-bromo-3-ethoxypyridine (CAS Number 89694-54-2) in step a. LCMS: Method H, 4.50 min, MS: ES+ 382.9; ¹H NMR (400 MHz, DMSO-d6) δ ppm 8.20 (d, J=8.8 Hz, 1H), 7.89 (t, J=5.6 Hz, 2H), 5.14-5.17 (m, 1H), 4.31 (q, J=6.8 Hz, 2H), 3.76 (s, 3H), 3.51-3.58 (m, 2H), 2.33-2.45 (m, 1H), 2.04-2.09 (m, 1H), 1.91-1.99 (m, 1H), 1.79-1.86 (m, 1H), 1.41 (t, J=6.8 Hz, 3H).

Example 140 (S)-1-cyano-N-(4-(6-cyano-5-(dimethylamino)pyridin-2-yl)thiazol-2-yl)-N-methyl-pyrrolidine-2-carboxamide

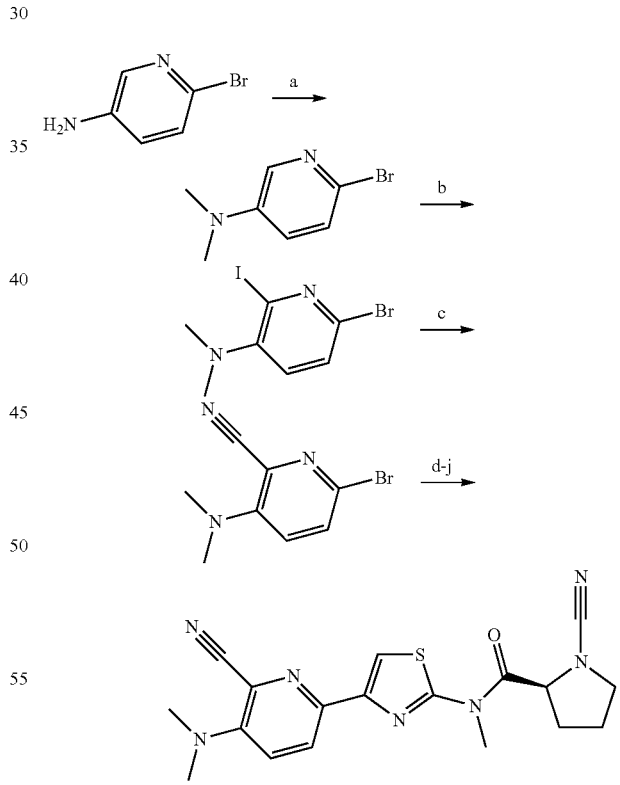

Step a. To a solution of 6-bromopyridin-3-amine (CAS Number 97-65-4) (1 g, 5.78 mmol) in formic acid (5 ml) was added para-formaldehyde (1.5 g, 1.5 eq w/w) at rt. The reaction mixture was heated at 90° C. for 16 hr. The resulting reaction mixture was poured into ice cold water, basified using solid sodium carbonate and extracted using EtOAc (30 ml×3). The organic layer was combined and dried over Na₂SO₄ concentrated under reduced pressure. The obtained residue was purified using column chromatography (20% EtOAc in hexane) yielding 6-bromo-N,N-dimethylpyridin-3-amine (0.43 g, 2.160 mmol). LCMS: Method C, 1.77 min, MS: ES+ 201.14. ¹H NMR (400 MHz, DMSO-d6) δ ppm 8.31-8.32 (d, 1H), 7.84-7.85 (d, 1H), 7.33-7.35 (d, 1H), 2.91 (s, 6H).

Step b. To a solution of 6-bromo-N,N-dimethylpyridin-3-amine (1.2 g, 6.03 mmol) in ethanol (20 ml) were added silver sulphate (2.067 g, 6.63 mmol) and iodine (1.81 g, 7.24 mmol) at rt. The resulting reaction mixture was stirred at rt for 2 hr. The resulting reaction mixture was poured into water (50 ml), basified using solid sodium bicarbonate and extracted using EtOAc (50 ml×2). The organic layer was combined and washed with solution of sodium thiosulphate (50 ml), dried over Na₂SO₄ and concentrated under reduced pressure. The obtained residue was purified using column chromatography (30% EtOAC in hexane) yielding 6-bromo-2-iodo-N,N-dimethylpyridin-3-amine (1.45 g, 4.45 mmol). LCMS: Method C, 2.17 min, MS: ES+ 327.13.

Step c. To a solution of 6-bromo-2-iodo-N,N-dimethylpyridin-3-amine (1.4 g, 4.29 mmol) in DMSO (10 ml) was added copper cyanide (0.382 g, 4.294 mmol) at rt. The resulting reaction mixture was stirred at 100° C. for 7 hrs. The resulting reaction mixture was poured into cold water (100 ml) and extracted using EtOAc (50 ml×2). The organic layer was combined, dried over Na₂SO₄ and concentrated under reduced pressure. The obtained residue was purified using column chromatography (30% EtOAc in hexane) yielding 6-bromo-3-(dimethylamino) picolinonitrile (0.56 g, 2.48 mmol). LCMS: Method C, 2.32 min, MS: ES+ 226. ¹H NMR (400 MHz, DMSO-d6) δ ppm 12.795 (s, 1H), 7.63-7.66 (m, 2H), 7.35-7.39 (m, 2H), 7.12-7.16 (t, 1H), 4.03-4.08 (m, 1H), 3.94-3.98 (m, 1H), 3.32-3.39 (m, 1H), 2.76-2.83 (m, 1H), 2.66-2.77 (m, 1H).

Steps d-j. The title compound was synthesised from the intermediate above using a procedure similar to that described for Example 77. LCMS: Method H, 4.41 min, MS: ES+ 382.00; ¹H NMR (400 MHz, DMSO-d6) δ ppm 8.10 (d, J=9.2 Hz, 1H), 7.78 (s, 1H), 7.59 (d, J=9.2 Hz, 1H), 5.13-5.18 (m, 1H), 3.75 (s, 3H), 3.50-3.59 (m, 2H), 3.10 (s, 6H), 2.34-2.40 (m, 1H), 2.02-2.09 (m, 1H), 1.91-1.96 (m, 1H), 1.85-1.87 (m, 1H).

Example 141 (S)-1-cyano-N-(4-(6-cyano-3-(2-methoxyethoxy)pyridin-2-yl)thiazol-2-yl)-N-methylpyrrolidine-2-carboxamide

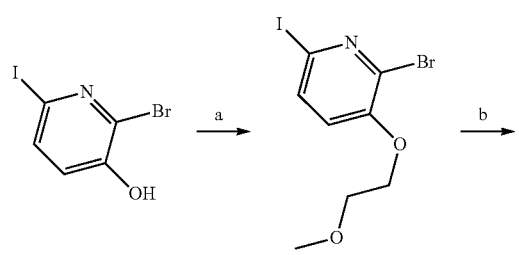

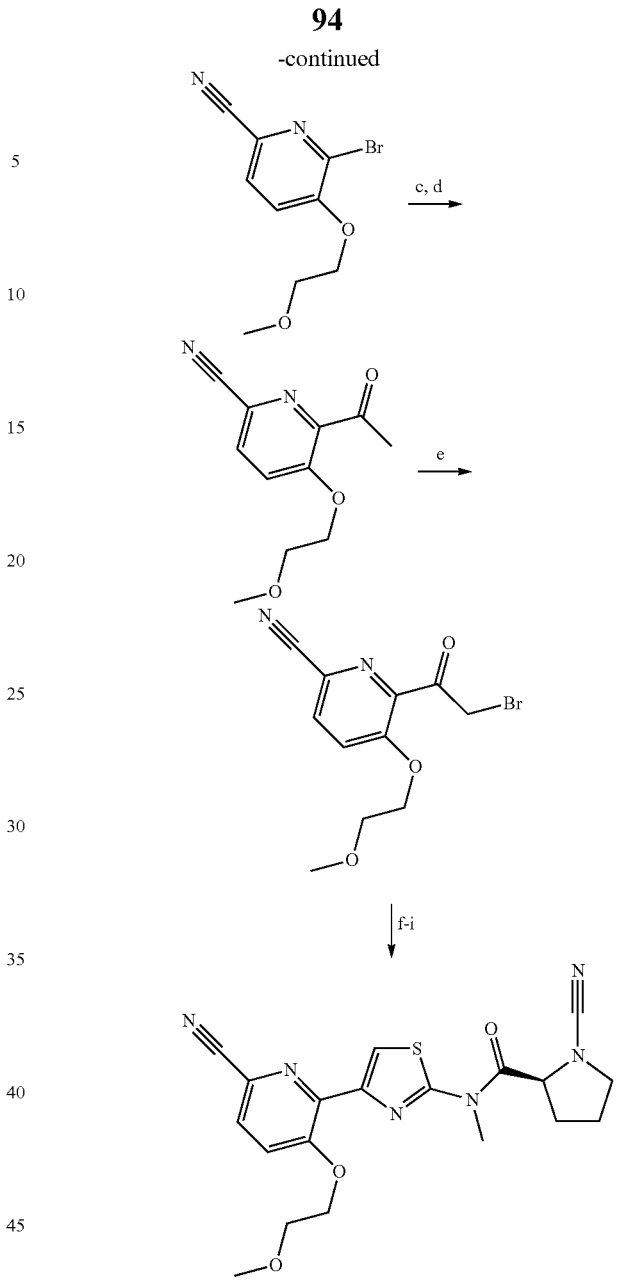

Step a. To a stirred solution of 2-bromo-3-hydroxy-6-iodopyridine (CAS Number 129611-32-1) (2.4 g, 8.027 mmol) in DMF (10 ml) was added sodium hydride (60% dispersion in mineral oil) (0.64 g, 16.05 mmol) at 0° C. under nitrogen atmosphere and stirred at 0° C. for 10 min. 2-Bromoethyl methyl ether (CAS Number 6482-24-2) (2.26 g, 16.29 mmol) was added to the reaction mixture at 0° C. The reaction mixture was heated at 80° C. for 16 h. The resulting reaction mixture was cooled to rt, diluted with brine solution (200 ml) and extracted with EtOAc (3×50 ml). The combined organic phase was separated and washed with water (2×100 ml). The organic phase was separated, dried over Na₂SO₄, filtered and concentrated under reduced pressure. The resulting crude material was purified by column chromatography (8.6% EtOAc in hexane) yielding tert-butyl 2-bromo-6-iodo-3-(2-methoxyethoxy)pyridine (2.37 g, 6.64 mmol). LCMS: Method C, 2.10 min, MS: ES+ 358.2, 360.13; ¹H NMR (400 MHz, DMSO-d6) δ ppm 7.79 (d, J=8.4 Hz, 1H), 7.32 (d, J=8.4 Hz, 1H), 4.23 (t, J=4.4 Hz, 2H), 3.68 (t, J=4.4 Hz, 2H), 3.32 (s, 3H).

Step b. To a stirred solution of 2-bromo-6-iodo-3-(2-methoxyethoxy)pyridine (2.3 g, 6.44 mmol) in DMF (12 ml) was added zinc cyanide (0.753 g, 6.44 mmol) at rt under nitrogen atmosphere. Pd(PPh₃)₄ (0.521 g, 0.451 mmol) was added to the reaction mixture at rt and heated at 90° C. for 9 h. The resulting reaction mixture was cooled to rt, poured into water (150 ml) and extracted with EtOAc (3×50 ml). The combined organic phase was washed with water (100 ml). The organic phase was separated dried over Na₂SO₄, filtered and concentrated under reduced pressure. The resulting crude material was purified by flash chromatography (23% EtOAc in hexane) yielding 6-bromo-5-(2-methoxyethoxy)picolinonitrile (1.22 g, 4.76 mol). LCMS: Method C, 2.15 min, MS: ES+ 257, 259.0; ¹H NMR (400 MHz, DMSO-d6) δ ppm 8.10 (d, J=4.8 Hz, 1H), 7.71 (d, J=4.4 Hz, 1H), 4.36 (t, J=4.4 Hz, 2H), 3.73 (t, J=4.4 Hz, 2H), 3.35 (s, 3H).

Steps c, d. Using a procedure similar to that described for Example 77, steps a, b.

Step e. To a stirred solution of 6-acetyl-5-(2-methoxyethoxy)picolinonitrile (1.14 g, 5.18 mmol) in THF (15 ml) was added pyridine hydrobromide perbromide (CAS Number 39416-48-3) (1.98 g, 6.218 mmol) at rt. The reaction mixture was stirred at rt for 2 h. The resulting reaction mixture was diluted with DM water (100 ml) and extracted with EtOAc (3×50 ml). The combined organic phase was separated and washed with DM water (50 ml). The organic phase was separated, dried over Na₂SO₄, filtered and concentrated under reduced pressure. The resulting crude material was purified by column chromatography (50% EtOAc in hexane) yielding 6-(2-bromoacetyl)-5-(2-methoxyethoxy)picolinonitrile (1.3 g, 4.36 mmol). LCMS: Method C, 1.83 min, MS: ES+ 299.2, 301.3

Steps f-i. The title compound was synthesised from the intermediate above using a procedure similar to that described for Example 77, steps g-j. LCMS: Method H, 3.71 min, MS: ES+ 413.01; ¹H NMR (400 MHz, DMSO-d6) δ ppm 8.04 (s, 1H), 8.02 (d, J=8.8 Hz, 1H), 7.77 (d, J=8.8 Hz, 1H), 5.15-5.18 (m, 1H), 4.38 (t, J=4.0 Hz, 2H), 3.79 (t, J=4.0 Hz, 2H), 3.76 (s, 3H), 3.51-3.58 (m, 2H), 3.34 (s, 3H), 2.36-2.45 (m, 2H), 2.03-2.07 (m, 1H), 1.93-1.96 (m, 1H), 1.79-1.86 (m, 1H).

Example 142 (S)-1-cyano-N-(4-(6-cyano-3-ethoxy-pyridin-2-yl)thiazol-2-yl)-N-methylpyrrolidine-2-carboxamide

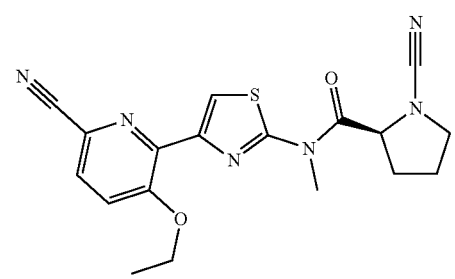 [SMILES: CCOc1ccc(C#N)nc1-c1csc(N(C)C(=O)[C@@H]2CCCN2C#N)n1]

The title compound was synthesised using a procedure similar to that described for Example 141. LCMS: Method H, 3.98 min, MS: ES+ 383.03; ¹H NMR (400 MHz, DMSO-d6) δ ppm 8.0-8.02 (m, 2H), 7.73 (d, J=8.8 Hz, 1H), 5.14-5.17 (dd, J=3.6 Hz, 8.4 Hz, 1H), 4.29 (q, J=6.8 Hz, 2H), 3.75 (s, 3H), 3.51-3.60 (m, 2H), 2.36-2.47 (m, 1H), 2.02-2.09 (m, 1H), 1.92-1.98 (m, 1H), 1.81-1.88 (m, 1H), 1.43-1.50 (m, 3H).

Example 85

1-(Cyano-L-prolyl)-4-phenylindoline-6-carboxamide

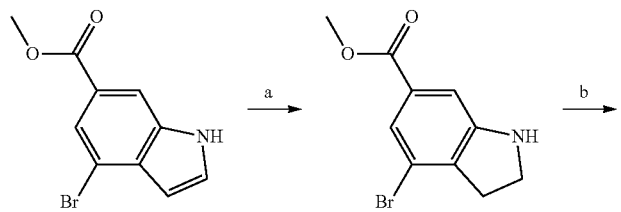

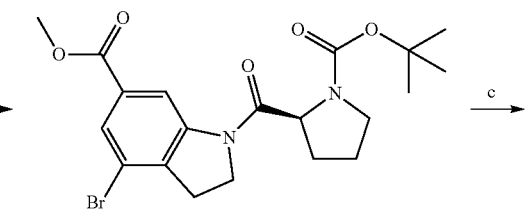

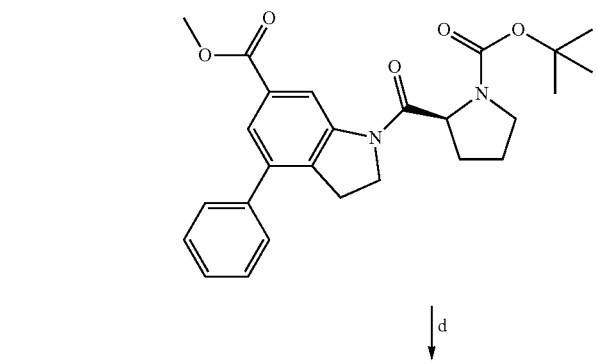

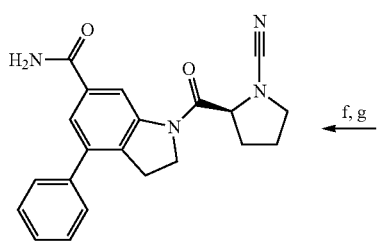 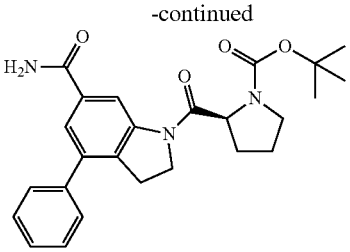 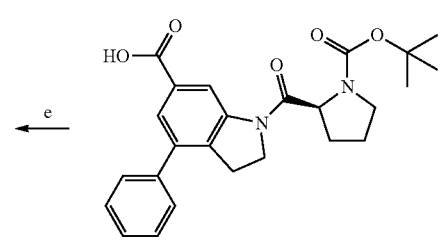

Step a. To a solution of methyl 4-bromo-1H-indole-6-carboxylate (CAS Number 882679-96-1) (1.0 g, 3.95 mmol) in TFA (5 ml) was added triethylsilane (1.9 ml, 11.86 mmol) at rt. The reaction mixture was stirred at 60° C. for 45 min. The resulting reaction mixture was cooled to rt, poured into saturated NaHCO$_3$ solution (50 ml) extracted with EtOAc (3×30 ml). The combined organic layer was dried over Na$_2$SO$_4$, filtered and concentrated under reduced pressure. The resulting residue was purified by flash chromatography (10% EtOAc in hexane) yielding methyl 4-bromoindoline-6-carboxylate (0.75 g, 29.4 mmol). LCMS: Method C, 2.31 min, MS: ES+ 256.3, 258.3; $^1$H NMR (400 MHz, DMSO-d6) δ ppm 7.20 (d, J=1.2 Hz, 1H), 6.94 (d, J=1.6 Hz, 1H), 6.19 (s, 1H), 3.80 (s, 3H), 3.54 (t, J=8.8 Hz, 2H), 2.97 (t, J=8.8 Hz, 2H).

Step b. A suspension of BOC-L-proline (0.70 g, 3.230 mmol), methyl 4-bromoindoline-6-carboxylate (0.55 g, 2.150 mmol), DCC (0.89 g, 4.310 mmol) in DMF (0.1 ml) was heated in a microwave at 130° C. for 40 min. The resulting reaction mixture was cooled to rt. The reaction mixture was poured into water (50 ml) and extracted with EtOAc (3×25 ml). The combined organic phase was dried over Na$_2$SO$_4$, filtered and concentrated under reduced pressure. The resulting residue was purified by flash chromatography (15% EtOAc in hexane) and dried well yielding methyl 4-bromo-1-((tert-butoxycarbonyl)-L-prolyl)indoline-6-carboxylate (0.26 g, 0.575 mmol). LCMS: Method C, 2.62 min, MS: ES+ 453.7, 455.7.

Step c. To a solution of methyl 4-bromo-1-((tert-butoxycarbonyl)-L-prolyl)indoline-6-carboxylate (0.25 g, 0.55 mmol) in DMF:water (9:1) (8 ml) was added phenylboronic acid (0.07 g, 0.61 mmol) and Na$_2$CO$_3$ (0.176 g, 1.66 mmol) at rt. The reaction mixture was degassed for 15 min before adding PdCl$_2$(dppf) (0.04 g, 0.055 mmol) at rt. The reaction mixture was heated at 100° C. for 2 h. The resulting reaction mixture was cooled to rt, poured into water (25 ml) and extracted with EtOAc (3×25 ml). The combined organic phase was dried over Na$_2$SO$_4$, filtered and concentrated under reduced pressure. The resulting residue was purified by flash chromatography (15% EtOAc in hexane) yielding methyl 1-((tert-butoxycarbonyl)-L-prolyl)-4-phenylindoline-6-carboxylate (0.25 g, 0.555 mmol). LCMS: Method C, 2.60 min, MS: ES+ 451.56.

Step d. To a solution of methyl 1-((tert-butoxycarbonyl)-L-prolyl)-4-phenylindoline-6-carboxylate (0.25 g, 0.55 mmol) in methanol:water (9:1) (8 ml) was added NaOH (0.067 g, 1.66 mmol) at rt. The reaction mixture was heated at 90° C. for 1 h. The resulting reaction mixture was cooled to rt and concentrated under reduced pressure. The resulting residue was quickly poured in water (20 ml), filtered through celite hyflow. The pH of the resulting filtrate was adjusted up to 2 by addition of 1M HCl. The resulting solids were filtered off under vacuum and dried well yielding 1-((tert-butoxycarbonyl)-L-prolyl)-4-phenylindoline-6-carboxylic acid (0.19 g, 0.436 mmol). LCMS: Method C, 2.36 min, MS: ES+ 437.8; $^1$H NMR (400 MHz, DMSO-d6) δ ppm. 12.95 (br s, 1H), 8.68-8.71 (m, 1H), 7.63-7.66 (m, 1H), 7.48-7.53 (m, 4H), 7.40-7.44 (m, 1H), 4.50-4.58 (m, 1H), 4.13-4.31 (m, 2H), 3.23-3.43 (m, 4H), 2.22-2.32 (m, 1H), 1.83-1.93 (m, 3H), 1.27-1.41 (m, 9H).

Step e. To a solution of 1-((tert-butoxycarbonyl)-L-prolyl)-4-phenylindoline-6-carboxylic acid (0.17 g, 0.39 mmol) in THF (7 ml) was added HATU (0.30 g, 0.78 mmol) and DIPEA (0.2 ml, 1.12 mmol) at rt. The reaction mixture was stirred at rt for 30 min. Ammonium bicarbonate (0.06 g, 0.78 mmol) was added to the reaction mixture at rt. The reaction mixture was stirred at rt for 1.5 h. The resulting reaction mixture was poured into water (25 ml) and extracted with EtOAc (3×25 ml). The combined organic phase was dried over Na$_2$SO$_4$, filtered and concentrated under reduced pressure. The resulting residue was purified by flash chromatography (1% MeOH in DCM) yielding tert-butyl (S)-2-(6-carbamoyl-4-phenylindoline-1-carbonyl)pyrrolidine-1-carboxylate (0.115 g, 0.264 mmol). LCMS: Method C, 2.21 min, MS: ES+ 436.8; $^1$H NMR (400 MHz, DMSO-d6) δ ppm 8.57-8.62 (m, 1H), 8.01 (br s, 1H), 7.48-7.61 (m, 5H), 7.41 (t, J=6.8 Hz, 1H), 7.32 (br s, 1H), 4.51-4.58 (m, 1H), 4.15-4.29 (m, 2H), 3.21-3.44 (m, 4H), 2.22-2.33 (m, 1H), 1.81-1.99 (m, 3H), 1.27-14 (m, 9H).

Steps f, g. The title compound was synthesised from the intermediate above using a procedure similar to that described for steps b and c of Example 1. LCMS: Method J, 3.59 min, MS: ES+ 361.61; $^1$H NMR (400 MHz, DMSO-d6) δ ppm 8.61 (s, 1H), 8.04 (br s, 1H), 7.63 (d, J=1.2 Hz, 1H), 7.40-7.55 (m, 5H), 7.33 (br s, 1H), 4.75-4.78 (m, 1H), 4.30-4.32 (m, 1H), 4.05-4.07 (m, 1H), 3.51-3.57 (m, 2H), 3.22-3.34 (m, 2H), 2.29-2.34 (m, 1H), 1.89-1.99 (m, 3H).

Example 86 1-(Cyano-L-prolyl)-N-ethyl-4-phenylindoline-6-carboxamide

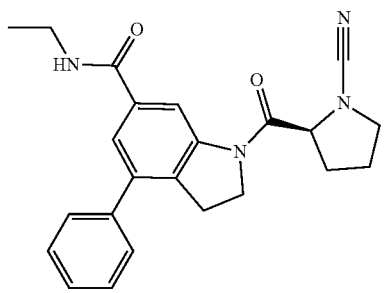 [SMILES: CCNC(=O)c1cc(-c2ccccc2)c2c(c1)N(C(=O)[C@@H]1CCCN1C#N)CC2]

The title compound was synthesised using a procedure similar to that described for Example 85 using ethylamine in step e. LCMS: Method J, 3.93 min, MS: ES+ 389.77; $^1$H NMR (400 MHz, DMSO-d6) δ ppm 8.59 (d, J=1.2 Hz, 1H), 8.54 (t, J=5.2 Hz, 1H), 7.58 (d, J=1.2 Hz, 1H), 7.48-7.55 (m, 4H), 7.40-7.44 (m, 1H), 4.76-4.79 (m, 1H), 4.28-4.35 (m, 1H), 4.03-4.09 (m, 1H), 3.49-3.59 (m, 2H), 3.20-3.32 (m, 4H), 2.29-2.34 (m, 1H), 1.89-2.02 (m, 3H), 1.12 (t, J=3.2 Hz, 3H).

Example 87 1-(Cyano-L-prolyl)-4-(3-ethylphenyl)-N-methylindoline-6-carboxamide

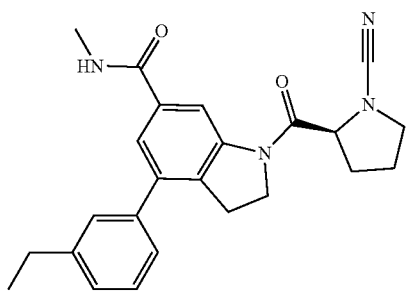 [SMILES: CCc1cccc(-c2cc(C(=O)NC)cc3c2CCN3C(=O)[C@@H]2CCCN2C#N)c1]

The title compound was synthesised using a procedure similar to that described for Example 85 using 3-ethylphenylboronic acid in step c and methylamine in step e. LCMS: Method H, 4.38 min, MS: ES+ 403.14; ¹H NMR (400 MHz, DMSO-d6) δ ppm 8.59 (s, 1H), 8.48 (d, J=4.4 Hz, 1H), 7.57 (d, J=1.2 Hz, 1H), 7.33-7.42 (m, 3H), 7.26 (d, J=7.6 Hz, 1H), 4.75-4.78 (m, 1H), 4.28-4.34 (m, 1H), 4.03-4.10 (m, 1H), 3.50-3.59 (m, 2H), 3.20-3.32 (m, 2H), 2.79 (d, J=4.4 Hz, 3H), 2.66-2.72 (m, 2H), 2.28-2.37 (m, 1H), 1.89-2.03 (m, 3H), 1.22-1.26 (m, 3H).

Example 88 1-(Cyano-L-prolyl)-N-methyl-4-(quinolin-6-yl)indoline-6-carboxamide

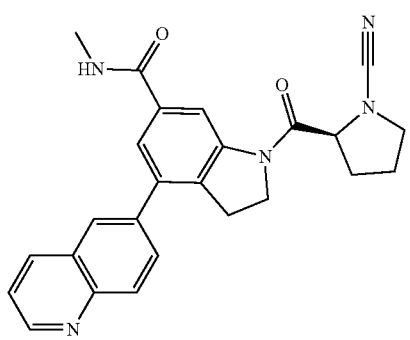 [SMILES: CNC(=O)c1cc(-c2ccc3ncccc3c2)c2c(c1)N(C(=O)[C@@H]1CCCN1C#N)CC2]

The title compound was synthesised using a procedure similar to that described for Example 85 using quinoline-6-boronic acid in step c and methylamine in step e. LCMS: Method H, 3.40 min, MS: ES+426.30; ¹H NMR (400 MHz, DMSO-d6) δ ppm 8.96 (d, J=2.4 Hz, 1H), 8.65 (s, 1H), 8.55 (s, 1H), 8.46 (d, J=8 Hz, 1H), 8.12-8.16 (m, 2H), 7.96 (d, J=8 Hz, 1H), 7.73 (s, 1H), 7.59-7.62 (m, 1H), 4.79-4.80 (m, 1H), 4.35-4.37 (m, 1H), 4.09-4.13 (m, 1H), 3.52-3.58 (m, 2H), 3.38-3.45 (m, 2H), 2.79 (d, J=4.4, 3H), 2.30-2.35 (m, 1H), 1.91-2.01 (m, 3H).

Example 89 1-(Cyano-L-prolyl)-N-methyl-4-(1H-pyrrolo[2,3-b]pyridin-3-yl)indoline-6-carboxamide

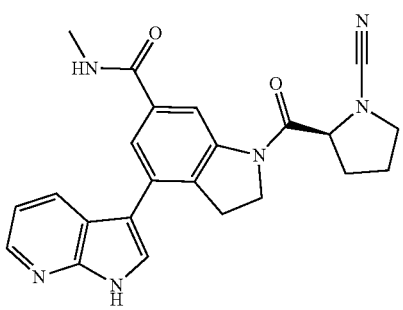 [SMILES: CNC(=O)c1cc(-c2c[nH]c3ncccc23)c2c(c1)N(C(=O)[C@@H]1CCCN1C#N)CC2]

The title compound was synthesised using a procedure similar to that described for Example 85 using tert-butyl 3-(4,4,5,5-tetramethyl-1,3,2-dioxaborolan-2-yl)-1H-pyrrolo[2,3-b]pyridine-1-carboxylate (CAS Number 942070-47-5) in step c and methylamine in step e. LCMS: Method H, 3.11 min, MS: ES+ 415.19; ¹H NMR (400 MHz, DMSO-d6) δ ppm 12.03 (s, 1H), 8.53 (s, 1H), 8.46 (d, J=4.4 Hz, 1H), 8.30-8.31 (dd, J=4.4, 1.6 Hz, 1H), 8.11 (d, J=8 Hz, 1H), 7.74-7.76 (m, 2H), 7.15-7.19 (m, 1H), 4.76-4.79 (m, 1H), 4.33-4.35 (m, 1H), 4.08-4.10 (m, 1H), 3.52-3.57 (m, 2H), 3.26-3.38 (m, 2H), 2.79 (d, J=4.4 Hz, 3H), 2.30-2.35 (m, 1H), 1.87-2.01 (m, 3H).

Example 90 (S)-2-(6-(H-Imidazol-2-yl)-4-phenylindoline-1-carbonyl)pyrrolidine-1-carbonitrile

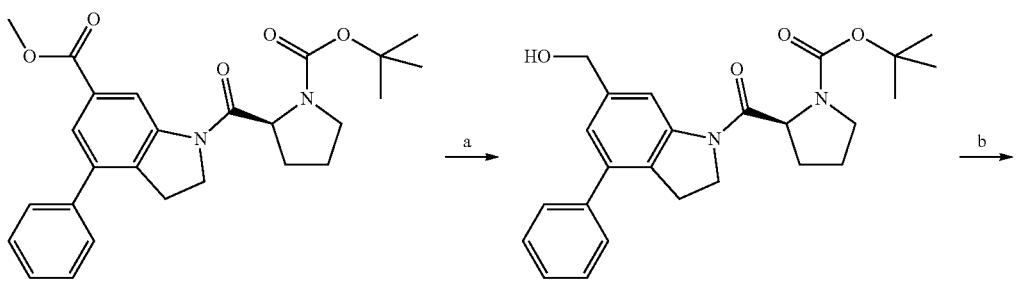

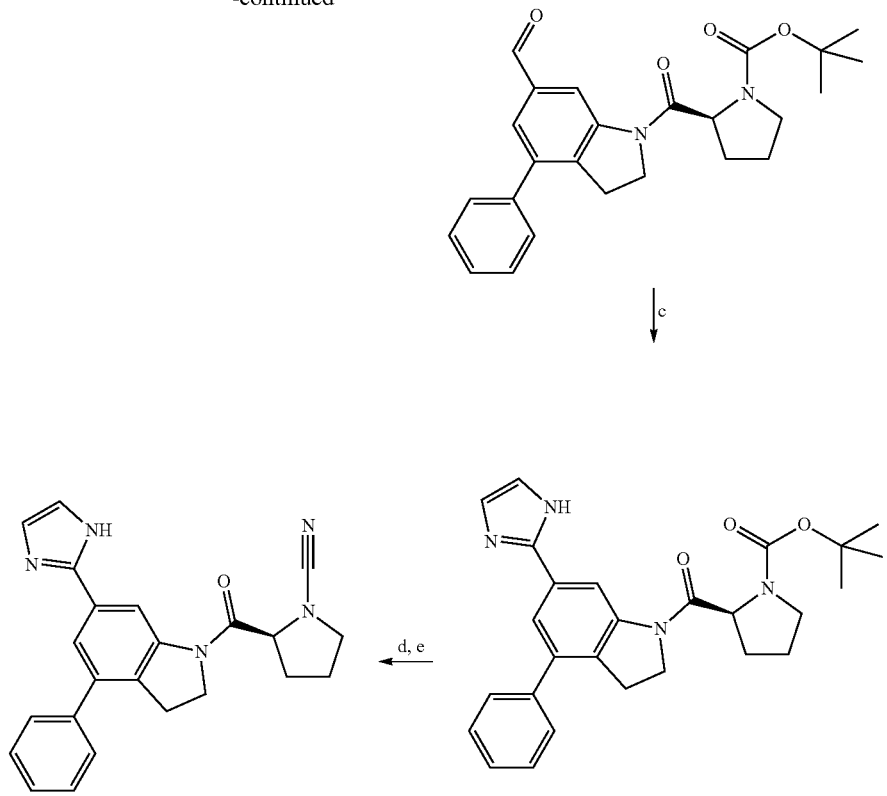

Step a. To a solution of methyl 1-((tert-butoxycarbonyl)-L-prolyl)-4-phenylindoline-6-carboxylate (described in steps a-c of Example 85) (1.500 g, 3.33 mmol) in THF (15 ml) was added 1M LiAlH₄ solution in THF (4 ml, 4.00 mmol) at −78° C. The reaction mixture was gradually warmed to −20° C. and stirred for a further 2 h. The resulting reaction mixture was quenched with slow addition of water (50 ml) and extracted with EtOAc (3×20 ml). The combined organic phase was dried over Na₂SO₄, filtered and concentrated under reduced pressure. The obtained residue was purified by column chromatography (40% EtOAc in hexane) yielding tert-butyl (S)-2-(6-(hydroxymethyl)-4-phenylindoline-1-carbonyl) pyrrolidine-1-carboxylate (1.20 g, 2.84). LCMS: Method C, 2.36 min, MS: ES+ 423.38.

Step b. To a solution of tert-butyl (S)-2-(6-(hydroxymethyl)-4-phenylindoline-1-carbonyl)pyrrolidine-1-carboxylate (1.200 g, 2.84) in DCM (15 ml) was added Dess-Martin periodinane (2.40 g, 5.66 mmol) at 0° C. The reaction mixture was stirred at rt for 16 h. The resulting reaction mixture was filtered through celite bed and washed with DCM (50 ml). The combined filtrate was dried over Na₂SO₄, filtered and concentrated under reduced pressure. The obtained residue was purified by column chromatography (50% EtOAc in hexane) yielding tert-butyl (S)-2-(6-formyl-4-phenylindoline-1-carbonyl) pyrrolidine-1-carboxylate (0.60 g, 1.43 mmol). LCMS: Method C, 2.59 min, MS: ES+ 365.30 (M-56).

Step c. To a solution of tert-butyl (S)-2-(6-formyl-4-phenylindoline-1-carbonyl)pyrrolidine-1-carboxylate (0.60 g, 1.43 mmol) in ethanol (6 ml) was added glyoxal solution (40% w/w in water) (0.2 ml, 1.57 mmol) at 0° C. NH₄OH solution (25% aqueous solution) (0.9 ml, 13.1 mmol) was added to the reaction mixture at 0° C. The reaction mixture was stirred at rt for 46 h. The resulting reaction mixture was concentrated under reduced pressure. The obtained residue was purified by column chromatography (3% MeOH in DCM) yielding tert-butyl (S)-2-(6-(1H-imidazol-2-yl)-4-phenylindoline-1-carbonyl) pyrrolidine-1-carboxylate (0.150 g, 0.327 mmol). LCMS: Method C, 2.017 min, MS: ES+ 459.28.

Steps d, e. The title compound was synthesised from the intermediate above using a procedure similar to that described for steps b and c of Example 1. LCMS: Method H, 3.89 min, MS: ES+ 384.11; ¹H NMR (400 MHz, DMSO-d6) δ ppm 12.60 (s, 1H), 8.78 (s, 1H), 7.71 (d, J=1.6 Hz, 1H), 7.49-7.57 (m, 4H), 7.40-7.44 (m, 1H), 7.21 (s, 1H), 7.01 (s, 1H), 4.77-4.80 (m, 1H), 4.28-4.35 (m, 1H), 4.02-4.10 (m, 1H), 3.50-3.58 (m, 2H), 3.20-3.28 (m, 2H), 2.30-2.35 (m, 1H), 1.86-2.03 (m, 3H).

Example 91 (S)-2-(4-Phenyl-6-(4H-1,2,4-triazol-3-yl)indoline-1-carbonyl)pyrrolidine-1-carbonitrile

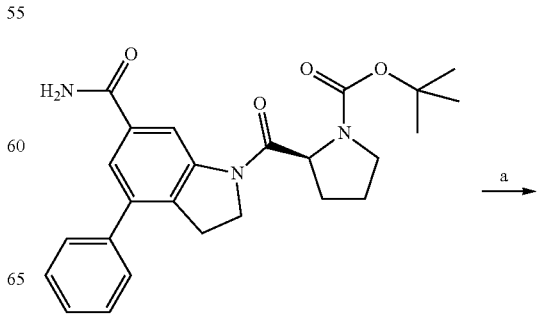

-continued

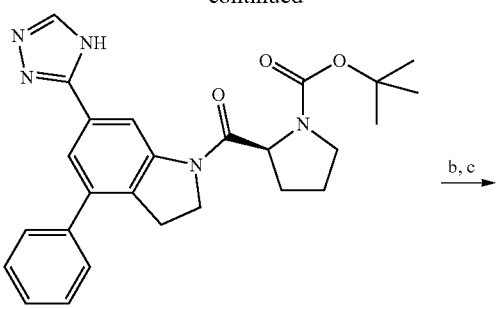

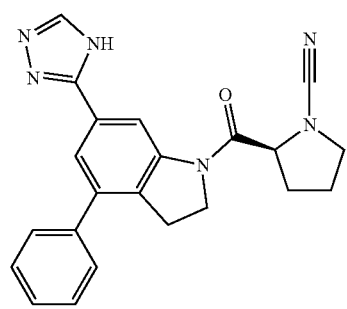

Step a. A mixture of tert-butyl (S)-2-(6-carbamoyl-4-phenylindoline-1-carbonyl)pyrrolidine-1-carboxylate (described as steps a-e of Example 85) (0.22 g, 0.505 mmol) and N,N-dimethylformamide dimethylacetal (10 ml) was heated at 90° C. for 3 h. The resulting reaction mixture was cooled to rt and concentrated under reduced pressure. The resulting residue was dissolved in acetic acid (10 ml) at rt. Hydrazine hydrate (0.05 ml, 1.01 mmol) was added to the reaction mixture at rt. The reaction mixture was heated at 80° C. for 2 h. The resulting reaction mixture was cooled to rt and concentrated under reduced pressure. The resulting residue was suspended in saturated NaHCO$_3$ solution (50 ml) and the resulting solid were filtered off under vacuum. The obtained solids were dried well yielding tert-butyl (S)-2-(4-phenyl-6-(4H-1,2,4-triazol-3-yl)indoline-1-carbonyl)pyrrolidine-1-carboxylate (0.19 g, 0.414 mmol). LCMS: Method C, 2.17 min, MS: ES+460.85; $^1$H NMR (400 MHz, DMSO-d6) δ ppm. 13.86 (br s, 1H), 8.82-8.85 (m, 1H), 8.38-8.43 (m, 1H), 7.74-7.75 (m, 1H), 7.48-7.56 (m, 4H), 7.40-7.44 (m, 1H), 4.52-4.59 (m, 1H), 4.15-31 (m, 2H), 3.16-3.50 (m, 4H), 2.23-2.33 (m, 1H), 1.83-1.94 (m, 3H), 1.27-1.40 (m, 9H).

Steps b, c. The title compound was synthesised from the intermediate above using a procedure similar to that described for steps b and c of Example 1. LCMS: Method J, 3.71 min, MS: ES+ 385.68; $^1$H NMR (400 MHz, DMSO-d6, 80° C.) δ ppm 14.10-14.4 (m, 1H), 8.84 (m, 1H), 8.63 (m, 1H), 7.78 (s, 1H), 7.42-7.52 (m, 5H), 4.75 (d, J=5.2 Hz, 1H), 4.29-4.35 (m, 1H), 4.09-4.16 (m, 1H), 3.45-3.62 (m, 2H), 3.16-3.28 (m, 2H), 2.31-2.40 (m, 1H), 1.93-2.07 (m, 3H).

Example 92 (S)-2-(6-(5-Methyl-4H-1,2,4-triazol-3-yl)-4-phenylindoline-1-carbonyl)pyrrolidine-1-carbonitrile

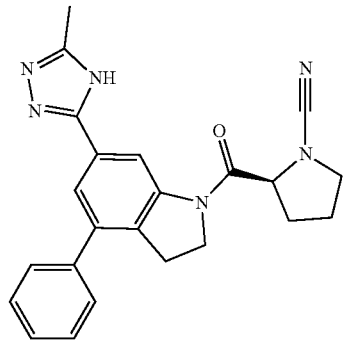 [SMILES: Cc1nnc(-c2cc(-c3ccccc3)c3c(c2)N(C(=O)[C@@H]2CCCN2C#N)CC3)[nH]1]

The title compound was synthesised using a procedure similar to that described for Example 91 using N,N-dimethylacetamide dimethylacetal in step a. LCMS: Method H, 3.70 min, MS: ES+ 399.08; $^1$H NMR (400 MHz, DMSO-d6) δ ppm 13.69 (s, 1H), 8.83 (s, 1H), 7.72 (s, 1H), 7.42-7.54 (m, 5H), 4.76-4.79 (m, 1H), 4.28-4.35 (m, 1H), 4.06-4.10 (m, 1H), 3.52-3.57 (m, 2H), 3.21-3.29 (m, 2H), 2.37 (s, 3H), 2.28-2.35 (m, 1H), 1.88-2.01 (m, 3H).

Example 93 (S)-2-(4-(4-Cyanophenyl)-6-(5-methyl-4H-1,2,4-triazol-3-yl)indoline-1-carbonyl)-pyrrolidine-1-carbonitrile The title compound was synthesised using a procedure similar to that described for Example 92. LCMS: Method J, 3.62 min, MS: ES+ 424.40; $^1$H NMR (400 MHz, DMSO-d6) δ ppm 13.71-14.15 (m, 1H), 8.84-8.81 (m, 1H), 7.95-8.01 (m, 2H), 7.73-7.78 (m, 3H), 4.78-4.79 (m, 1H), 4.30-4.33 (m, 1H), 4.06-4.10 (m, 1H), 3.52-3.57 (m, 2H), 3.16-3.25 (m, 2H), 2.41 (s, 3H), 2.28-2.37 (m, 1H), 1.89-2.00 (m, 3H).

Example 94 (S)-2-(4-(3-Cyanophenyl)-6-(5-methyl-4H-1,2,4-triazol-3-yl)indoline-1-carbonyl)-pyrrolidine-1-carbonitrile

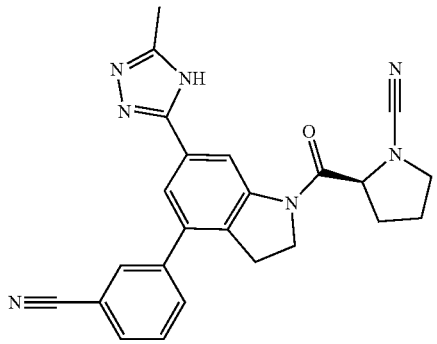 [SMILES: Cc1nnc(-c2cc(-c3cccc(C#N)c3)c3c(c2)N(C(=O)[C@@H]2CCCN2C#N)CC3)[nH]1]

The title compound was synthesised using a procedure similar to that described for Example 92. LCMS: Method H, 3.63 min, MS: ES+ 424.40; $^1$H NMR (400 MHz, DMSO-d6) δ ppm 13.71-14.09 (m, 1H), 8.83-8.86 (m, 1H), 8.02-8.05 (m, 1H), 7.87-7.90 (m, 2H), 7.69-7.73 (m, 2H), 4.78-4.79 (m, 1H), 4.32-4.36 (m, 1H), 4.06-4.08 (m, 1H), 3.50-3.57 (m, 2H), 3.21-3.31 (m, 2H), 2.41 (s, 3H), 2.30-2.35 (m, 1H), 1.89-2.01 (m, 3H).

Example 95 (2S,4S)-4-Fluoro-2-(4-(5-methyl-1H-pyrazol-4-yl)indoline-1-carbonyl)pyrrolidine-1-carbonitrile (Prepared According to Scheme 3)

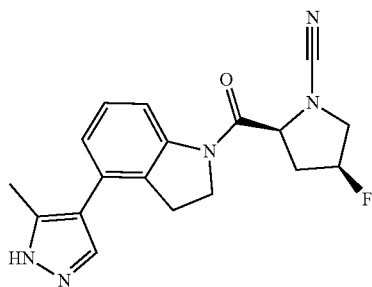 [SMILES: Cc1[nH]ncc1-c1cccc2c1CCN2C(=O)[C@@H]1C[C@H](F)CN1C#N]

The title compound was synthesised using a procedure similar to that described for Example 19 using (2S,4S)-1-(tert-butoxycarbonyl)-4-fluoro-2-pyrrolidinecarboxylic acid (CAS Number 203866-13-1) in step a. LCMS: Method H, 3.19 min, MS: ES+ 339.93; $^1$H NMR (400 MHz, DMSO-d6+drop of TFA) δ ppm 8.07 (d, J=6 Hz, 2H), 7.27 (t, J=8 Hz, 1H), 7.04 (d, J=7.2 Hz, 1H), 5.33 (d, J=53.2, 1H), 4.86 (d, J=10.0 Hz, 1H), 4.19-4.23 (m, 1H), 3.98-4.04 (m, 1H), 3.87-3.91 (m, 2H), 3.10-3.16 (m, 2H), 2.63-2.72 (m, 1H), 2.31-2.43 (m, 2H), 2.07 (s, 3H).

Example 96 N-(4-(1-(Cyano-L-prolyl)indolin-4-yl)pyridin-2-yl)acetamide

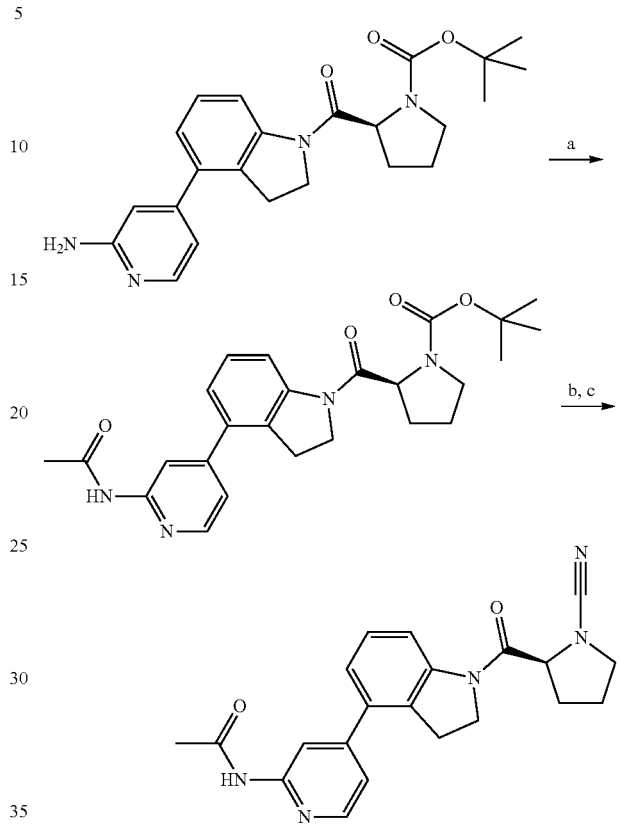

Step a. To a solution of tert-butyl (S)-2-(4-(2-aminopyridin-4-yl)indoline-1-carbonyl) pyrrolidine-1-carboxylate (prepared using a procedure similar to that described for steps a and b of Example 19) (0.228 g, 0.56 mmol) in DMF (5 ml) was added pyridine (0.06 ml, 0.73 mmol) at 0° C. Acetic anhydride (0.06 ml, 0.56 mmol) was added drop wise to the reaction mixture at 0° C. The reaction mixture was heated to 60° C. for 3 h. The resulting reaction mixture was poured into water (50 ml) and extracted with EtOAc (2×50 ml). The combined organic layer was washed with aqueous citric solution (50 ml) and water (50 ml). The organic phase was dried over Na$_2$SO$_4$, filtered and concentrated under reduced pressure. The resulting residue was triturated with n-pentane (3×10 ml), diethyl ether (2×5 ml) and dried under high vacuum yielding tert-butyl (S)-2-(4-(2-acetamidopyridin-4-yl) indoline-1-carbonyl) pyrrolidine-1-carboxylate (0.166 g, 0.37 mmol). LCMS: Method C, 2.06, MS: ES+ 451.80

Steps b, c. The title compound was synthesised from the intermediate above using a procedure similar to that described for steps b and c of Example 1. LCMS: Method C, 1.79 min, MS: ES+ 376.60; $^1$H NMR (400 MHz, DMSO-d6) δ ppm 10.62 (s, 1H), 8.37 (d, J=5.2 Hz, 1H), 8.20-8.22 (m, 2H), 7.36 (t, J=8 Hz, 1H), 7.22 (dd, J=7.6 Hz, 1H), 7.14-7.16 (m, 1H), 4.73-4.74 (m, 1H), 4.26-4.30 (m, 1H), 4.02-4.09 (m, 1H), 3.50-3.58 (m, 2H), 3.22-3.32 (m, 2H), 2.27-2.36 (m, 1H), 2.13 (s, 3H), 1.95-2.03 (m, 1H), 1.86-1.93 (m, 2H).

Example 97 (S)-2-(4-(5-(Trifluoromethyl)-1H-pyrazol-4-yl)-2,3-dihydro-H-pyrrolo[3,2-c]pyridine-1-carbonyl)pyrrolidine-1-carbonitrile (Prepared According to Scheme 5)

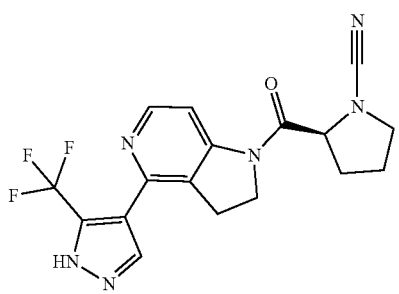 [SMILES: N#CN1CCC[C@H]1C(=O)N1CCc2c1ccnc2-c1cn[nH]c1C(F)(F)F]

The title compound was synthesised using a procedure similar to that described for Example 39 using 4-chloro-2,3-dihydro-1H-pyrrolo[3,2-c]pyridine (CAS Number 494767-29-2) and 4-(4,4,5,5-tetramethyl-1,3,2-dioxaborolan-2-yl)-3-(trifluoromethyl)-1H-pyrazole (CAS Number 1218790-40-9) in step a. LCMS: Method J, 2.78 min, MS: ES+ 377.64; $^1$H NMR (400 MHz, DMSO-d6) δ ppm 13.84 (s, 1H), 8.40 (d, J=5.2 Hz, 1H), 8.33 (s, 1H), 7.90 (d, J=5.2 Hz, 1H), 4.76-4.77 (m, 1H), 4.34-4.38 (m, 1H) 4.04-4.11 (m, 1H), 3.48-3.58 (m, 2H), 3.17-3.25 (m, 2H), 2.27-2.36 (m, 1H), 1.94-2.02 (m, 1H), 1.82-1.92 (m, 2H).

Example 98 1-(Cyano-L-prolyl)-N-methyl-4-(4-(trifluoromethyl)phenyl)indoline-6-carboxamide (Prepared According to Scheme 11)

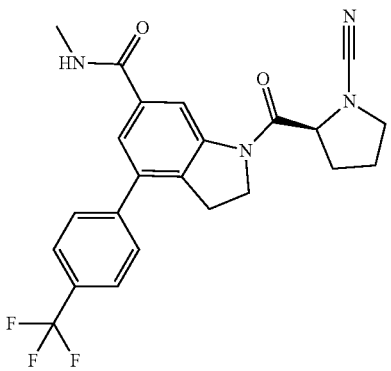 [SMILES: CNC(=O)c1cc(-c2ccc(C(F)(F)F)cc2)c2c(c1)N(C(=O)[C@@H]1CCCN1C#N)CC2]

Step a. To a solution of 4-bromo-1H-indole-6-carboxylic acid (8.00 g, 33.3 mmol) in DCM (150 ml) was added HATU (12.67 g, 33.3 mmol), DIPEA (14.0 ml, 80.0 mmol) and methylamine hydrochloride (2.25 g, 33.3 mmol). The reaction mixture was stirred at rt for 16 h. The reaction mixture was diluted with water (200 ml) and extracted with DCM (100 ml×3). The combined organic layers were washed with aqueous NaCl (150 ml), dried over Na$_2$SO$_4$, filtered and concentrated under reduced pressure to provide 4-bromo-N-methyl-1H-indole-6-carboxamide (8.00 g, crude) as an off-white solid. MS: ES+ 254.8.

Scheme 11

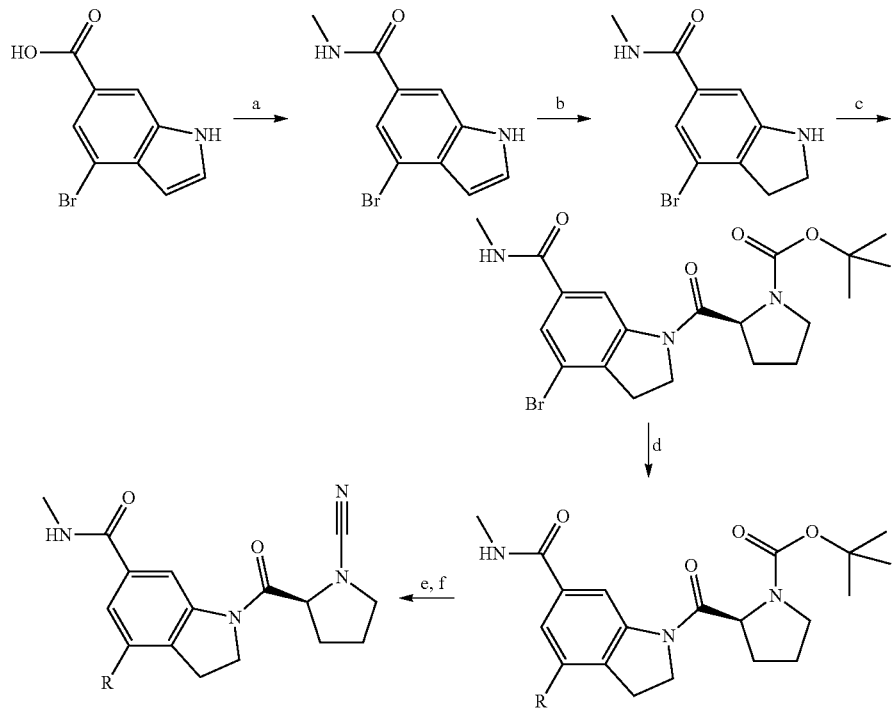

Reagents and conditions: a) Methylamine, HATU, DIEA, DCM, rt, 16 h b) Et$_3$SiH, TFA, 0° C., 4 h c) BOC-L-proline, HATU, DIPEA, DMF, rt, 16 h d) Pd(PPh$_3$)$_4$, Cs$_2$CO$_3$, 1,4-dioxane, water, 100° C., 16 h e) HCl/EtOAc, rt, 2 h f) cyanogen bromide, NaHCO$_3$, EtOH, rt, 16 h Step b. To a solution of 4-bromo-N-methyl-1H-indole-6-carboxamide (8.00 g, 31.6 mmol) in TFA (50 ml) was added triethylsilane (10.1 ml, 63.2 mmol) at 0° C., then the reaction mixture was stirred at 0° C. for 4 h. The reaction mixture was quenched by addition 1M HCl (300 ml) and washed with EtOAc (50 ml). The combined aqueous phase was adjusted to pH 10 by 50% NaOH, the mixture was extracted with EtOAc (300 ml×2), washed with brine (300 ml), dried over Na$_2$SO$_4$, filtered and concentrated under reduced pressure to provide 4-bromo-N-methyl-indoline-6-carboxamide (4.00 g, crude) as a yellow oil. MS: ES+ 254.8.

Step c. To a solution of 4-bromo-N-methyl-indoline-6-carboxamide (4.00 g, 15.7 mmol) in DMF (15 ml) was added DIPEA (3.56 ml, 20.4 mmol), HATU (5.96 g, 15.7 mmol) and (2S)-1-tert-butoxycarbonylpyrrolidine-2-carboxylic acid (3.38 g, 15.7 mmol). The reaction mixture was stirred at rt for 16 h. The reaction mixture was partitioned between EtOAc (300 ml) and water (200 ml). The organic phase was separated, washed with water (100 ml×2), dried over Na$_2$SO$_4$, filtered and concentrated under reduced pressure to give a residue. The residue was purified by column chromatography on silica gel (PE:EtOAc=10:1 to 1:1) to provide tert-butyl (2S)-2-[4-bromo-6-(methylcarbamoyl)indoline-1-carbonyl]pyrrolidine-1-carboxylate (3.00 g, 6.63 mmol, 42% yield) as a white solid. $^1$H NMR (400 MHz, DMSO-d6) δ ppm 8.54 (s, 1H), 8.49 (s, 1H), 7.68 (d, J=4.8 Hz, 1H), 4.47-4.54 (m, 1H), 4.21-4.32 (m, 2H), 3.16-3.21 (m, 2H), 2.76 (d, J=4.4 Hz, 3H), 2.27-2.31 (m, 1H), 1.83-1.91 (m, 3H), 1.40 (s, 3H), 1.25 (s, 6H).

Step d. To a solution of tert-butyl (2S)-2-[4-bromo-6-(methylcarbamoyl)indoline-1-carbonyl]pyrrolidine-1-carboxylate (0.2 mmol), (4-(trifluoromethyl)phenyl)boronic acid (0.2 mmol) and Cs$_2$CO$_3$ (0.6 mmol) in 1,4-dioxane (1 ml) and water (0.2 ml) was added Pd(PPh$_3$)$_4$ (0.2 eq) at rt under nitrogen. The reaction mixture was stirred at 100° C. for 16 h. The resulting mixture was concentrated under reduced pressure. The resulting residue was purified by prep-TLC (PE/EtOAc=1:1) yielding (S)-tert-butyl 2-(6-(methylcarbamoyl)-4-(4-(trifluoromethyl)phenyl)indoline-1-carbonyl)pyrrolidine-1-carboxylate. MS: ES+ 518.5.

Step e. To a solution of (S)-tert-butyl 2-(6-(methylcarbamoyl)-4-(4-(trifluoromethyl)phenyl)indoline-1-carbonyl)pyrrolidine-1-carboxylate in EtOAc (1 ml) was added HCl/EtOAc (4 M, 1 ml). The reaction mixture was stirred at rt for 2 h. The resulting mixture was concentrated under reduced pressure. The residue (S)—N-methyl-1-(pyrrolidine-2-carbonyl)-4-(4-(trifluoromethyl)phenyl)indoline-6-carboxamide was used for next step directly without further purification. MS: ES+ 418.4.

Step f. To a solution of (S)—N-methyl-1-(pyrrolidine-2-carbonyl)-4-(4-(trifluoromethyl) phenyl)indoline-6-carboxamide in EtOH (2 mL) was added cyanogen bromide (0.2 mmol) and NaHCO$_3$ (0.6 mmol). The reaction mixture was stirred at rt for 16 h. The resulting mixture was concentrated under reduced pressure. The crude was purified by preparative reverse phase HPLC (A: 0.078% CH$_3$COONH$_4$ in water, B: MeCN) yielding (54.3 mg, 0.127 mmol). LCMS: Method X, 2.78 min, MS: ES+ 442.9.

Compounds in Table 19 were synthesised using a procedure similar to that described for Example 98.

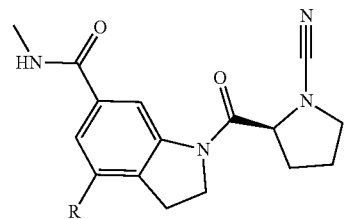

TABLE 19

| Example Number | R | Name | Boronic acid CAS Number | LCMS method | LCMS RT | MS ES+ |
|---|---|---|---|---|---|---|
| 99 | 3-cyanophenyl | 1-(cyano-L-prolyl)-4-(3-cyanophenyl)-N-methylindoline-6-carboxamide | 150255-96-2 | X | 2.69 | 400.1 |
| 100 | 4-cyanophenyl | 1-(cyano-L-prolyl)-4-(4-cyanophenyl)-N-methylindoline-6-carboxamide | 126747-14-6 | X | 2.69 | 400.0 |
| 101 | 4-chlorophenyl | 4-(4-chlorophenyl)-1-(cyano-L-prolyl)-N-methylindoline-6-carboxamide | 1679-18-1 | Y | 2.44 | 409.1 |
| 102 | m-tolyl | 1-(cyano-L-prolyl)-N-methyl-4-(m-tolyl)indoline-6-carboxamide4 | 17933-03-8 | X | 2.83 | 389.1 |
| 103 | 2-chlorophenyl | 4-(2-chlorophenyl)-1-(cyano-L-prolyl)-N-methylindoline-6-carboxamide | 3900-89-8 | X | 2.79 | 409.0 |

TABLE 19-continued

| Example Number | R | Name | Boronic acid CAS Number | LCMS method | LCMS RT | MS ES+ |
|---|---|---|---|---|---|---|
| 104 | 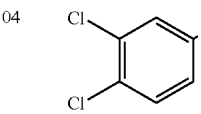 | 1-(cyano-L-prolyl)-4-(3,4-dichlorophenyl)-N-methylindoline-6-carboxamide | 151169-75-4 | Z | 2.51 | 443.1 |
| 105 | 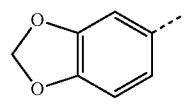 | 4-(benzo[d][1,3]dioxol-5-yl)-1-(cyano-L-prolyl)-N-methylindoline-6-carboxamide | 94839-07-3 | X | 2.26 | 419.3 |

Example 106 (S)—N-(5-(3-Chlorophenyl)isoxazol-3-yl)-1-cyano-N-methylpyrrolidine-2-carboxamide

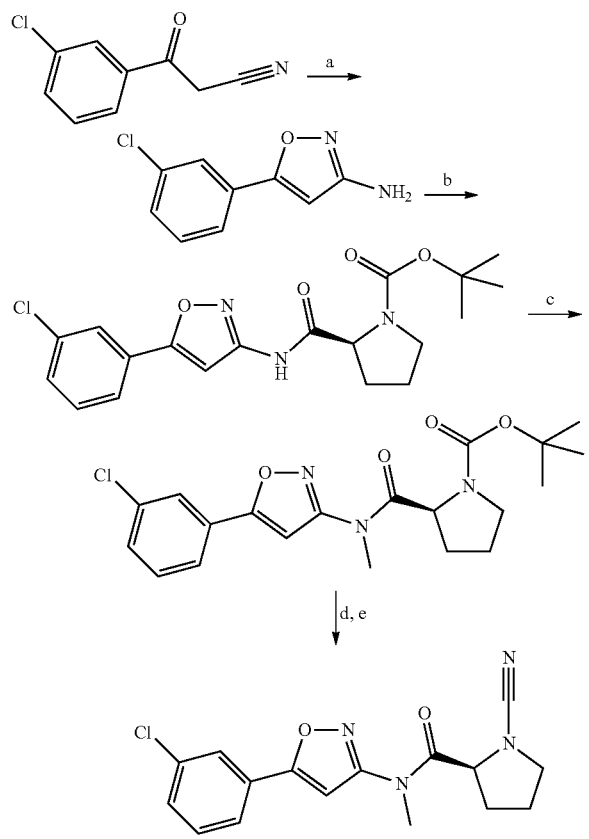

Step a. To a solution of 3-(3-chlorophenyl)-3-oxopropanenitrile (CAS Number 21667-62-9) (1 g, 5.59 mmol) in methanol:water (2:1, 15 ml) was added hydroxylamine hydrochloride (0.388 g, 5.59 mmol) and NaHCO$_3$ (0.516 g, 6.14 mmol) at rt. The reaction mixture was heated at 60° C. for 16 h. The reaction mixture was cooled to rt and treated with concentrated HCl (3 ml). The reaction mixture was heated at 60° C. for 1 h. The resulting reaction mixture was cooled to rt and concentrated under reduced pressure. The obtained residue was poured into dilute NaOH solution (100 ml) and extracted with CHCl$_3$ (3×20 ml). The combined organic phase was dried over Na$_2$SO$_4$, filtered and concentrated under reduced pressure. The resulting residue was purified by column chromatography (19% EtOAc in hexane) to yield 5-(3-chlorophenyl)isoxazol-3-amine (0.09 g, 0.463 mmol). LCMS: Method C, 2.06 min, MS: ES+ 195.12; $^1$H NMR (400 MHz, CDCl$_3$) δ ppm 7.72 (s, 1H), 7.61-7.63 (m, 1H), 7.37-7.42 (m, 2H), 6.13 (s, 1H), 4.04 (s, 2H).

Step b. To a solution of 5-(3-chlorophenyl)isoxazol-3-amine (0.12 g, 0.618 mmol) in pyridine (10 ml) was added BOC-L-proline (0.199 g, 0.927 mmol) at 0° C. and stirred for 20 min. POCl$_3$ (0.11 ml, 1.23 mmol) was added drop wise to the reaction mixture at 0° C. The resulting reaction mixture was stirred at 0° C. for 15 min and then allowed to stir at rt for 30 min. The resulting reaction mixture was poured into water (60 ml) and extracted with EtOAc (2×20 ml). The combined organic phase was dried over Na$_2$SO$_4$, filtered and concentrated under reduced pressure yielding tert-butyl (S)-2-((5-(3-chlorophenyl)isoxazol-3-yl)carbamoyl)pyrrolidine-1-carboxylate (0.493 g, quantitative). LCMS: Method C, 2.35 min, MS: ES+ 392.41. This material was used directly for the next step without further purification.

Step c. To a solution of tert-butyl (S)-2-((5-(3-chlorophenyl) isoxazol-3-yl)carbamoyl) pyrrolidine-1-carboxylate (0.200 g, 0.511 mmol) in DMF (10 ml) was added NaH (60% dispersion in paraffin oil) (0.030 g, 1.27 mmol) at 0° C. and stirred for 15 min. Methyl iodide (0.072 g, 0.51 mmol) was added drop wise to reaction mixture at 0° C. and stirred for 30 min. The resulting reaction mixture was poured into water (60 ml) and extracted with EtOAc (2×20 ml). The combined organic phase was dried over Na$_2$SO$_4$, filtered and concentrated under reduced pressure. The resulting residue was purified by column chromatography (22% EtOAc in hexane) yielding tert-butyl (S)-2-((5-(3-chlorophenyl)isoxazol-3-yl)(methyl)carbamoyl) pyrrolidine-1-carboxylate (0.082 g, 0.20 mmol). LCMS: Method C, 2.68 min, MS: ES+ 406.30.

Steps d, e. The title compound was synthesised from the intermediate above using a procedure similar to that described for steps b and c of Example 1. LCMS: Method J, 4.49 min, MS: ES+ 331.24; $^1$H NMR (400 MHz, DMSO-d6) δ ppm 8.02 (s, 1H), 7.87-7.90 (m, 1H), 7.56-7.62 (m, 3H), 4.96-4.98 (m, 1H), 3.49-3.53 (m, 2H), 3.40 (s, 3H), 2.32-2.33 (m, 1H), 1.79-1.96 (m, 3H).

Example 107 (S)-1-Cyano-N-(5-(3-cyanophenyl)isoxazol-3-yl)-N-methylpyrrolidine-2-carboxamide

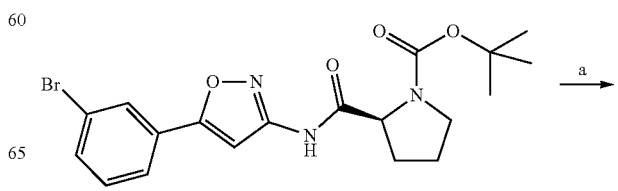

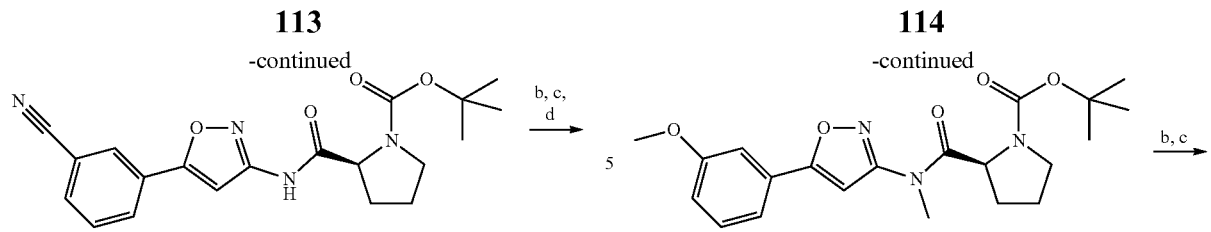

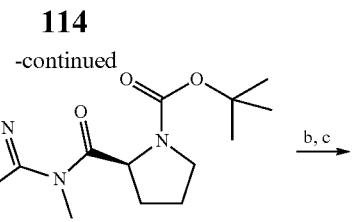

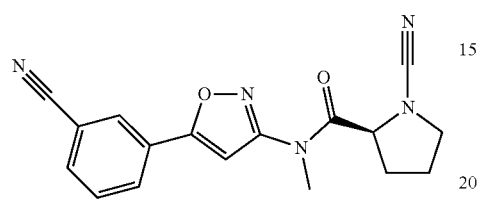

Step a. A solution tert-butyl (S)-2-((5-(3-bromophenyl)isoxazol-3-yl)carbamoyl)pyrrolidine-1-carboxylate (prepared using a procedure similar to that described for steps a and b of Example 106) (0.170 g, 0.39 mmol) in DMA (10 ml) was degassed at rt for 15 min. Zinc dust (0.005 g, 0.07 mmol), Zn(CN)$_2$ (0.036 g, 0.31 mmol), Pd$_2$(dba)$_3$ (0.007 g, 0.007 mmol) and 1,1'-ferrocenediyl-bis(diphenylphosphine) (0.008 g, 0.01 mmol) were added to the reaction mixture at rt. The reaction mixture was heated at 140° C. for 4 h. The resulting reaction mixture was cooled to rt and poured into water (60 ml). The obtained mixture was extracted with EtOAc (3×20 ml). The combined organic phase was dried over Na$_2$SO$_4$, filtered and concentrated under reduced pressure. The resulting residue was purified by column chromatography (25% EtOAc in hexane) to yield tert-butyl (S)-2-((5-(3-cyanophenyl)isoxazol-3-yl)carbamoyl) pyrrolidine-1-carboxylate (0.080 g, 0.20 mmol). LCMS: Method C, 2.30 min, MS: ES+ 383.48.

Steps b-d. The title compound was synthesised from the intermediate above using a procedure similar to that described for steps c-e of Example 106. LCMS: Method J, 3.98 min, MS: ES+ 322.09; $^1$H NMR (400 MHz, DMSO-d6) δ ppm 8.46 (s, 1H), 8.24 (d, J=8.0 Hz, 1H), 8.00 (d, J=8.0 Hz, 1H), 7.75-7.79 (t, J=8.0 Hz, 1H), 7.71-7.75 (m, 1H), 4.99-5.00 (m, 1H), 3.50-3.53 (t, J=6.8 Hz, 2H), 3.29-3.44 (m, 3H), 2.25-2.39 (m, 1H), 1.80-1.99 (m, 3H).

Example 108 (S)-1-Cyano-N-(5-(3-methoxyphenyl)isoxazol-3-yl)-N-methylpyrrolidine-2-carboxamide

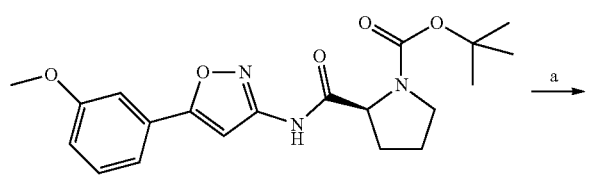

Step a. To a solution of tert-butyl (S)-2-((5-(3-methoxyphenyl)isoxazol-3-yl)carbamoyl) pyrrolidine-1-carboxylate (prepared using a procedure similar to that described for steps a and b of Example 106) (0.220 g, 0.56 mmol) in DMF (8 ml) was added K$_2$CO$_3$ (0.235 g, 1.70 mmol) at 0° C. The reaction mixture was stirred at 0° C. for 20 min. Methyl iodide (0.080 g, 0.56 mmol) was added drop wise and the reaction mixture was stirred at 0° C. for 15 min and then rt for 1 h. The resulting reaction mixture was poured into water (50 ml) and extracted with EtOAc (2×20 ml). The combined organic phase was dried over Na$_2$SO$_4$, filtered and concentrated under reduced pressure. The resulting residue was purified by column chromatography (25% EtOAc in hexane) yielding tert-butyl (S)-2-((5-(3-methoxyphenyl)isoxazol-3-yl)(methyl)carbamoyl)pyrrolidine-1-carboxylate (0.150 g, 0.37 mmol). LCMS: Method C, 2.44 min, MS: ES+ 402.51.

Steps b, c. The title compound was synthesised from the intermediate above using a procedure similar to that described for steps b and c of Example 1. LCMS: Method J, 4.06 min, MS: ES+ 327.38; $^1$H NMR (400 MHz, DMSO-d6) δ ppm 7.43-7.51 (m, 4H), 7.09-7.12 (m, 1H), 4.95-4.97 (m, 1H), 3.85 (s, 3H), 3.49-3.53 (m, 2H), 3.39 (s, 3H), 2.29-2.32 (m, 1H), 1.80-1.99 (m, 3H).

Example 109 (S)—N-(4-(3-Chlorophenyl)thiazol-2-yl)-1-cyano-N-ethylpyrrolidine-2-carboxamide

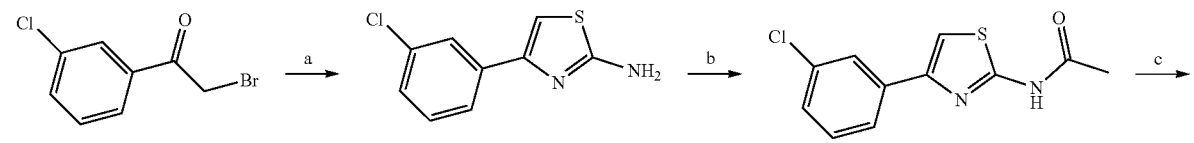

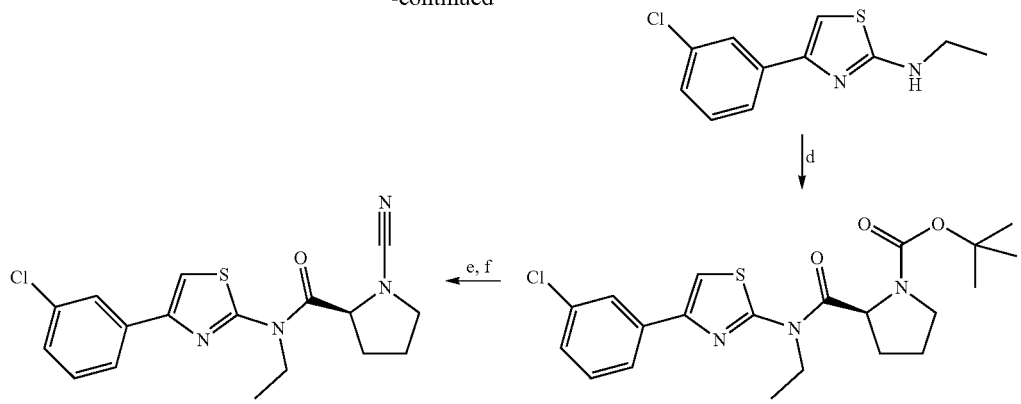

Step a. To a solution of 2-bromo-1-(3-chlorophenyl)ethan-1-one (CAS Number 41011-01-2) (0.3 g, 1.28 mmol) in ethanol (5 ml) was added thiourea (0.108 g, 1.41 mmol) at rt. The resulting reaction mixture was stirred at rt for 1 h. The reaction mixture was concentrated under reduced pressure. The obtained residue was poured into 1M NaOH solution (70 ml) and extracted with DCM (2×30 ml). The combined organic phase was dried over $Na_2SO_4$, filtered and concentrated under reduced pressure yielding 4-(3-chlorophenyl) thiazol-2-amine (0.350 g, quantitative). LCMS: Method C, 2.03 min; MS: ES+ 213.04. This material was used directly for the next step without further purification.

Step b. To a solution of 4-(3-chlorophenyl) thiazol-2-amine (0.350 g, 1.66 mmol) in THF (7 ml) was added acetic anhydride (0.682 g, 6.66 mmol) at rt. The reaction mixture was heated at 80° C. for 18 h. The reaction mixture was cooled to rt and diluted with EtOAc (65 ml). The reaction mixture was washed with saturated $NaHCO_3$ (50 ml), dried over $Na_2SO_4$, filtered and concentrated under reduced pressure yielding N-(4-(3-chlorophenyl)thiazol-2-yl)acetamide (0.35 g, 1.38 mmol). LCMS: Method C, 2.26 min, MS: ES+ 253.11; $^1$H NMR (400 MHz, DMSO-d6) δ ppm 12.29 (s, 1H), 7.95 (t, J=2 Hz, 1H), 7.86 (d, J=8 Hz, 1H), 7.76 (s, 1H), 7.46 (t, J=7.6 Hz, 1H), 7.37-7.39 (m, 1H), 2.16 (s, 3H).

Step c. To a solution of N-(4-(3-chlorophenyl) thiazol-2-yl) acetamide (0.350 g, 1.38 mmol) in THF (7 ml) was added lithium aluminium hydride (2 M in THF) (2.08 ml, 4.16 mmol) drop wise at 0° C. The reaction mixture was heated at 80° C. for 1.5 h. The resulting reaction mixture was cooled to rt and poured into saturated $NH_4Cl$ solution (50 ml). The obtained mixture was extracted with EtOAc (2×25 ml). The combined organic phase was dried over $Na_2SO_4$, filtered and concentrated under reduced pressure to yield 4-(3-chlorophenyl)-N-ethylthiazol-2-amine (0.240 g, 1.0 mmol). LCMS: Method C, 2.53 min, MS: ES+ 239.15.

Steps d-f. The title compound was synthesised from the intermediate above using a procedure similar to that described for Example 1. LCMS: Method H, 5.38 min, MS: ES+ 360.95; $^1$H NMR (400 MHz, DMSO-d6) δ ppm 7.99-8.00 (m, 1H), 7.92-7.93 (m, 2H), 7.46-7.50 (t, J=7.6 Hz, 1H), 7.39-7.41 (m, 1H), 5.06-5.09 (m, 1H), 4.44-4.47 (m, 1H), 4.10-4.15 (m, 1H), 3.54-3.58 (m, 2H), 2.40-2.45 (m, 1H), 1.88-2.03 (m, 3H), 1.36-1.39 (t, J=13.6 Hz, 3H).

Example 110 (S)-1-Cyano-N-(4-(5-cyanopyridin-3-yl)thiazol-2-yl)-N-methylpyrrolidine-2-carboxamide

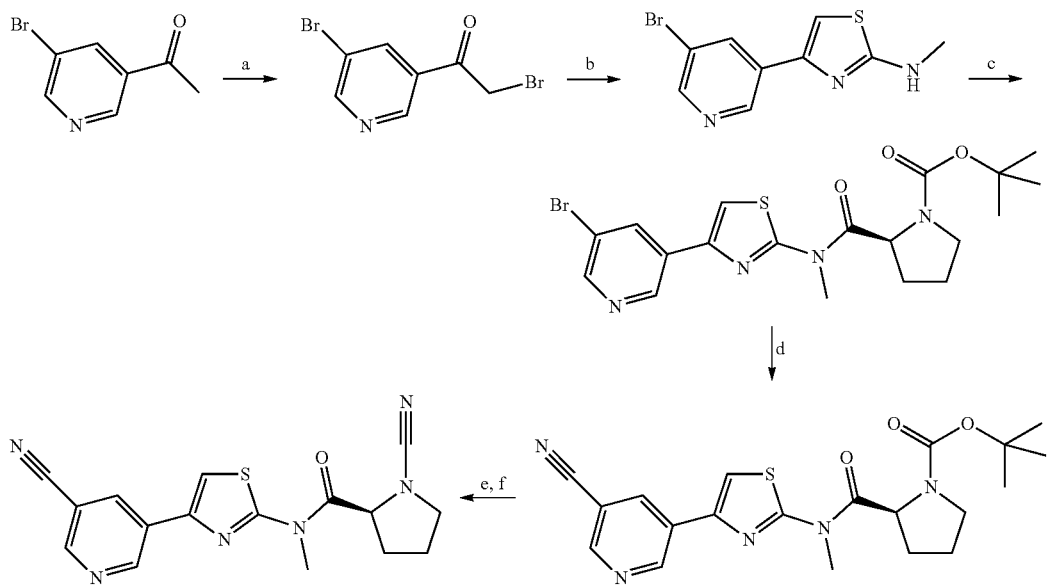

Step a. To a solution of 1-(5-bromopyridin-3-yl)ethan-1-one (CAS Number 38940-62-4) (0.75 g, 3.75 mmol)) in HBr (33% solution in acetic acid) (7.5 ml, 10 vol.) was added bromine (0.59 g, 3.75 mmol) in acetic acid (7.5 ml) drop wise at 0° C. The resulting reaction mixture was stirred at rt for 1 h. The reaction mixture was filtered and the obtained solids were neutralized by quickly pouring in saturated NaHCO$_3$ solution at rt. The obtained mixture was extracted with EtOAc (3×50 ml) and washed with brine (50 ml). The combined organic phase was dried over Na$_2$SO$_4$, filtered and concentrated under reduced pressure yielding 2-bromo-1-(5-bromopyridin-3-yl) ethan-1-one (0.91 g, 3.26 mmol). LCMS: Method C, 2.12 min, MS: ES+ 279.93.

Step b. To a solution 2-bromo-1-(5-bromopyridin-3-yl) ethan-1-one (0.91 g, 3.26 mmol) in EtOH (14 ml) was added N-methylthiourea (0.35 g, 3.91 mmol) at rt. The reaction mixture was heated at 80° C. for 1 h. The reaction mixture was concentrated under reduced pressure and the obtained residue suspended in saturated NaHCO$_3$ solution (50 ml). The suspension was extracted with EtOAc (2×100 ml) and the combined organic phase dried over Na$_2$SO$_4$, filtered and concentrated under reduced pressure to yield 4-(5-bromopyridin-3-yl)-N-methylthiazol-2-amine (0.9 g, 3.33 mmol). LCMS: Method C, 1.94 min, MS: ES+ 272.21.

Step c. To a solution of BOC-L-proline (0.86 g, 4.0 mmol) in DCM (27 ml) was added HATU (1.9 g, 5.0 mmol) and TEA (1.4 ml, 10.0 mmol) at rt and stirred for 30 min. 4-(5-Bromopyridin-3-yl)-N-methylthiazol-2-amine (0.9 g, 3.33 mmol) was added to a reaction mixture and stirred for 16 h. The resulting reaction mixture was poured into water (100 ml) and extracted with EtOAc (3×50 ml). The combined organic phase was washed with brine solution (50 ml), dried over Na$_2$SO$_4$, filtered and concentrated under reduced pressure. The resulting residue was purified by column chromatography (10% EtOAc in hexane) to yield tert-butyl (S)-2-((4-(5-bromopyridin-3-yl)thiazol-2-yl)(methyl)carbamoyl)pyrrolidine-1-carboxylate (1.15 g, 2.46 mmol). LCMS: Method C, 2.48 min, MS: ES+ 469.56.

Step d. A solution (S)-2-((4-(5-bromopyridin-3-yl)thiazol-2-yl)(methyl)carbamoyl)pyrrolidine-1-carboxylate (1.0 g, 2.13 mmol) in DMA (15 ml) was degassed at rt for 15 min. Zn(CN)$_2$ (0.25 g, 2.13 mmol), zinc dust (0.014 g, 0.21 mmol), Pd$_2$(dba)$_3$ (0.098 g, 0.10 mmol) and 1,1'-bis(diphenylphosphino)ferrocene (0.12 g, 0.21 mmol) were added to the reaction mixture at rt. The reaction mixture was heated at 130° C. for 2 h. The resulting reaction mixture was cooled to rt and poured into water (100 ml). The obtained mixture was extracted with EtOAc (3×50 ml). The combined organic phase was washed with brine solution (50 ml), dried over Na$_2$SO$_4$, filtered and concentrated under reduced pressure. The resulting residue was purified by column chromatography (30% EtOAc in hexane) to yield tert-butyl (S)-2-((4-(5-cyanopyridin-3-yl) thiazol-2-yl)(methyl)carbamoyl)pyrrolidine-1-carboxylate (0.62 g, 1.49 mmol). LCMS: Method C, 2.20 min, MS: ES+ 414.65.

Steps e, f. The title compound was synthesised from the intermediate above using a procedure similar to that described for steps b and c of Example 1. LCMS: Method H, 3.84 min, MS: ES+ 339.06; 1H NMR (400 MHz, DMSO-d6) δ ppm 9.45 (d, J=2.4 Hz, 1H), 8.98 (d, J=2.0 Hz, 1H), 8.83 (t, J=2.0 Hz, 1H), 8.12 (s, 1H), 5.15-5.18 (m, 1H), 3.78 (s, 3H), 3.53-3.57 (m, 2H), 2.36-2.45 (m, 1H), 2.02-2.09 (m, 1H), 1.91-1.97 (m, 1H), 1.82-1.91 (m, 1H).

Example 111 (S)-2-(1-Phenyl-1,4,5,6-tetrahydropyrrolo[3,2-c]pyrazole-4-carbonyl)pyrrolidine-1-carbonitrile

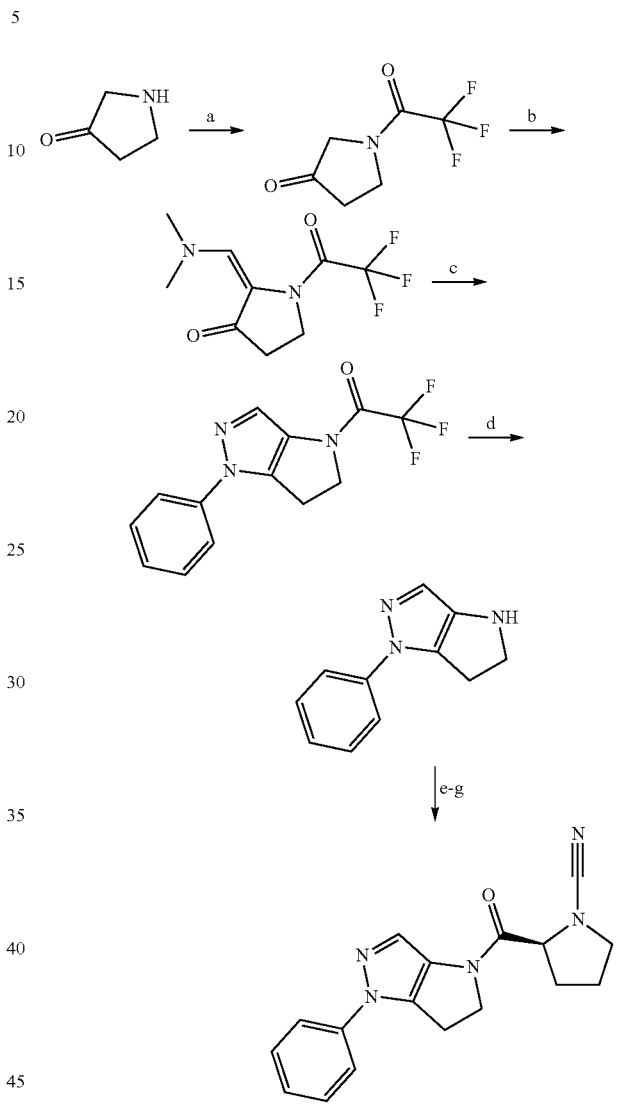

Step a. A mixture of pyrrolidin-3-one (2.5 g, 20.6 mmol) and trifluoroacetic anhydride (12.5 ml) was stirred at rt for 1.5 h. The resulting reaction mixture was concentrated under reduced pressure. The obtained residue was azeotropically distilled with DCM (2×15 ml) and dried under reduced pressure to yield 1-(2,2,2-trifluoroacetyl)pyrrolidin-3-one (4.0 g, 2.20 mmol). This material was used for the next step without further purification.

Step b. To a solution 1-(2,2,2-trifluoroacetyl)pyrrolidin-3-one (4.0 g, 2.20 mmol) in 1,4-dioxane (20 ml) was added N,N-dimethylformamide dimethylacetal (5.9 ml, 4.41 mmol) at rt. The reaction mixture was heated at 90° C. for 3 h. The resulting reaction mixture was cooled to rt and concentrated under reduced pressure. The obtained residue was purified by column chromatography (40% EtOAc in hexane) to yield (E)-2-((dimethylamino) methylene)-1-(2,2,2-trifluoroacetyl)pyrrolidin-3-one (1.59 g, 6.73 mmol). LCMS: Method C, 1.72 min, MS: ES+ 237.58.

Step c. To a solution of (E)-2-((dimethylamino) methylene)-1-(2,2,2-trifluoroacetyl)pyrrolidin-3-one (1.58 g, 6.69 mmol) in glacial acetic acid (20 ml) was added phenylhydrazine (0.950 g, 8.03 mmol) at rt. The reaction mixture was heated at 110° C. for 4 h. The resulting reaction mixture was cooled to rt and poured into water (80 ml). The obtained mixture was neutralized with solid Na$_2$CO$_3$ and extracted with EtOAc (5×150 ml). The combined organic phase was dried over Na$_2$SO$_4$, filtered and concentrated under reduced pressure. The resulting residue was purified by column chromatography (11% EtOAc in hexane) yielding 2,2,2-trifluoro-1-(1-phenyl-5,6-dihydropyrrolo[3,2-c]pyrazol-4 (1H)-yl)ethan-1-one (0.63 g, 2.24 mmol). LCMS: Method C, 2.21 min, MS: ES+ 282.51.

Step d. To a solution 2,2,2-trifluoro-1-(1-phenyl-5,6-dihydropyrrolo[3,2-c]pyrazol-4(1H)-yl)ethan-1-one (0.050 g, 0.17 mmol) in THF (5 ml) was added NaOH (0.021 g, 0.53 mmol) at rt. The reaction mixture was stirred at rt for 2 h. The resulting reaction mixture was concentrated under vacuum to yield 1-phenyl-1,4,5,6-tetrahydropyrrolo[3,2-c]pyrazole (0.033 g, 0.17 mmol). LCMS: Method C, 1.51 min, MS: ES+ 186.19.

Steps e-g. The title compound was synthesised from the intermediate above using a procedure similar to that described for Example 1. LCMS: Method J, 3.55 min, MS: ES+ 308.26; $^1$H NMR (400 MHz, DMSO-d6) δ ppm 7.66-7.70 (m, 2H), 7.60 (s, 1H), 7.49-7.54 (m, 2H), 7.30-7.35 (m, 1H), 4.71-4.72 (m, 1H), 4.61-4.64 (m, 1H), 4.45-4.58 (m, 1H), 3.38-3.60 (m, 4H), 2.25-2.29 (m, 1H), 1.81-1.96 (m, 3H).

Example 143 (S)-1-cyano-N-(4-(6-cyanopyridin-2-yl)-5-ethylthiazol-2-yl)-N-methylpyrrolidine-2-carboxamide

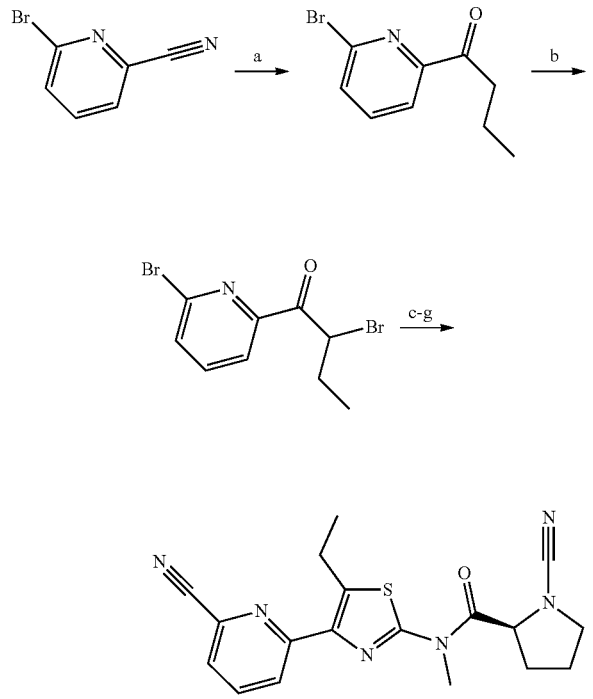

Step a. To a stirred solution of 2-cyano-6-bromopyridine (CAS Number 122918-25-6) (2.0 g, 10.93 mmol) in THF (250 ml) was added drop wise propylmagnesium bromide solution (27% in THF) (4.0 g, 27.3 mmol) at −20° C. for 30 min. The reaction mixture was stirred at rt for 1 h. The reaction mixture was cooled to 0° C. and diluted with saturated ammonium chloride (100 ml) solution and extracted with EtOAc (3×100 ml). The combined organic phase was separated, dried over Na$_2$SO$_4$, filtered and concentrated under reduced pressure. The resulting crude material was purified by column chromatography (5% EtOAc in hexane) yielding 1-(6-bromopyridin-2-yl)butan-1-one (1.1 g, 4.846 mmol). LCMS: Method C, 2.21 min, MS: ES+ 228.3, 230.3

Step b. To a stirred solution of 1-(6-bromopyridin-2-yl)butan-1-one (0.9 g, 3.96 mmol) in THF (15 ml) was added trimethylphenylammonium tribromide (CAS Number 4207-56-1) (1.6 g, 4.36 mmol) at rt. The reaction mixture was heated to 60° C. for 2 h. The resulting reaction mixture was cooled to rt, quenched with water (120 ml) and extracted with EtOAc (3×50 ml). The combined organic phase was separated, dried over Na$_2$SO$_4$, filtered and concentrated under reduced pressure yielding 2-bromo-1-(6-bromopyridin-2-yl)butan-1-one (1.0 g, 3.26 mmol). This material was directly used for next step without further purification. LCMS: Method C, 2.74 min, MS: ES+ 308.0, 310.0

Steps c-g. The title compound was synthesised from the intermediate above using a procedure similar to that described for Example 110. LCMS: Method H, 4.80 min, MS: ES+ 367.0; $^1$H NMR (400 MHz, DMSO-d6) δ ppm 8.34-8.37 (dd, J=0.8 Hz, 8.0 Hz, 1H), 8.14 (t, J=8.0 Hz, 1H), 7.95-7.98 (dd, J=0.8 Hz, 7.6 Hz, 1H), 5.13-5.15 (dd, J=4.0 Hz, 8.4 Hz, 1H), 3.71 (s, 3H), 3.53-3.57 (m, 2H), 3.26-3.36 (m, 1H), 2.33-2.40 (m, 2H), 2.04-2.05 (m, 1H), 1.92-1.96 (m, 1H), 1.82-1.86 (m, 1H), 1.30 (t, J=7.2 Hz, 3H).

Example 144 (S)-1-cyano-N-(4-(6-cyanopyridin-2-yl)-5-methylthiazol-2-yl)-N-methylpyrrolidine-2-carboxamide

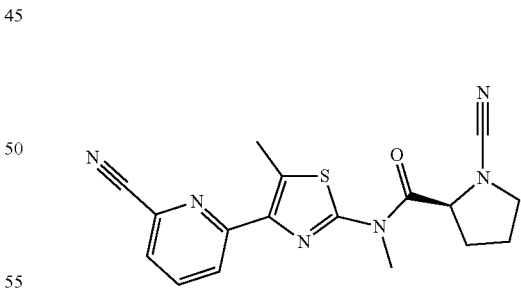

The title compound was synthesised using a procedure similar to that described for Example 143. LCMS: Method H, 4.58 min, MS: ES+ 353.0; $^1$H NMR (400 MHz, DMSO-d6+drop of TFA) δ ppm 8.35-8.37 (dd, J=0.8 Hz, 8.0 Hz, 1H), 8.14 (t, J=7.6 Hz, 1H), 7.95-7.97 (dd, J=0.8 Hz, 7.6 Hz, 1H), 5.13-5.16 (dd, J=4.0 Hz, 8.4 Hz, 1H), 3.711 (s, 3H), 3.53-3.59 (m, 2H), 2.76 (s, 3H), 2.33-2.47 (m, 1H), 2.03-2.08 (m, 1H), 1.91-1.97 (m, 1H), 1.78-1.85 (m, 1H).

Example 145 (S)-1-cyano-N-(4-(3-(methoxymethyl)phenyl)thiazol-2-yl)-N-methylpyrrolidine-2-carboxamide

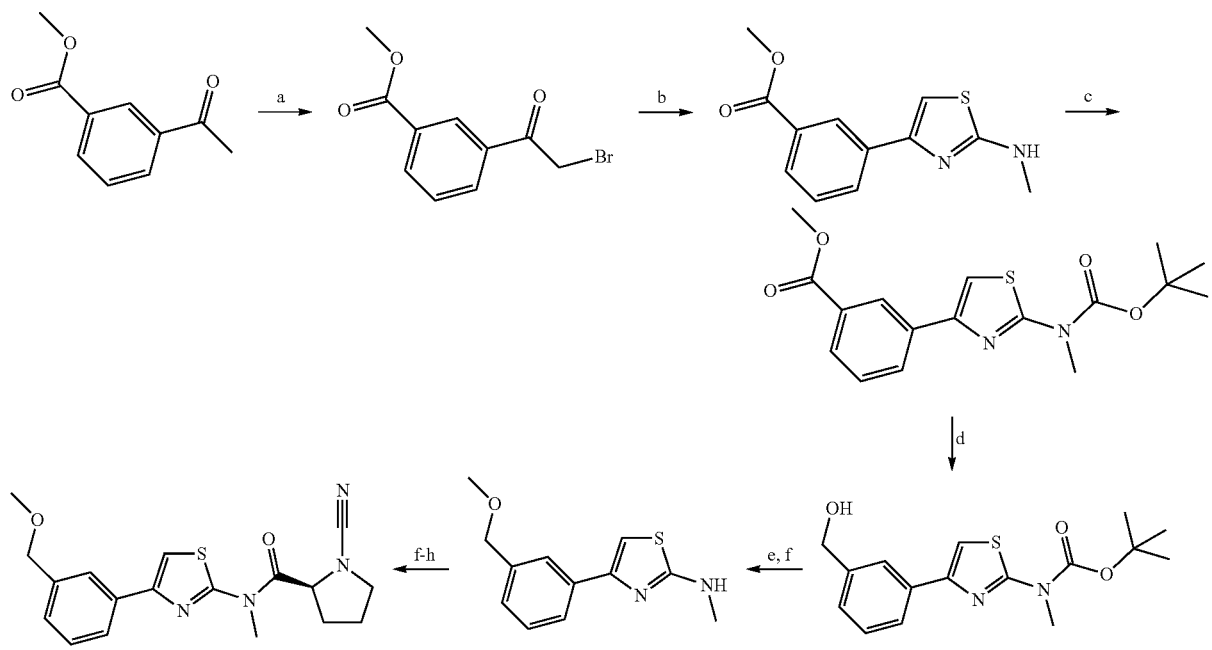

Step a. To a stirred solution of methyl 3-acetylbenzoate (CAS Number 21860-07-1) (0.7 g, 3.93 mmol) in chloroform (15 ml) was added bromine (0.69 g, 4.32 mmol) drop wise and 33% HBr in acetic acid (5 drops) at 0° C. The resulting reaction mixture was stirred at rt for 16 h. The reaction mixture was carefully quenched with saturated NaHCO$_3$ (50 ml) solution and extracted with EtOAc (2×100 ml). The combined organic phase was washed with brine (50 ml). The organic phase was separated, dried over Na$_2$SO$_4$, filtered and concentrated under reduced pressure yielding methyl 3-(2-bromoacetyl)benzoate (0.988 g, 3.84 mmol). This material was directly used for the next step without further purification.

Step b. To a stirred solution of 3-(2-bromoacetyl)benzoate (0.95 g, 3.695 mmol) in EtOH (10 ml) was added N-methylthiourea (0.366 g, 4.065 mmol) at rt. The reaction mixture was heated at 80° C. for 5 h. The resulting reaction mixture was cooled to rt, excess solvent was distilled off and the obtained residue was dissolved in water (50 ml). The reaction mixture was extracted with EtOAc (100 ml) and 10% MeOH in DCM (3×100 ml). The combined organic phase was washed with brine (50 ml). The organic phase was separated, dried over Na$_2$SO$_4$, filtered and concentrated under reduced pressure. The resulting crude material was purified by flash chromatography (27% EtOAc in hexane) yielding methyl 3-(2-(methylamino)thiazol-4-yl)benzoate (0.65 g, 2.01 mmol). LCMS: Method C, 1.82 min, MS: ES+ 249.28; $^1$H NMR (400 MHz, DMSO-d6) δ ppm 8.43 (t, J=1.6 Hz, 1H), 8.09-8.11 (m, 1H), 7.85-7.87 (m, 1H), 7.68 (q, J=4.8 Hz, 1H), 7.53 (t, J=8.0 Hz, 1H), 7.23 (s, 1H), 3.88 (s, 3H), 2.88 (d, J=4.8 Hz, 3H).

Step c. To a stirred solution of methyl 3-(2-(methylamino)thiazol-4-yl)benzoate (0.4 g, 1.61 mmol) in THF (5 ml) was added TEA (0.489 g, 4.833 mmol) and DMAP (0.019 g, 0.161 mmol) at rt. BOC anhydride (0.702 g, 3.22 mmol) was added slowly to the reaction mixture at rt. The reaction mixture was stirred at rt for 5 h. The resulting reaction mixture was poured into water (50 ml), extracted with EtOAc (2×50 ml). The combined organic phase was separated, dried over Na$_2$SO$_4$, filtered and concentrated under reduced pressure. The resulting crude material was purified by flash chromatography (6% EtOAc in hexane) yielding methyl 3-(2-((tert-butoxycarbonyl) (methyl)amino)thiazol-4-yl)benzoate (0.53 g, 1.521 mmol). LCMS: Method C, 2.84 min, MS: ES+349.38; $^1$H NMR (400 MHz, DMSO-d6) δ ppm 8.48 (t, J=5.6 Hz, 1H), 8.18-8.21 (m, 1H), 7.90-7.92 (m, 1H), 7.82 (s, 1H), 7.59 (t, J=7.6 Hz, 1H), 3.89 (s, 3H), 3.58 (s, 3H), 1.56 (s, 9H).

Step d. To a stirred solution of methyl 3-(2-((tert-butoxycarbonyl) (methyl)amino)thiazol-4-yl)benzoate (0.5 g, 1.435 mmol) in THF (10 ml) was added lithium aluminium hydride (1M in THF) (1.58 ml, 1.58 mmol) drop wise at −78° C. The resulting reaction mixture was stirred at −40° C. for 2 h. The resulting reaction mixture was quenched with saturated Na$_2$SO$_4$ solution (10 ml) at −30° C., diluted with water (50 ml) and extracted with EtOAc (3×50 ml). The combined organic phase was washed with brine (30 ml). The organic phase was separated, dried over Na$_2$SO$_4$, filtered and concentrated under reduced pressure yielding methyl 3-(2-((tert-butoxycarbonyl) (methyl)amino)thiazol-4-yl)benzoate (0.44 g, 1.37 mmol). This material was directly used for the next step without further purification. LCMS: Method C, 2.35 min, MS: ES+ 321.33; $^1$H NMR (400 MHz, DMSO-d6) δ ppm 7.88 (s, 1H), 7.78 (d, J=7.6 Hz, 1H), 7.63 (s, 1H), 7.37 (t, J=7.6 Hz, 1H), 7.26 (d, J=7.6 Hz, 1H), 5.25 (t, J=6.0 Hz, 1H), 4.54 (d, J=6.0 Hz, 2H), 3.57 (s, 3H), 1.55 (s, 9H).

Step e. To a stirred solution of methyl 3-(2-((tert-butoxycarbonyl) (methyl)amino)thiazol-4-yl)benzoate (0.4 g, 1.25 mmol) in DCM (5 ml) was added trimethyloxonium tetrafluoroborate (CAS Number 420-37-1) (0.203 g, 1.37 mmol) at rt. The reaction mixture was stirred at rt for 18 h.

The resulting reaction mixture was basified with saturated NaHCO₃ solution (10 ml), diluted with water (20 ml) and extracted with 10% MeOH in DCM (2×50 ml). The combined organic phase was washed with brine (30 ml). The organic phase was separated, dried over Na₂SO₄, filtered and concentrated under reduced pressure. The resulting crude material was purified by flash chromatography (27% EtOAc in hexane) yielding 4-(3-(methoxymethyl)phenyl)-N-methylthiazol-2-amine (0.18 g, 0.767 mmol). LCMS: Method C, 1.589 min, MS: ES+ 235.28; ¹H NMR (400 MHz, DMSO-d6) δ ppm 7.79 (s, 1H), 7.75 (d, J=8.0 Hz, 1H), 7.57 (q, J=4.4 Hz, 1H), 7.43 (t, J=7.6 Hz, 1H), 7.20 (d, J=7.6 Hz, 1H), 7.07 (s, 1H), 4.43 (s, 2H), 3.30 (s, 3H), 2.87 (4.4 Hz, 3H).

Steps f-h. The title compound was synthesised from the intermediate above using a procedure similar to that described for Example 1. LCMS: Method H, 4.61 min, MS: ES+ 357.08; ¹H NMR (400 MHz, DMSO-d6) δ ppm 7.90 (s, 1H), 7.88 (s, 1H), 7.77 (s, 1H), 7.42 (t, J=7.6 Hz, 1H), 7.28 (d, J=7.2 Hz, 1H), 5.13-5.17 (m, 1H), 4.47 (s, 2H), 3.77 (s, 3H), 3.50-3.60 (m, 2H), 3.32 (s, 3H), 2.33-2.42 (m, 1H), 2.04-2.10 (m, 1H), 1.92-2.00 (m, 1H), 1.88-1.90 (m, 1H).

Example 146 (S)-1-cyano-N-(5-cyano-4-phenylthiazol-2-yl)-N-methylpyrrolidine-2-carboxamide

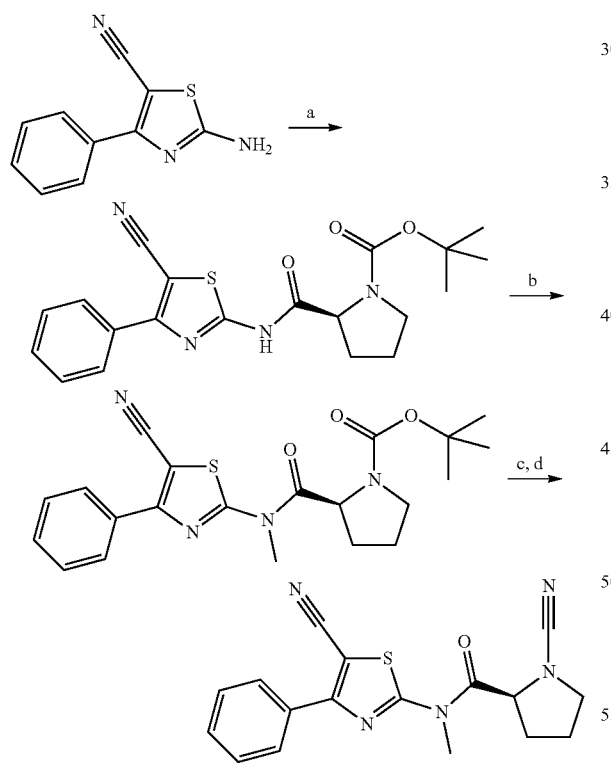

Step a. To a stirred solution of 2-amino-5-cyano-4-phenylthiazole (CAS Number 704870-71-3) (0.3 g, 1.49 mmol) and BOC-L-proline (0.64 g, 2.98 mmol) in pyridine (3 ml) was added POCl₃ (0.3 ml, 2.98 mmol) at 0° C. The reaction was stirred at 0° C. for 1 h. The resulting reaction mixture was poured into saturated NaHCO₃ solution (50 ml), extracted with EtOAc (3×25 ml). The combined organic phase was separated, dried over Na₂SO₄, filtered and concentrated under reduced pressure. The resulting crude material was purified by column chromatography (20% EtOAc in hexane) yielding tert-butyl (S)-2-((5-cyano-4-phenylthiazol-2-yl)carbamoyl)pyrrolidine-1-carboxylate (0.39 g, 0.98 mmol). LCMS: Method C, 2.35 min, MS: ES+ 399.48; ¹H NMR (400 MHz, DMSO-d6) δ ppm 13.35 (s, 1H), 8.00-8.01 (m, 2H), 7.56-7.61 (m, 3H), 4.39-4.51 (m, 1H), 3.43-3.49 (m, 1H), 3.36-3.38 (m, 1H), 2.20-2.33 (m, 1H), 1.80-1.98 (m, 3H), 1.20 (s, 9H).

Step b. To a stirred solution of tert-butyl (S)-2-((5-cyano-4-phenylthiazol-2-yl)carbamoyl)pyrrolidine-1-carboxylate (0.3 g, 0.753 mmol) in DMF (6 ml) was added Cs₂CO₃ (0.27 g, 0.83 mmol) at rt. The reaction mixture was stirred at rt for 15 min. Methyl iodide (0.12 g, 0.83 mmol) was added to the reaction mixture at rt. The reaction mixture was heated at 110° C. for 30 min. The resulting reaction mixture was cooled to rt, poured into water (50 ml) and extracted with EtOAc (3×25 ml). The combined organic phase was separated, dried over Na₂SO₄, filtered and concentrated under reduced pressure. The resulting crude material was purified by column chromatography (20% EtOAc in hexane) yielding tert-butyl (S)-2-((5-cyano-4-phenylthiazol-2-yl)(methyl)carbamoyl)pyrrolidine-1-carboxylate (0.26 g, 0.63 mmol). LCMS: Method C, 2.47 min, MS: ES+ 413.47; ¹H NMR (400 MHz, DMSO-d6) δ ppm 8.06-8.09 (m, 2H), 7.53-7.65 (m, 3H), 4.97-5.04 (m, 1H), 3.85 (s, 3H), 3.38-3.85 (m, 2H), 2.30-2.38 (m, 1H), 1.98-2.04 (m, 1H), 1.87-1.91 (m, 2H), 1.25 (s, 9H).

Steps c, d. The title compound was synthesised from the intermediate above using a procedure similar to that described for Example 1. LCMS: Method H, 4.69 min, MS: ES+ 337.9; ¹H NMR (400 MHz, DMSO-d6) δ ppm 8.06-8.09 (dd, J=1.6 Hz, 8.4 Hz, 2H), 7.54-7.62 (m, 3H), 5.20-5.23 (dd, J=3.6 Hz, 8.8 Hz, 1H), 3.78 (s, 3H), 3.52-3.61 (m, 2H), 2.38-2.46 (m, 1H), 2.07-2.14 (m, 1H), 1.92-1.98 (m, 1H), 1.80-1.84 (m, 1H).

Example 147 (S)-1-cyano-N-(4-(6-cyclopropylpyridin-2-yl)thiazol-2-yl)-N-methylpyrrolidine-2-carboxamide

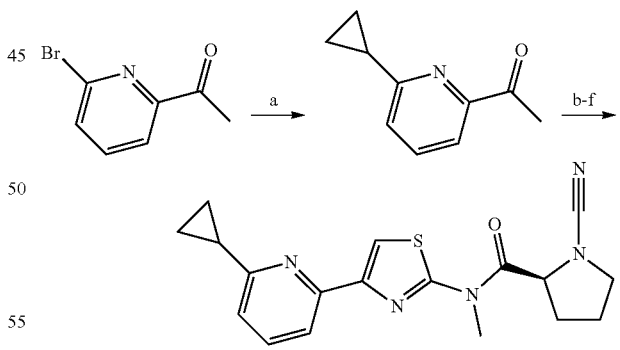

Step a. To a stirred solution of 2-acetyl-6-bromopyridine (CAS Number 49669-13-8) (2.0 g, 10.0 mmol) and cyclopropylboronic acid (1.3 g, 15.0 mmol) in THF (40 ml) was added potassium phosphate tribasic (5.3 g, 25.0 mmol) at rt. The reaction mixture was degassed using nitrogen for 15 min. (1,1'-Bis(diphenylphosphino)ferrocene)palladium(II) dichloride (0.73 g, 0.1 mmol) was added to the reaction mixture at rt. The reaction mixture was heated at 80° C. for 3 h. The resulting reaction mixture was cooled to rt, poured into water (150 ml) and extracted with EtOAc (3×50 ml).

The combined organic phase was separated, dried over Na$_2$SO$_4$, filtered and concentrated under reduced pressure. The crude material was purified by column chromatography (5% EtOAc in hexane) yielding 1-(6-cyclopropylpyridin-2-yl)ethan-1-one (1.2 g, 7.44 mmol). LCMS: Method C, 2.08 min, MS: ES+163.37; $^1$H NMR (400 MHz, DMSO-d6) δ ppm 7.83 (t, J=7.6 Hz, 1H), 7.68 (dd, J=0.8 Hz, 7.6 Hz, 1H), 7.54 (dd, J=0.8 Hz, 7.6 Hz, 1H), 2.54 (s, 3H), 2.17-2.23 (m, 1H), 0.96-1.05 (m, 4H).

Steps b-f. The title compound was synthesised from the intermediate above using a procedure similar to that described for Example 77, steps c-g. LCMS: Method H, 5.07 min, MS: ES+ 353.97; $^1$H NMR (400 MHz, DMSO-d6) δ ppm 7.85 (s, 1H), 7.78-7.80 (m, 1H), 7.73-7.75 (m, 1H), 7.22 (d, J=6.8 Hz, 1H), 5.12-5.16 (dd, J=4.0 Hz. 8.8 Hz, 1H), 3.76 (s, 3H), 3.51-3.60 (m, 2H), 2.33-2.45 (m, 1H), 2.03-2.16 (m, 2H), 1.77-1.99 (m, 2H), 0.95-1.01 (m, 4H).

Example 148 (S)-1-cyano-N-(4-(3-cyanophenyl)-5-fluorothiazol-2-yl)-N-methylpyrrolidine-2-carboxamide

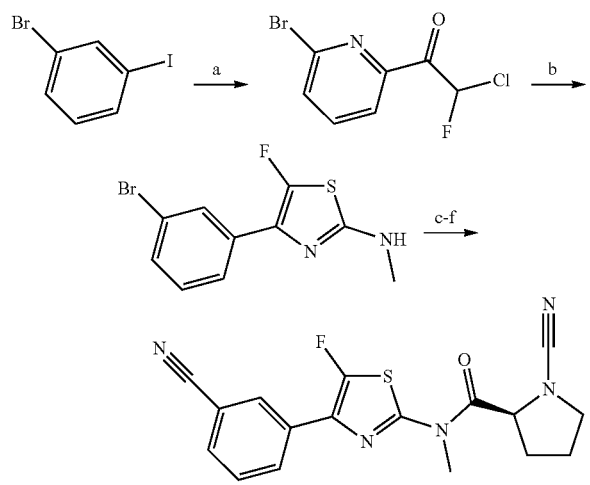

Step a. To a stirred solution of 1-bromo-3-iodobenzene (CAS Number 591-18-4) (3.0 g, 10.6 mmol) in dry THF (60 ml) was added n-butyl lithium (1.6M in hexane) (6.62 ml, 10.6 mmol) drop wise at −78° C. The reaction mixture was stirred at −78° C. for 30 min. Ethyl chlorofluoroacetate (CAS Number 401-56-9) (2.53 g, 18.0 mmol) was added drop wise to the reaction mixture at −78° C. The reaction mixture was stirred at −78° C. for 0.5 h. The resulting reaction mixture was quenched with saturated NH$_4$Cl solution (100 ml) and was extracted with EtOAc (10×100 ml). The combined organic extracts were dried over anhydrous Na$_2$SO$_4$, filtered and concentrated under reduced pressure. The resulting crude material was purified by flash chromatography (10% EtOAc in hexane) yielding 1-(3-bromophenyl)-2-chloro-2-fluoroethan-1-one (2.01 g, 8.01 mmol). $^1$H NMR (400 MHz, CDCl$_3$) δ ppm 8.22 (s, 1H), 8.03 (d, J=7.6 Hz, 1H), 7.82 (d, 8.0 Hz, 1H), 7.44 (t, J=7.6 Hz, 1H), 6.73-6.85 (d, J$_{HF}$=50.8 Hz, 1H).

Step b. To a stirred solution of 1-(3-bromophenyl)-2-chloro-2-fluoroethan-1-one (1.0 g, 3.98 mmol) in THF (20 ml) was added N-methylthiourea (0.897 g, 9.96 mmol) at rt. The reaction mixture was heated at 90° C. for 5 h. The resulting reaction mixture was cooled to rt and combined with one other batch prepared on the same scale by an identical method. The reaction mixture was diluted with water (100 ml) and extracted with EtOAc (5×100 ml). The combined organic extracts were dried over anhydrous Na$_2$SO$_4$, filtered and concentrated under reduced pressure. The resulting crude material was purified by flash chromatography (4.8% EtOAc in hexane) yielding 4-(3-bromophenyl)-5-fluoro-N-methylthiazol-2-amine (1.75 g, 6.10 mmol). LCMS: Method C, 2.512 min, MS: ES+ 287.1, 289.1; $^1$H NMR (400 MHz, DMSO-d6) δ ppm 7.78 (s, 1H), 7.74 (d, J=8.0 Hz, 1H), 7.57 (q, J=4.8 Hz, 1H), 7.51 (d, J=8.0 Hz, 1H), 7.40 (t, J=8.0 Hz, 1H), 2.83 (d, J=4.8 Hz, 3H).

Steps c-f. The title compound may be synthesised from the intermediate above using a procedure similar to that described for steps c-f of Example 110.

BIOLOGICAL ACTIVITY OF COMPOUNDS OF THE INVENTION

Abbreviations:
TAMRA carboxytetramethylrhodamine
PCR polymerase chain reaction
PBS phosphate buffered saline
EDTA ethylenediaminetetraacetic acid
Tris 2-amino-2-(hydroxymethyl)-1,3-propanediol
NP-40 Nonidet P-40, octylphenoxypolyethoxyethanol
BSA bovine serum albumin
PNS peripheral nervous system
BH3 Bcl-2 homology domain 3
PTEN phosphatase and tensin homologue
In Vitro UCHL1 Inhibition Assay
Expression and Purification of UCHL1

The UCHL1 construct was PCR amplified and cloned into a pFLAG-CMV-6a vector (Sigma-Aldrich) with an N-terminal FLAG tag. HEK293T cells were transfected with FLAG-UCHL1 using TransIT-LT1 transfection reagent (Mirus) according to the manufacturer's instructions. Cells were harvested 40 hours after transfection. Cells were washed once with PBS and scraped in lysis buffer (50 mM Tris, pH 7.5, 150 mM NaCl, 3 mM EDTA, 0.5% NP40, 10% glycerol, 5 mM beta-mercaptoethanol, protease inhibitors (complete mini, Roche) and phosphatase inhibitors (PhosSTOP mini, Roche). Lysates were incubated for 30 min on ice and centrifuged at 1200 rpm for 10 min at 4° C. Soluble supernatant was added to FLAG affinity resin (EZview Rad ANTI-FLAG M2 affinity gel, Sigma-Aldrich) equilibrated in low salt buffer (20 mM Tris, pH 7.5, 150 mM NaCl, 0.5 mM EDTA, 5 mM beta-mercaptoethanol) and incubated at 4° C. for 3 hours rotating. The resin was spun at 2000 rpm for 2 min and the supernatant was removed. The resin was washed two times with low salt buffer and one time with high salt buffer (20 mM Tris, pH 7.5, 500 mM NaCl, 0.5 mM EDTA, 5 mM beta-mercaptoethanol, protease inhibitors (complete mini, Roche) and phosphatase inhibitors (PhosSTOP mini, Roche). To elute the bound UCHL1, elution buffer (10 mM Tris, pH 7.5, 150 mM NaCl, 0.5 mM EDTA, 10% glycerol, 0.5% NP40, 5 mM beta-mercaptoethanol, 0.15 mg/ml 3×FLAG peptide (Sigma-Aldrich)) was added to the resin and incubated at 4° C. for 2.5 hours rotating. The resin was centrifuged at 4000 rpm for 30 seconds, and the supernatant containing purified FLAG-UCHL1 was removed and stored at −80° C.

UCHL1 Biochemical Kinetic Assay

Reactions were performed in duplicate in black 384 well plates (small volume, Greiner 784076) in a final reaction volume of 21 μl. UCHL1 was diluted in reaction buffer (20 mM Tris, pH 7.5, 100 mM NaCl, 0.05% Tween 20, 0.5 mg/ml BSA, 5 mM—beta mercaptoethanol) to the equivalent of 0, 0.01, 0.05, 0.1, 0.5, and 1 µl/well. Buffer was optimised for optimal temperature, pH, reducing agent, salts, time of incubation, and detergent. Reactions were initiated by the addition of 50 nM of TAMRA labelled peptide linked to ubiquitin via an iso-peptide bond as fluorescence polarisation substrate. Reactions were incubated at room temperature and read every 2 min for 120 min. Readings were performed on a Pherastar Plus (BMG Labtech). λ Excitation 540 nm; λ Emission 590 nm.

UCHL1 Biochemical IC50 Assay

Dilution plates were prepared at 21 times the final concentration (2100 µM for a final concentration of 100 µM) in 50% DMSO in a 96-well polypropylene V-bottom plate (Greiner #651201). A typical 8-point dilution series to be 30, 10, 3, 1, 0.3, 0.1, 0.03, 0.01 µM final. Reactions were performed in duplicate in black 384 well plates (small volume, Greiner 784076) in a final reaction volume of 21 µl. Either 1 µl of 50% DMSO or diluted compound was added to the plate. UCHL1 was diluted in reaction buffer (20 mM Tris, pH 7.5, 100 mM NaCl, 0.05% Tween 20, 0.5 mg/ml BSA, 5 mM—beta mercaptoethanol) to the equivalent of 0.05 µl/well and 10 µl of diluted UCHL1 was added to the compound. Enzyme and compound were incubated for 30 min at room temp. Reactions were initiated by the addition of 50 nM of TAMRA labelled peptide linked to ubiquitin via an iso-peptide bond as fluorescence polarisation substrate. Reactions were read immediately after addition of substrate and following a 2 hr incubation at room temperature. Readings were performed on a Pherastar Plus (BMG Labtech). λ Excitation 540 nm; λ Emission 590 nm.

Activity of Exemplary Compounds in UCHL1 biochemical IC50 assay

Ranges:
A<0.1 µM;
0.1<B<1 µM;
1<C<10 µM;
10 µM<D<100 µM

| Example | IC50 range |
|---|---|
| 1 | C |
| 2 | C |
| 3 | C |
| 4 | C |
| 5 | C |
| 6 | C |
| 7 | C |
| 8 | C |
| 9 | C |
| 10 | C |
| 11 | C |
| 12 | C |
| 13 | C |
| 14 | C |
| 15 | C |
| 16 | C |
| 17 | C |
| 18 | C |
| 19 | A |
| 20 | B |
| 21 | B |
| 22 | D |
| 23 | C |
| 24 | C |
| 25 | B |
| 26 | C |
| 27 | A |
| 28 | B |
| 29 | A |
| 30 | B |
| 31 | D |
| 32 | C |
| 33 | C |
| 34 | D |
| 35 | D |
| 36 | C |
| 37 | B |
| 38 | B |
| 39 | B |
| 40 | C |
| 41 | C |
| 42 | C |
| 43 | C |
| 44 | C |
| 45 | D |
| 46 | B |
| 47 | B |
| 48 | D |
| 49 | C |
| 50 | C |
| 51 | C |
| 52 | B |
| 53 | B |
| 54 | B |
| 55 | D |
| 56 | C |
| 57 | D |
| 58 | C |
| 59 | D |
| 60 | C |
| 61 | C |
| 62 | C |
| 63 | C |
| 64 | C |
| 65 | D |
| 66 | D |
| 67 | D |
| 68 | D |
| 69 | D |
| 70 | C |
| 71 | B |
| 72 | C |
| 73 | C |
| 74 | B |
| 75 | D |
| 76 | B |
| 78 | C |
| 79 | C |
| 81 | B |
| 85 | C |
| 86 | C |
| 87 | C |
| 88 | C |
| 89 | B |
| 90 | C |
| 91 | C |
| 92 | C |
| 95 | A |
| 96 | B |
| 97 | B |
| 103 | C |
| 104 | C |
| 105 | C |
| 109 | B |
| 110 | D |
| 112 | C |
| 115 | A |
| 116 | B |
| 117 | A |
| 118 | D |
| 119 | C |
| 120 | B |
| 121 | D |
| 122 | B |
| 123 | B |

| Example | IC50 range |
|---|---|
| 124 | B |
| 125 | C |
| 126 | B |

In Vitro USP30 Inhibition Assay

USP30 biochemical kinetic assay. Reactions were performed in duplicate in black 384 well plates (small volume, Greiner 784076) in a final reaction volume of 21 µl. USP30 CD (57-517, #64-0057-050 Ubiquigent) was diluted in reaction buffer (40 mM Tris, pH 7.5, 0.005% Tween 20, 0.5 mg/ml BSA, 5 mM—beta-mercaptoethanol) to the equivalent of 0, 0.005, 0.01, 0.05, 0.1 and 0.5 µl/well. Buffer was optimised for optimal temperature, pH, reducing agent, salts, time of incubation, and detergent. Reactions were initiated by the addition of 50 nM of TAMRA labelled peptide linked to ubiquitin via an iso-peptide bond as fluorescence polarisation substrate. Reactions were incubated at room temperature and read every 2 min for 120 min. Readings were performed on a Pherastar Plus (BMG Labtech). λ Excitation 540 nm; λ Emission 590 nm.

USP30 Biochemical IC50 Assay

Dilution plates were prepared at 21 times the final concentration (2100 µM for a final concentration of 100 µM) in 50% DMSO in a 96-well polypropylene V-bottom plate (Greiner #651201). A typical 8-point dilution series would be 100, 30, 10, 3, 1, 0.3, 0.1, 0.03 µM final. Reactions were performed in duplicate in black 384 well plates (small volume, Greiner 784076) in a final reaction volume of 21 µl. Either 1 µl of 50% DMSO or diluted compound was added to the plate. USP30 was diluted in reaction buffer (40 mM Tris, pH 7.5, 0.005% Tween 20, 0.5 mg/ml BSA, 5 mM—beta-mercaptoethanol) to the equivalent of 0.05 µl/well and 10 µl of diluted USP30 was added to the compound. Enzyme and compound were incubated for 30 min at room temp. Reactions were initiated by the addition of 50 nM of TAMRA labelled peptide linked to ubiquitin via an iso-peptide bond as fluorescence polarisation substrate. Reactions were read immediately after addition of substrate and following a 2 hr incubation at room temperature. Readings were performed on a Pherastar Plus (BMG Labtech). λ Excitation 540 nm; λ Emission 590 nm.

Activity of Exemplary Compounds in USP30 biochemical IC50 assay

Ranges:
A<0.1 µM;
0.1<B<1 µM;
1<C<10 µM;
10 µM<D<100 µM

| Example | IC50 range |
|---|---|
| 6 | D |
| 8 | D |
| 22 | C |
| 23 | C |
| 24 | C |
| 33 | C |
| 43 | D |
| 46 | B |
| 47 | B |
| 48 | C |
| 49 | C |
| 50 | C |
| 52 | A |
| 53 | C |
| 54 | C |
| 57 | D |
| 59 | C |
| 61 | B |
| 62 | D |
| 64 | C |
| 65 | C |
| 66 | C |
| 67 | C |
| 68 | C |
| 69 | C |
| 77 | A |
| 78 | B |
| 79 | B |
| 80 | A |
| 81 | C |
| 82 | B |
| 83 | A |
| 84 | B |
| 85 | C |
| 86 | D |
| 87 | C |
| 88 | C |
| 89 | C |
| 90 | C |
| 91 | C |
| 92 | B |
| 93 | B |
| 94 | B |
| 98 | C |
| 99 | C |
| 100 | C |
| 101 | C |
| 102 | C |
| 104 | C |
| 105 | C |
| 106 | C |
| 107 | C |
| 108 | C |
| 109 | B |
| 110 | B |
| 111 | D |
| 112 | C |
| 113 | C |
| 114 | B |
| 115 | C |
| 122 | C |
| 124 | B |
| 125 | A |
| 126 | B |
| 127 | A |
| 128 | C |
| 129 | C |
| 130 | C |
| 131 | C |
| 132 | C |
| 133 | B |
| 134 | C |
| 135 | C |
| 136 | B |
| 137 | A |
| 138 | C |
| 139 | B |
| 140 | A |
| 141 | B |
| 142 | A |
| 143 | B |
| 144 | B |
| 145 | B |
| 146 | C |
| 147 | B |

The invention claimed is:
1. A compound of formula (I)

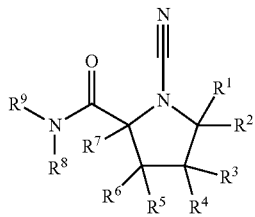

a tautomer thereof, or a pharmaceutically acceptable salt of said compound or tautomer, wherein:

$R^1$, $R^2$ and $R^7$ each independently represent a hydrogen atom or $C_1$-$C_6$ alkyl;

$R^3$, $R^4$, $R^5$ and $R^6$ each independently represent a hydrogen atom, a halogen atom, cyano, $C_1$-$C_6$ alkyl, $C_1$-$C_6$ alkoxy, a 3 to 10 membered cycloalkyl or heterocyclyl, or a 5 to 10 membered heteroaryl or aryl;

$R^8$ represents $C_1$-$C_3$ alkyl;

$R^9$ represents a 3 to 10-membered monocyclic or bicyclic cycloalkyl or heterocyclyl or a 5 to 10-membered monocyclic or bicyclic heteroaryl or aryl;

wherein $R^9$ is optionally substituted with one or more $R^{10}$ substituents;

each $R^{10}$ is independently selected from a halogen atom, oxo, cyano, $-OR^{11a}$, $-SR^{11a}$, $-NO_2$, $-NR^{11a}R^{12a}$, $-CONR^{11a}R^{12a}$, $-NR^{11a}COR^{12a}$, $-NR^{11a}CONR^{12a}R^{13a}$, $-COR^{11a}$, $-C(O)OR^{11a}$, $-SO_2R^{11a}$, $-SO_2NR^{11a}R^{12a}$, $-NR^{11a}SO_2R^{12a}$, $-NR^{11a}SO_2NR^{12a}R^{13a}$, $-NR^{11a}C(O)OR^{12a}$, $-C_1$-$C_6$ alkyl, $-C_1$-$C_6$ alkoxy, and $-C_2$-$C_6$ alkenyl;

$R^{11a}$, $R^{12a}$ and $R^{13a}$ each independently represent a hydrogen atom or $C_1$-$C_6$ alkyl;

wherein $R^9$ is also optionally substituted with one, two, or more, $R^{14}$ substituents, which are each attached to the ring through Q;

Q is selected from a covalent bond, an oxygen atom, a sulphur atom, $-NR^{11}-$, $-CONR^{11}-$, $-NR^{11}CO-$, $-NR^{11}CONR^{12}-$, $-CO-$, $-C(O)O-$, $-SO-$, $-SO_2-$, $-SO_2NR^{11}-$, $-NR^{11}SO_2-$, $-NR^{11}SO_2NR^{12}-$, $-NR^{11}C(O)O-$, $-NR^{11}C(O)OR^{13}-$, $-C_1$-$C_6$ alkylene, $-C_1$-$C_6$ alkyleneoxy and $-C_2$-$C_6$ alkenylene;

$R^{11}$ and $R^{12}$ each independently represent a hydrogen atom or $C_1$-$C_6$ alkyl;

$R^{13}$ represents a $C_1$-$C_6$ alkylene group;

$R^{14}$ represents a 3 to 10-membered monocyclic or bicyclic cycloalkyl or heterocyclyl or a 5 to 10-membered monocyclic or bicyclic heteroaryl or aryl;

and each occurrence of $R^{14}$ and Q is the same or different;

wherein $R^{14}$ is optionally substituted with one or more substituents each independently selected from a halogen atom, oxo, cyano, $-OR^{15}$, $-SR^{15}$, $-NO_2$, $-NR^{15}R^{16}$, $-CONR^{15}R^{16}$, $-NR^{15}COR^{16}$, $-NR^{15}CONR^{16}R^{17}$, $-COR^{15}$, $-C(O)OR^{15}$, $-SO_2R^{15}$, $-SO_2NR^{15}R^{16}$, $-NR^{15}SO_2R^{16}$, $-NR^{15}SO_2NR^{16}R^{17}$, $-NR^{15}C(O)OR^{16}$, $-C_1$-$C_6$ alkyl, $-C_1$-$C_6$ alkoxy, $-C_1$-$C_6$ alkylene, $-C_1$-$C_6$ alkyleneoxy, $-C_2$-$C_6$ alkenyl, methoxymethyl, methoxyethoxy, $-C_2$-$C_6$ alkenylene, 3 to 10-membered cycloalkyl or heterocyclyl, and 5 to 10-membered heteroaryl or aryl, wherein the $-C_1$-$C_6$ alkylene, $-C_1$-$C_6$ alkyleneoxy or $-C_2$-$C_6$ alkenylene group is attached to a 3 to 10-membered cycloalkyl or heterocyclyl or 5 to 10-membered heteroaryl or aryl;

$R^{15}$, $R^{16}$ and $R^{17}$ each independently represent a hydrogen atom, $C_1$-$C_6$ alkyl, a 3 to 10-membered cycloalkyl or heterocyclyl or 5 to 10-membered heteroaryl or aryl;

each $C_1$-$C_6$ alkyl, $C_1$-$C_6$ alkoxy, $C_2$-$C_6$ alkenyl, $C_1$-$C_6$ alkylene, $C_1$-$C_6$ alkyleneoxy and $C_2$-$C_6$ alkenylene, is optionally substituted with one or more substituents, which may be the same or different, selected from halogen, hydroxyl, thiol, cyano, amino, nitro and $SF_5$; and each cycloalkyl, aryl, heterocyclyl and heteroaryl ring of $R^3$, $R^4$, $R^5$ and $R^6$ is optionally substituted with one or more substituents, which may be the same or different, selected from halogen, hydroxyl, thiol, cyano, amino, nitro, $SF_5$, $C_1$-$C_6$ alkyl and $C_1$-$C_6$ alkoxy, wherein the alkyl and alkoxy groups are optionally substituted with one or more halogen.

2. The compound according to claim 1, wherein $R^1$, $R^2$, $R^5$, $R^6$ and $R^7$ are each hydrogen.

3. The compound according to claim 1, wherein $R^3$ and $R^4$ independently represent a hydrogen atom, a halogen atom, optionally substituted $C_1$-$C_3$ alkyl, optionally substituted $C_1$-$C_3$ alkoxy or an optionally substituted 6-membered aryl.

4. The compound according to claim 1, wherein the optionally substituted heterocyclyl, heteroaryl or aryl ring of $R^9$ is selected from morpholinyl, piperidinyl, pyrrolidinyl, diazepanyl, piperazinyl, pyridazinyl, pyrazinyl, pyrazolyl, cyclopropyl, cyclohexyl, cyclopentyl, pyridinyl, imidazolyl, indolinyl, isoindolinyl, pyrimidinyl, isoxazolyl, dihydroindenyl, dihydroisoquinolinyl, tetrahydropyranyl, benzothiazolyl, phenyl, oxadiazolyl, triazolyl and thiazolyl.

5. The compound according to claim 4, wherein the optionally substituted heteroaryl ring of $R^9$ is selected from thiazolyl, benzothiazolyl and isoxazolyl.

6. The compound according to claim 1, wherein $R^{10}$ is selected from a halogen atom, cyano, optionally substituted $C_1$-$C_6$ alkyl, optionally substituted $C_1$-$C_6$ alkoxy, $-NR^{11a}R^{12a}$, and $-CONR^{11a}R^{12a}$.

7. The compound according to claim 1, wherein $R^9$ is substituted with one or more $R^{10}$ substituents selected from methyl, ethyl, cyano and fluorine.

8. The compound according to claim 1, wherein $R^{14}$ represents an optionally substituted 5 to 6-membered monocyclic heteroaryl, aryl or heterocyclyl, or an optionally substituted 9 to 10-membered bicyclic heteroaryl or heterocyclyl, or an optionally substituted 3 to 5-membered cycloalkyl.

9. The compound according to claim 8, wherein the optionally substituted heteroaryl, aryl, heterocyclyl, or cycloalkyl ring of $R^{14}$ is selected from phenyl, isoxazolyl, pyridinyl, pyrazolyl, cyclopropyl, tetrahydrofuran, pyrimidinyl, pyrrolopyridinyl, pyrazinyl, imidazopyridinyl, benzodioxolyl, triazolyl, imidazolyl, indazolyl, pyrrolopyrazinyl, pyridazinyl, pyrazolopyridinyl, and quinolinyl.

10. The compound according to claim 1, wherein Q is selected from a covalent bond, an oxygen atom, optionally substituted $C_1$-$C_6$ alkylene, and optionally substituted $C_1$-$C_6$ alkyleneoxy.

11. The compound according to claim 1, wherein $R^{14}$ is substituted with one or more substituents selected from fluorine, chlorine, cyano, nitro, methyl, ethyl, cyclopropyl, $CF_3$, methoxy, ethoxy, methoxymethyl, methoxyethoxy, propoxy, $OCF_3$, $C(O)NHMe$, $NHC(O)Me$, $NMeC(O)Me$, $NMeS(O)_2Me$, $S(O)_2Me$, $NH_2$, $NHMe$ and $N(Me)_2$.

12. The compound according to claim 1, having the stereochemistry of formula (II)

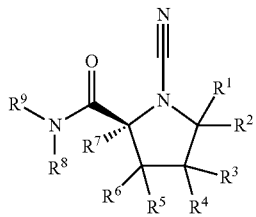

a tautomer thereof, or a pharmaceutically acceptable salt of said compound or tautomer.

13. The compound according to claim 1, which is selected from:
- (S)-1-cyano-N-ethyl-N-(4-phenylthiazol-2-yl)pyrrolidine-2-carboxamide;
- (S)-1-cyano-N-(4-(2-methoxyphenyl)thiazol-2-yl)-N-methylpyrrolidine-2-carboxamide;
- (S)-1-cyano-N-(4-(3-methoxyphenyl)thiazol-2-yl)-N-methylpyrrolidine-2-carboxamide;
- (S)-1-cyano-N-methyl-N-(4-(pyridin-2-yl)thiazol-2-yl)pyrrolidine-2-carboxamide;
- (S)-1-cyano-N-methyl-N-(4-(pyridin-3-yl)thiazol-2-yl)pyrrolidine-2-carboxamide;
- (S)-1-cyano-N-methyl-N-(4-(pyridin-4-yl)thiazol-2-yl)pyrrolidine-2-carboxamide;
- (2S)-1-cyano-N-methyl-N-(4-(tetrahydrofuran-3-yl)thiazol-2-yl)pyrrolidine-2-carboxamide;
- (S)—N-(4-(3-chlorophenyl)thiazol-2-yl)-1-cyano-N-methylpyrrolidine-2-carboxamide;
- (S)—N-(4-(2-chlorophenyl)thiazol-2-yl)-1-cyano-N-methylpyrrolidine-2-carboxamide;
- (S)-1-cyano-N-methyl-N-(4-phenylthiazol-2-yl)pyrrolidine-2-carboxamide;
- (S)-1-cyano-N-methyl-N-(1-phenyl-1H-pyrazol-3-yl)pyrrolidine-2-carboxamide;
- (S)-1-cyano-N-(4-isopropylthiazol-2-yl)-N-methylpyrrolidine-2-carboxamide;
- (S)-1-cyano-N-methyl-N-(3-phenylisoxazol-5-yl)pyrrolidine-2-carboxamide;
- (S)—N-(5-benzylthiazol-2-yl)-1-cyano-N-methylpyrrolidine-2-carboxamide;
- (S)-1-cyano-N-methyl-N-(5-phenylthiazol-2-yl)pyrrolidine-2-carboxamide;
- (S)—N-(4-(tert-butyl)thiazol-2-yl)-1-cyano-N-methylpyrrolidine-2-carboxamide;
- (S)—N-(4-(4-chlorophenyl)thiazol-2-yl)-1-cyano-N-methylpyrrolidine-2-carboxamide;
- (S)—N-(3-(2-chlorophenyl)isoxazol-5-yl)-1-cyano-N-methylpyrrolidine-2-carboxamide;
- (2S,4S)-1-cyano-N-methyl-4-phenyl-N-(4-phenylthiazol-2-yl)pyrrolidine-2-carboxamide;
- (S)—N-(3-(3-chlorophenyl)isoxazol-5-yl)-1-cyano-N-methylpyrrolidine-2-carboxamide;
- (S)-1-cyano-N-(3-(3-methoxyphenyl)isoxazol-5-yl)-N-methylpyrrolidine-2-carboxamide;
- (S)-1-cyano-N-methyl-N-(5-phenylisoxazol-3-yl)pyrrolidine-2-carboxamide;
- (S)—N-(3-(4-chlorophenyl)isoxazol-5-yl)-1-cyano-N-methylpyrrolidine-2-carboxamide;
- (S)—N-(4-(4-acetamidophenyl)thiazol-2-yl)-1-cyano-N-methylpyrrolidine-2-carboxamide;
- (S)—N-(4-(3-acetamidophenyl)thiazol-2-yl)-1-cyano-N-methylpyrrolidine-2-carboxamide;
- (2S,4S)-1-cyano-4-methoxy-N-methyl-N-(4-phenylthiazol-2-yl)pyrrolidine-2-carboxamide;
- (S)-1-cyano-N-(4-(6-cyanopyridin-2-yl)thiazol-2-yl)-N-methylpyrrolidine-2-carboxamide;
- (S)-1-cyano-N-(4-(2-cyanopyridin-4-yl)thiazol-2-yl)-N-methylpyrrolidine-2-carboxamide;
- (S)-1-cyano-N-(4-(4-cyanopyridin-2-yl)thiazol-2-yl)-N-methylpyrrolidine-2-carboxamide;
- (S)-1-cyano-N-(4-(6-cyano-3-methylpyridin-2-yl)thiazol-2-yl)-N-methylpyrrolidine-2-carboxamide;
- (S)-1-cyano-N-(4-(6-methoxypyridin-2-yl)thiazol-2-yl)-N-methylpyrrolidine-2-carboxamide;
- (S)-1-cyano-N-methyl-N-(4-(6-(trifluoromethyl)pyridin-2-yl)thiazol-2-yl)pyrrolidine-2-carboxamide;
- (S)-1-cyano-N-(4-(6-cyano-5-methoxypyridin-2-yl)thiazol-2-yl)-N-methylpyrrolidine-2-carboxamide;
- (S)-1-cyano-N-(4-(6-cyano-5-methylpyridin-2-yl)thiazol-2-yl)-N-methylpyrrolidine-2-carboxamide;
- (S)—N-(5-(3-chlorophenyl)isoxazol-3-yl)-1-cyano-N-methylpyrrolidine-2-carboxamide;
- (S)-1-cyano-N-(5-(3-cyanophenyl)isoxazol-3-yl)-N-methylpyrrolidine-2-carboxamide;
- (S)-1-cyano-N-(5-(3-methoxyphenyl)isoxazol-3-yl)-N-methylpyrrolidine-2-carboxamide;
- (S)—N-(4-(3-chlorophenyl)thiazol-2-yl)-1-cyano-N-ethylpyrrolidine-2-carboxamide;
- (S)-1-cyano-N-(4-(5-cyanopyridin-3-yl)thiazol-2-yl)-N-methylpyrrolidine-2-carboxamide;
- (S)—N-(4-(3-chloro-4-fluorophenyl)thiazol-2-yl)-1-cyano-N-methylpyrrolidine-2-carboxamide;
- (S)-1-cyano-N-methyl-N-(4-(3-(trifluoromethyl)phenyl)thiazol-2-yl)pyrrolidine-2-carboxamide;
- (S)-1-cyano-N-(4-(3-cyanophenyl)thiazol-2-yl)-N-methylpyrrolidine-2-carboxamide;
- (S)-1-cyano-N-(4-(3-ethylphenyl)thiazol-2-yl)-N-methylpyrrolidine-2-carboxamide;
- (S)-1-cyano-N-methyl-N-(4-(3-(N-methylacetamido)phenyl)thiazol-2-yl)pyrrolidine-2-carboxamide;
- (S)-1-cyano-N-methyl-N-(4-(3-(N-methylmethylsulfonamido)phenyl)thiazol-2-yl)pyrrolidine-2-carboxamide;
- (S)-1-cyano-N-(4-(6-cyano-3-methoxypyridin-2-yl)thiazol-2-yl)-N-methylpyrrolidine-2-carboxamide;
- (S)-1-cyano-N-(4-(6-isopropoxypyridin-2-yl)thiazol-2-yl)-N-methylpyrrolidine-2-carboxamide;
- (S)-1-cyano-N-(4-(6-cyano-5-ethoxypyridin-2-yl)thiazol-2-yl)-N-methylpyrrolidine-2-carboxamide;
- (S)-1-cyano-N-(4-(6-cyano-5-(dimethylamino)pyridin-2-yl)thiazol-2-yl)-N-methylpyrrolidine-2-carboxamide;
- (S)-1-cyano-N-(4-(6-cyano-3-(2-methoxyethoxy)pyridin-2-yl)thiazol-2-yl)-N-methylpyrrolidine-2-carboxamide;
- (S)-1-cyano-N-(4-(6-cyano-3-ethoxypyridin-2-yl)thiazol-2-yl)-N-methylpyrrolidine-2-carboxamide;
- (S)-1-cyano-N-(4-(6-cyanopyridin-2-yl)-5-ethylthiazol-2-yl)-N-methylpyrrolidine-2-carboxamide;
- (S)-1-cyano-N-(4-(6-cyanopyridin-2-yl)-5-methylthiazol-2-yl)-N-methylpyrrolidine-2-carboxamide;
- (S)-1-cyano-N-(4-(3-(methoxymethyl)phenyl)thiazol-2-yl)-N-methylpyrrolidine-2-carboxamide;
- (S)-1-cyano-N-(5-cyano-4-phenylthiazol-2-yl)-N-methylpyrrolidine-2-carboxamide;
- (S)-1-cyano-N-(4-(6-cyclopropylpyridin-2-yl)thiazol-2-yl)-N-methylpyrrolidine-2-carboxamide; and
- (S)-1-cyano-N-(4-(3-cyanophenyl)-5-fluorothiazol-2-yl)-N-methylpyrrolidine-2-carboxamide;

a tautomer thereof, or a pharmaceutically acceptable salt of said compound or tautomer.

14. A method of inhibiting USP30, comprising the step of administering the compound according to claim 1, a tautomer thereof, or a pharmaceutically acceptable salt of said compound or tautomer, to a patient in need thereof.

15. A pharmaceutical composition comprising the compound according to claim 1, a tautomer thereof, or a pharmaceutically acceptable salt of said compound or tautomer, and one or more pharmaceutically acceptable excipients.

* * * * *